Figure 1A:
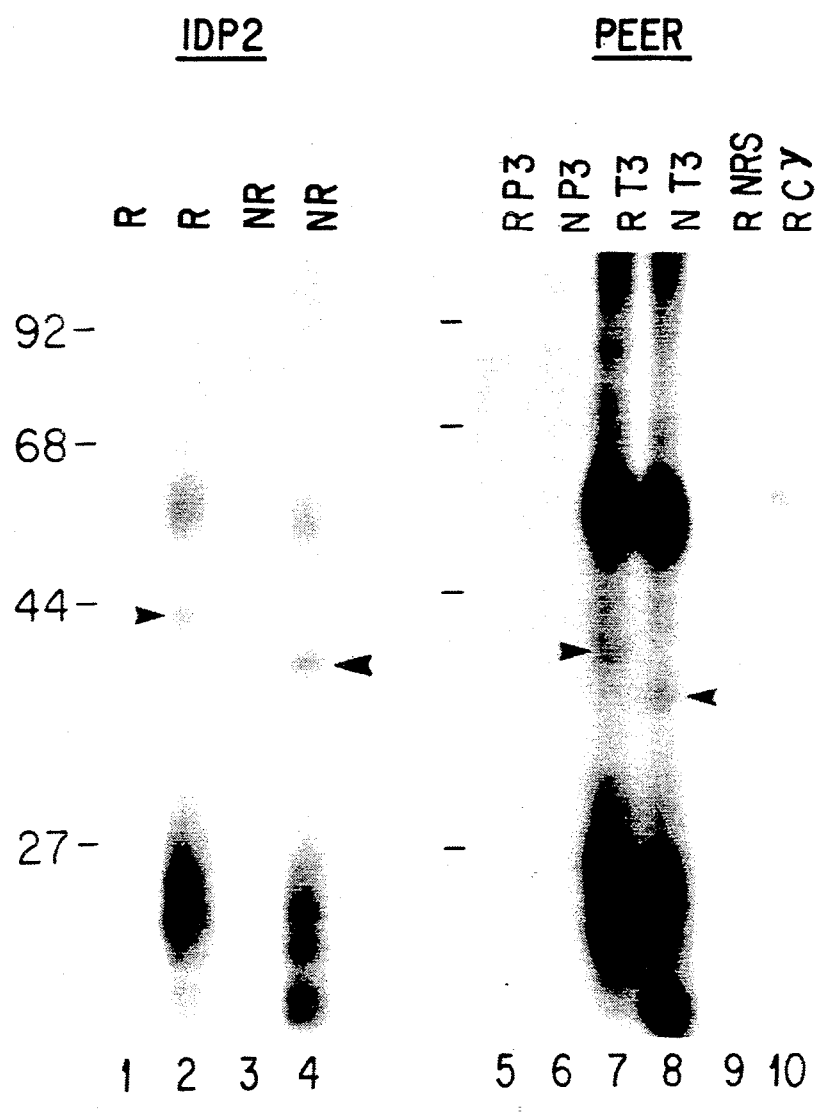

United States Patent [19]
Brenner et al.

[11] Patent Number: 5,185,250
[45] Date of Patent: Feb. 9, 1993

[54] HUMAN γ, δ T CELL ANTIGEN RECEPTOR POLYPEPTIDES AND NUCLEIC ACIDS

[75] Inventors: Michael B. Brenner, Sherborn; Jonathan Seidman, Milton; Jack L. Strominger, Lexington; Stephen H. Ip, Sudbury, all of Mass.; Michael S. Krangel, Chapel Hill, N.C.; Hamid Band, Boston, Mass.

[73] Assignees: T Cell Sciences, Inc., Cambridge; Dana Farber Cancer Institute; President & Fellows of Harvard College, both of Boston, all of Mass.

[21] Appl. No.: 297,661

[22] Filed: Jan. 13, 1989

Related U.S. Application Data

[63] Continuation-in-part of Ser. No. 187,698, Apr. 29, 1988, which is a continuation-in-part of Ser. No. 115,256, Oct. 29, 1987, Pat. No. 5,024,940, which is a continuation-in-part of Ser. No. 16,252, Feb. 19, 1987, which is a continuation-in-part of Ser. No. 882,100, Jul. 3, 1986, abandoned.

[51] Int. Cl.[5] .............. C12P 21/06; C12N 5/02; A61K 35/14; C07H 15/12
[52] U.S. Cl. ................ 435/69.3; 435/69.1; 435/7.24; 435/172.2; 435/240.27; 530/350; 530/387.9; 530/388.22; 530/388.75; 536/23.5
[58] Field of Search ............ 435/7, 69.1, 172.2, 435/172.3, 68.1, 70, 6, 240.27, 69.3; 536/27; 530/387, 359

[56] References Cited

PUBLICATIONS

Loh et al. (1987), Nature, vol. 330, pp. 569-572.
Littman et al. (1987), Nature, vol. 326, pp. 85-88.
Picker et al. Am. J. Pathol. 132:401 (Sep. 1988).
Nakanishi et al.; Nature 325:720 (Feb. 1987).
Satyanarayana et al.; Proc. Natl. Acad. Sci. USA 85:8166 (Nov. 1988).
Dembic et al.; Nature 320:232 (Mar. 1986).
Gascoigne et al.; Proc. Natl. Acad. Sci. USA 84:2936 (May 1987).
Ohashi et al.; Nature 316:606 (Aug. 1985).
Hochstenbach et al.; J. Exp. Med. 168:761 (Aug. 1988).
Brenner et al.; Adv. Immunol. 43:133-192 (1988).
Pardoll et al.; Nature 326:79-81 (1987).

*Primary Examiner*—David L. Lacey
*Assistant Examiner*—Gian P. Wang
*Attorney, Agent, or Firm*—Pennie & Edmonds

[57] ABSTRACT

The present invention is directed to purified polypeptides comprising the γ T cell antigen receptor (TCR) polypeptide, the δ TCR polypeptide, a γ, δ TCR complex, or a fragment thereof containing an epitope. The invention also relates to nucleic acid sequences encoding such polypeptides, and subsequences thereof. In specific embodiments, the invention relates to nucleic acid sequences comprising variable, diversity, joining, or constant regions of the δ TCR gene sequence. The invention also relates to monoclonal antibodies specifically reactive with an epitope of the gamma or delta TCR polypeptides. In specific embodiments, these antibodies are reactive with the delta constant region, the delta variable region, or gamma constant region. Such antibodies can be identified by detecting co-modulation of the CD3 antigen. In another embodiment, the invention relates to compositions comprising substantially purified cells which express both a γ, δ TCR and the CD4 antigen. The invention also relates to a composition comprising cells which express a γ, δ TCR that is not associated with a CD3 complex.

25 Claims, 50 Drawing Sheets

FIG. 3A

```
       K   P   S   V   F   V   M   K   N   G   T   N   V   A  |C   L  | V   K   E   F   Y   P   K   D   I   R   I   N   L   V
                              |140─── |                        |       |150                                 160
       AAA CCA TCC GTT TTT GTC ATG AAA AAT GGA ACA AAT GTC GCT |TGT CTG| GTG AAG GAA TTC TAC CCC AAG GAT ATA AGA ATA AAT CTC GTG
       ─── ─── ──T ─── ─── ──T ─── ─── ─── ─── ─── ─── ──T ─── |─── ───| ─── ──A ──T ─── ─── ──T ─── ──A ──G ─G─ ─CT ─── ──GC AGA

S   S   K   K   I   T   E   F   D   P   A   I   V   I   S   P   S   G   K   Y   N   A   V   K   L   G   K   Y   E   D
                                       170                                  180                                 190
       TCA TCC AAG AAG ATA ACA GAG TTT GAT CCT GCT ATT GTC ATC TCT CCC AGT GGG AAG TAC AAT GCT GTC AAG CTT GGT AAA TAT GAA GAT
       ─── ─── ─── ─── ─── ──T GTG ──A ──C ──C ─── ──A ─── ─── ─── ──C ─── ─── ──C ─── ──G ─── ─── ─── ─── ─── ─── ─── C─G ──G
```

FIG.3A(cont.)

FIG.3B

TGACTGGGCATGAGGAAGCTACACTCCTGAAGAAACCAAAGGCTTACAAAAATGCATCTCCTTGACTTCTTTGTGATTCAAGTTGACCTGTCATAGCCTTGTTAAAATGGCTG

CTAGCAAACCAATTTTTCTTCAAAGACAACAAACCCAGCTCTATCCTCCAGCTTGATGGGAAGACAAAAGTCCTGGGGAAGGGGGTTTATGTCCTAACTGCTTTGTATGCTGTTTTATA

AAGGGATAGAAGGATATAAAAAGATATAGGACTCTTTTTTTTACTCCTACAAGTGATACACTTTGAAAATGATGTTTGTTCCTTTTGACTTTCTTTACCTTTTGAAGTAGAAAGTGGGA

ACCAACAGGTTCACAGCTTCATTCCTCATGAGGAAAATAGGCCTTGGGAGAAGAAGAGCGGGTGCCCTTTATCTAAACATGGAAGGCTCTGCTCAACTGAGCACTAGATTTGCTACAA

ACCAGCATCATCTTCTTCCCTCCTGTCCTCACGGCTTGTCCCACCCTCTATGTTCACTTCAGGAGCCACACTAGAGATTCTGCAAAATCTCATCTATTAGCAAAAATCAGAGTA

CTCTCCTAATACTTTACAAATGAGATTACATTTGAATTTGCTAATACTTTATGAGCAGGCAATGAGGTTTCCAAAATCTCATCTAAATACTCCAATCTATTAGCAAAAATCAGAGTA

AAATACAGAGGAAAGGCACTGCTTTCTGTTAATTGATTAACATGATGAATTAGCTCCCTCTGAGTTCCAGGCACTATGCTGAGAGTACAAAGAAGACACAAGTCTGCTTTCAAGCAA

CTCACTGTGAAAGTGTTTTGAAGGGAGGAACAGAAATGAGACCCTATCTTCCCTATAAAAACAACATTTTACTGTCTTTTGCCTGCCAATCTGTATTTGAAACCATTGGACACTG

ATTCTCTGGCCTGGGACTTTGGCATGATGGTTTTCTGCCTTTCTCTCAGCCTCTGCCCTCTATTGCATTTATTAAACTGCATTGTGTGCAAAAAAAAAAAAAA

FIG.3B(cont.)

MAb: CONTROL | Anti-TCRδ | CONTROL | Anti-TCRδ   Mr
—69

—46

—30

Lane: 1  2  3  4

FIG.5

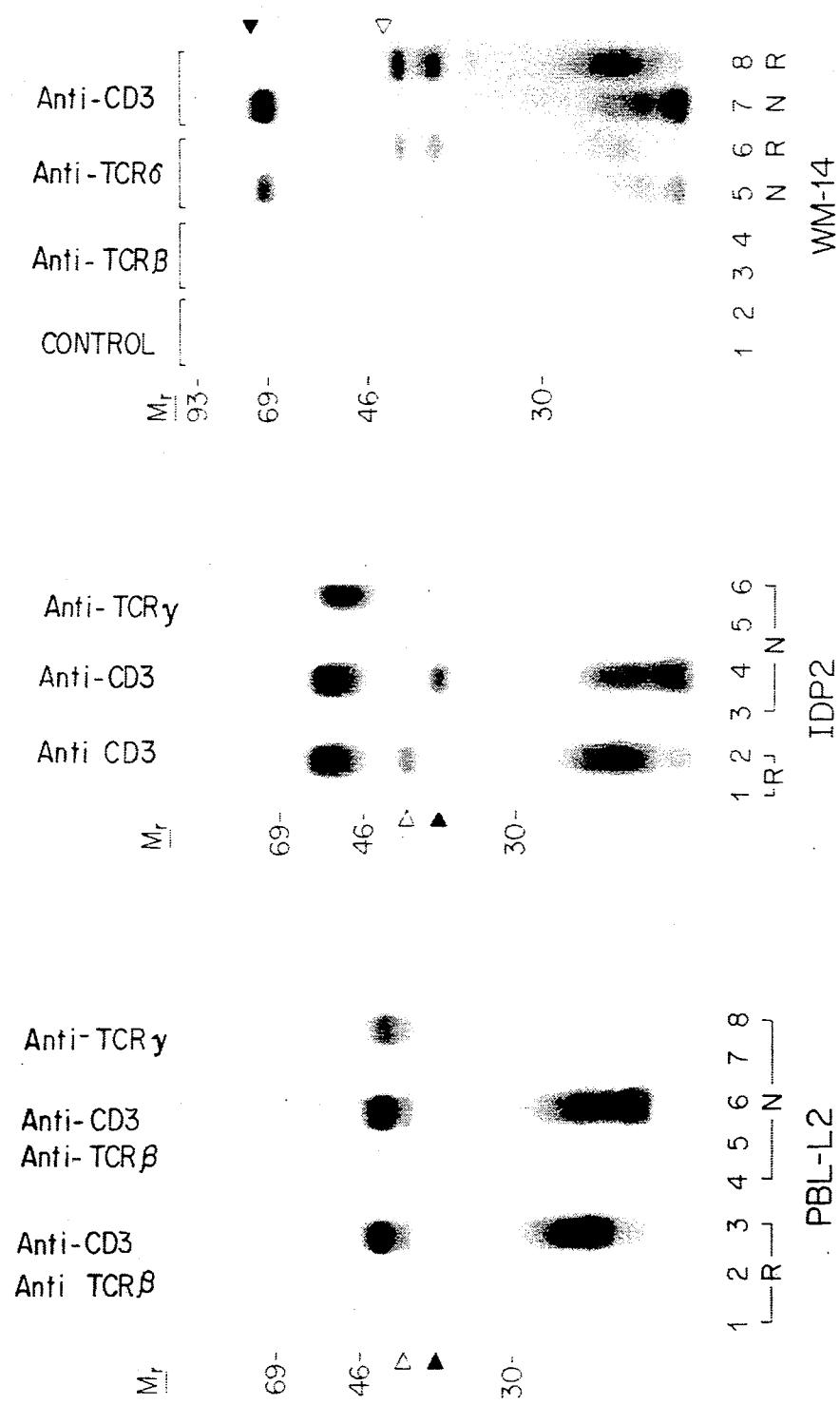

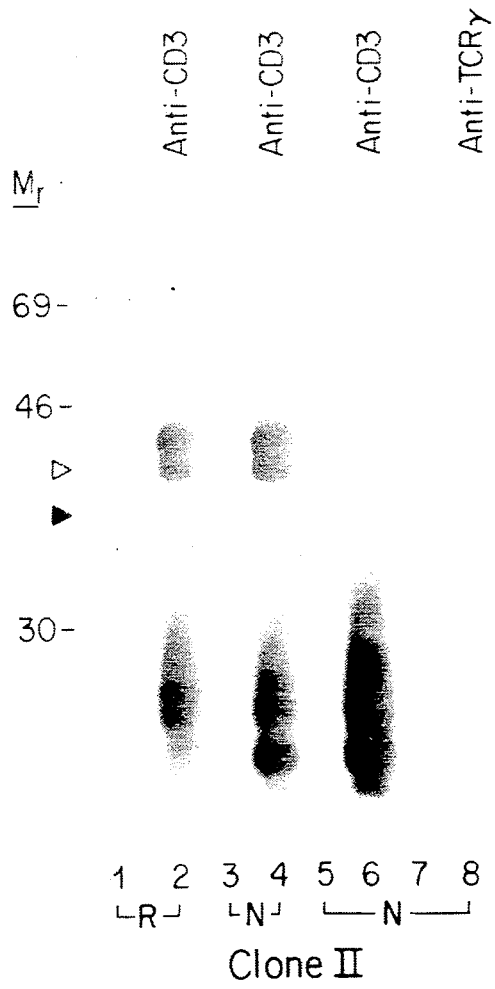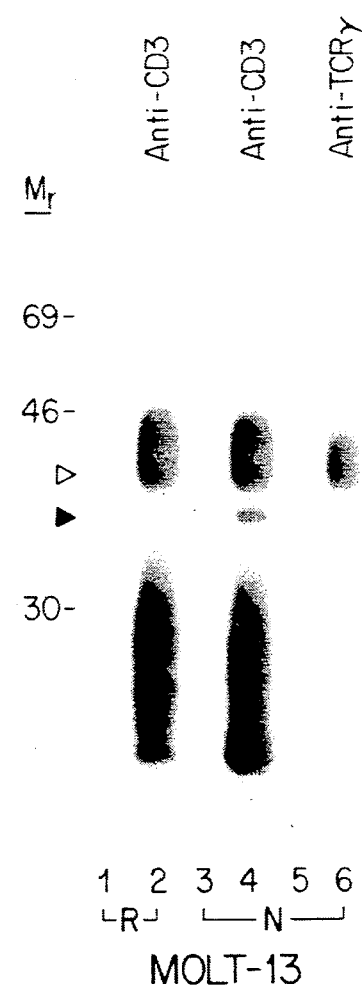

```
                                                                                          ──→ V
1   TGGTCCCTTCCTTCCAAGGCCCCGAGAGGAAGGC ATG CGG TGG GCC CTA GTG GTG CTT CTA GCT TTC CTG TCT CCT GCC AGT CAG
                                       M   R   W   A   L   V   V   L   L   A   F   L   S   P   A   S   Q
                        ──→ B
88  AAA TCT TCC AAC TTG GAA GGG AGA ACG AAG TCA GTC ACC AGG CAG ACT GGG TCA TCT GCT GAA ATC ACT TGC GAT CTT ACT GTA ACA
    K   S   S   N   L   E   G   R   T   K   S   V   T   R   Q   T   G   S   S   A   E   I   T   C   D   L   T   V   T

175 AAT ACC TTC TAC ATC CAC TGG TAC CTA CAC CAG GAG GGG AAG GCC CCA CAG CGT CTT CTG TAC TAT GAC GTC TCC ACC GCA AGG GAT
    N   T   F   Y   I   H   W   Y   L   H   Q   E   G   K   A   P   Q   R   L   L   Y   Y   D   V   S   T   A   R   D

262 GTG TTG GAA TCA GGA CTC AGT CCA GGA AAG TAT TAT ACT CAT CCA CGG AGG TGG AGC TGG ATA TTG AGA CTG CAA AAT CTA ATT
    V   L   E   S   G   L   S   P   G   K   Y   Y   T   H   P   R   R   W   S   W   I   L   R   L   Q   N   L   I
                                                                  ──→ N
                                                                                            ──→ J
349 GAA AAT GAT TCT GGG GTC TAT TAC TGT GCC ACC TGG GAC AGG CCC CGC CTT AAG AAA CTC TTT GGC AGT GGA ACA ACA CTT GTT GTC
    E   N   D   S   G   V   Y   Y   C   A   T   W   D   R   P   R   L   K   K   L   F   G   S   G   T   T   L   V   V
        ──→ C1
436 ACA GAT AAA CAA CTT GAT GCA GAT GTT TCC CCC AAG CCC ACT ATT TTT CTT CCT TCG ATT GCT GAA ACA AAG CTC CAG AAG GCT GGA
    T   D   K   Q   L   D   A   D   V   S   P   K   P   T   I   F   L   P   S   I   A   E   T   K   L   Q   K   A   G
```

FIG. 10B

```
523
ACA TAC CTT TGT CTT CTT GAG AAA TTT TTC CCA GAT ATT ATT AAG ATA CAT TGG CAA GAA AAG AAG AGC AAC ACG ATT CTG GGA TCC
 T   Y   L   C   L   L   E   K   F   F   P   D   I   I   K   I   H   W   Q   E   K   K   S   N   T   I   L   G   S

610
CAG GAG GGG AAC ACC ATG AAG ACT AAC GAC ACA TAC ATG AAA TTT AGC TGG TTA ACG GTG CCA GAA GAG TCA CTG GAC AAA GAA CAC
 Q   E   G   N   T   M   K   T   N   D   T   Y   M   K   F   S   W   L   T   V   P   E   E   S   L   D   K   E   H

←C11b
697
AGA TGT ATC GTC AGA CAT GAG AAT AAT AAA AAC GGA ATT GAT CAA GAA ATT TTC CCA ATA AAG ACA GAT GTC ACC ACA GTG
 R   C   I   V   R   H   E   N   N   K   N   G   I   D   Q   E   I   F   P   P   I   K   T   D   V   T   T   V

←C11c
784
GAT CCC AAA TAC AAT TAT TCA AAG GAT GCA AAT GAT GTC ATC ACA ATG GAT CCC AAA GAC AAT TGG TCA AAA GAT GCA AAT GAT ACA
 D   P   K   Y   N   Y   S   K   D   A   N   D   V   I   T   M   D   P   K   D   N   W   S   K   D   A   N   D   T

←C11l
871
CTA CTG CTG CAG CTC ACA AAC ACC TCT GCA TAT TAC ACG TAC CTC CTC CTC CTG CTC AAG AGT GTG GTC TAT TTT GCC ATC ATC ACC
 L   L   L   Q   L   T   N   T   S   A   Y   Y   T   Y   L   L   L   L   L   K   S   V   V   Y   F   A   I   I   T

958
TGC TGT CTG CTT AGA AGA ACG GCT TTC TGC TGC AAT GGA GAG AAA TCA TAA CAGACGGTGGCACAAGGAGGCCATCTTTCCTCATCGGTTATTGTCC
 C   C   L   R   R   T   A   F   C   C   N   G   E   K   S   U

1056
CTAGAAGCGTCCCGAATTCAAGGT
```

FIG. 10B (cont.)

| FORM | GENE SEGMENTS | | CELL LINES | POLYPEPTIDE SIZES | | | |
|---|---|---|---|---|---|---|---|
| | V J C | CI—CII—CIII | | BACKBONE | | GLYCOSYLATED | |
| | | | | PRED. | Obs. | PRED. | Obs. |
| 1 | Vγ2 Jγ1.3 Cγ1 (S-S) | Cys | PBL C1 | 34.7 | 31 | 46.7 | 40,36 |
| 2bc | Vγ13 Jγ2.3 Cγ2 (S-S) | b c | MOLT-13 | 34.8 | 35 | 52.3 | 40 |
| 2abc | Vγ2 Jγ2.3 Cγ2 (S-S) | a b c | IDP2 | 38.5 | 40 | 53.5 | 55 |

48 aa

FIG. 14A

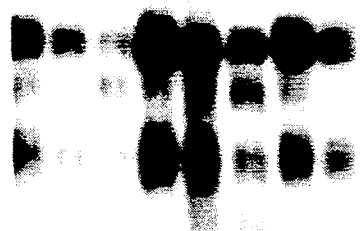
Probe    A             E            Probe
$C_\delta$            $V_\gamma 1$
FIG.17A           FIG.17E
B            F
$V_\delta 1$           $V_\gamma 2$
FIG.17B           FIG.17F
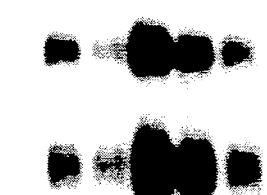
C            G
$V_\delta 2$           $V_\gamma 3$
FIG.17C           FIG.17G
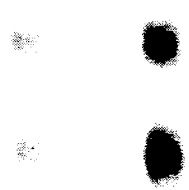
D            H
$V_\delta 3$           $V_\gamma 4$
FIG.17D           FIG.17H

Probe $J_\delta 1$

FIG. 18A

$J_\delta 3$

```
              M Q R I S S L I H
LB117  AACACTTGTGTGTTGGTTCAGAGGAGGACCAGGCAGAAGTGGTTGAGAGGCAGAGCTGCCCCTGAGTGAGCCATGCAGAGGATCTCCTCATCCA
LB210                                                                                   CTCATCCA
LB207                                                                                  CCTCATCCA

L S L F W A G V M S A I E L V P E H Q T V P V S I G V P A T L R C
LB117  TCTCTCTCTCTCTGGGCAGGAGTCATGTCAGCATTGAGTTGGTGCCTGAACACCAAACAGTGCCTGTTCAATAGGGGTCCTGCCACCCTCAGGTGC
LB210  TCTCTCTCTCTCTGGGCAGGAGTCATGTCAGCATTGAGTTGGTGCCTGAACACCAAACAGTGCCTGTTCAATAGGGGTCCTGCCACCCTCAGGTGC
LB207  TCTCTCTCTCTCTGGGCAGGAGTCATGTCAGCATTGAGTTGGTGCCTGAACACCAAACAGTGCCTGTTCAATAGGGGTCCTGCCACCCTCAGGTGC

S M K G E A I G N Y Y Y I N W Y R K T Q G N T I I T F I Y R E K D I Y
LB117  TCCATGAAAGGAGAAGCGATCGGTAACTACTACTATATCAACTGGTACAGAAAGACCCAAGGTAACACAATCACTTTCATATACCGAGAAAAGGACATCTATG
LB210  TCCATGAAAGGAGAAGCGATCGGTAACTACTACTATATCAACTGGTACAGAAAGACCCAAGGTAACACAATCACTTTCATATACCGAGAAAAGGACATCTATG
LB207  TCCATGAAAGGAGAAGCGATCGGTAACTACTACTATATCAACTGGTACAGAAAGACCCAAGGTAACACAATCACTTTCATATACCGAGAAAAGGACATCTATG

G P G F K D N F Q G D I D I A K N L A V L K I L A P S E R D E G S Y
LB117  GCCCTGGTTTCAAAGACAATTTCCAAGGTGACATTGATATTGCAAAGAACCTGGCTGTACTTAAGATACTTGCACCATCAGAGAGAGATGAAGGGTCTTA
LB210  GCCCTGGTTTCAAAGACAATTTCCAAGGTGACATTGATATTGCAAAGAACCTGGCTGTACTTAAGATACTTGCACCATCAGAGAGAGATGAAGGGTCTTA
LB207  GCCCTGGTTTCAAAGACAATTTCCAAGGTGACATTGATATTGCAAAGAACCTGGCTGTACTTAAGATACTTGCACCATCAGAGAGAGATGAAGGGTCTTA
```

Jδ1

```
       K L I F G K G T
LB117  TAAACTCATCTTTGGAAAAGGAACCC
```

```
         Y C A C D    N  Dδ1  N   T   Dδ2   N   M G   H P R G
LB117  CTACTGTGCCTGTGA    CA      CC   A     TGGG      CACCCACGGGG
```

```
                Y  C  A  C  D         H  T  S           D  W              T  G  N  Q                                D  T  D  K  L  I  F  G  K  G  T
LB210           CTACTGTGCCTGTGA       TCATA CTTCC       ACTGG             ACTGGTAATCAGG                              ACACCGATAAAACTCATCTTTGGAAAAGGAACCC
                                                                                                                                    Jδ3

Y  C  A  C  D                          R     L  G     V  S                       S  W  D  T  R  Q  M  F  F  G  T  G  I
LB207           CTACTGTGCCTGTGA                    CC  G  ACTGGGGG     TTAG                       CTCCTGGGACACCCGACAGATGTTTTCGGAACTGGCATCA
                                                                                                               Cδ

R  V  T  V  E  P           R  S  Q  P  H  T  K  P  S  V  F  V  M  K  N  G  T  N  V  A  C  L  V  K  E  F
LB117           GTGTGACTGTGGAACCAA         GAAGTCAGCCTCATACCAAACCATCCGTTTTTGTCATGAAAAATGGAACAAATGTCGCTTGTCTGGTGAAGGAATTC
LB210           GTGTGACTGTGGAACCAA         GAAGTCAGCCTCATACCAAACCATCCGTTTTTGTCATGAAAAATGGAACAAATGTCGCTTGTCTGGTGAAGGAATTC

K  L  F  V  E  P           R  S  Q  P  H  T  K  P  S  V  F  V  M  K  N  G  T  N  V  A  C  L  V  K  E  F
LB207           AACTCTTCGTGGAGCCCC         GAAGTCAGCCTCATACCAAACCATCCGTTTTTGTCATGAAAAATGGAACAAATGTCGCTTGTCTGGTGAAGGAATTC
```

FIG.19A(cont.)

```
                                              M   I   L   T   V   G   F   S   F
WM14                        GAGACTATCTTAGGAACCCTGTTTTGTTGTATATCCTCTGCCCTGATATGAAGAAAGATGATTCTTACTGTGGCTTAGCTT

L   F   F   Y   R   G   T   L   C   D   K   V   T   Q   S   S   P   D   Q   T   V   A   S   G   S   E   V   V   L   L   C   T   Y
WM14    TTTGTTTTTCTACAGGGGCACGCTGTGTGACAAAGTAACCCAGAGTTCCCCGGACAGACGGTGGCGAGTGGCAGTGGTACTGCTCTGCACTTAC

D   T   V   Y   S   N   P   D   L   F   W   Y   R   I   R   P   D   Y   S   F   Q   F   V   F   Y   G   D   N   S   R   S   E   G
WM14    GACACTGTATATTCAAATCCAGATTTATTCTGGTACCGGATAAGGCCAGATTATTCCTTCAGTTTGTCTTTTATGGGGATAACAGCAGATCAGAAGGTG

A   D   F   T   Q   G   R   F   S   V   K   H   I   L   T   Q   K   A   F   H   L   V   I   S   P   V   R   T   E   D   S   A   T   Y
WM14    CAGATTTTACTCAAGGACGGTTTTCTGTGAAACACATTCTGACCCAGAAAGCCTTTCACTTGGTGATCTCCCAGTAAGGACTGAAGACAGTGCCACTTA

N       D_δ1    N       D_δ2    N           V   R   P   F   E               Y   T   D   K   L   I   F   G   K   G   T
WM14            GAA     CCTAC   TCCT    CTGG    TACGACCGTTCGAAT                             ACACCGATAAACTCATCTTTGGAAAAGGAACCC
                E       P   C   P       L
                Y   C   A   F
        CTACTGTGCCTTT

R   V   T   V   E   P   R   S   Q   P   H   T   K   P   S   V   F   V   M   K   N   G   T   N   V   A   C   L   V   K   E   F
WM14    GTGTGACTGTGGAACCAAGAAGTCAGCCTCATACCAAACCATCCGTTTTTGTCATGAAAAATGGAACAAATGTCGCTTGTGTGAAGGAATTC
```

FIG. 19B

```
HUMAN  V1    QKVTQAQSSVSMPVRKAVTLNCLYETSWWS YYIFWYKQLP  SKEMIFLIRQGSDEQNA KSGRYSVNFKKAAKSVA LTISALQLEDSAKYFCALGE
HUMAN  V2    IELVPEHQT-PVSIGVPA-R-SMKGEAIGN---N-RKTQ    GNTIT-IY-EKDIYGPGF- DNFQGDI DI--NL-V-K-L-PSER-EGS-Y--CD
HUMAN  V3    D-----SSPDQTVASGSE-V-L-T-D-  VY-NPDL---RIR-DY-FQFV-YGDNSRS-GADFTQ--F--KHILTQ-AFH -V-PVRT----T-Y-F

HUMAN  V1    QKVTQAQSSVSMPVRKAVTLNCLYETSWWSYYIFWYKQLPSKEMIFLIRQGSD EQNAKSGRYSVNFKKAAKSVALTISALQLEDSAKYFCALGE
MOUSE  V6    A-----V--TG-SQWGE ---H-S----EYF-V-L-----F-G--V--Y-T-FTD--QRNS----V-Q-SL--IS-V--S-P---GT-----S

HUMAN  V3    DKVTQSSPDQTVASGSEVVLLCTYDTVYSNPDLFWYRIRPDYSFQFVFYGDNSRSEGADFTQGRFSVKHILTQKAFHLVISPVRTEDSATYYCAF
MOUSE  V5    ITL-----T----T-AT-----NASPD--------K--R----IL-R-DTS-HD---V------SKANRT------SL--------S
```

FIG. 19 C

FIG. 21A

| Probe | | |
|---|---|---|
| | | −Vγ2−Jγ1.2 (12.0) |
| | | −Vγ1 or 3−Jγ1.1 (8.5) |
| | | −Vγ2−Jγ1.3 or 2.3 (7.5) |
| | | −Vγ4−Jγ1.3 or 2.3 (6.0) |
| | | −Vγ1 or 3−Jγ2.1 (4.7) |
| F7 | | |
| WM14 | | |
| LB213 | | |
| LB210 | | |
| LB207 | | |
| LB117 | | |
| MOLT-13 | | |
| IDP2 | | |
| HL60 | | |
| SB | | | kb
23.1—
9.4— GL→
6.6— GL→
4.4—

Jγ1.3/2.3

−Vγ1 or 3−Jγ1.3 or 2.3 (1.8)

2.3—
2.0—

FIG. 21B

−Vγ2−Jγ1.2 (12.0)
−Vγ2−Jγ1.3 or 2.3 (7.5)

23.1— GL→
9.4—
6.6— GL→
4.4—

Vγ2

Vδ3

TTCCTCTTGTTTCCTCCGTCTCTTTCATTAGAACGTCAGATAGTCTCTGAGATCTTAGGAACCCTGTGTTTGTTGTAT

M I L T V G F S F L F F
ATCCTCTGCCCTGATATGAAGAAAAAGATGATTCTACTGTGGGCTTAGTGTTTTGTTTTTCTGTAAGTAGTTCATTTG

TTTACATTCCACTTGTCTCTATAACCCCATTTCTCTCTTCTGACTCTCTGAAGGCTTTTCTCTCTGCACTCTTGGTTTTTG

GTTATTTGCTGCTTTGGCTTTATTTCTGTGCCTCTCTTCTGCCTCATTGAGTTCTCTGGGCTAGGCATGTGCT
                                                    Y R G T L C D K
GTACTCACTGTCTCTGGGGGGTGCAGAATTCACTATTCCTCATTGTCTTTTTCCAGACAGGGCACGCTGTGTGACAAAG

V T Q S S P D Q T V A S G S E V V L L C T Y D T V Y S
TAACCCAGAGTTCCCCGGACAGACGGTGGCAGTGGGAGTGGAGGTGCTCCTGTGCACTTACGACACTGTATATTCA

N P D L F W Y R I R P D Y S F Q F V F Y G D N S R S E
AATCCAGATTTATTCTGGTACCGGATAAGGCCAGATTATTCCTTCAGTTTGTCTTTTATGGGGATAACAGCAGATCAGA

G A D F T Q G R F S V K H I L T Q K A F H L V I S P
AGGTGCAGATTTTACTCAAGGACGGTTTCTGTGAAACACATTCTGACCCAGAAAGCCTTTCACTTGGTGATCTCTCCAG

V R T E D S A T Y Y C A F
TAAGGACTGAAGACAGTGCCACTTACTACTGTGCCTTTAGCACTACTATGATGCAGGTGCCAGGAAGTCATAACACAAACTC

FIG.23

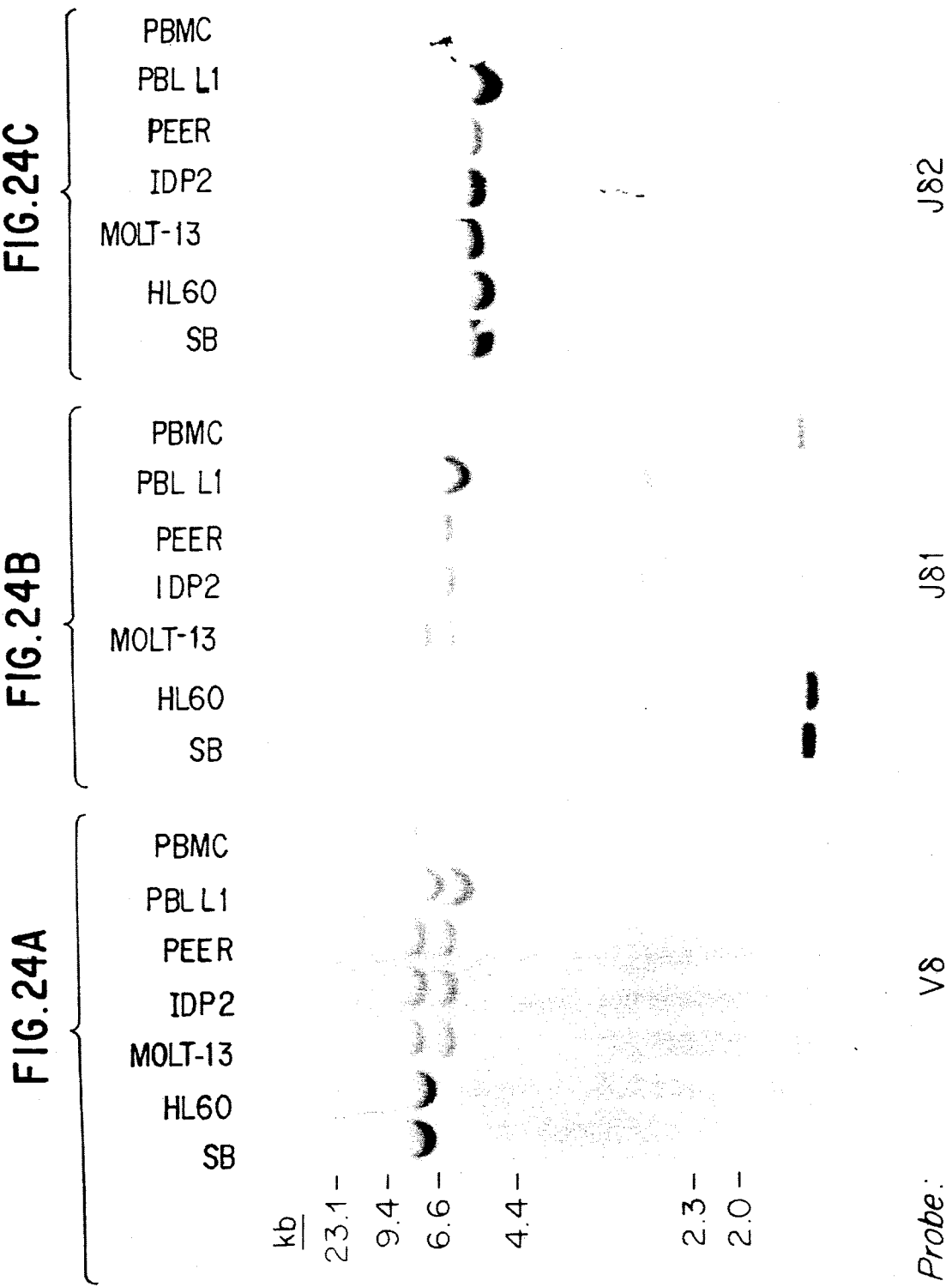

|  | V | | | | | | | | | | | | | | J | |
|---|---|---|---|---|---|---|---|---|---|---|---|---|---|---|---|---|
|  | 90 | | | | | | 100 | | | | | | | | 110 | |
| IDP2 | C A L<br>TGT GCT CTT | G | | A V R G K L L E R N G G Y A V F P<br>CT GTA CGG GGA AAA CTC CTA GAA AGG AAT GGG GGA TAC GCG GTC TTT CCA | T | S D K L<br>CC GAT AAA CTC | — |
| PBL C1 | — — —<br>— — — | — | G E<br>-GG GAA C | | | | | | | | | | | | — | — — —<br>— — — |
| Molt-13 | — — —<br>— — — | — | G E<br>-GG GAA C | P G S L Q W G W G R G I G G<br>CC GGC TCC CTA CAG TGG GGG TGG GGT CGT GGG ATA GGT | G<br>GG | Y T —<br>AC A— | — — —<br>— — — |
| PBL L1a | — — —<br>— — — | — | G E<br>-GG GAA | P G G<br>CT GGG GGG T | | | | | | | | | | | Y T —<br>AC A— | — — —<br>— — — |
| PBL L1a | — — —<br>— — — | — | G E<br>-GG GAA | S Q P P Y W G I R R I L<br>TCC CAA CCT CCC TAC TGG GGG ATA CGC AGG ATC CTG | T | N T —<br>AC A— | — — —<br>— — — |
| PBL L1a | — — —<br>— — — | — | G E<br>-GG GAA | K W T D F P K T Y W G I R<br>AAA TGG ACG GAC TTC CCA AAA ACG TAC TGG GGG ATA CGG | A | | |

GERMLINE
V: — — — — — —GG GAA CT cacagtg....(23)...acaaaaacc    GERMLINE    J: ggtttttgg....(12)...tgctgtg    AC A— — — —

FIG. 25A

|  | V | N? | P? | N? | D | N? | J |
|---|---|---|---|---|---|---|---|
| IDP2 | TGTGCTCTTG | CTGTACGGGAAAA | CTCC | TAGAAAGGAA | TGGGGGATACG | CGGTCTTTCCAT | CCGATAAACTCAT |
| PBL C1 | TGTGCTCTTGGGGAAC | CCGG | CTCCCT | ACAG | TGGGGG | TGGGGTCGTGGGATAGGTGG | ACTCAT |
| Molt-13 | TGTGCTCTTGGGGAAC |  | CTCCCT |  | CTGGGGG | GT | ACACCGATAAACTCAT |
| PBL L1a | TGTGCTCTTGGGGAA | TCCCAAC |  |  | ACTGGGGGATACG | CAGGATCCTGT | ACACCGATAAACTCAT |
| PBL L1b | TGTGCTCTTGGGGAA | AAATGGACGGACT | TCCC | AAAAAACGT | ACTGGGGGATACG | GA | ACACCGATAAACTCAT |
| PBL L1c | TGTGCTCTTGGGGAACT |  | CC | ACAG | CTGGGGGATACG | GAGG | CCGATAAACTCAT |
| PEER | TGTGCTCTTGGG | ACGGGGTGA |  |  | GGGGA | CTCCAGG | ACACCGATAAACTCAT |

Germline D    agtttttgt...(12)...cactgtg    ACTGGGGGATACG cacagtg...(23)...acaaaact

```
1    CACCGCAGGGCCCTGGTAGGCACTGAACTTGAGCTTCAGGCAGCAGCAACTCACATTGTGCAAAGAGCT
           M  L  F  S  S  L  L  C  V  F  V  A  F  S  Y  S
71   ACATGCCACATGCTGTTCTCCAGCCTGCTGTGTGTATTGTGGCCTTCAGCTACTCTGGTATGGATGGTT
           C  Q  V  E  V  K  K  V  K  E  D  I  P  K  T  G  I  I  L  V  L
141  CCAAGTGTGAGTAAAAATGTTAAGGATGGAAGATTCCAAACAGGCATATGTTAGTTTCTCTGGGTCCTAAA
           G  E  K  R  E  N  V  K  K  A  E  L  I  I  L  V  L  V  L  V  L  K
211  GGAGGAAAAGAGAGAAATTGTAAAAAAGCGAGCATATTATGATTTTAGTTTGTTGTCTCTGGGTCCTAAA
           L  V  L  T  L  R  I  F  Y  I  I  K  R  I  R  V  F  L  F  P  H
281  TTAGTCTAGTCTTACGATATTTATTCACTATATCAAGGATCAGCTCTGTTTCTGATTTTTCCCACA
           G  S  S  V  A  Q  K  V  T  Q  A  Q  S  S  V  S  M  P  V  R  K  A  V
351  GGATCAAGTGTGGCCCAGAAGGTTACTCAAGCCCAGTCATCAGTATCCATGCCAGTGAGGAAGCAGTCA
           T  L  N  C  L  Y  E  T  S  W  W  S  Y  Y  I  F  W  Y  K  Q  L  P  S  K
421  CCCTGAACTGCCTGTATGAAACAAGTTGGTGGTCATATTATATTTTTGGTACAAGCAACTTCCCAGCAA
           E  M  I  F  L  I  R  Q  G  S  D  E  Q  N  A  K  S  G  R  Y  S  V  N
491  AGAGATGATTTCCTTATTCGCCAGGGTTCTGATGAACAGAATGCAAAAAGTGGTCGCTATTCTGTCAAC
           F  K  K  A  A  K  S  V  A  L  T  I  S  A  L  Q  L  E  D  S  A  K  Y
561  TTCAAGAAAGCAGCAAATCCGTGCCTTAACCATTTCAGCCTTACAGCTAGAAGATTCAGCAAAGTACT
           F  C  A  L  G  E
631  TTTGTGTCTCTTGGGAACTCACAGTGTTTGAAGTGATAGTAGTAAAAGCAAAACAAAAACCCTAGGGCTCAAT
701  AAGAGAACCCCTCTACTCCCCATCCTTTGCTACAGGAGCCAATCTGAAATGCACACCTGCAGATCTCAGG
```

FIG. 28B

Vα13.1

```
      Y  Q  Q  F  P  G  K  G  P  A  L  L  I  A  I  R  P  D  V  S  E  K  K
  1   GGTACCAACAATTCCCTGGGAAAGGCCCTGCATTATTGATAGCCATACGTCCAGATGTGAGTGAAAAGAA

E  G  R  F  T  I  S  F  N  K  S  A  K  Q  F  S  L  H  I  M  D  S  Q
 71   AGAAGGAAGATTCACAATCTCCTTCAATAAAAGTGCCAAGCAGTTCTCATTGCATATCATGGATTCCCAG

P  G  D  S  A  T  Y  F  C  A  A  R
141   CCTGGAGACTCAGCCACCTACTTCTGTGCAGCAAGACACAGTGCTCCCCAGGCACCTGAAGCCTGTACCC

211   AAACCTGCAGTTGAGGTTCCAGCAAACCCACAGTGGGAGCTTACGTAGGCAGAGATGTAGCCTAGTTT
```

FIG. 28C

Jδ1

```
421  AAGCAAACCTGTCCCTACCTGCAGATGATTAACCATCTATGAACCGGCTGGGTAAGCAACAAGTGCCATC
491  TTTCATGGAGCTGAGCCTTAAAGATCCTCCAGTCCTAAAGCTGACGGGAAGAAGGTAGGTGGGAGCAGCG
                                        T  D  K  L  I  F  G  K  G  T  R  V
561  CTGAGGTTTTTGGAACGTCCTCAAGTGCTGTGACACCGATAAACTCATCTTTGGAAAAGGAACCCGTGTG
      T  V  E  P
631  ACTGTGGAACCAAGTAAGTAACTCATTTATTTATCTGAAGTTTAAGGTTAAGGCATCCTCCATCTAAGGA
701  GGCAGAAATAATCCTGAAATGGGAAATGGGTGAAATAGCTAGCATTTAGGAGGACTCCTGGGAAGAGGTG
```

FIG.30A

Jδ2

```
581  GCCCCTTGGTCTCATCAAGAGCAGCTTTGTAGTTCTCTGAGCTGTGGGGTCTCTAGGCTGAGAACTGAGG
651  CTGGGGAGGCAGGGCACAGATGTTACAGCTCAGGCCCCAGGGCCAGCTCCAGGCTAGTTACCTGTGAGGC
         S  W  D  T  R  Q  M  F  F  G  T  G  I  K  L  F  V  E
721  ACTGTCATAATGTGCTCCTGGGACACCCGACAGATGTTTTTCGGAACTGGCATCAAACTCTTCGTGGAGC
      P
791  CCCGTGAGTTGATCTTTTTCCTATATTTCTGGGATAATTTGAGTCCTGGCACTGGGGCTGCAATCCAGTT
861  TGCATTATAAATTATAATAGTAAATGAAATTATAACAAGGAGACAGAGTATTACAGATGTGAAATAGGCC
```

FIG.30B $D_6V$

3361 AGCCCCAGAGACAGAAGCACCTGAGCCAGCTTGGCCTGACCTAACTGTCAGGACCCTTTGATCTTGCTGGAG

3431 CTTGACTTGGAGAAAACATCTGGTTCTCAGGGGCCATATAGTGTGAAACCGAGGGGAAGTT

3501 TTTGTAAAGCTCTGTGTAGCACTGTGACTGGGGGATACGCACAGTGCTACAAAACCTACAGAGACCTGTACA

3571 AAAACTGCAGGGGCAAAAGTGCCATTTCCCTGGATATCCTCACCCTGGGTCCCATGCCTCAGGAGACAA

3641 ACACAGCAAGCAGCTTCCCTCCCTGCTTTGGGGCCTGGAAGGGATAGCAGGAAGTTGACTGGACCAGGGA

FIG. 30C

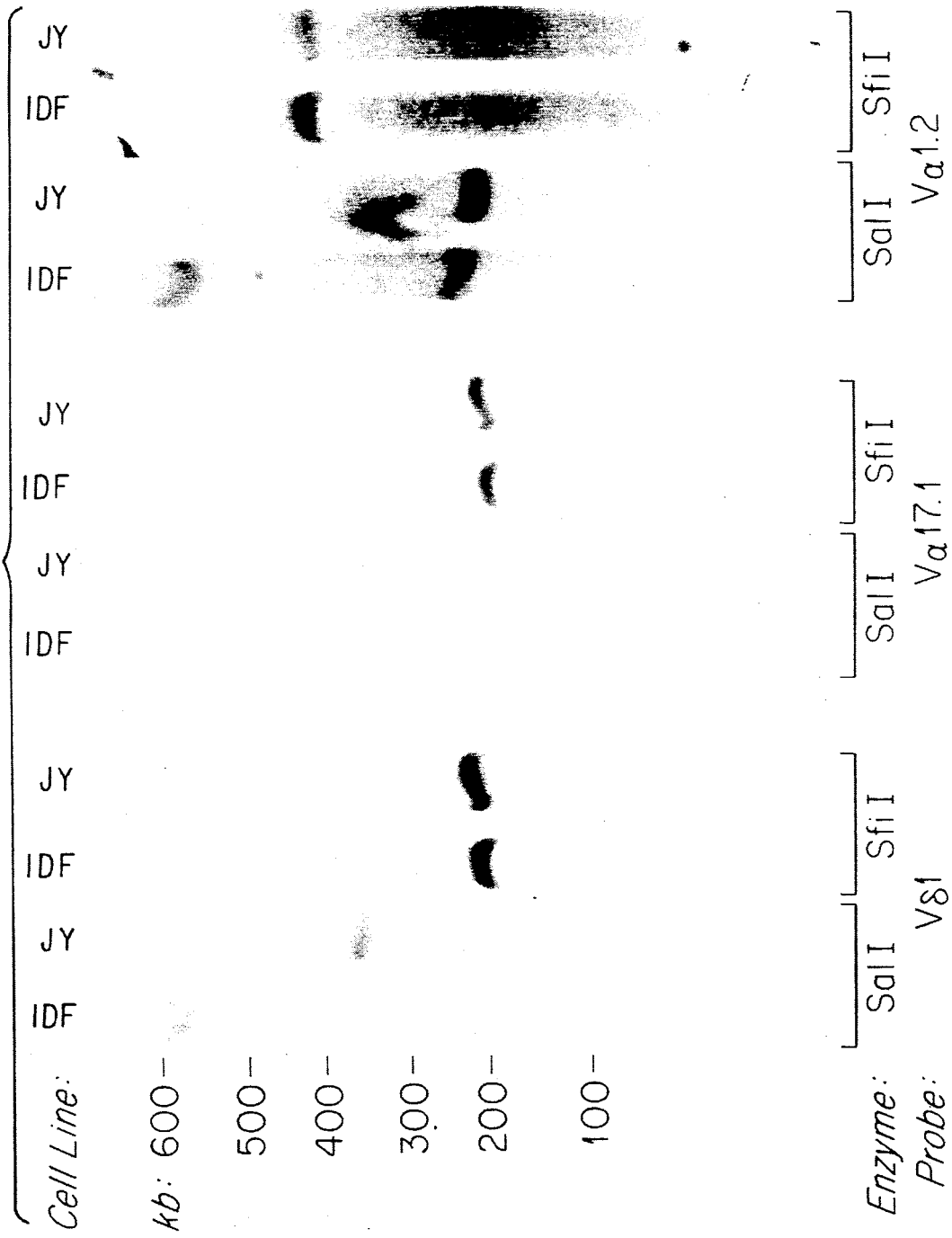

# HUMAN γ, δ T CELL ANTIGEN RECEPTOR POLYPEPTIDES AND NUCLEIC ACIDS

This invention was supported by several NIH grants, and the U.S. Government has certain rights to the invention.

This application is a continuation-in-part of U.S. patent application Ser. No. 187,698, filed Apr. 29, 1988, which is a continuation-in-part of Ser. No. 115,256, filed Oct. 29, 1987, now U.S. Pat. No. 5,024,940 which is a continuation-in-part of Ser. No. 016,252, filed Feb. 19, 1987, which is a continuation-in-part of Ser. No. 882,100 filed Jul. 3, 1986, now abandoned, each of which is incorporated by reference herein in its entirety.

TABLE OF CONTENTS

1. Introduction
2. Background of the Invention
3. Summary of the Invention
   3.1. Definitions
4. Description of the Figures
5. Detailed Description of the Invention
   5.1. γTCR Polypeptids and Nucleic Acids
   5.2. Polypeptide Complexes Containing γTCR Form 1
   5.3. Polypeptide Complexes Containing γTCR Form 2abc
   5.4. Polypeptide Complexes Containing γTCR Form 2bc
   5.5. γTCR Polypeptides and Nucleic Acids
   5.6. Diagnostic Methods
   5.7 Monoclonal Antibodies Reactive with the γδTCR Polypeptides
6. Example: Identification of a Putative Second T Cell Receptor
   6.1. Materials and Methods
      6.1.1. Lymphocyte Culture and Cell Population Analysis
      6.1.2. Reactivity and Characterization of Cell Culture Using Monoclonal Antibodies
      6.1.3. Analysis of Cell Surface Protein Molecules Associated with T3 Molecules on IDP1 and IDP2 Cell Lines
      6.1.4. Northern Blot Analysis of RNA Isolated From IDP2 Cell Line Using TCR α, TCR β and TCR γ cDNA Probes
      6.1.5. Immunoprecipitation of IDP2 Cell Line 7 Surface Molecules Using Anti-γ Antiserum
      6.1.6. Isolation of DNA Sequences of the δ Polypeptide
      6.1.7. Preparation of Monoclonal Antibodies Against the γ,δ Complexes.
      6.1.8. Immunoprecipitations of TCR γ,δ and T3 From a Human Tumor and Peripheral Blood Lymphocyte Lines
      6.1.9. Northern Blot Analysis of RNA Isolated From PBL C1
      6.1.10. Two-Dimensional Gel Analysis of TCR γ Polypeptides and Precursors
      6.1.11. Rearrangements of the γ and β Genes In T Cells Expressing the TCR γ Polypeptides
      6.1.12. Cytolysis by IDP2 and PBL C1 Cells
   6.2. Experimental Results
      6.2.1. A βF1−WT31−T3+T Cell Population
      6.2.2. WT31−T3+Cell Lines Created From Peripheral Blood Lymphocytes of Immunodeficiency Patients
      6.2.3. Immunoprecipitation Shows That WT31−T3+Cells are βF1−
      6.2.4. Northern Blot Analysis to Determine the Expression of αTCR, βTCR and γTCR mRNA
      6.2.5. Association of the γ,δ Polypeptides With T3 in WT31−T3+Cell Lines
      6.2.6. Antibodies to Synthetic γTCR Peptides Recognize a Protein that Co-Precipitates With T3
      6.2.7. Cell Lines Created From WT31−T3+Cells in Normal WT31−T3+Peripheral Blood
      6.2.8. Different Species of γTCR can be Identified by Gel Electrophoresis.
      6.2.9. γTCR Species Have Different Peptide Backbone Sizes
      6.2.10. Both Disulphide Linked and Non-Covalently Associated γTCR Are Present in Normal Peripheral Blood
      6.2.11. Genomic Rearrangements of γTCR and γTCR Genes
      6.2.12. γTCR Cells have Spontaneous Effector Cytotoxic Capability
   6.3. Discussion
7. Example: Production of Monoclonal Antibodies Specific for the γTCR and γTCR Chains
   7.1. Materials and Methods
      7 1.1. Culture Method
      7.1.2. Hybridoma Production for Monoclonal Antibodies Specific for the TCR γ Chain
      7.1.3. Hybridoma Screening for Monoclonal Antibodies Specific for the TCR γ Chain
      7.1.4. Immunoprecipitation
      7.1.5. Production and Screening of Hybridomas Which Produce a Monoclonal Antibody Specific for the TCR δ Chain
   7.2. Results and Discussion
8. Example: Cloning of the T Cell Antigen Receptor Delta Gene
   8.1. Materials and Methods
      8.1.1. Northern Blot Analysis
      8.1.2. Southern Blot Analysis Using Group O Clones
      8.1.3. Sequence Analysis of Group O cDNA Clones
   8.2. Experimental Results
      8.2.1. Selection of Putative γTCR cDNA Clones
      8.2.2. Northern Blot Analysis
      8.2.3. Evidence for Rearrangement of the Locus Defined by the Group O Clones
      8.2.4. Sequencing of Group O Clones
   8.3. Discussion
9. Example: Generation of Monoclonal Antibody Anti-TCRδ1 Specifically Reactive with the γTCR Sub-Unit Constant Rgion, and Characterization of the δ Polypeptide
   9.1. Materials and Methods
      9.1.1. Cytofluorographic Analysis of T Cell Lines with Anti-TCRδ1
      9.1.2. Immunochemical Analysis of the Specificity of mAb Anti-TCRδ1
      9.1.3. N-Linked Glycosylation of the γTCR Polypeptide
      9.1.4. Recognition of In Vitro Translation Products of cDNA Clone IDP2 O-240/38 by mAb Anti-TCRδ1
   9.2. Results
   9.3 Discussion 10. Example: Generation of Monoclonal Antibody δTCAR-3 Specifically Reactive With the TCR Delta Subunit Variable Region
  10.1. Materials and Methods
    10.1.1. Immunoprecipitation and SDS-PAGE Analysis of T Cell Antigen Receptor
    10.1.2. Immunoprecipitation of δ Chain by γTCAR-3 Antibody
    10.1.3. Analysis of Cell Surface Staining by Flow Cytometry
    10.1.4. Two Color Cytofluorographic Analysis of a γTCAR-3+ and OKT®3+ Peripheral Blood Lymphocytes
    10.1.5. Measurement of Intracytoplasmic $Ca^{2+}$-Concentration ($[Ca^{2+}]_i$) Versus Time
  10.2. Results and Discussion
11. Example: Three Forms of the Human T Cell Receptor γδ: Preferential Use of One Form in Selected Healthy Individuals
  11.1. Materials and Methods
    11.1.1. Antibodies
    11.1.2. Cell Lines
    11.1.3. Iodination and Immunoprecipitation
    11.1.4. Biosynthetic Labelling
    11.1.5. Gel Purification of γTCR Proteins.
    11.1.6. Endoglycosidase Digestion
    11.1.7. Production of Monoclonal Antibody Anti-Cγml
    11.1.8. Isolation and Sequencing of a Molt-13 γTCR cDNA Clone
  11.2. Results
    11.2.1. Novel γδTCR Protein Complex
    11.2.2. Core Polypeptide Size of Molt-13 γTCR Subunit
    11.2.3. Primary Sequence of Molt-13 γTCR
    11.2.4. Preferential Cγ Gene Segment Usage
    11.2.5. Characterization of the γTCR Subunit
  11.3. Discussion
12. Example: Characterization of a Human δ T Cell Antigen Receptor Gene and a Vδ Specific Monoclonal Antibody
  12.1. Materials and Methods
    12.1.1. Isolation and Sequencing of AK119 γTCR cDNA Clones
    12.1.2. Cloning a Rearranged γTCR Gene
    12.1.3. DNA Preparation
    12.1.4. Southern Blot Analysis
    12.1.5. Cytofluorometric Analysis
  12.2. Results
    12.2.1. Diversity of δTCR Gene Rearrangements
    12.2.2. Determining the Specificity of mAb TCSδ1
  12.3. Discussion
13. Example: T Cell γδ Complex, Not Associated With CD3, is Identified in Human Endometrial Glandular Epithelium
  13.1. Materials and Methods
    13.1.1. Specimens
    13.1.2. Monoclonal Antibodies
    13.1.3. Immunohistology
    13.1.4. Immunofluorescence
    13.1.5. Double-Labeling Experiment
    13.1.6. Immunoperoxidase Staining
    13.1.7. Microscopy
  13.2. Results
    13.2.1. Detection of TCR
    13.2.2. Detection of Leukocyte Antigens and MHC Antigens
    13.2.3. Detection of Epithelial Antigens and Trophoblast Antigens
  13.3. Discussion
14. Example: Human Lymphocytes Bearing γδTCR Are Phenotypically Diverse
  14.1. Materials and Methods
    14.1.1. Tissue Sampling
    14.1.2. Monoclonal Antibodies
    14.1.3. Immunofluoresence Analysis of Thymocytes, peripheral Blood Mononuclear Cells (PBMC) and Splenocytes
    14.1.4. Immunohistologic Analysis of Cryostat Sections of Lymphoid and Nonlymphoid Organs
  14.2. Results
    14.2.1. Reactivity of mAb Anti-TCRδ1
    14.2.2. The Number and Phenotype of γδTCR Lymphocytes in Peripheral Blood and Spleen
15. Three T Cell Antigen Receptor γ, δ Isotypic Forms Reconstituted by Pairing of Distinct Transfected γTCR Chains With a Single δTCR Subunit
  15.1. Materials and Methods
    15.1.1. Cell Lines
    15.1.2. Antibodies
    15.1.3. Isolation and Sequencing of Molt-13 δCR cDNA Clones
    15.1.4. Construction of Expression Plamids and Transfections
    15.1.5. Iodination and Immunoprecipitation
    15.1.6. Biosynthetic Labeling
  15.2. Results
    15.2.1. A Single Functional γTCR Chain is Present in the Molt-13 Cell Line
    15.2.2. γTCR Gene Product Determines the Form of the Receptor
    15.2.3. Polypeptide Backbone Sizes of the Transfected γTCR Chain Proteins
  15.3. Discussion
16. Example: Diversity and Organization of Human T Cell Receptor δ Variable Gene Segments
  16.1. Materials and Methods
    16.1.1. γδTCR+ Cell Lines
    16.1.2. DNA Probes
    16.1.3. Preparation and Blot Hybridization Analysis of RNA and DNA Samples
    16.1.4. cDNA Library Construction and Analysis
    16.1.5. Analysis of Genomic Clones
  16.2. Results
    16.2.1. Two Novel Human Vδ Segments
    16.2.2. Rearrangement and Expression of δTCR and γTCR Gene Segments
    16.2.3. Additional Jδ1 Rearrangements in Newborn Thymus DNA
    16.2.4. Dispersed Organization of Human Vδ Segments Within the α/δTCR Gene Locus
  16.3. Discussion
17. Example: Extensive Junctional Diversity of Rearranged Human T Cell Receptor δ Genes
  17.1. Materials and Methods
    17.1.1. Detection of γTCR Gene Rearrangements in γδTCR+ Cell Lines
    17.1.2. Determining the Structure of δTCR V-J Junctional Regions
  17.2. Results and Discussion
18. Example: Genomic Organization of the Human T Cell Antigen Receptor α/δ Locus
  18.1. Materials and Methods
    18.1.1. Isolation and Characterization of Genomic Clones 18.1.2. Field Inversion Gel Electrophoresis (FIGE)
18.2. Results
  18.2.1. Isolation and Characterization of Cosmids Containing Vδ and Cδ Gene Segments
  18.2.2. Vδ1 Genomic Segment
  18.2.3. Vα Segments Lie Upstream and Downstream of Vδ1
  18.2.4. Dδ, Jδ and Cδ Segments
  18.2.5. Linkage of the Cδ and Jα Regions
  18.2.6. Field Inversion Gel Electrophoresis (FIGE)
18.3. Discussion
19. Deposit of Hybridomas

1. INTRODUCTION

The present invention is directed to purified polypeptides which comprise at least a portion of a γTCR polypeptide, a γTCR polypeptide, or a γ,δTCR complex, and also to nucleic acids encoding these polypeptides. The invention is also directed to substances capable of forming complexes with these polypeptides. The invention provides monoclonal antibodies specifically reactive with an epitope of the γ or δ T cell antigen receptor polypeptides.

2. BACKGROUND OF THE INVENTION

The T cell antigen receptor (TCR) was shown to be a clone specific disulfide-linked heterodimer on T cells, composed of two glycosylated subunits, one of which is designated the α chain and the other of which is designated the β chain. The α and γTCR subunits have a relative molecular mass ($M_r$) of approximately 50,000 and 40,000 daltons, respectively (Allison et al., 1982, Immunol. 129:2293-2300; Meuer et al., 1983, J. Exp. Med. 157:705-719; Haskins et al., 1983, J. Exp. Med. 157:1149-1169). Genes that rearrange during T cell ontogeny and encode the γTCR (Yanagi et al., 1984, Nature 308:145-149; Hedrick et al., 1984, Nature 308:153-158) and γTCR (Chien et al., 1984, Nature 312:31-35; Saito et al., 1984, Nature 312:36-40, Sim et al., 1984, Nature 312:771-775) subunits were isolated either by subtractive hybridization or by probing with oligonucleotides.

The alpha and beta chains of the T cell antigen receptor of a T cell clone are each composed of a unique combination of domains designated variable (V), diversity (D), joining (J), and constant (C) (Siu et al., 1984, Cell 37:393; Yanagi et al., 1985, Proc. Natl. Acad. Sci. USA 82:3430). Hypervariable regions have been identified (Patten et al., 1984, Nature 312:40; Becker et al., 1985, Nature 317:430). In each T cell clone, the combination of V, D and J domains of both the alpha and the beta chains participates in antigen recognition in a manner which is uniquely characteristic of that T cell clone and defines a unique binding site, also known as the idiotype of the T cell lone. In contrast, the C domain does not participate in antigen binding.

A unique feature of the human α,βTCR was the observed comodulation (Meuer et al., 1983, J. Exp. Med. 157:705-719), coimmunoprecipitation (Oettgen, et al., 1984, J. Biol. Chem. 259:12,039-12,048), and required coexpression (Weiss et al., 1984, J. Exp. Med. 160:1284-1299) of the α,βTCR molecules with a CD3 glycoprotein complex. Subsequently, the direct physical association of the two protein complexes was demonstrated by chemically cross-linking the α,βTCR molecules to the T3 glycoprotein and identifying the components of the cross-linked complex as the TCR subunit and the T3 glycoprotein ($M_r$ 28,000) subunit (Brenner et al., 1985, Cell 40:183-190). A T3 counterpart is similarly associated with murine α,βTCR (Allison et al., 1985, Nature 314:107-109; Samelson et al., 1984, Immunol. Rev. 81:131-144).

A third gene that rearranges in T cells, designated γTCR, was identified, first in mice (Saito et al, 1984, Nature 309:757-762; Kranz et al., 1985, Nature 313:762-755; Hayday et al., 1985, Cell 40:259-269) and then in humans (Lefranc et al., 1985, Nature 316:464-466; Murre et al., 1985, Nature 316:549-552). The human γTCR locus appears to consist of between five and ten variable, five joining, and two constant region genes (Dialynas et al., 1986, Proc. Natl. Acad. Sci. U.S.A. 83: 2619). Although the total number of functional variable and joining regions is limited, significant diversity is introduced during the process of V-J joining (Kranz et al., 1985, Nature 313:752-755; Lefranc et al., 1986, Cell 45:237-246; Quertermaus et al., 1986, Nature 322:184). The γTCR gene rearrangements occur in lymphocytes with suppressor-cytotoxic as well as helper phenotypes (Lefranc et al., 1985, Nature 316:464-466; Murre et al., 1985, Nature 316:549-552, Quertermaus et al., 1986, Science 231:252-255; Lefranc et al., 1986, Cell 45:237-246, Iwamoto et al., 1986, J. Exp. Med. 163:1203-1212; Zauderer et al., 1986, J. Exp. Med. 163:1314-1318).

During T cell ontogeny, it has been shown that γTCR gene rearrangement precedes β and αTCR gene rearrangement (Roulet et al., 1985, Nature 314:103-107; Snodgrass et al., 1985, Nature 315:232-233).

3. SUMMARY OF THE INVENTION

The present invention provides a purified polypeptide which comprises at least a portion of a δTCR polypeptide, a γTCR polypeptides or a γ,δTCR complex. The invention also relates to fragments of the γTCR polypeptide which contain an epitope thereof.

In one embodiment, the δTCR polypeptides of the invention may comprise at least a portion of the primary amino acid sequence shown in FIG. 3 or FIG. 19.

In a specific embodiment, a purified polypeptide which comprises at least a portion of a γTCR polypeptide is provided by the present invention. In one embodiment of the invention the γTCR polypeptide has a molecular weight of about 40,000 daltons (Form 1). In another embodiment of the invention the γTCR polypeptide has a molecular weight of about 55,000 daltons (Form 2abc). Form 2abc γTCR polypeptide has a slightly larger peptide backbone and contains one extra potential N-linked glycan than Form 1 γTCR polypeptide. In yet another embodiment of the invention, the γTCR polypeptide has a molecular weight of about 40,000 daltons (Form 2bc). Form 2bc γTCR polypeptide possesses a slightly smaller peptide backbone and 2-3 less potential N-linked glycans. Additionally, the γTCR polypeptide may be a human γTCR polypeptide.

The present invention also provides a substance capable of specifically forming a complex with at least one γTCR polypeptide or γTCR polypeptide. The substance may be an antibody. In one embodiment of the invention, the antibody is a polyclonal antibody. In another embodiment of the invention, the antibody is a monoclonal antibody. In a specific embodiment, the monoclonal antibody is reactive with the constant region of γTCR. In another embodiment, the monoclonal antibody is reactive with the constant region of γTCR.

In yet another specific embodiment, the monoclonal antibody is reactive with the variable region of δTCAR. The present invention also provides a method for identifying monoclonal antibodies to TCR polypeptides, by detecting the comodulation of CD3 antigen.

The invention further provides a purified complex which comprises at least a portion of a δTCR polypeptide and at least a portion of a γTCR polypeptide herein referred to as a γ,δTCR complex. Also provided are substances capable of specifically forming a complex with at least one γ,δTCR complex. These may be used to detect T cells, each of which has a γ,δTCR complex. The γ,δTCR complexes may be present on the surface of the T cells. Alternatively, the γ,δTCR complexes may be present in the cytoplasm of the T cells.

The invention is also directed to nucleic acid sequences encoding γTCR or δTCR, or hybridizable subsequences thereof comprising about 15 nucleotides. In specific embodiments, the invention relates to nucleic acid sequences of the variable, joining, diversity or constant regions of the δTCR, and their encoded peptides. Such variable regions include but are not limited to Vδ1, Vδ2, and Vδ3. Such joining regions include but are not limited to Jδ1 or Jδ2. Such diversity regions include but are not limited to Dδ2.

The invention further relates to nucleic acid sequences of γTCR Form 2bc, and hybridizable subsequences thereof comprising about 15 nucleotides.

In another embodiment, the invention is directed to a composition comprising substantially purified cells which express both a γδTCR and the CD4 antigen on their cell surface. In another embodiment, the invention provides substantially purified cells which express a γδTCR on their surface which is not associated with a CD3 complex.

3.1. Definitions

As used herein, the following terms will have the meanings indicated:

TCR = T cell antigen receptor
V = variable
D = diversity
J = joining
C = constant
mAb = monoclonal antibody

4. DESCRIPTION OF FIGURES

FIG. 1: Immunoprecipitations of TCR γ,δ and T3 from a human tumour and peripheral blood lymphocyte lines. Immunoprecipitations from $^{125}$I-labelled cell lysates were analysed by SDS-PAGE (10% acrylamide) under reducing (R) and nonreducing (N or NR) conditions. Size markers, $M_r$ in thousands.

Part A. TCR γ,δ and T3 subunits on IDP2 and PEER cells. Immunoprecipitations were performed using 1 μg control mAb P3 (mAb secreted by the P3×63.Ag8 myeloma lanes 1, 3, 5 and 6): 1 μg UCHT (anti-T3) (Beverley and Callard, 1981, Eur. J. Immunol. 11:329-334) (lanes 2, 4,7 and 8); 10 μl normal rabbit serum (NRS lane 9) and 10 μl anti-C peptide sera (anti-TCR γ) (lane 10). Arrows indicate positions of TCR γ subunits which change mobility under R and NR conditions.

Part B. TCR γ,δ and T3 subunits on peripheral blood T cell clone, PBL Cl and the WT31−PBL Line. Immunoprecipitations were performed using control mAb P3 (lanes 1,4,9 and 12), 1 μg βF1 (anti-TCR β) (lanes 2, 5, 10 and 13). NMS (lanes γ and 15) and anti-C peptide sera (lanes 8 and 16). Open arrow indicates disulphide-linked βF1 and unreactive T3-associated species; solid arrow indicates non-disulphide-linked T3-associated material that displays increased SDS-PAGE mobility under nonreducing conditions (like TCR δ in A).

Figure 2:
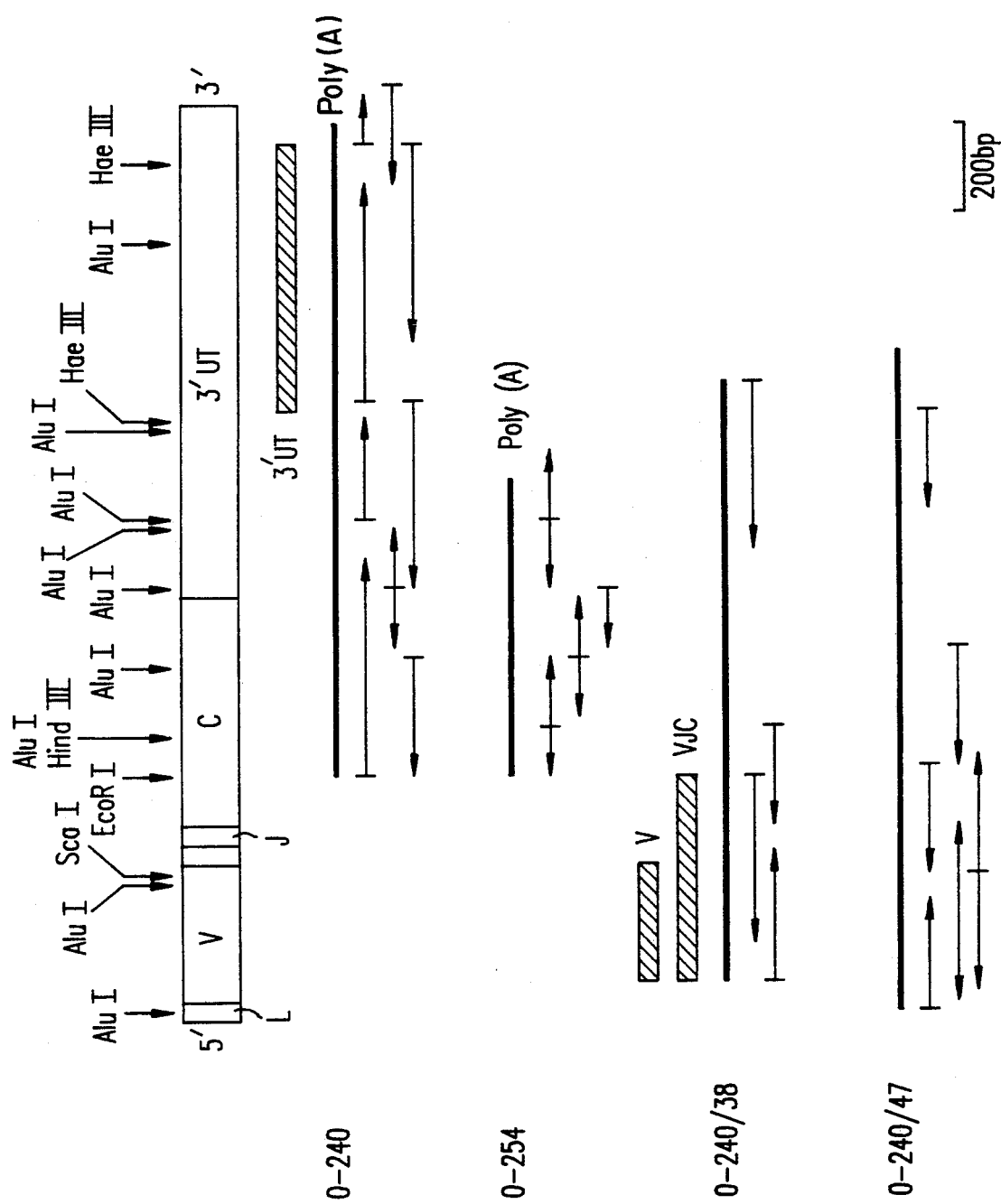

FIG. 2: Organization and sequencing strategy of group O cDNA clones.

Figure 3A:
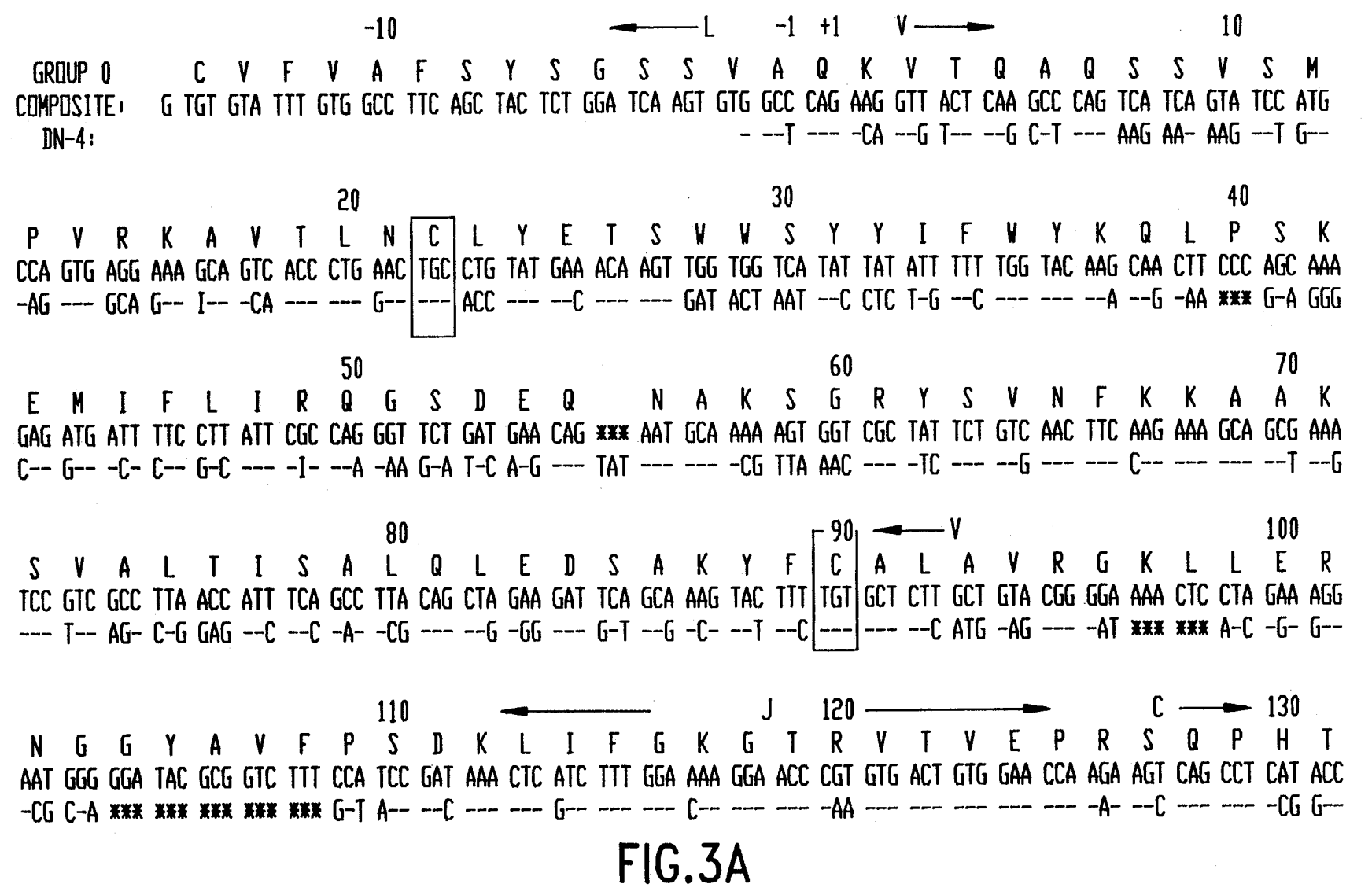
Figure 3B:
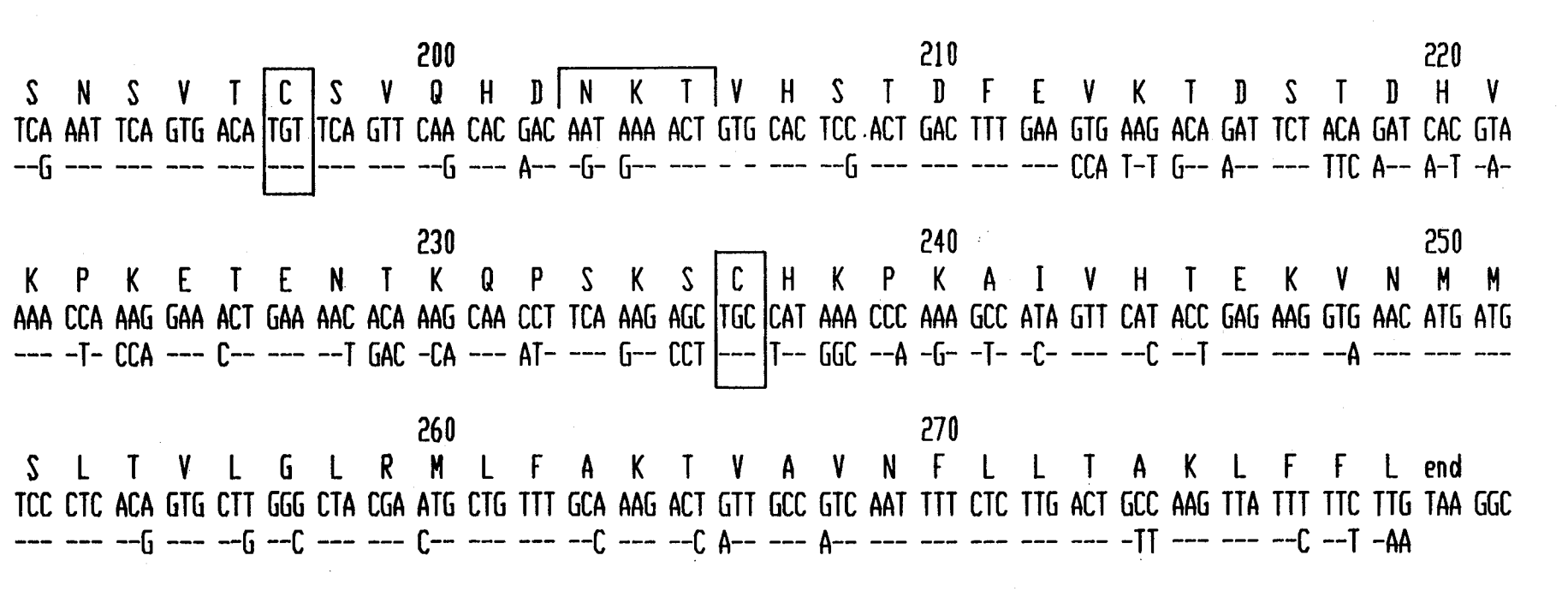

FIGS. 3A-3B: Composite nucleotide sequence of group O cDNA clones encoding δTCR protein. Amino acid residues are numbered from the presumed amino terminal processing point. Cysteine residues are boxed, potential N-linked glycosylation sites are bracketed, and polyadenylation signals used in the clones are underlined. The composite nucleotide sequence is compared with that of the coding region of murine cDNA clone DN-4 (Chien, et al., 1987, Nature 327:677). (−) denotes identity and (*) denotes a gap.

Figure 4:
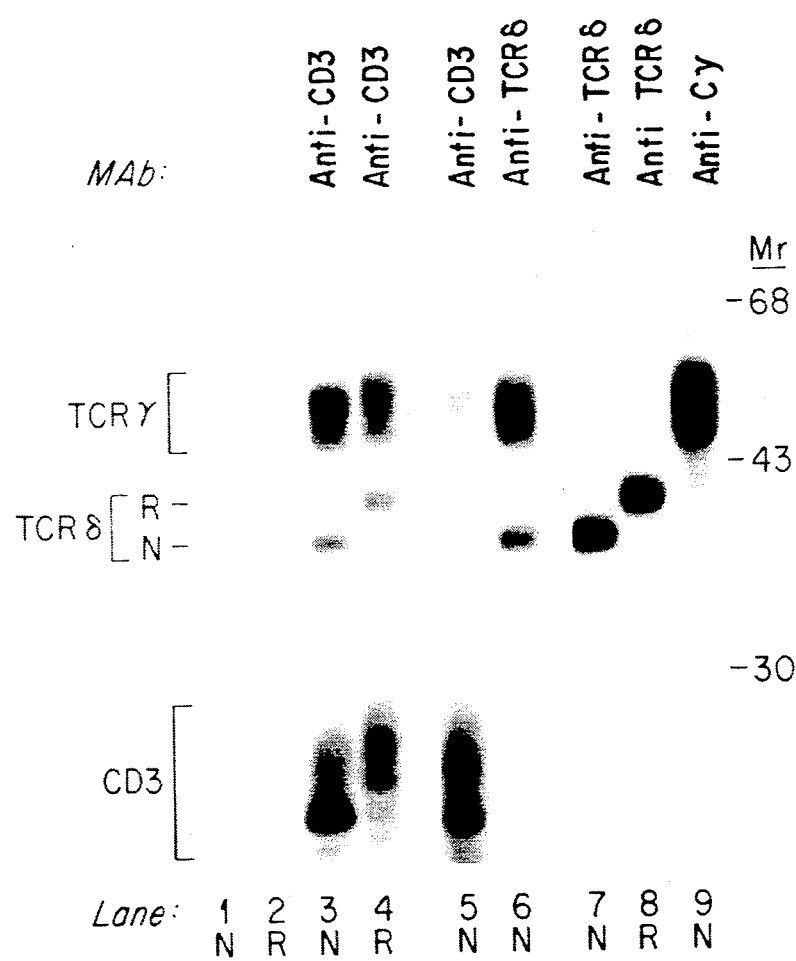

FIG. 4: Immunochemical analysis of the specificity of mAb anti-TCRδ1. Surface $^{125}$I-labeled IDP2 cells were immunoprecipitated using control mAb P3 (lanes 1 and 2), anti-Leu 4 (lanes 3-5), anti-TCRδ1(lanes 6-8) or anti-Cγ serum (lane 9) and were then resolved by SDS-PAGE and visualized by autoradiography. N=nonreducing conditions, R=reducing conditions.

FIG. 5: Immunoprecipitations of in vitro translation products of cDNA clone IDP2 0-240/38 by mAb anti-TCRδ1.

Figure 6:
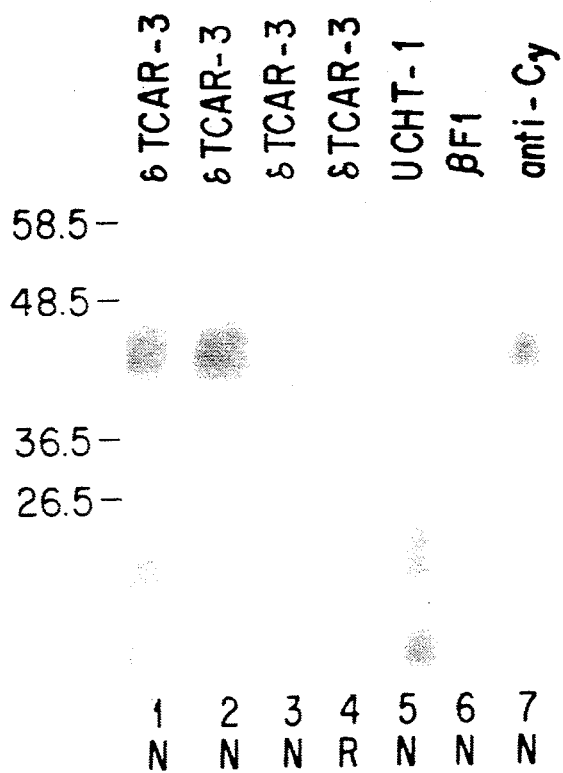

FIG. 6: Immunoprecipitation of δ chain by δTCAR-3 antibody. Molt-13 cells solubilized in Tris-buffered saline (pH 8) containing 0.3% CHAPS (lane 1) or in 1% Triton X-100 (lanes 2-7). Lane 1, δTCAR-3 immunoprecipitates γδTCR heterodimer with Lane 2, δTCAR-3 immunoprecipitates γδTCR heterodimer without the CD3 proteins. Lanes 3 and 4, δTCAR-3 immunoprecipitates single δchain from denatured lysates (N) and reducing (R) conditions respectively. Lane 5, UCHT-immunoprecipitates the CD3 proteins. Lane 6, βF1 antibody does not immunoprecipitate a heterodimer from MOLT-13 cells. Lane 7, anti-Cγ antiserum immunoprecipitates a single γ chain.

FIG. 7: Immunoprecipitation of the three forms of γ,δTCR. For parts A-E, the antibodies used for immunoprecipitation are anti-Leu4 (anti-CD3), βF1 (anti-TCRβ), anti-TCRδ1 (anti-δTCR), anti-Cγb serum (anti-γTCR) and P3 (unlabelled lanes, control). Immunoprecipitations from $^{125}$I-labelled cell lysates were analyzed by SDS-PAGE (10% polyacrylamide) under reducing (R) or nonreducing (N) conditions. An open arrow indicates the position of TCR δ under reducing conditions, whereas the solid arrow denotes the position of δTCR under nonreducing conditions. Size markers, $M_r$ in thousands, are shown on the left.

Part A: Nondisulfide-linked γTCR (40 kD) on PBL-L2. In lanes 1-6 the radiolabelled cells were solubilized in 0.3% CHAPS detergent which preserves the TCR-CD3 association, whereas in lanes γ and 8, immunoprecipitations were performed after chain separation (see methods).

Part B: Nondisulfide-linked γTCR (55 kD) on IDP2 cells. In lanes 1-4 radiolabelled cells were solubilized in 0.3% CHAPS detergent, whereas in lanes 5 and 6 imunoprecipitations were carried out after chain separation.

Part C: Disulfide-linked γTCR (40 kD) on WM-14 cells. All lanes correspond to immunoprecipitations from 1% digitonin solubilized radiolabelled cells.

Part D: Nondisulfide-linked γTCR (40 kD) thymic Clone II cells. Radiolabelled cells were solubilized in 1% digitonin (lanes 1-4) or in 0.1% Triton X-100 (lanes 5 and 6), whereas in lanes 7 and 8 immunoprecipitations were carried out after chain separation.

Part E: Nondisulfide-linked γTCR (40 kD) on MOLT-13 leukemia T cells. In lanes 1-4 immunoprecipitations were carried out after solubilization of cells in 0.3% CHAPS detergent, whereas in lanes 5 and 6 immunoprecipitations were carried out after chain separation.

Figure 8:
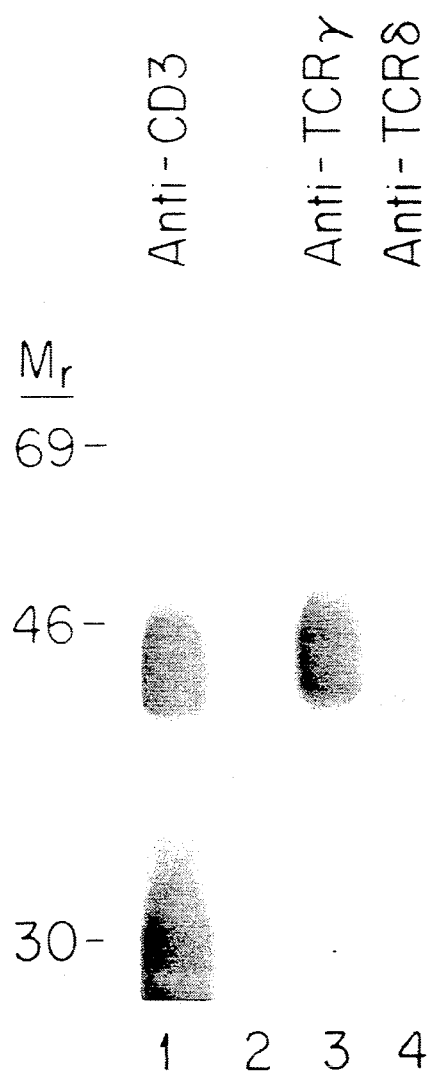

FIG. 8. Immunoprecipitation of γTCR and δTCR chain by anti-Cγml antibody and anti-TCRδI antibody, respectively. Cell surface radiolabelled MOLT-13 cells were solubilized in 0.3% CHAPS detergent and the γ,δTCR-CD3 complex was isolated with anti-CD3 monoclonal antibody. Immunoprecipitates were analyzed by 10% SDS-PAGE under reducing conditions.

Lane 1: Immunoprecipitation with anti-Leu4 (anti-CD3) mAb

Lane 3: Immunoprecipitation with anti-Cγml (anti-TCRγ) mAb after separating chains of isolated γ,δTCR-CD3 complexes.

Lane 4: Immunoprecipitation with anti-TCRδ1 (anti-TCRδ) mAb after separating chains of isolated γ,δTCR-CD3 complexes.

FIG. 9. Determination of peptide backbone sizes and glycosylation of γ and δTCRs from PEER and MOLT-13 cells. Monoclonal antibodies used for immunoprecipitation were anti-Cjγml (anti-TCRγ), anti-TCRγ1 (anti-TCRδ) and P3 (labelled control) as shown at the top of each lane. The labelled cell lines used are shown at the bottom of each 10% SDS-PAGE autoradiograph or fluorograph. All samples were resolved under reducing conditions. Size markers, $M_r$ in the thousands.

Part A: Peptide backbone sizes of γTCR from PEER and MOLT-13 cells. Cells were biosynthetically labelled with $^{35}S$-cysteine and $^{35}S$-methionine for 15 minutes. Samples were either treated with Endo H (+) or mock treated (−). Immunoprecipitation with anti-Cγml shows the positions of immature γTCR of peer cells (lane 3) and of MOLT-13 cells (lane 7), while the corresponding polypeptide backbone sizes are visualized after treatment with endo H (lanes 4 and 8).

Part B: Glycosylation of TCR δ from MOLT-13 cells. $^{125}I$-labelled cells were immunoprecipitated with anti-CD3 mAb and the δTCR polypeptides were gel purified (see methods) before incubation with N-glycanase (lane 4), endo H (lane 2), or mock treated (lanes 1, and 3).

Figure 10A:
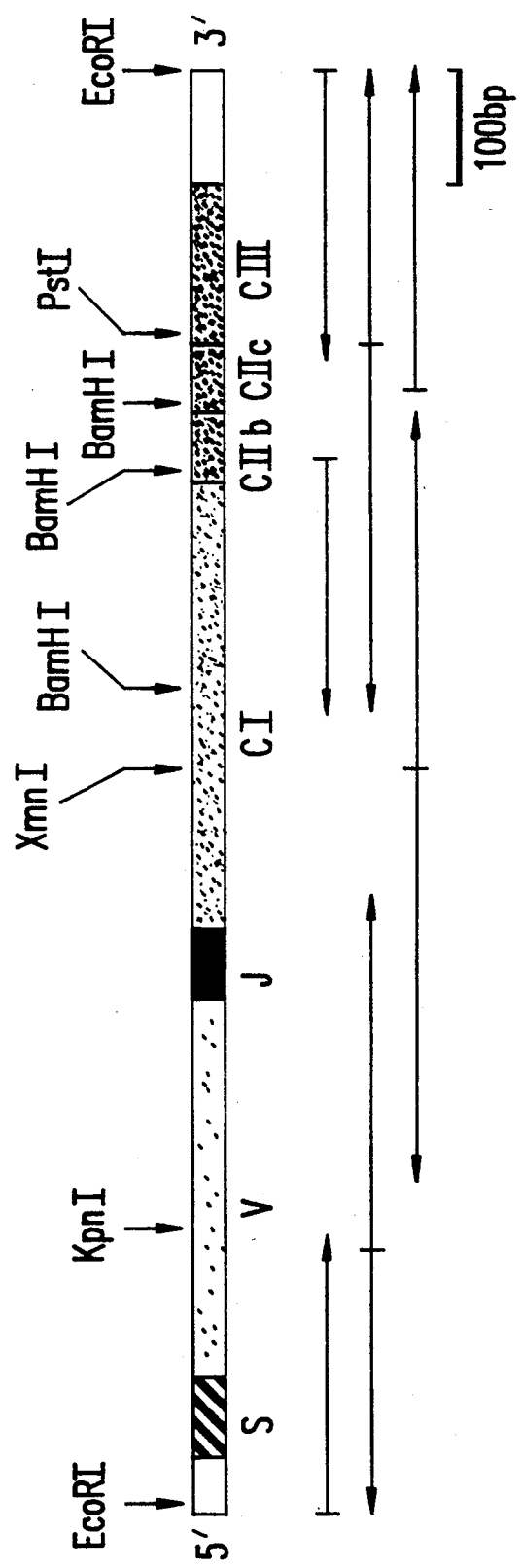

FIG. 10. Nucleotide sequence of MOLT-13 γTCR (Form 2bc).

Part A: Sequencing strategy of clone M13k. A partial restriction map of the 1.1 kb cDNA clone M13k is shown.

Part B: Nucleotide and deduced amino acid sequence of clone M13k. Signal sequence (S), variable (V), N-region (N), joining (J) and constant (CI, CIIb, CIIc and CIII) region gene segments are indicated by arrows and were identified by comparison to genomic sequences, described by Lefranc et al. (1986, Cell 45:237-246) (for S and V), Lefranc et al. (1986, Nature, 319:420-422) and Quertermous et al. (1987, Immunol. 138:2687-2690) (for J), and Lefranc et al. (1986, Proc. Natl. Acad. Sci. U.S.A. 83:9596-9600) and Pellicci et al. (1987, Science 237:1051-1055) (for C). The deduced amino acid sequence beginning at the initiator methionine is presented below the nucleotide sequence. Extracellular cysteines are highlighted by boxes, and potential N-linked carbohydrate attachment sites (N-X-S or N-X-T; Marshall, 1977, Ann. Rev. Biochem. 41:673-702) are indicated by brackets.

Figure 11:
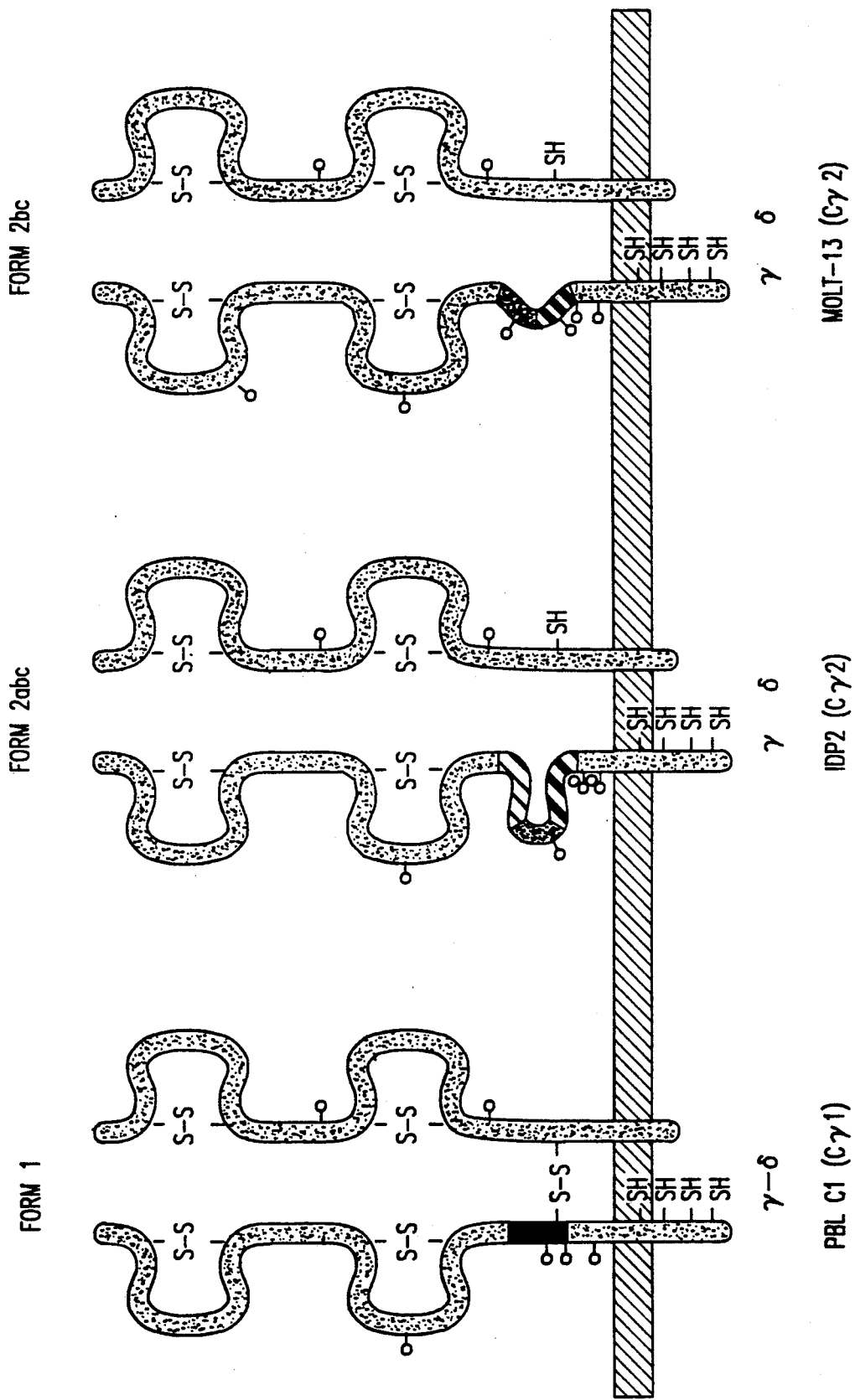

FIG. 11. Schematic representation of the three γ,δTCR forms in man. The CII exon encoded connector peptides are highlighted by filled areas ( ) as Cγl CII exon encoded peptide;   as CγCII exon copy a, copy b, and copy c encoded peptides, respectively). Potential N-linked glycan attachment sites (o), and sulfhydryl groups (-SH) and putative disulfide bridges (-S-S-) are indicated.

Figure 12:
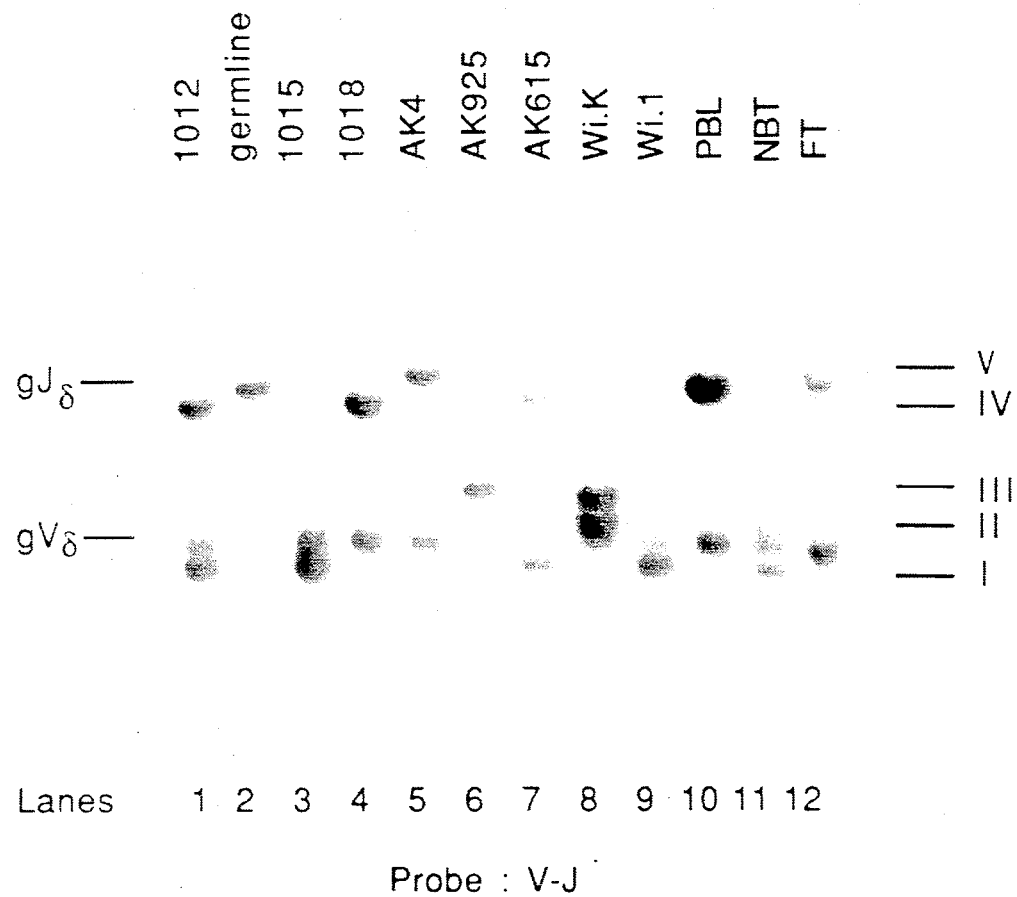

FIG. 12. Southern blot analysis of γ,δ T cell clones and polyclonal human T cell populations. Genomic DNA was digested with EcoRI and probed with the V-J probe. DNA sources are: PBL T cell clones, (lanes 1, 3-9), PBL (lane 10), newborn thymocytes (NBT-lane 11), fetal thymocytes (FT-lane 12), and B cells (germline-lane 2). The germline 3 kb Vδ and 6.7 kb Jδ fragment are indicated on the left of the blot, while the 5 common rearrangements, numbered I-V are indicated on the right. The sizes of the rearrangements from I-V are 2.9 kb, 3.5 kb, 4.2 kb, 6.2 kb and 7.1 kb respectively.

Figures 13A, 13B:
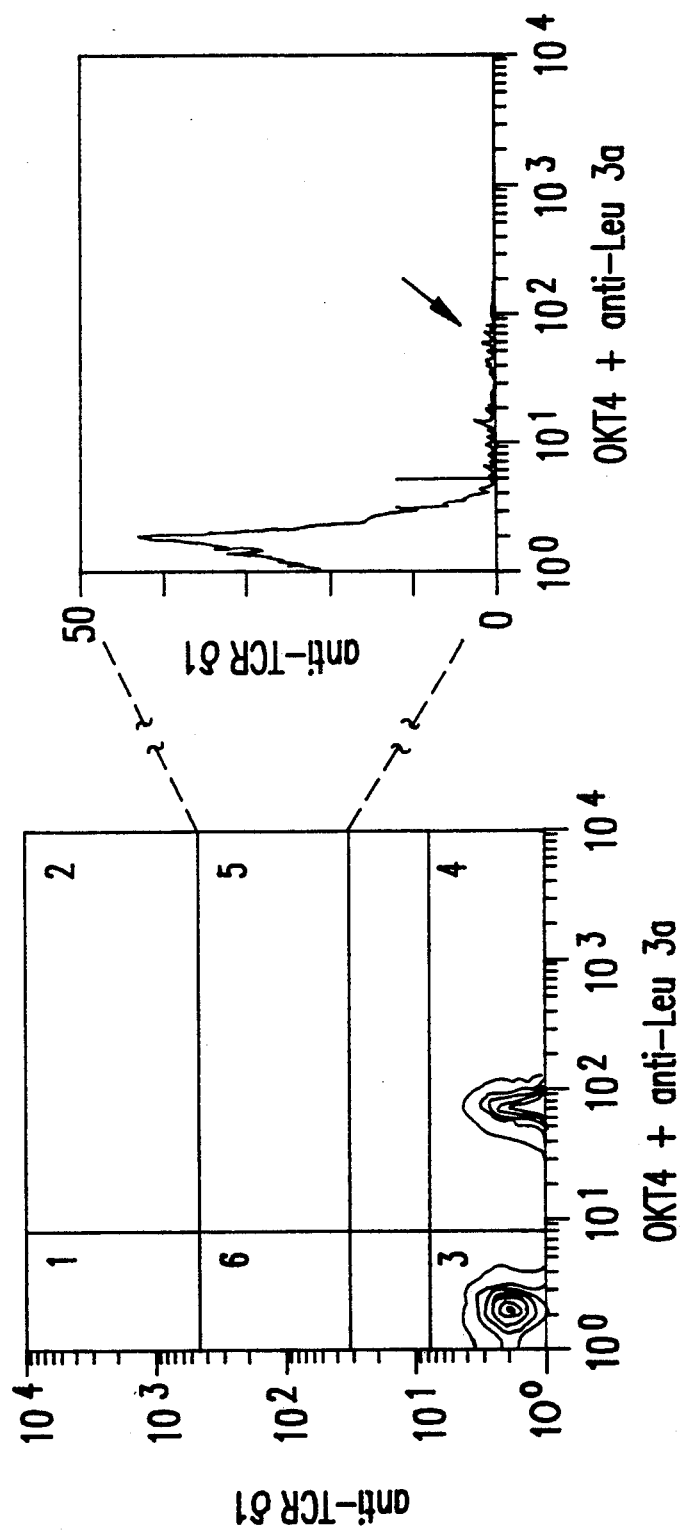
Figures 13C, 13D:
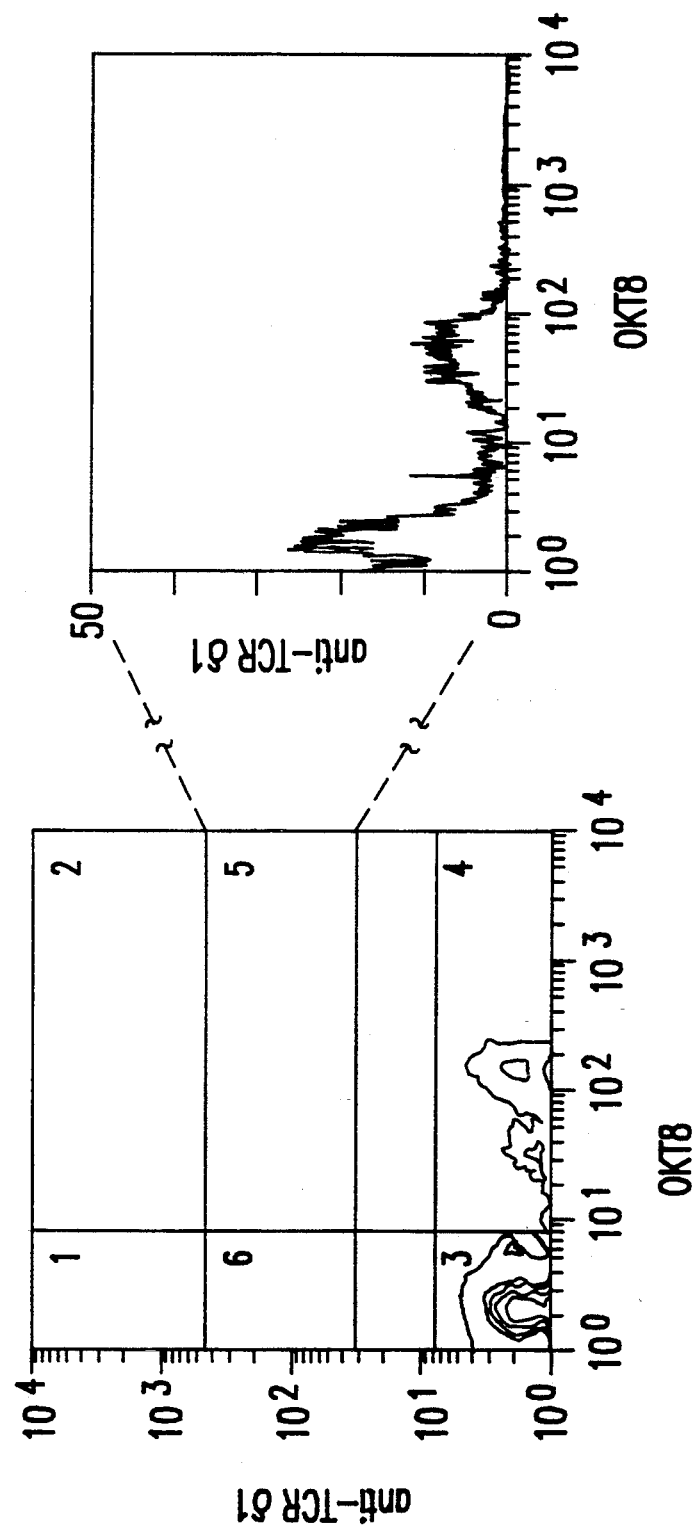

FIG. 13. Two color cytofluorographic analysis of CD4 and CD8 expression by TCRγδ+peripheral blood lymphocytes. Contour maps (FIG. 13a, 13c) show two channel fluorescence of PBMC gated by forward and side light scatter for lymphocytes. A second gate was set to include all anti-TCRδ1+cells and 1000 cells falling within this gate were analyzed for CD4 and CD8 expression respectively (FIG. 13b, 13d).

FIG. 13a and 13b. A small but distinct number of anti-TCRδ1+cells also react with anti-CD4 mAb (see dots in quadrant 5, FIG. 13a; as well as arrow pointing to small population of gated anti-TCRδ1+cells reactive with anti-CD4, FIG. 13b). The majority of PBL reactive with anti-CD4 mAb however are unreactive with anti-TCRδ1 and presumably express TCRαβ (quadrant 4 and 6, FIG. 13a).

FIG. 13c and 13d. A sizeable number of anti-TCRδ1+cells also react with anti-CD8 (see dots in quadrant 5, FIG. 13c; as well as the profile located to the right of vertical marker line representing gated anti-TCRδ1+cells that also react with anti-CD8, FIG. 13d. The majority of CD8+PBL are unreactive with anti-TCRδ1 and presumably express TCRαβ (quadrant 4 and 6, FIG. 13d). CD8 expression by anti-TCRδ1+cells is slightly weaker than that observed on anti-CD8+anti-TCRδ1−PBL.

PBMC were first incubated with FITC-OKT4 together with FITC-anti-Leu3a (FIG. 13a, 13b) or FITC-OKT8 (FIG. 13c, 13d) and second with biotinylated anti-TCRδ1 followed by PE-streptavidin.

FIG. 14A. Schematic representation of the TCR γ chains used for transfection into MOLT-13 cell line. Pred., predicted; Obs., observed. The predicted glycosylated polyeptide size assumes that all available N-linked glycosylation sites (shown as lollipops), each containing 3 kD of attached carbohydrate, are used, and that no significant size differences are introduced by other post-translational modifications. The intra-chain disulfide linkages typical of Ig-like molecules are shown. Note that a cysteine residue (cys) is encoded by the CII exon in PBL C1 TCR γ, but such a cysteine is absent from all the copies of CII exon used in the two other TCR γ chains. TCR γ constant region in the γδT leukemia cell line PEER (Littman, D. R., et al., 1987, Nature 326:85-88) that also expresses a 55 kD TCR γ protein is identical to that of IDP2.

Figure 14B:
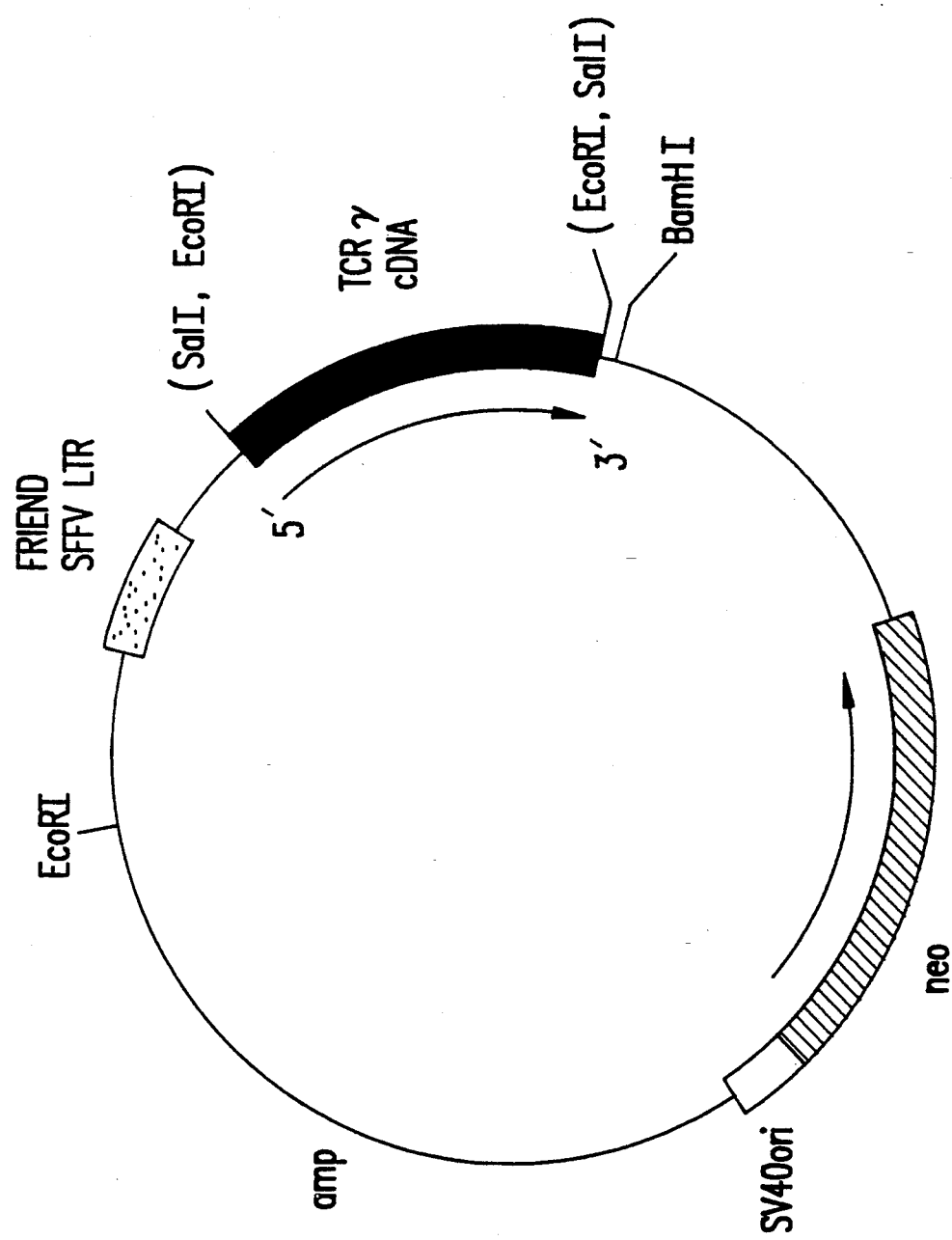

FIG. 14B. The expression plasmid constructs pFneo.PBL Clγ and pFneo.IDP2γ used to introduce TCR γ cDNa clones into MOLT-13 cell line. PBL C1 TCR γ cDNA clones (PBL C1.15) and repaired IDP2 TCR γ cDNA clone (IDP2.11r) (Krangel, M. S., et al., 1987, Science 237:64–67) were cleaved from their parent plasmid vector (pUC 18) by EcoRI digestion, the ends were made blunt with Klenow fragment of DNA Polymerase I, and the cDNAs were then ligated into a SalI-cut, and Klenow-treated pFneo mammalian expression vector. Clones containing the cDNA inserts in appropriate orientation with respect to the spleen focus forming virus (SFFV) LTR were selected based on restriction mapping. pFneo (Saito et al., 1987, Nature 325:125–130) is a derivative of pTβFneo (Ohashi et al., 1985, Nature 316:606–609) 609) obtained by BamHI digestion, to delete the murine TCR β cDNA insert, followed by ligation with T4 DNA ligase. As shown, this vector contains a bacterial neomycin resistance gene (neo$^r$ under the control of SV40 promoter, thus conferring resistance to the antibiotic G418 on the mammalian recipient cells. The restriction sites within parentheses were destroyed during contruction.

FIGS. 15A-15E. Immunoprecipitation analysis of TCR γδ on MOLT-13 TCR γ transfectants. Surface $^{125}$I-labeled cells were solubilized in 0.3% CHAPS detergent to preserve the chain association, immunoprecipitated with mAb P3 (control), anti-leu-4 (anti-CD3), anti-TCR δ1 (anti-TCR δ), or anti-Ti-γA (anti-Vγ2), and were then resolved by SDS-PAGE under nonreducing (N) or reducing (R) conditions and visualized by autoradiography as described earlier (Brenner et al., 1986, Nature 322:145–149; Brenner et al., 1987, Nature 689–694). Anti-Ti-γA shows a pattern of reactivity on different T cell clones consistent with its recognition of Vγ2 segment. M13.PBL C1γ, MOLT-13 cells transfected with the PBL C1-derived TCR γ chain; Clone #γ was used for this analysis. M13.IDP2γ, MOLT-13 cells transfected with the IDP2-derived TCR γ chain; Clone #10 was used for this analysis. Size markers, M$_r$(molecular weight) in thousands of daltons. Open arrow, resident MOLT-13 TCR γ chain; solid arrow, transfected (PBL C1- or IDP2-derived) TCR γ cDNA; asterisk, MOLT-13 TCR δ chain under nonreducing conditions. Upon reduction the TCR δ chain undergoes a mobility shift and comigrates with the 40 kD TCR γ chain. However, TCR γ chain is distinctly visualized as a 40 kD band under reducing conditions when the 40 kD TCR γ protein is not coimmunoprecipitated, as is seen in anti-Vγ2 immunoprecipitates of M13.1Dp2γ (FIG. 15, lane 8).

Figure 16:
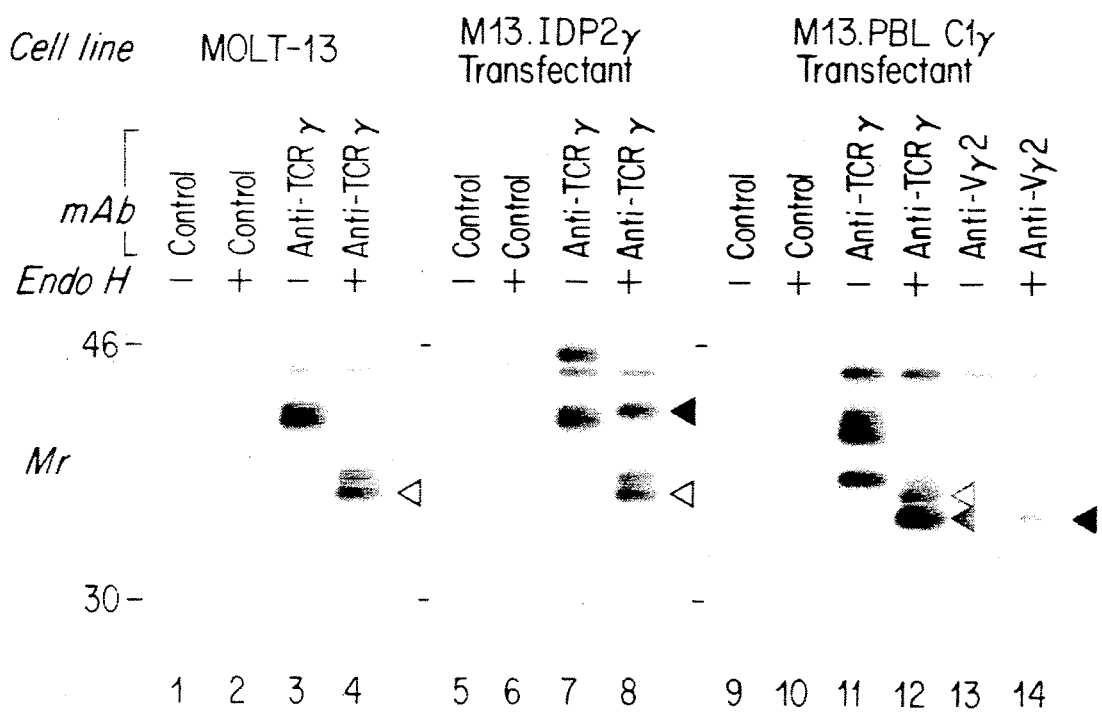

FIG. 16. Analysis of backbone polypeptide sizes of TCR γ chains of transfectants. Cells were pulse labeled with $^{35}$S-methionine and $^{35}$S-cysteine for 15 minutes and immunoprecipitated with P3 (control), anti-Cγml (anti-TCR γ), or anti-Ti-γA (anti-Vγ2) mAb, as indicated. Immunoprecipitates were treated with endoglycosidase-H (Endo-H, +), or were mock-incubated (−), resolved by SDS-PAGE, and visualized by fluorography. All Samples were run reduced. M$_r$, markers in thousands. The 43 kD contaminating actin band serves as an additional internal marker. M13.IDP2γ: MOLT-13 cells transfected with the IDP2 γTCR cDNA, clone #10; M13.PBL C1γ: MOLT-13 cells transfected with the PBL C1 γTCR cDNA, clone #10.

FIGS. 17A-17H. Blot hybridization analysis of TCR δ and TCR γ transcripts. 5 μg samples of total RNA was electrophoresed though 1.5% agarose containing 2.2 M formaldehyde, transferred to Hybond-N membranes, and serially probed with the indicated $^{32}$P-labelled DNA fragments.

Figures 18A, 18B:
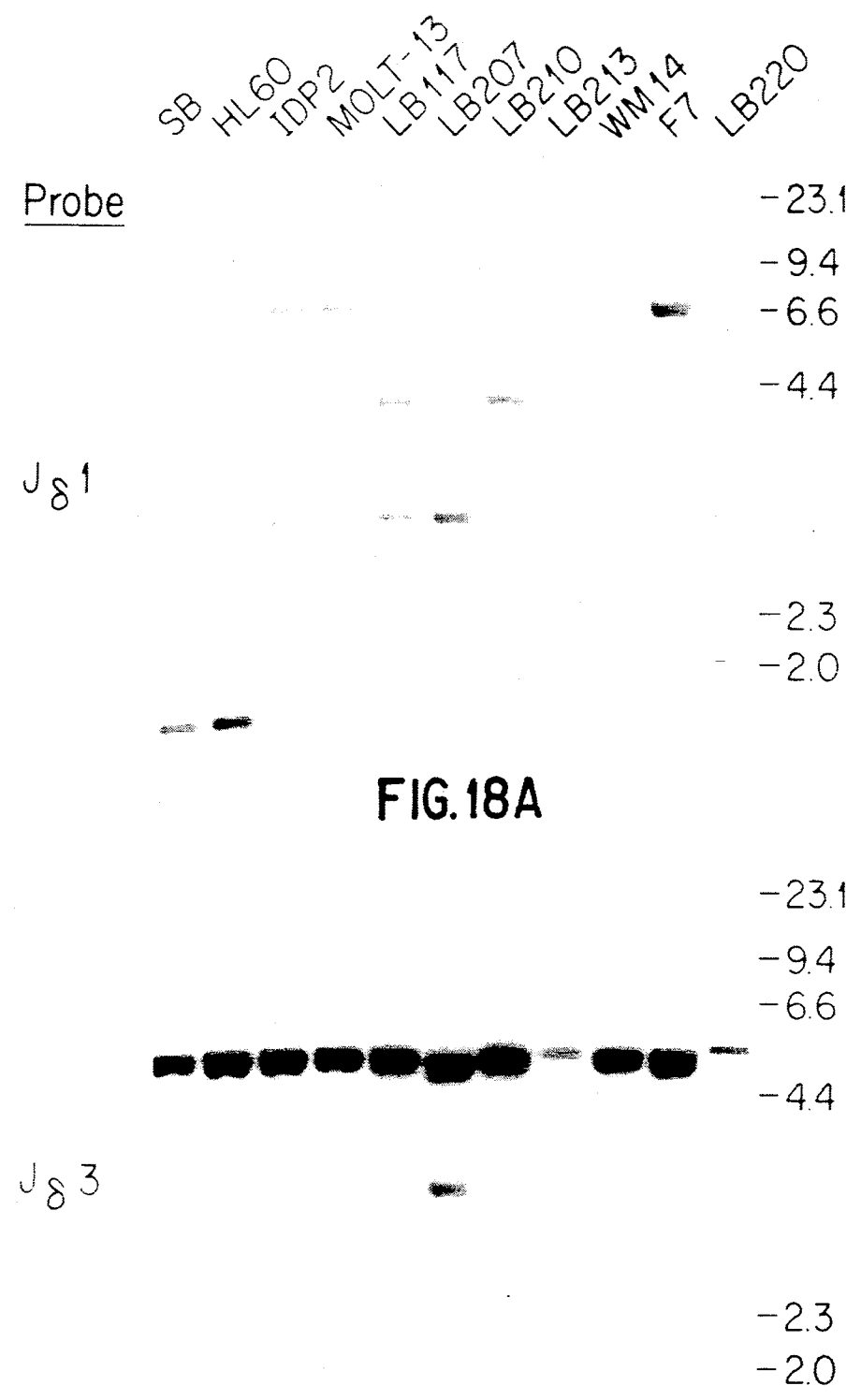

FIGS. 18A-18B. Blot hybridization analysis of J$_δ$ rearrangements. Samples of genomic DNA were digested with XbaI, electrophoresed through 0.7% agarose, transferred to Hybond-N membranes, and serially probed with the indicated $^{32}$P-labelled DNA fragments. The amount of DNA loaded was 5 μg in most instances, but was approximately 2.5 μg for LB213 and 1 μg for LB220. The data for LB220 in panel A derives from a longer exposure of the autoradiograph than the data for the remaining samples. SB and HL60 served as germline controls. A phage λ HindIII digest served as molecular weight markers.

FIG. 19. Nucleotide and deduced amino acid sequences of V$_δ$2 and V$_δ$3 cDNA clones.

A. Sequences of V$_δ$2 cDNAs from cell lines LB117, LB210 and LB207 are presented from near the EcoRI linker at the 5' end of each clone to the EcoRI site situated 77 bp into the C$_δ$ segment. Putative contributions of N and D segments within the junctional region are noted.

B. Sequence of a V$_δ$3 cDNA from WM14.

C. Homologies among the deduced amino acid sequences of human and murine V$_δ$ segments. Mouse V$_δ$5 and V$_δ$6 sequences are from Elliott et al., 1988, Nature 331:627. Dashes denote identities and blanks denote gaps introduced to maximize the alignment.

Figure 20A:
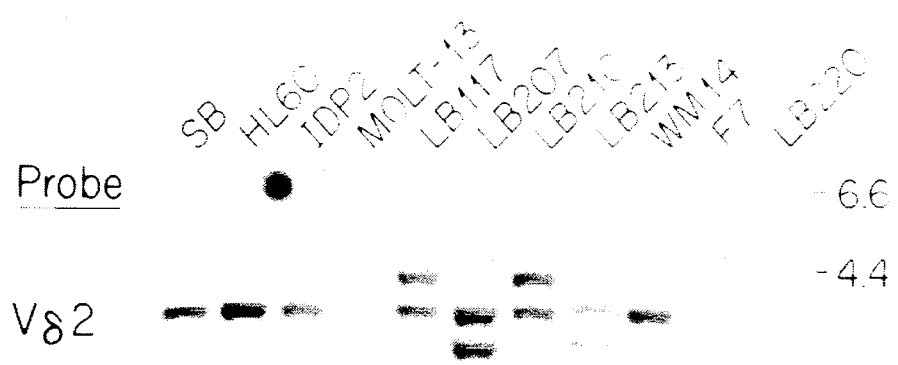
Figure 20B:
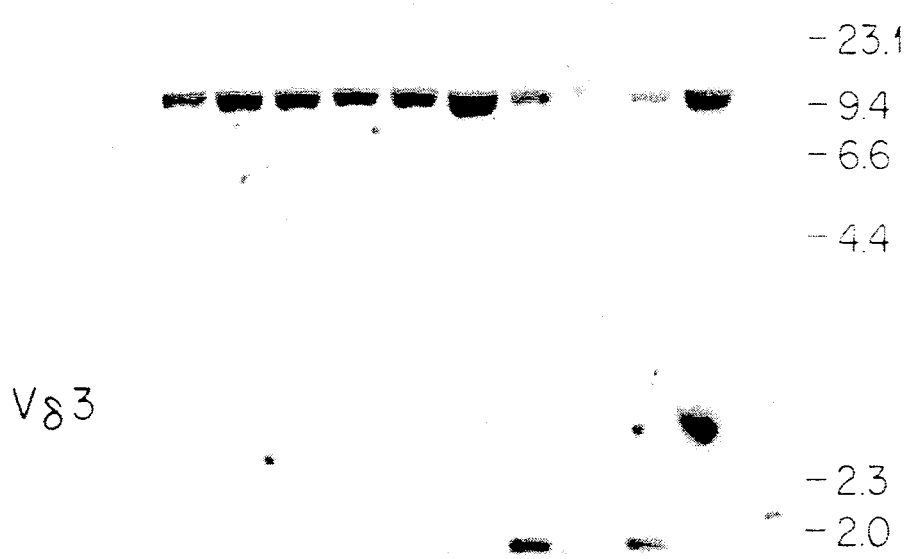
Figure 20C:
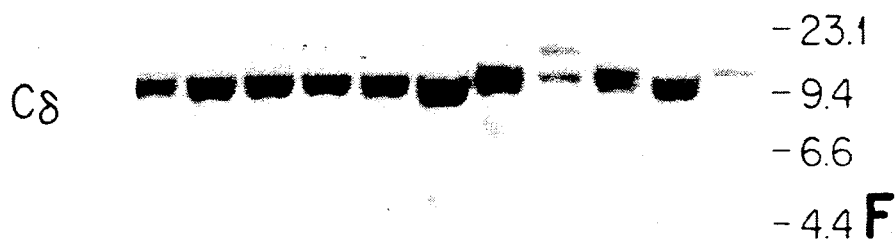

FIG. 20. Blot hybridization analysis of V$_δ$2 and V$_δ$3 rearrangements. The blot carrying XbaI digested DNA samples used in FIG. 18 was serially reprobed with $^{32}$P-labelled V$_δ$2 (A), V$_δ$3 (B), and C$_δ$ (C) DNA fragments.

FIG. 21. Blot hybridization analysis of TCRγ gene rearrangements. Samples of genomic DNA (5 μg) were digested with KpnI, electrophoresed through 0.7% agarose transferred to Hybond-N membranes, and serially probed with the indicated $^{32}$P-labelled DNA fragments.

A. The J$_γ$1.3/2.3 probe detects both the J$_γ$1 and J$_γ$2 clusters (germline fragments [GL]of 9 kb and 16 kb, respectively). The migration of HindIII fragments of phage λ DNA are noted on the left border of the figure, whereas the predicted sizes (in kb) and assignments of rearrangements according to Huck and Lefranc (1987, FEBS Lett. 224:291) are shown on the right border.

B. The V$_γ$2 probe detects two apparent germline fragments in KpnI digests [GL]. The analysis of XbaI digests with this probe reveals that Molt-13, LBI17, LB207 and WM14 retain no germline copies of V$_γ$2, a result which correlates with the presence or absence of the larger germline KpnI fragment. It is on this basis that distinction is made between V$_γ$1 and V$_γ$3 rearrangments on the nonproductive chromosome (Table V). The 11 kb fragment in F7 DNA corresponded to neither of the J$_γ$ rearrangements in these cells.

Figure 22:
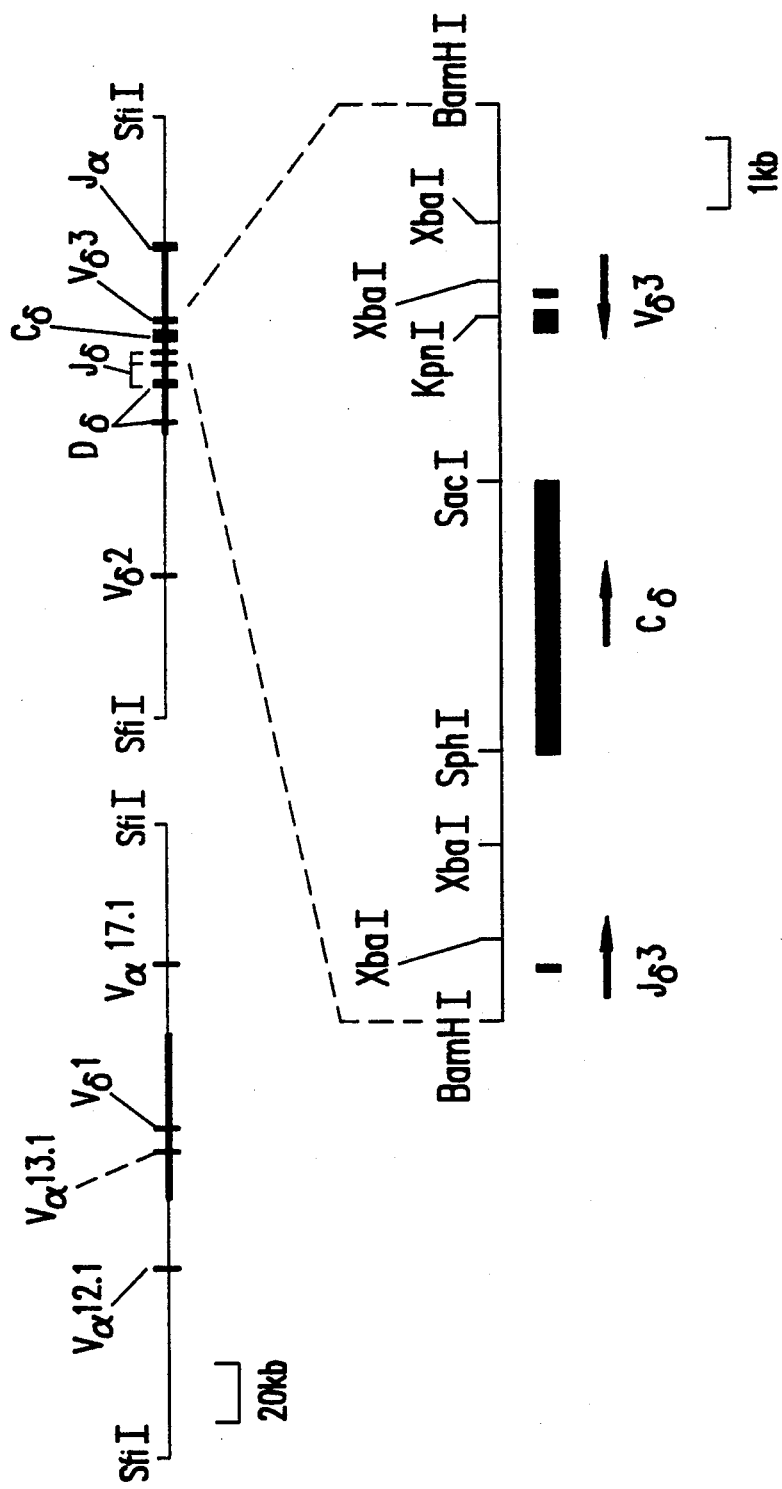

FIG. 22. Dispersed genomic organization of V$_δ$ gene segments. SfiI fragments of 190 kb and 180 kb carrying the V$_δ$1 and C$_δ$ segments are shown. The order of the gene segments mapping onto these fragments has been established in genomic Southern blotting experiments, and by the mapping of cosmid clones (in the regions covered by the bold horizontal lines). However, the precise distances between the segments mapping out-side the regions covered by cosmid clones is uncertain. The nomenclature for $V_\alpha$ segments is according to Klein et al. (1987, Proc. Natl. Acad. Sci. U.S.A. 84:6884). Since we have only attempted to map a limited number of $V_\alpha$ segments, additional unidentified $V_\alpha$ segments may also map to these fragments. More detailed restriction maps of two adjacent subcloned BamHI-KpnI fragments that carry the $J_\delta 3$, $C_\delta$ and $V_\delta 3$ segments is also presented. Transcription orientations are denoted by arrows. The orientation of the $J_\delta 3$ and $V_\delta 3$ segments with respect to mapped restriction sites has been directly established by nucleotide sequence analysis. The orientation of the $C_\delta$ segment has been established elsewhere.

FIG. 23. Nucleotide and deduced amino acid sequence of the $V_\delta 3$ genomic segment. Splice donor and acceptor sequences, as well as hepamer and nonamer recombination signals, are underlined.

FIG. 24. $\delta$TCR gene rearrangements in $\gamma\delta$TCR cell lines.

(A) $V\delta$ probe, a 300-bp EcoRI-ScaI fragment of IDP2 $\delta$TCR clone O-240/47 (see Section 8).

(B) $J\delta 1$ probe, a genomic 1.7 kb XbaI fragment carrying the $J\delta 1$ segment (see Section 18).

(C) $J\delta 2$ probe, a genomic 1.1 kb XbaI-BamHI fragment carrying the $J\delta 2$ segment.

FIG. 25. Structure of human $\delta$TCR V-J junctional regions.

(A) Nucleotide and deduced amino acid sequences of the junctional regions of cDNA clones representing functional $\delta$TCR transcripts in PBL C1, Molt-13, and PBL L1 (PBL L1a and PBL L1b) are presented and compared with those of IDP2.

(B) Nucleotide sequences presented in (A) are compared with those of $\delta$TCR cDNA clone representing an out-of-frame transcript in PBL L1 (PBL L1c) (PBL L1a, b, and c were found in ratios of 8:4:1) and that reported for PEER $\delta$TCR (Loh et al., 1987, Nature 330:569). Sequences are aligned to emphasize segments shared by the majority of the clones. The sequence of one germline D element including heptamer and nonamer recombination signals, is presented. Assignments of other potential N and D nucleotides are based on homologies and are tentative.

Abbreviations for the amino acid residues are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

Figure 26:
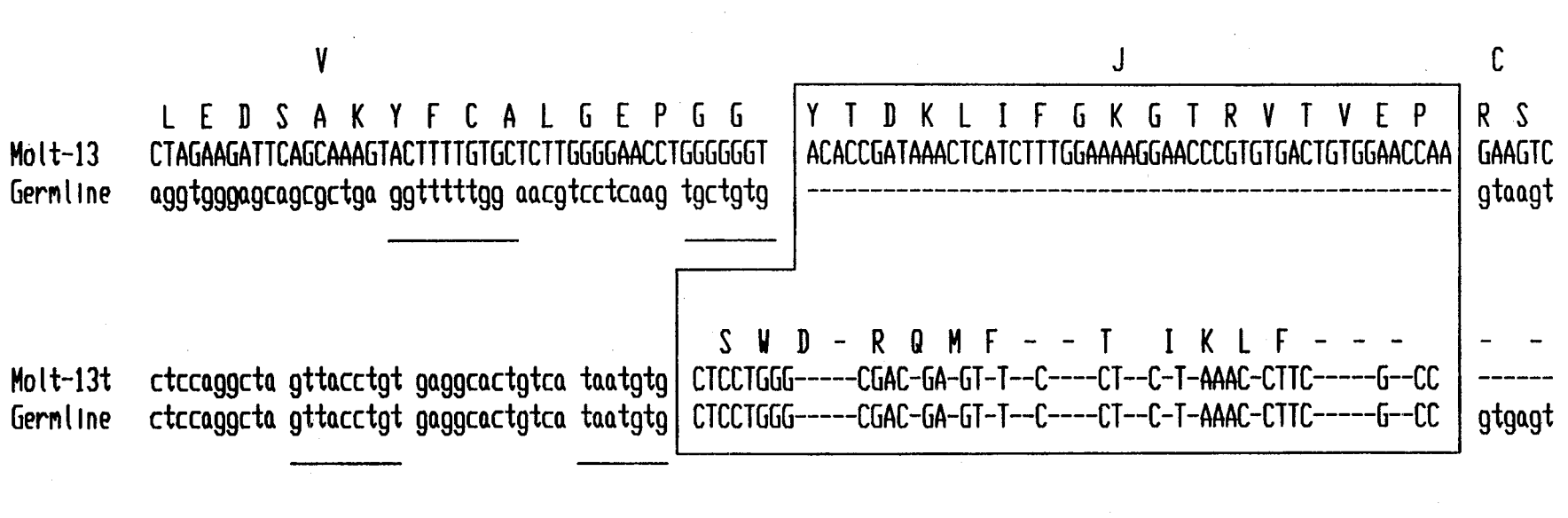

FIG. 26. Structure of the Molt-13t $\delta$TCR cDNA clone. The nucleotide and deduced amino acid sequences of the Molt-13t (truncated) cDNA are aligned with the Molt-13 (functional) cDNA. These sequences are compared with the sequences of the germline J segments, and the J coding segments are boxed. Identities in the J and C segments are noted (—). Heptamer- and nonamer-like elements are underlined. The underlined nonamer-like element flanking the Molt-13t J segment ($J_\delta 2$) diverges significantly from the consensus nonamer.

Figure 27:
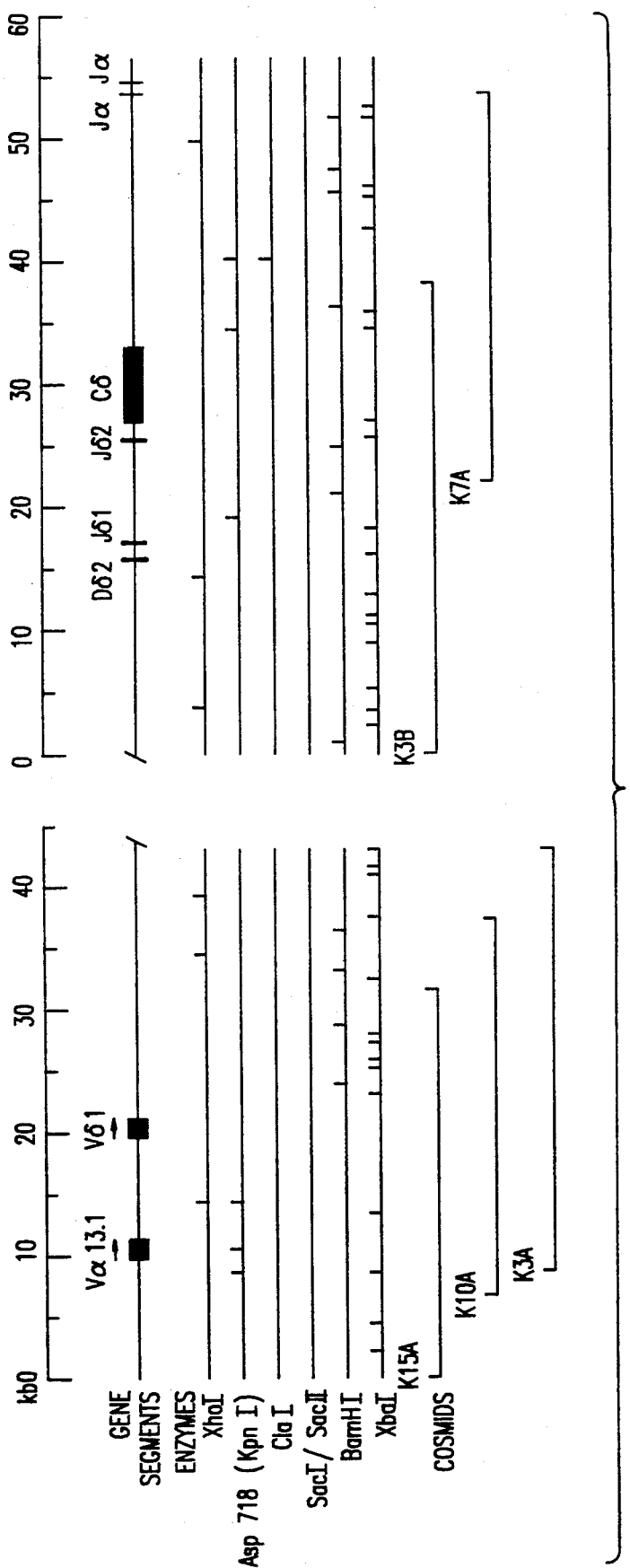

FIG. 27. Cosmid maps of the TCR $\alpha/\delta$ locus. Part A: $V\delta 1$ region. Part B: $C_\delta$ region. Black boxes represent gene segments. Arrows show the direction of transcription. Note that the placement of some of the small (1 kb) XbaI framents remains tentative. (kb=kilobases).

FIG. 28. (A) Fine map of the $V\alpha 13.1$-$V\delta 1$ region. Restriction enzyme sites: A, Asp718; B, BglII, X, XbaI; Xh, XhoI; E, EcoRI; H, HindIII. Asterisks denote those restriction sites mapped only on the subclones. Solid lines and broken lines denote regions of the subclones whose sequences were determined or not determined, respectively.

(B) Sequence of the $V_\delta 1$ segment. A portion of the sequence of the 3 kb EcoRI fragment is presented. Splice donor and acceptor sequences and heptamer and nonamer recombination signals are underlined. Numbering is from the beginning of the region presented. Predicted amino acid sequences are given in standard one-letter code above the nucleotide sequence.

(C) Sequence of the $V\alpha$ segment. The sequence of a portion of the Asp718-BglII fragment extending 3' from the Asp718 site within the coding region is presented. The sequence of only one strand was determined. Numbering is from the 5' end of the fragment.

Figure 28A:
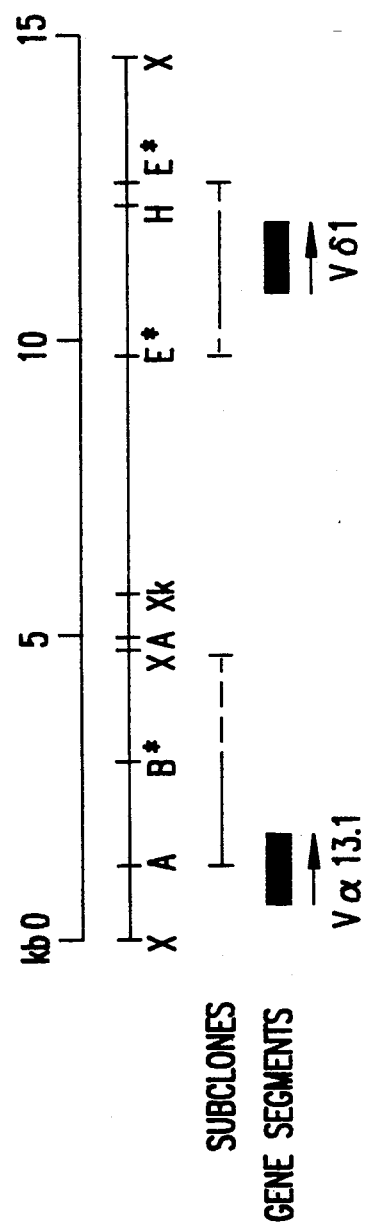
Figure 29:
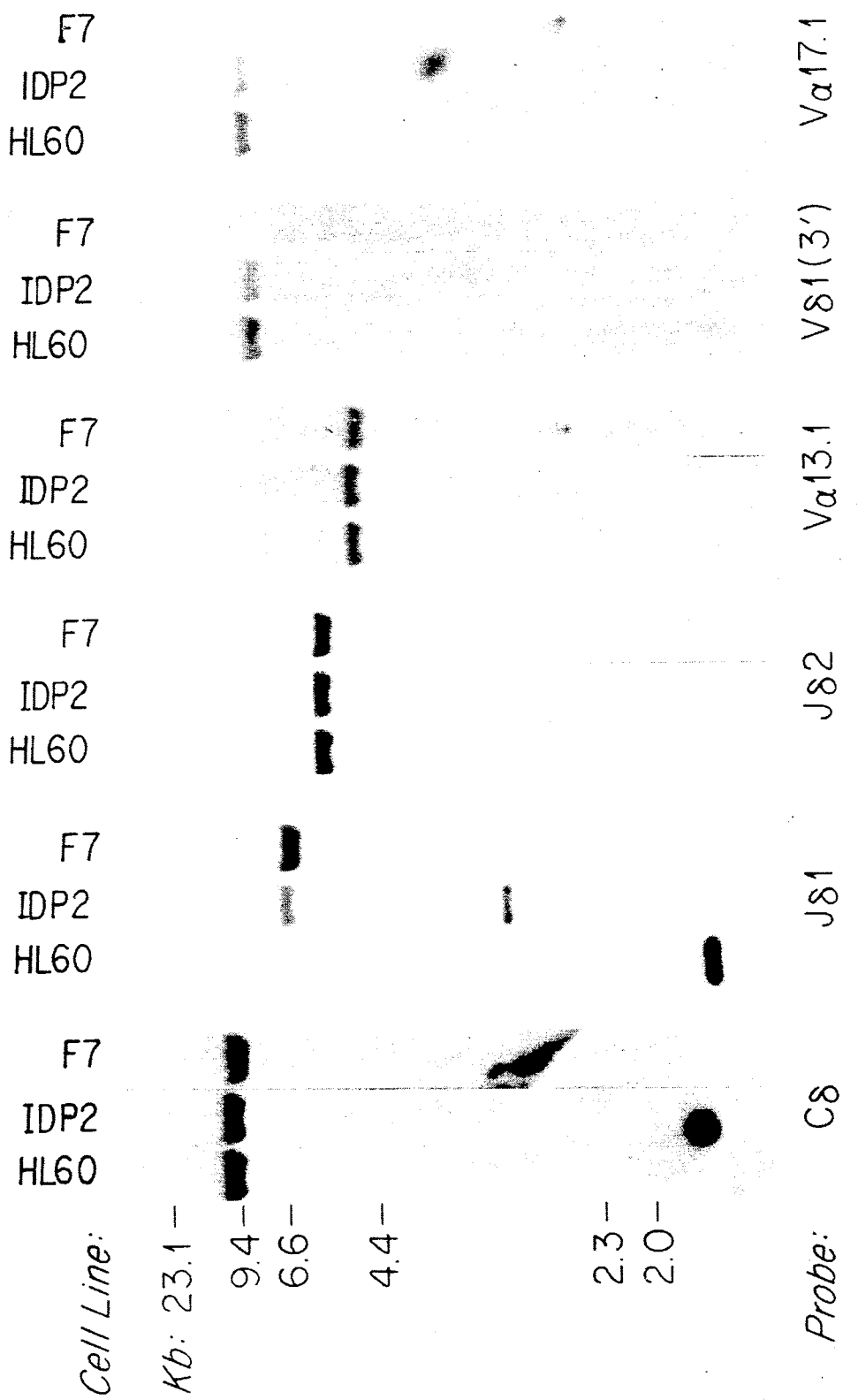

FIG. 29. A $V\alpha$ segment 3' of $V_\delta 1$. XbaI-digested genomic DNA samples (5 $\mu$g) from the cell lines HL60 (myeloid), IDP2 ($\gamma\delta$TCR) and F7 ($\gamma\delta$TCR) were electrophoresed in 0.7% agarose, blotted onto a Hybond-N membrane and analyzed by hybridization with the indicated probes. Probes were $C\delta$ (O-240), $J\delta 1$ (1.7 kb XbaI fragment of K3B), $J\delta 2$ (1.1 kb BamHI-XbaI fragment of K3B), $V\alpha 13.1$ (220 bp Asp718-PstI fragment carrying the sequenced portion of the coding region), $V_\delta 1(3')$ (300 bp HindIII-EcoRI fragment mapped just 3' to the coding region; see FIG. 28A), and $V\alpha 17.1$ (340 bp PstI-BamHI fragment of L17a; Leiden et al., 1986, Immunogenetics 24:17–23). A single blot was serially analyzed with all probes. A phage $\lambda$ HindIII digest served as size markers.

FIG. 30. Structure of the $J\delta 1$, $J\delta 2$ and $D\delta 2$ elements.

(A) Sequence of the $J\delta 1$ segment. The sequence of the 1.7 kb XbaI fragment of cosmid K3B was determined, and the region surrounding $J\delta 1$ is presented. Heptamer and nonamer recombination signals and a splice donor signal are underlined. Numbering is from the 5' end of the XbaI fragment.

(B) Sequence of the $J\delta 2$ segment. The sequence of the 1.1 kb BamHI-XbaI fragment of cosmid K3B was determined and the region surrounding $J\delta 2$ is presented. Numbering is from the 5' end of the fragment.

(C) Sequence of the $D\delta 2$ element. The sequence of the 3.9 kb XbaI fragment of cosmid K3B was determined; the region surrounding $D\delta 2$ is presented. Heptamer and nonamer recombination signals are underlined, and the $D\delta 2$ segment is overlined. Numbering is from the 5' end of the fragment.

Figure 31A:
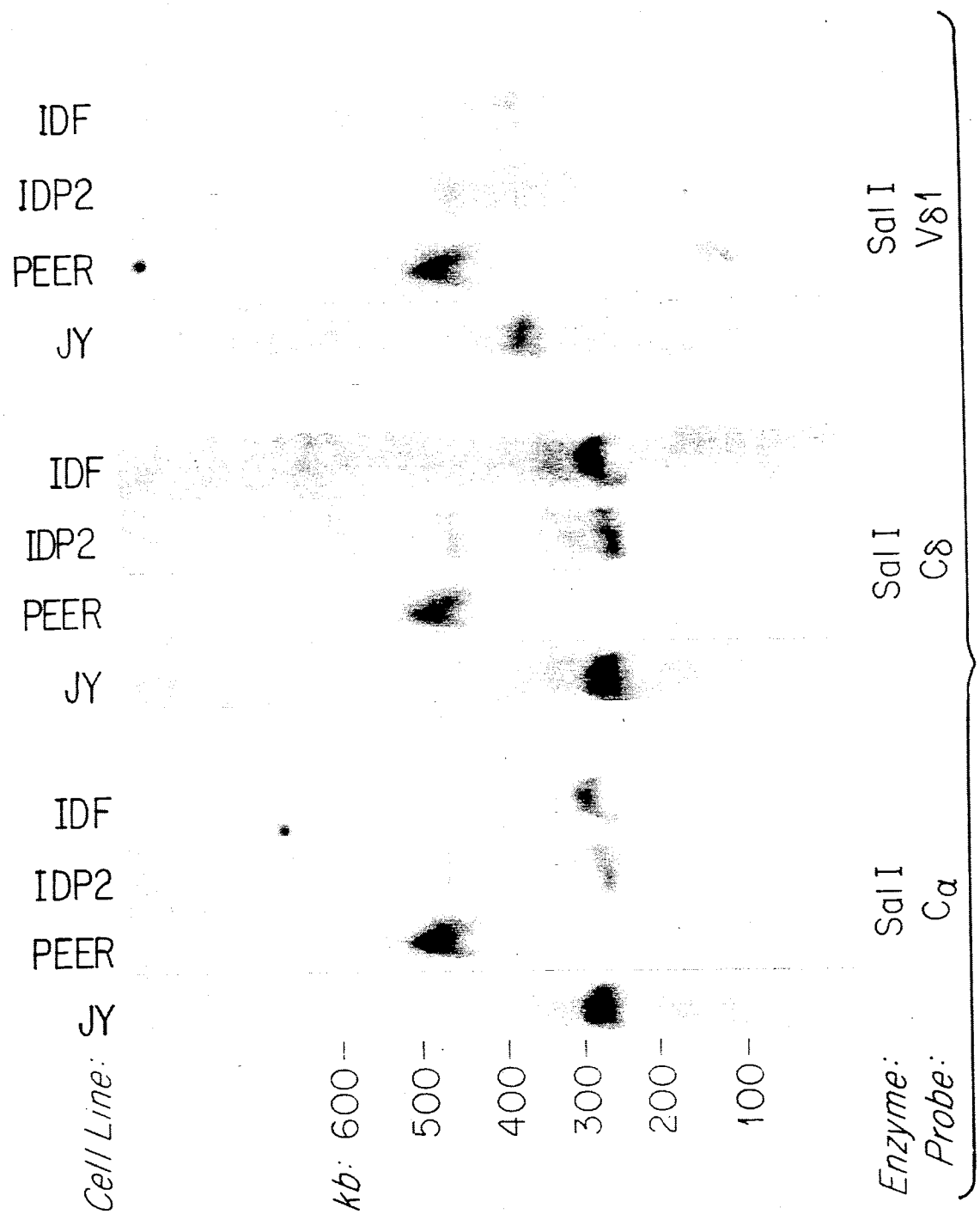

FIG. 31. Field inversion gel electrophoresis (FIGE). (A) SalI digests of JY and IDF DNA (B cells) and PEER and IDP2 DNA ($\gamma\delta$TCR T cells) were analyzed by FIGE at 200 V, with a ratio of forward to reverse pulse times of 3 and a ramp of forward pulse times from 2.4 sec to 84 sec. A single blot was serially probed with $C_\alpha$ (400 bp PvuII fragment of cDNA L17$\alpha$), $C_\delta$ (clone O-240), and $V\delta 1$ (300 bp EcoRI-ScaI fragment of clone O-240/47) probes labeled by random priming. Ligated phage $\lambda$ concatamers served as size markers.

(B) SfiI- and SalI/SfI-digested DNA samples were analyzed by FIGE at 167 V, with a ratio of forward to reverse pulse times of 3 and a ramp of forward pulse times from 3 sec to 20 sec. A single blot was analyzed with probes identical to those in A. Molt-13 is a $\gamma\delta$TCR T cell line.

(C) SalI- and SfiI-digested DNA samples were analyzed by FIGE as in A. A single blot was analyzed with $V\delta 1$, $V\alpha 17.1$, and $V\alpha 1.2$ (500 bp BamHI-ScaI fragment of PY14; Yanagi et al., 1985, Proc. Natl. Acad. Sci. U.S.A. 82:3430–3434) probes labeled as above.

(D) Germ-line and rearranged maps of the TCR α/δ locus determined by FIGE. Numbers denote distances in kb.

5. DETAILED DESCRIPTION OF THE INVENTION

The present invention is directed to the γTCR polypeptide, the δTCR polypeptide, γδTCR, and fragments thereof containing an epitope.

The γTCR polypeptides of the invention include but are not limited to γTCR Form 1, γTCR Form 2abc, and γTCR Form 2bc.

The invention further provides a purified complex which comprises at least a portion of a δTCR polypeptide and at least a portion of γTCR polypeptide herein referred to as a γδTCR complex.

The present invention also provides a substance capable of specifically forming a complex with at least one γTCR polypeptide or δTCR polypeptide. In a specific embodiment, such a substance is a monoclonal antibody. The present invention also provides a method for identifying monoclonal antibodies reactive with TCR polypeptides by detecting the comodulation of CD3 antigen.

The invention is also directed to nucleic acid sequences encoding γTCR or δTCR, or hybridizable subsequences thereof comprising about 15 nucleotides. In specific embodiments, the invention relates to nucleic acid sequences of the variable, joining, diversity or constant regions of the δTCR, and their encoded peptides.

The invention further relates to nucleic acid sequences of γTCR Form 2bc, and hybridizable subsequences thereof comprising about 15 nucleotides.

In another embodiment, the invention is directed to a composition comprising substantially purified cells which express both a γδTCR and the CD4 antigen on their cell surface. In a particular aspect of this embodiment, the substantially purified cells can be γδTCR+, CD4+ and CD8-negative. In another embodiment, the invention provides substantially purified cells which express a γδTCR on their surface which is not associated with a CD3 complex.

5.1. δTCR Polypeptides and Nucleic Acids

The present invention is directed to γTCR polypeptides and nucleic acids. In particular, the invention to forms of the γTCR polypeptide termed Form 2bc, Form 1, and Form 2abc. The invention also relates to nucleic acids encoding γ Form 2bc, such as DNA and RNA, and their complementary nucleic acids. γ Form 2bc is detailed infra in Sections 11 and 15. Form 1 and Form 2abc γTCR polypeptides are described in copending U.S. application Ser. No. 882,100, incorporated by reference herein in its entirety. The Form 1 γTCR polypeptide has a molecular weight of about 40,000 daltons. The Form 2abc γTCR polypeptide has a molecular weight of about 55,000 daltons. Form 2abc γTCR chain has a slightly larger peptide backbone and contains one extra potential N-linked glycan than Form 1. Form 2bc has a molecular weight of about 40,000 daltons and possesses a slightly smaller peptide backbone and 2-3 less N-linked glycans.

γTCR chain Form 2bc differs in size by more than 15 kD (40 kD versus 55 kD) compared to Form 2abc. This difference is accounted for by a 5 kD smaller polypeptide backbone size (35 kD versus 40 kD) and by a reduction in the amount of carbohydrates (5 kD versus 15 kD). The approximately 35 kD polypeptide backbone size of Form 2bc also serves to distinguish it from Form 1; Form 1 has a 40 kD backbone size.

γTCR polypeptide Form 2bc also differs from Form 1 and Form 2abc in constant region (Cγ) gene segment usage. Form 1 γTCR chains have a constant region encoded by the Cγ1 gene segment (Krangel et al., 1987, Science 237:64-67) containing a single CII exon. The Form 2abc γ polypeptide is encoded by Cγ2 gene segments containing three CII exon copies, namely copy a, copy b and copy c (Krangel et al., 1987, Science 237:64-67; Littman et al., 1987, Nature 326:85-88) In contrast, Form 2bc lacks one copy of the sequence encoded by the Cγ2 second exon that is present in the cDNA of Form 2abc. This, Form 2bc contains two Cγ2 CII exon copies, namely copy b and copy c. Copy a of CII, which is missing in Form 2bc, encodes a part of a connector region between the membrane spanning region and the extracellular constant domain.

Six potential N-linked carbohydrate attachment sites exist on the Form 2bc polypeptide. Since the biochemical data suggest that only 2-3 N-linked glycans are attached to the polypeptide chain, it indicates that not all potential sites are used.

In specific embodiments, γTCR polypeptide Form 2bc can be obtained from cells of the MOLT-13 (Loh et al., 1987, Nature 330:569-572) T cell line or thymus-derived Clone II (Bank et al., 1986, Nature 322:179-181). δTCR chain Form 2bc can also be obtained from T lymphocytes of a human subject which express that γTCR form.

Form 2bc γTCR polypeptide comprises the primary amino acid sequence of the γTCR polypeptide shown in FIG. 10, or any portion thereof comprising a constant region consisting of copy b and copy c of Cγ2 CII.

The present invention also provides a nucleic acid molecule encoding a γTCR Form 2bc polypeptide having a molecular weight of about 40,000 daltons. The constant region of γTCR Form 2bc polypeptide results from translation of a nucleic acid sequence which has only two of the three Cγ2 cII exons. The invention is also directed to nucleic acid sequences comprising a Cγ2 constant region having only two cII exons. The nucleic acid can be a DNA, cDNA, RNA, and complementary nucleic acids and derivatives thereof. In a specific embodiment of the invention, the DNA molecule comprises at least a portion of the nucleic acid sequence shown in FIG. 10.

In an example to be discussed in Section 11, the 2bc γTCR polypeptide and its encoding nucleic acid sequence are described. In an example to be discussed in Section 15, it is shown that the ability of the γTCR polypeptide to form disulfide bonds or be glycosylated is determined by its constant region primary sequence.

5.2. Polypeptide Complexes Containing γTCR FORM 1

The present invention relates to polypeptide complexes which comprise the γTCR chain Form 1, having a molecular weight of approximately 40,000 kD. In a specific embodiment, the polypeptide complex consists of a T cell antigen receptor dimer. In particular, such a dimer can be a heterodimer (including but not limited to a γ,δ heterodimer, a γ,β heterodimer, and a α,γ heterodimer, or a γ,γ' heterodimer in which γ' can be γTCR polypeptide Form 2abc, or 2bc; alernatively, the dimer can be a homodimer.

In a particular embodiment of the invention, the polypeptide complex comprising γTCR Form 1 is a γδTCR heterodimer. Thus, a purified complex which comprises at least a portion of a δTCR polypeptide and γTCR Form 1 polypeptide is provided by the present invention. The δ polypeptide may have at least one intrachain, covalent disulphide bridge. Additionally, the polypeptide may comprise a δTCR polypeptide having about 40,000 daltons.

γTCR polypeptide Form 1 is more fully described in copending U.S. applications Ser. Nos. 187,698, filed Apr. 29, 1988; 115,256, filed Oct. 29, 1987; and 016,252, filed Feb. 19, 1987, which are incorporated by reference herein in their entirety. As detailed in examples infra, the γTCR Form 1 chain can be covalently associated in a complex with the δTCR chain forming a disulfide-linked TCR complex.

As discussed in section 6, infra, the PBL-Cl cell line expresses γTCR Form 1, wherein γTCR Form 1 is encoded by the $C_\gamma 1$ gene segment containing a single CII exon, which encodes amino acids permissive of disulfide binding. As illustrated in example section 15, infra, disulfide binding within the γδTCR complex is determined by the presence or absence of this exon. Accordingly, the present invention provides a method for producing expression of γδTCR heterodimers of defined intermolecular linkage (disulfide or non-disulfide-linked).

5.3. Polypeptide Complexes Containing δTCR Form 2abc

The present invention also relates to polypeptide complexes which comprise the γTCR chain Form 2abc. In a specific embodiment, the polypeptide complex consists of a T cell antigen receptor dimer. In particular, such a dimer can be a heterodimer (including but not limited to a γδ heterodimer, a γ,β heterodimer, a α,γ heterodimer, or a γ,γ' heterodimer in which γ' can be δTCR polypeptide Form 1 or 2bc); alternatively, the dimer can be a homodimer.

In a particular embodiment of the invention, the polypeptide complex comprising γTCR Form 2abc is a γδTCR heterodimer. Thus, a purified complex which comprises at least a portion of δTCR polypeptide and γTCR Form 2abc polypeptide is provided by the present invention. The δ polypeptide may have at least one intrachain, covalent disulfide bridge. Additionally, the polypeptide may comprise a δTCR polypeptide having a molecular weight of about 40,000 daltons.

As detailed in the examples infra, the γTCR Form 2abc chain is noncovalently associated in a complex with the δTCR chain. Thus, γ Form 2abc forms a non-disulfide-linked TCR complex, as does γ Form 2bc. As discussed in the example of section 8, infra, Form 2abc (e.g., on I DP2 and PEER cells) utilizes the Cγ2 gene segment containing CII exon copy a, copy b, and copy c, which account for inability to form disulfide bonds as well as the amount of potential carbohydrate binding. γTCR polypeptide, Form 2abc, is more fully described in copending applications serial numbers 187,698, filed Apr. 29, 1988; 115,256, filed Oct. 29, 1987; and 016,252, filed Feb. 19, 1987, incorporated by reference herein in their entirety.

5.4. Polypeptide Complexes Containing γTCR Form 2bc

The present invention also relates to polypeptide complexes which comprise the γTCR chain Form 2bc. In a specific embodiment, the polypeptide complex consists of a T cell antigen receptor dimer. In particular, such a dimer can be a heterodimer (including but not limited to a γ, δ heterodimer, a γ, β heterodimer, and a α,γ heterodimer, or a γ,γ' heterodimer in which γ' can be γTCR polypeptide Form 1, 2abc, or 2bc), or a homodimer.

In a particular embodiment of the invention, the polypeptide complex comprising γTCR Form 2bc is a γδTCR heterodimer. Thus, a purified complex which comprises at least a portion of a γTCR polypeptide and δTCR Form 2bc polypeptide is provided by the present invention. The δ polypeptide may have at least one intrachain, covalent, disulphide bridge. Additionally, the polypeptide may comprise a δTCR polypeptide having a molecular weight of about 40,000 daltons.

As detailed in the examples infra, the γTCR Form 2bc chain is noncovalently associated in a complex with the δTCR chain. Thus, γ Form 2bc forms a nondisulfide-linked TCR complex. γTCR chain Form 2abc also forms a nondisulfide-linked complex with a δTCR chain (e.g., on IDP2 cells), while γTCR chain Form 1 forms a disulfide-linked complex with a δTCR polypeptide.

As shown in the example of Section 15, infra, γTCR constant region CII exon usage (and thus the primary sequence of the γTCR chain) determines not only the presence or absence of disulfide linkage between TCR γ and δ, but also the amount of carbohydrate attached to γTCR, which is largely responsible for the differences in size of the cell surface γTCR proteins. Thus, the present invention also provides a method for producing expression of γδTCR heterodimers of defined intermolecular linkage (disulfide or nondisulfide-linked) and extent of γTCR glycosylation, which comprises introducing a γTCR gene encoding a particular γ polypeptide form into a cell capable of expressing the γ gene, which cell expresses the δTCR chain.

The present invention further provides a purified complex which comprises a γTCR Form 2bc polypeptide of the present invention associated with another γTCR polypeptide (e.g., Form 1, 2abc, or 2bc). In one embodiment of the invention, the two γTCR polypeptides are associated with each other through at least one interchain, covalent, disulfide linkage. In another embodiment of the invention, the two γTCR polypeptides are noncovalently associated with each other. In still another embodiment of the invention, the two γTCR polypeptides have the same constant domain. In yet a further embodiment of the invention, the two γTCR polypeptides have different constant domains.

5.5. δTCR Polypeptides and Nucleic Acids

The present invention provides a purified polypeptide which comprises at least a portion of a δTCR polypeptide (hereinafter referred to as δTCR), more fully described in copending application serial number 187,698, filed Apr. 29, 1988, and U.S. application Ser. No. 115,256, filed Oct. 29, 1987, incorporated by reference in their entirety herein. According to the present invention, this polypeptide may have at least one intrachain, covalent, disulfide bridge, and may have a molecular weight of approximately 40,000. In a particular embodiment of the invention, the δTCR polypeptide may be incorporated TCR complex as part of a heterodimer including, but not limited to, a γδ heterodimer, a αδ heterodimer, or a βδ heterodimer; alternatively, the dimer could be a homodimer. In another embodiment of the invention the polypeptide comprises at least a portion of the amino acid sequence shown in FIG. 15. In particular, such a portion of the sequence can be a fragment encoding an epitope.

The present invention also provides a nucleic acid molecule encoding a δTCR molecule, comprising at least a part of the sequence depicted in FIG. 15. In particular, the invention relates to a hybridizable portion of the sequence of FIG. 15, such as that comprising about 15 nucleotides.

In a specific embodiment, the present invention relates to protein and nucleic acid sequences of the delta variable region, e.g., Vδ1, Vδ2, and Vδ3 (see section 16, infra). In particular, the invention relates to nucleic acid molecules encoding at least a part of the δTCR variable region, comprising all or part of the nucleic acid sequences presented in FIG. 19. The present invention also relates to δTCR polypeptides comprising all or part of the amino acid sequences presented in FIG. 19. In one embodiment, γδTCR polypeptide comprising Vδ2 can be obtained from the LB117 cell line (Ysell et al., 1984, J. Immunol. Methods 72:219). In another embodiment, γδTCR polypeptide comprising Vδ3 can be obtained from the WM14 cell line (Alarconon et al., 1987, Proc. Natl. Acad. Sci. U.S.A. 84:3861).

In another specific embodiment, the invention relates to protein and nucleic acid sequences of the delta joining region. For example, such a joining region can be Jδ1 or Jδ2.

In another specific embodiment, the invention relates to protein and nucleic acid sequences of the delta diversity region. For example, such a diversity region can be Dδ2.

In yet another embodiment, the invention relates to protein and nucleic acid sequences of the delta constant region.

5.6. Diagnostic Methods

The present invention also provides methods for diagnosing an immune system abnormality, comprising detecting the presence or absence of the γTCR or δTCR polypeptides described herein either on the surface of cells or in the cytoplasm of cells. The term "immune system abnormality" as used herein shall be construed to mean any condition of immunological responsiveness to antigens characterized by an increased or decreased immune response compared to a normal, or standard, immune response. Accordingly, immune system abnormalities include, but are not limited to, immunodeficiency conditions and diseases such as acquired immune deficiency syndrome and congenital imunodeficiencies, and also hyperimmune conditions and diseases, such as allergies and hay fever, as well as autoimmune diseases. Lymphatic malignancy is another example of an immune system abnormality.

In one embodiment of the invention, the amount of γTCR or δTCR molecules present on T cells is quantitated and compared with normal values. In another embodiment of the invention, the number of T cells expressing a particular γTCR or δTCR molecule is measured, and compared with normal population distributions of T cells.

In another embodiment of the invention, γTCR or δTCR is measured on the surface of, or in the cytoplasm of, non-T cells. A specific embodiment is described in Example 13, infra, in which γ,δTCR is quantitated in uterine endometrium.

γTCR or δTCR may be detected by various methods according to the invention. In one embodiment, these polypeptides may be detected using polyclonal antiserum. In another embodiment, they may be detected using monoclonal antibodies or fragments thereof. In still another embodiment, the mRNA encoding the γTCR or δTCR polypeptides may be detected by using nucleic acid hybridization.

5.7. Monoclonal Antibodies Reactive with the γδTCR Polypeptides

A monoclonal antibody (mAb) to an epitope of the δ or δ T cell antigen receptor can be prepared by using any technique which provides for the production of antibody molecules by continuous cell lines in culture. These include but are not limited to the hybridoma technique originally described by Kohler and Milstein (1975, Nature 256:495-497), and the more recent human B cell hybridoma technique (Kozbor et al., 1983, Immunology Today 4:72) and EBV-hybridoma technique (Cole et al., 1985, Monoclonal Antibodies and Cancer Therapy, Alan R. Liss, Inc., pp. 77-96).

In one embodiment, the monoclonal antibodies may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308-7312; Kozbor et al., 1983, Immunology Today 4:72-79; Olsson et al., 1982, Meth. Enzymol, 92:3-16). Chimeric antibody molecules may be prepared containing a mouse (or rat, or other species) antigen-binding domain with human constant regions (Morrison et al., 1984, Proc. Natl. Acad. Sci. U.S.A. 81:6851; Takeda et al., 1985, Nature 314:452).

The invention is also directed to a method of identifying a monoclonal antibody reactive with a T cell antigen receptor. Such a mAb can be identified by detecting its ability to comodulate the CD3 antigen upon binding of the mAb to a cell which expresses both a T cell antigen receptor and CD3 complex. The CD3 comodulation can be detected, for example, by measuring the amount of labeled anti-CD3 antibody which is bound by the cell. This method is illustrated by way of example in Section 10.1.1, infra, in which it is used to identify hybridomas secreting anti-Vδ mAb δTCAR-3.

A molecular clone of an antibody to an epitope of a γ or δTCR polypeptide can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

One embodiment of the invention is directed to monoclonal antibodies reactive with the variable region of the δTCR chain. Such an antibody is δTCAR-3 (aka TCSδ1)(see Section 10, infra), which recognizes an epitope expressed from a specific δ gene rearrangement. As described in Section 10.2, infra, mAb δTCAR-3 is capable of stimulating the proliferation of a γ,δ+T lymphocyte. Monoclonal antibody δTCAR-3 is also able to stimulate a rise in cytoplasmic free calcium ion concentration of γ, δ+T lymphocytes.

In another embodiment, the invention relates to antibodies reactive with the constant region of the γ or δTCR polypeptide. In a specific embodiment, the invention is directed to mAb TCRδ1 which is reactive with the constant region of the δTCR chain (see Section 9, infra). In another specific embodiment, the invention relates to mAb anti-Cγm1, which is reactive with the constant region of the γTCR chain (see Section 11.1.7, infra).

6. EXAMPLE: IDENTIFICATION OF A PUTATIVE SECOND T CELL RECEPTOR

6.1. Materials and Methods

6.1.1. Lymphocyte Culture and Cell Population Analysis

Viable lymphocytes were isolated by Ficoll-hypaque density centrifugation and stained with 0.5 micrograms of a specific monoclonal antibody, e.g. WT31 (Brenner, et al., 1984, J. Exp. Med. 160:541-551; Tax, et al., 1983, Nature 304:445-447) or OKT®3, OKT®4 or OKT®8 (Ortho Diagnostic Systems, Inc., Raritan, N.J.), for 30 minutes at 4° C. After washing, the cell pellets were stained again with fluorescein isothiocyanate (FITC)-conjugated goat antimouse IgG(ab),2 fragments. Fluorescence activated cell sorter (FACS) analyses were performed on an Ortho cytofluorograph or a Coulter Epics as previously described (Raulet et al., 1985, Nature 314:103-107). Specifically stained positive cells were determined relative to a negative control profile for each cell line (stained with a nonspecific control monoclonal antibody). Cells having fluorescence intensity channel numbers greater than the intercept of the negative control profile with the baseline were counted as positive, and the % positive was calculated relative to the total number of cells counted.

All IL-2 dependent cell lines were propagated in vitro in media composed of RPMI 1640, 10% human serum and conditioned media containing 2-5 units of interleukin-2 activity as previously described (Brenner et al., 1985, J. Immunol. 135:384-390).

Alloantigen (allo) activated cultures were stimulated with irradiated allogeneic peripheral blood lymphocytes at weekly intervals. Mitogen, i.e. phytohemagglutinin (PHA), activated lines were stimulated with a 1:1,000 dilution of PHA (Difco, Detroit, Mich.) at culture initiation.

6.1.2. Reactivity and Characterization of Cell Culture using Monoclonal Antibodies Immunoprecipitates from $^{125}$I-labeled lymphocyte lysates were analyzed by sodium dodecyl sulfate-polyacrylamide gel electrophoresis (SDS-PAGE). The radioiodinated T leukemia cell lines HPB-MLT and Jurkat, the HTLV-1 transformed cell line ANITA and resting peripheral blood lymphocytes were solubilized in 1% Triton-X-100 (TX-100) and immunoprecipitated with a control antibody, normal mouse serum (NMS) or a framework antibody to TCR α,β i.e., βF1 (Brenner et al., 1986, Fed. Proc. 45:1292). The βF1 monoclonal antibody was prepared according to standard procedures (Brenner et al., 1987, J. Immunol. 138:1502-1509; Kenneth et al., 1980, in Monoclonal Antibodies: A New Dimension in Biological Analysis, Plenum Press, N.Y.). Spleen cells from mice immunized with purified TCR α,β as described by Brenner et al. (1984, J. Exp. Med. 160:541-551) were used for the fusion experiments. A positive clone, βF1, was obtained by immunoprecipitation with T cell lines and peripheral blood lymphocytes as described above.

$^{125}$I-labeled lymphocytes were solubilized in 0.1% TX-100 and immunoprecipitated with NMS, the anti-T3 antibody UCHT-1 (Beverly and Callard, 1981, Eur. J. Immunol. 11:329-334) and a framework antibody to TCR i.e., WT31. The efficiency of immunoprecipitation with WT31 was improved at the lower TX-100 concentration used here and the monoclonal antibody 187.1 (Yelton et al., 1981, Hybridoma 1, 5-11) was used as a second antibody.

Two-color FACS analysis of normal adult peripheral blood lymphocytes was performed using an anti-TCR α,β monoclonal antibody and an anti-T3 monoclonal antibody. Peripheral blood lymphocytes were stained first with an FITC-conjugated anti-T3 monoclonal antibody (OKT®3) and then with a biotinyl-anti-TCR α,β monoclonal antibody (βF1) followed by phycoerythrin-conjugated avidin (PE-avidin, Becton Dickinson, Mt. View, Calif.).

Viable lymphocytes were isolated by Ficoll-hypaque density centrifugation for SDS-PAGE and FACS analyses. For SDS-PAGE analysis, lymphocytes were radioiodinated by the lactoperoxidase technique, solubilized in 1% TX-100 and immunoprecipitated using 1 microgram of a specific antibody, i.e. monoclonal antibody βF1 or monoclonal antibody UCHT-1, or 1 microliter of NMS. The immunoprecipitates were then analysed by 10.5% SDS-PAGE under reducing conditions. The $^{125}$I-labeled molecules were visualized by autoradiography as previously described (Brenner et al., 1984, J. Exp. Med. 160:541-551).

Two-colored cytofluorographic analysis was performed by first staining with FITC-OKT®3 monoclonal antibody for 45 minutes at 4° C. After washing, the lymphocytes were fixed in 1% paraformaldehyde for 15 minutes at 23° C. then incubated in 70% ethanol in phosphate buffered saline (PBS) for 5 minutes at −20° C. After further washing, the cells were stained with the biotinyl-βF1 monoclonal antibody followed by PE-avidin. Analysis was performed on an Ortho® cytofluorograph (Ortho Diagnostic Systems, Inc., Westwood, Mass.).

6.1.3. Analysis of Cell Surface Protein Molecules Associated with T3 Molecules on IDP1 and IDP2 Cell Lines IDP1 CELL LINE 2 (WT31+) and cell line 3 (WT31−) were $^{125}$I-labeled as described above. Radioiodinated, intact lymphocytes were then either crosslinked by incubation in PBS (pH 8) containing 50 micrograms/ml dithio-bis-succinimidyl propionate (DSP) or mock incubated. The cells were then solubilized in 1% TX-100 and immunoprecipitated as previously described (Brenner et al., 1985, Cell 40:1983-190). T3 associated molecules ($M_r$ 40,000-55,000) in t anti-T3 immunoprecipitations were detected at low levels in the noncrosslinked samples and at higher levels in the crosslinked samples.

IDP2 cell line 7 (88% WT31−T3+) was $^{125}$I-labeled and treated with DSP or mock incubated. Immunoprecipitations were performed using NMS, the anti-T3 monoclonal antibody UCHT-1 and the anti-TCR α,β monoclonal antibody βF1 either without or with preclearing TCR α,β molecules with the monoclonal antibody βF1. A small fraction of radiolabeled TCR α,β was detected in samples which were not precleared but not in samples which were precleared with βF1.

IDP2 cell line 5 (WT3+T3+) and cell line 7 (88% WT31−T3+) were $^{125}$I-labeled, solubilized in 1% TX-100 and immunoprecipitated using NMS or the anti-T3 monoclonal antibody UCHT-1. The T3 heavy subunit ($M_r$ 27,000) appeared similar on these two cell lines, while the T3 light subunits ($M_r$ 19,000–25,000) did not.

$^{125}$I-labeling, solubilization in 1% TX-100, immunoprecipitation and visualization after 10.5% SDS-PAGE analysis by autoradiography were performed as previously described (Brenner et al., 1988, J. Exp. Med. 160:541–551). Chemical cross-linking was performed for 30 minutes at 23° C. on intact radiolabeled lymphocytes using DSP (50 micrograms/ml) in PBS (pH 8) as previously described (Brenner et al., 1984, Cell 40:183–190). After immunoprecipitation, all samples were examined by SDS-PAGE under reducing conditions using 5% 2-mercaptoethanol, which cleaved both the disulfide bonds between protein subunits and the DSP chemical cross-link.

6.1.4. Northern Blot Analysis of RNA Isolated from IDP2 Cell Line Using TCR α, TCR β and TCR γ cDNA PROBES Total RNA (15 micrograms) isolated from IDP2 cell line 6 (WT31−) and from T leukemic cell line HBP-MLT was fractionated on a 1.5% agarose gel containing 2.2 M formaldehyde, transferred to nitrocellulose and hybridized with TCR α, TCR β and TCR γ probes.

Total RNA (3 micrograms) isolated from IDP2 cell line 5 (WT31+T3+), IDP2 cell line 7 (88% WT31−T3+) and HPB-MLT was analyzed as described above.

RNA preparation, electrophoresis, transfer to nitrocellulose and hybridization with $^{32}$P-labeled, nick translated probes (1–3×10$^8$ cpm/microgram) were as described previously (Krangel, 1985, EMBO J., 4:1205–1210). α-chain probes were either the human cDNA clones pGA5 (Sim et al., 1984, Nature 312:771–775) or L17 α (Leiden et al., 1986 immunogenetics). β chain probes were either the human cDNA clones 12AI or L17 (Leiden and Strominger, 1986, Proc. Natl. Acad. Sci.: U.S.A.). The γ-chain probe was an EcoRI to AccI fragment derived from human cDNA clone Tγ-1 (Dialynas et al., 1986, Proc. Natl. Acad. Sci. U.S.A. 83:2619–2623). Radioactive bands were visualized by autoradiography using intensifying screens. All probes were labeled to nearly identical specific activity, and identical exposure times are presented.

6.1.5. Immunoprecipitation of IDP2 Cell Line 7 Surface Molecules using Anti-γ Antiserum TX-100 solubilized $^{125}$I-labeled IDP2 cell line 7 (88% WT31−T3+) was denatured (see below) and then immunoprecipitated with NMS or normal rabbit serum and with anti-V γ peptide serum or anti-γ peptide serum. A specific band was observed at $M_r$ 55,000 in both the anti-V γ and anti-C γ immunoprecipitations. The additional band at $M_r$ 90,000 was not reproducibly observed in the anti-C γ immunoprecipitations (see below).

DSP cross-linked native lysates (1% TX-100) from $^{125}$I-labeled IDP2 cell line 7 were immunoprecipitated with NMS or with the anti-T3 monoclonal antibody UCHT-1. Alternatively, the lysate was denatured (as described below) and immunoprecipitated with either normal rabbit serum or with anti-C γ peptide serum.

An additional aliquot of lysate was subjected to a two stage immunoprecipitation. Polypeptides were immunoprecipitated with the anti-T3 monoclonal antibody UCHT-1, and were eluted from the immunoabsorbent under denaturing and reducing conditions, in order to break the DSP cross-link. Immunoprecipitation from this eluate was then performed using anti-C γ peptide serum.

$^{125}$I-labeling, solubilization in 1% TX-100 and immunoprecipitation were performed as described above. Native lysates (1% TX-100) were denatured by the addition of SDS (final concentration of 1%) and dithiothreitol (final concentration of 2 mM) followed by heating the mixture for 5 minutes at 68° C. After cooling, iodoacetamide was added (20 mM final concentration) and samples were diluted with the addition of 4 volumes of 1.5% TX-100 in Tris buffered saline (pH 8). The initial immunoprecipitate in the experiment was denatured and subsequently partially renatured (Brenner et al., 1984, J. Exp. Med. 160:541–555). Samples were immunoprecipitated with 10 microliters of anti-C γ or anti-V γ peptide sera, 1 microgram of UCHT-1 or 1 microliter of NMS or normal rabbit serum and analyzed by 10.5% SDS-PAGE under reducing conditions (5% 2-mercaptoethanol).

Peptides corresponding to deduced V γ or C γ amino acid sequences (residue numbers noted below in the Experimental Result section) were synthesized on a Beckman 990 peptide synthesizer using the method of Erickson and Merrifield (1976, in The Proteins, Neurath, H. and Hill, R. L., eds., Academic Press, N.Y., p. 255). Peptide purity was assessed by high pressure liquid chromatography and peptide sequence was confirmed by amino acid analysis. Peptides were coupled to keyhole limpet hemocyanin (KLH) at a ratio of 50 peptides per KLH molecule (Liv et al., 1979, Biochem. 18:690–697). Mice and rabbits were immunized with the V γ peptides or Cγ peptides, respectively. Animals were injected at three week intervals and the antisera screened for binding reactivity on peptide-KLH and peptide-bovine serum albumin conjugates to ascertain the presence of peptide-specific antibodies.

Monoclonal antibodies against the γ chain were generated by standard procedures as described in (Acuto et al., 1984 Proc. Natl. Acad. Sci. U.S.A.81:3851–3855). BALB/c mice were immunized with the KLH-coupled peptide to the variable region γ chain peptide described above using the method of Erickson and Merrifield (supra). After four immunizations at two week intervals, spleen cells were fused with P3-X63-Ag8UI myeloma cells. Positive hybridoma clones were screened and identified by the enzyme immunoassay (EIA) described in Ischimori et al. (1985, J. Immunol. Method. 80:55–66).

6.1.6. Isolation of DNA Sequences of the δ Polypeptide

In one embodiment, DNA sequences of the TCR δ gene may be isolated and determined by strategies utilized to isolate the TCR β gene as described in Royer et al. (1984, J. Exp. Med. 160:947–953) and Acuto (supra).

Briefly, the amino acid sequence of the TCR δ gene may be determined following isolation of the TCR δ polypeptide which is described hereinafter. After the amino acid sequence is determined, short, synthetic DNA sequences may be prepared using a commercial DNA synthesizer (Applied Biosystems, Inc., Foster City, Calif.). The synthetic DNA sequences may be used as probes for the isolation of the complete sequence of DNA from a cDNA library of cell lines containing the TCR δ polypeptide. The primary structure of the protein may then be determined (Maniatis et al., 1982, "Molecular Cloning, A Laboratory Manual," Cold Spring Harbor Laboratories, Cold Spring Harbor, N.Y.).

The isolation and sequence of DNA encoding the delta gene is described infra in Sections 8, 16, 17, and 18.

6.1.7. Preparation of Monoclonal Antibodies Against the δ Polypeptides and Against γ, δ Complexes Monoclonal antibodies against the δ polypeptide may be generated by standard procedures (Acuto et al., supra). Peptides derived from the TCR δ polypeptide may be prepared from nucleic acid sequences determined by the methods described above. Methods for the selection of such peptides useful for immunization have been described in detail (Hopp et al., 1981, Proc. Natl. Acad. Sci. U.S.A. 78:3824–3828; Kyte and Doolittle, 1982, J. Mol. Biol. 157:105–132; G®ysen et al., 1985, Proc. Natl. Acad. Sci. U.S.A. 82:178–182).

Monoclonal antibodies directed against γ,δ complexes may be prepared according to published procedures (Acuto, supra). γ,δ complexes may be isolated from the T cell lines described above and used to immunize BALB/c mice as described in previously published procedures (Brenner et al., 1984, supra). Alternatively, BALB/c mice may be immunized with cell lines, e.g., the IDP1 cell line or the IDP2 cell line.

Methods for the fusion, generation and maintenance of hybridoma cell lines have been widely published and are known to those skilled in the art. Hybridoma cells that produce monoclonal antibodies which are directed against specific TCR γ, δ cell lines but which do not cross react with other T cell lines may be selected and recovered.

In specific embodiments, the production and characterization of a monoclonal antibody is detailed in Sections 7, 9, 10, 11.1.7, and 12, infra.

6.1.8. Immunoprecipitations of TCR γ,δ and T3 from a Human Tumor and Peripheral Blood Lymphocyte Lines Viable lymphocytes were isolated by Ficoll-hypague density gradient centrifugation and $2 \times 10^7$ cells were radioiodinated by the lactoperoxidase technique as described (Brenner et al. 1984, J. Exp. Med. 160:541–551). Labelled cells were lysed in 5 ml of TBS (10 mM Tris pH 8, 140 mM NaCl) with 0.3% 3-[(3-cholamidopropyl) dimethylammonio]-1-propane-sulphonate (CHAPS), which preserves the TCR-T3 association (Samelson, L. E., et al., 1985, Proc. Natl. Acad. Sci. U.S.A. 82:1969–1973), containing 2 mM phenylmethylsulphonyl fluoride (PMSF) and 8 mM iodoacetamide (IAA). Immunoprecipitation was carried out using fixed *Staphylococcus aureus* Cowan I (SACI) as described (Brenner et al., 1985, Cell 40:183–190), and the immune complexes were washed ×5 in TBS containing 0.1% Triton X-100 (TX-100). Reduced samples were boiled in 2 mM dithiothreitol (DTT) and all samples incubated for 10 minutes at 23° C. in 10 mM IAA before analysis by SDS-PAGE. Immunoprecipitations using anti-C γ sera were performed on 1% TX-100 lysates that were dialysed to remove IAA and then denatured by the addition of one tenth volume of sodium dodecyl sulphate (SDS) containing 3 mM DTT with boiling for 3 minutes. After partial renaturation by the addition of 4 volumes of 1.5% TX-100 in TBS containing 30 mM IAA, anti-C γ sera or NRS were added and the immunoprecipitates were washed in TBS containing 0.5% TX-100, 0.5% deoxycholate, 0.05% SDS before analysis by SDS-PAGE. Rat anti-mouse α chain-specific mAb (187.1; 15 μg) was added as a second antibody to provide protein A binding of IgG₁ mAb βF1, UCHT and P3 (Yelton et al. 1981, Hybridoma 1:5–11).

6.1.9. Northern Blot Analysis of RNA Isolated from PBL C1

Approximately 1.5 μg RNA was loaded per lane, probes were labeled to similar specific activity, and identical autoradiographical exposures are presented. RNA sizes were determined based on previously published lengths for TCR β and TCR γ transcripts (Dialynas et al., 1986, Proc. Natl. Acad. Sci. U.S.A. 83:2619–2623; Yanagi et al., 1984, Nature 308:145–149).

6.1.10. Two-Dimensional Gel Analysis of TCR γ Polypeptides and Precursors

After radioiodination with lactoperoxidase, lymphocytes were treated with 100 U of neuraminidase (Gibco) in phosphate-buffered saline (PBS), 1 mg/ml bovine serum albumin, 1 mg/ml glucose for 90 minutes at 23° C., washed in PBS and solubilized in 0.3% CHAPS. Immunoprecipitates were prepared and NEPHGE (charge separation) was carried out using pH 3.5–10 ampholines (LKB, Sweden), or isoelectric focusing (IEF) using pH 3.5–10, 4–6, 9–11 ampholines (2:15.5:1.5) followed by 10.5% SDS-PAGE gels for size separation as described (Brenner et al., 1985, Cell 40:183-190). NEPHGE was carried out applying the iodinated IEF sample at the acidic end, while IEF was carried out for 20 hours at 400 V applying the sample at the other (basic) end. Brackets enclose the T3-associated species.

Cells ($2 \times 10^7$) were preincubated for 1 hour at 37° C. in 4 ml methionine-free RPMI 1640 supplemented with 10% fetal bovine serum. $^{35}$S-methionine was added to 250 μCi/ml and incubation was continued for 1 hour at 37° C. Cells were collected, washed and lysed in 0.4 ml of boiling solution of 1% SDS, 10 mM Tris-HCl (pH 8.0), 0.1 mM PMSF and 10 mM IAA. Lysates were diluted with 1.6 ml of 2.5% Nonidet-P40, 1% gelatin, 10 mM Tris-HCl (pH 8) and 0.2 ml of 1 mg/ml DNase. 0.5 mg/ml RNase, 0.5M Tris-HCl (pH 7), 50 mM MgCl₂ and incubated at 0° C. for 2–4 hours. After centrifugation for 15 minutes at 12,000×g to pellet insoluble debris, immunoprecipitations with anti-γ serum were performed using protein A sepharose preincubated with 1% gelatin and washing as described (Krangel et al., 1979, Cell 18:979–991). Elution from the immunoabsorbent and treatment with endo-H (Miles Scientific, Naperville, Ill.) were as described (Krangel et al., 1979, Cell 18:979–991). Samples were analysed with antiserum by two-dimensional gel electrophoresis employing NEPHGE in the first dimension and 10% SDS-PAGE in the second dimension, followed by fluorography (Bonner, et al., 1974, Eur. J. Biochem. 46:83–88).

6.1.11. Rearrangements of the γ and β Genes in T Cells Expressing the TCR γ Polypeptides Genomic DNA was isolated as described (BamHI or EcoRI), size-fractionated on 0.7% agarose (BamHI digests) or 0.9% agarose (EcoRI digest), and transferred to nitrocellulose as described (Southern, 1975, J. Exp. Med. 98:503-517). Filters were hybridized to a nick-translated $^{32}$P-labelled 0.8 kb HindIII-EcoRI Jγ $_{1.3}$ probe (Quertermous et al., 1986, Science 231:252-255) or a 1.1 kb EcoRI-HindIII C$_{\beta 2}$ probe (Duby and Seidman, 1986, Proc. Natl. Acad. Sci. U.S.A. 83:4890-4894). Filters were washed in 2×SSC and 0.1% SDS followed by 0.2% SSC and 0.1% SDS at 55° C. before autoradiography with intensifying screens.

6.1.12. Cytolysis by IDP2 and PBL C1 Cells

Cytolytic assays were performed in round-bottom 96-well tissue culture plates with $^{51}$Cr-labelling, harvesting and calculation of % specific release as described (Brenner et al., 1985 J. Immunol. 135:384-390). IDP2 or PBL C1 cells were either preincubated with UCHTI (1:300 dilution) (+anti-T3) for 30 minutes at 0° C., washed three times or mock incubated and placed together with labelled target cells. Anti-HLA Class I and Class II mAb and anti-T3 mAb were placed in wells containing the $^{51}$Cr-labelled MOLT 4 cells for 30 minutes at 0° C., then IDP2 cells were added at a 40:1 E:T ratio. All samples were assayed in triplicate, and each experiment was performed at least three times.

6.2. Experimental Results

6.2.1. A βF1−WT31−T3+ T Cell Population

A murine framework antiserum that recognizes the majority of human TCR α,β molecules has previously been reported (Brenner et al., 1984, J. Exp. Med. 160:541-551). Subsequently, a murine monoclonal antibody, designated Framework 1 (β F1), that is reactive with shared determinants on the human TCR β chain was obtained (Brenner et al., 1987, J. Immunol. 138:1502-1509). The βF1 monoclonal antibody reacts with the majority of T3 positive (T3+) human peripheral blood lymphocytes (PBLs) and is capable of immunoprecipitating the TCR α,β heterodimer from all human T cell lines examined that have α,β T cell receptors and express the T3 glycoprotein. Immunoprecipitations from a panel of T cell lines using this monoclonal antibody demonstrated this reactivity as well as the heterogeneity of the TCR α and TCR β subunits from different receptors. Like the framework antiserum (Brenner et al., 1984, J. Exp. Med. 160:541-551), this monoclonal antibody does not stain the surface of living T cells, but will specifically react with both membrane and cytoplasmic T cell receptors after partial solution of the lymphocyte plasma membrane with 70% ethanol. Double staining of human PBLs with a fluorescein-anti-T3 monoclonal antibody and a biotinyl-βF1 monoclonal antibody followed by PE avidin reveals that the βF1 monoclonal antibody recognizes 95-97% of peripheral blood T3+lymphocytes. However, it clearly defined a small population of T lymphocytes that is βF1 negative (β F1−) yet T3+(approximately 4% of the T3+cells).

A second framework monoclonal antibody designated WT31, initially thought to recognize the T3 antigen (Tax et al., 1983, Nature 304:445-447), has recently been shown to react with a common epitope of human TCR α,β (Spits et al., 1985, J. Immunol. 135:1922-1228). While double staining with an anti-T3 monoclonal antibody (OKT®3) and WT31 revealed that each of these monoclonal antibodies cross-block binding of the other, one-color fluorescence indicated that WT31 typically recognized 1-3% fewer cells in peripheral blood than do anti-T3 monoclonal antibodies. The WT31 monoclonal antibody efficiently binds to the surface of T cells (such as in FACS analyses) and is capable of immunoprecipitating the TCR α,β molecules, albeit inefficiently, from radiolabeled detergent lysates (Spits et al., 1985, J. Immunol. 135:1922-1928). Thus, the βF1 monoclonal antibody and the WT31 monoclonal antibody appear to recognize all but a small fraction of human peripheral blood T3+cells, and define a subpopulation that is T3+but unreactive with both of these framework monoclonal antibodies against the TCR α,β molecules. Evidence that the T3+lymphocytes that are unreactive with the monoclonal antibody βF1 are also unreactive with the monoclonal antibody WT31 is shown below. WT31 was used primarily for FACS analyses and βF1 was used primarily for immunoprecipitation studies.

6.2.2. WT31−T3+Cell Lines Created from Peripheral Blood Lymphocytes of Immunodeficiency Patients Efforts at growing the WT31 T3+population from normal adult PBLs proved difficult, since the WT31+T3+lymphocytes usually overgrew the WT31−T3+cells following mitogenic stimulation. However, growth of the WT31−T3+population from the PBLs of immunodeficiency patients was successful. Immunodeficiency patient 1 (IDP1) suffered from the bare lymphocyte syndrome and lacked class II MHC antigen expression on lymphoid cells (Griscelli et al., 1980, in Primary Immunodeficiencies, Seligman and Hitzig, eds., Elsevier, North-Holland, pp. 499-504; Hadman et al., 1984, in Progress in Immunodeficiency Research and Therapy I, Griscelli and Vossen, eds., Elsevier Science Publishers B. V., Amsterdam, pp. 43-50), while immunodeficiency patient 2 (IDP2) suffered from an ectodermal dysplasia syndrome (Levine et al., 1977, J. Ped. 90:55-61) and displayed poor in vitro T cell proliferative responses to mitogens.

After activation of PBLs from IDPI and alloantigen and propagation in conditioned media containing interleukin-2 (IL-2) activity (Brenner et al., 1985, J. Immunol. 135:384-390), the resultant cell line was observed to be approximately 50% WT31+T3+and 50% WT31−T3+(see Table I below, cell line 1). Subsequent sorting of this cell line yielded homogeneous populations of WT31+T3+cells and WT31−T3+cells (see Table I below, cell lines 2 and 3, respectively).

TABLE I

| Cell Line Number | Source | Cell Line Description[1] | % Positive | | | |
|---|---|---|---|---|---|---|
| | | | WT31 | T3 | T4 | T8 |
| 1 | IDP1 | allo | 50 | 100 | 11 | 50 |
| 2 | IDP1 | WT31+sort | 100 | 100 | 70 | 28 |
| 3 | IDP1 | WT31−sort | 0 | 100 | 0 | 62 |
| 4 | IDP2 | fresh PBL | 61 | 63 | 38 | 16 |
| 5 | IDP2 | PHA | 100 | 96 | 18 | 80 |
| 6 | IDP2 | allo | 2 | 100 | 0 | 43 |
| 7 | IDP2 | PHA | 12 | 93 | 1 | 18 |

[1]Cell line description indicates the conditions for activation or source of lymphocytes. WT31+ and WT31− sorted cell lines 2 and 3 (sort) were obtained by fluoresence activated cell sorting of IDPI cell line 1.

Cell lines were also obtained from IDP2. Fresh PBLs from IDP2 revealed that 63% of the PBLs were T3+ and 1-3% fewer cells (61%) were WT31+, which is typical of normal PBLs (Table I, cell line 4). Activation of these IDP2 PBLs with either phytohemagglutinin (PHA) or alloantigen and propagation in vitro with conditioned media resulted in several cell lines. These included a homogeneous WT31+T3+cell line (Table I, cell line 5), a homogeneous WT31−T3+cell line (Table I, cell line 6) and on a third occasion, a cell line that was 88% WT31−T3+(with 12% contaminating WT31+T3+cells( (Table I, cell line 7). The WT31−T3+population contained both T4−T8+ and T4−T8−cells (Table I, cell lines 3, 6 and 7). Further phenotypic analysis revealed that this population was T11+ but negative for natural killer cell markers such as Leu 7, Leu 11 and OKM1 and for the immature thymocyte marker T6.

6.2.3. Immunoprecipitation Shows that WT31−T3+Cells are βF1−

The βF1 monoclonal antibody immunochemically defined a heterodimeric structure on the surface of $^{125}$I-labeled WT31+T3+IDPI lymphocytes, yet failed to recognize a similar protein on the WT31−T3+population from this same individual. Similar analysis of IDP2 cell lines revealed a trace of α,βTCR on the 88% WT31−T3+cell line 7, consistent with the 12% contamination with the WT31−T3+cells. Thus, the WT31−T3+cells, identified by the lack of cell surface reactivity with the WT31 monoclonal antibody in FACS analysis, were also βF1−, as determined by the lack of TCR α,β on immunoprecipitation. All WT31+T3+ and WT31−T3+cell lines expressed similar amounts of T3 by FACS analysis and by immunoprecipitation with an anti-T3 monoclonal antibody. However, the T3 molecule found on WT31−βF1−T3+lymphocytes was not identical to the T3 molecule found on WT31+βF1 +T3+cells by SDS-PAGE. One-dimensional and two-dimensional gel analysis indicated that the difference in T3 was restricted to the light T3 subunits, which reproducibly displayed different SDS-PAGE mobilities.

6.2.4. Northern Blot Analysis to Determine the Expression of αTCR, βTCR and γTCR mRNA To determine if the WT31−βF1−T3+population lacked TCR α,β molecules, or alternatively expressed TCR α,β molecules that failed to react with these monoclonal antibodies, the presence of mRNAs encoding the TCR α and β proteins was investigated. $^{32}$P-labeled cDNA clones encoding αTCR βTCR, and γTCR were used to probe Northern blots containing whole cell RNA from WT31−γ F1−T3+ and WT31+βF1+T3+ IDP2 cell lines and from HPB-MLT, which is known to contain mRNA for αTCR, β TCR, and γ TCR. No αTCR or βTCR mRNA transcripts could be detected in the RNA from the WT31−βF1−$_{T3}$+IDP2 cell line 6, whereas expression of both was clearly detectable in RNA from HPB-MLT. Notably, TCR γmRNA was present in the WT31−T3+cells at levels comparable to that in HPB-MLT. Thus, the WT31βF1−T3+lymphocytes lacked TCR α and γ mRNA. Subsequent experiments on cell lines that were mostly WT31−T3+corroborated these results. For example, Northern blot analysis performed on IDP2 cell line 7 (88% WT31−T3+) and compared with IDP2 cell line 5 (WT31+T3+), as well as with HPB-MLT cells, revealed only a trace of TCR or TCR β mRNA in the 88% WT31−T3+cells (consistent with the 12% contamination with WT31+T3+cells). Further, the majority of the β transcripts that could be detected were 1.0 and not 1.3 kb and were probably nonfunctional (Yasunobu et al., 1984, Nature 312:521-524). In contrast, the IDP2 cell line 5 (WT31−T3+) expressed levels of both RNA species which were comparable to HBP-MLT. However, like the WT31−$_{T3}$+cell line, both the WT31−T3+ and the WT31+T3+cell lines showed TCR γ RNA levels comparable to HPB-MLT. Thus, the WT31−T3+cells lacked α and βT cell receptor proteins (immunoprecipitation and FACS analysis). The presence of γ mRNA in WT31−T3+cells, while consistent with TCR γ protein expression, could not be taken as strong evidence for this, since many human cell lines that express γTCR mRNA of normal size may express full length transcripts that are out of frame due to defective V-J joining (Dialynas et al., 1986, Proc. Natl. Acad. Sci. U.S.A. 83:2619-2623).

6.2.5. Association of the γ,δ Polypeptides with T3 in WT31−T3+Cell Lines

To determine if proteins analogous to the TCR molecules existed on the WT31−βF1−T3+cells, the technique of chemical cross-linking was utilized. This procedure has been used to show directly the physical association of the TCR α,β molecules with the T3 glycoprotein (Brenner et al., 1985, Cell 40:183-190). The bifunctional, cleavable reagent, dithio-bis-succinimidyl propionate (DSP) was employed to cross-link $^{125}$I-labeled surface proteins of viable T lymphocytes. After cross-linking, the lymphocytes were solubilized in a non-ionic detergent and immunoprecipitated with an anti-T3 monoclonal antibody. As expected, the WT31+βF1+T3+lymphocytes revealed that the TCR α and β chains were cross-linked to T3. For example, TCR α,β molecules and T3 were found in anti-T3 or βF1 monoclonal antibody immuniprecipates from cross-linked IDPI cell line 2 (WT31−T3+). However, despite the lack of reactivity with the βF1 monoclonal antibody and lack of TCR α or TCR β mRNA, IDP1 cell lines 3 (WT31−T3+) and IDP2 cell line 7 (88% WT31−T3+both expressed two protein subunits ($M_r$ 55,000 and 40,000) that specifically cross-linked to T3. The mobilities of these T3 associated molecules were clearly different from those of the TCR α and β chains from WT31+T3+cell lines.

Since IDP2 cell line 7 (88% WT31−T3+) contained 12% WT31+T3+cells, accounting for the weak βF1 immunoprecipitates noted, the lysate from these cells was precleared of TCR α,β protein using the βF1 monoclonal antibody. After preclearing, no residual βF1 reactive material could be detected. When this βF1 -precleared lysate from cross-linked cells was immunoprecipitated with an anti-T3 monoclonal antibody, $M_r$ 55,000 and 40,000 subunits were still detected.

Since these WT31−γ F1−T3+cell lines display undetectable levels of TCR α and TCR β mRNA, the molecules found specifically cross-linked to T3 on their cell surfaces cannot represent proteins encoded by the known TCR β or TCR α genes.

6.2.6. Antibodies to Synthetic γ TCR Peptides Recognize a Protein that Co-Precipitates with T3 cDNA clones representing the rearranging human TCR γ gene would encode a polypeptide with a predicted molecular weight of 40,000 daltons (Dialynas, 1986, Proc. Natl. Acad. Sci. U.S.A. 83:2619-2623).

However, unlike the murine TCR γ gene, which does not reveal any N-linked glycoslyation sites (Saito et al., 1984, Nature 309:757-762), the human TCR γ gene reveals five potential sites for N-linked glycosylation, four of which are located in the constant region (Dialynas, 1986, supra). Since a TCR γ protein has not previously been isolated, it is not known how many of these potential sites may be used. However, a fully glycosylated human TCR γ protein may have a $M_r$ of about 55,000. The heavy chain of the non-α-non-βT3-associated subunits identified on the WT31−βF1−T3+IDPI aND IDP2 cell lines has a relative mobility on SDS-PAGE of 55,000 daltons.

In order to determine if this T3-associated heavy chain was serologically cross-reactive with or identical to the TCR γ protein, antisera were raised to a synthetic peptide having the sequence:

RTKSVTRQTGSSAEITC (representing a 17 amino acid stretch of residues 5-21 from the variable region; anti-V γ peptide serum) and to a synthetic peptide having the sequence:

DKQLDADVSPKPTIFLPSIA (representing a 20 amino acid stretch of residues 117-136 from the constant region; anti-C γ peptide serum) of the TCR amino acid sequence deduced from a human cDNA clone (Dialynas, 1986, supra). Both the anti-C γ peptide serum and anti-V γ peptide serum immunoprecipitated a molecule with $M_r$ 55,000 from the denatured lysate of $^{125}$I-labeled WT31−βF1−T3+. Such molecules could not be immunoprecipitated from lysates of $^{125}$I-labeled HPB-MLT cells, which express only nonfunctional TCR γ mRNA (Dialynas, 1986, supra).

To demonstrate that the 55,000 dalton molecule immunoprecipitated by the anti-C γ and anti-V γ peptide sera was, in fact, the heavy chain subunit that crosslinked to T3, an additional experiment was performed. A sample of DSP crosslinked lysate from the WT31−βF1−T3+cells was first immunoprecipitated with an anti-T3 monoclonal antibody, again demonstrating the presence of $M_r$ 55,000 and 40,000 subunits associated with T3. In parallel, another aliquot of the cross-linked lysate was immunoprecipitated with an anti-T3 monoclonal antibody, and the immunoprecipitated T3 cross-linked polypeptides were eluted from the immunoabsorbent under denaturing and reducing conditions in order to break the DSP cross-link. This eluate was then reprecipitated with anti-C γ peptide serum. The $M_r$ 55,000 subunit that crosslinked to T3 was reprecipitated by anti-γ serum, indicating that the $M_r$ 55,000 subunits defined by these two approaches were identical.

Immunoprecipitations from lysates of surface-iodinated IDP2 lymphocytes using anti-T3 mAb (under conditions that do not dissociate TCR subunits from T3, see FIG. 1) yielded two species (55 kD and 40 kD) in addition to the T3 subunits (FIG. 1A). This result is identical to the one reported previously using chemical cross-linking. The 55 kD species was shown to react specifically with anti-C γ and anti-V γ peptide sera. The 40 kD polypeptide was unreactive with these anti-γ peptide sera and is thus likely to represent a non-TCR α,β or γ subunit. To determine if these subunits are covalently linked, like the TCR α and β subunits, the T3 co-immunoprecipitated polypeptides were examined under reducing and nonreducing conditions. In striking contrast to the TCR α,β subunits, which exist in a heterodimeric disulphide-linked form under nonreducing conditions, the TCR γ and δ subunits on the IDP2 cell line are not covalently linked (FIG. 1A). A small increase in relative mobility on SDS-polyacrylamide gel electrophoresis (PAGE) under nonreducing conditions was observed for the diffuse, heavily glycosylated (see below) TCR γ, whereas a dramatic increase in mobility was observed for the δ subunit, suggesting the presence of one or more intrachain disulphide loops (compare species at arrows, lanes 2 and 4).

Weiss et al. suggested that the PEER cell line might express the TCR γ polypeptide since it lacked expression of TCR mRNA yet expressed a T3-associated 55-60 kD polypeptide (1986, Proc. Natl. Acad. Sci. U.S.A. 83:6998-7002). On further examination, this cell line was found to lack reactivity with a mAb recognizing framework determinants on the TCR β chain, βF1 (FIG. 5A) and to express a strongly iodinated 38 kD polypeptide. The 55-60 kD polypeptide was specifically immunoprecipitated with anti-C γ peptide sera and thus appears to represent a further example of the TCR γ protein (FIG. 5A). The TCR γ and δ polypeptides on PEER were of similar size to those on the IDP2 cell line and similarly were not disulphide-linked. Like the δ subunit on IDP2 cells, the counterpart molecule on PEER underwent a marked shift in SDS-PAGE mobility when compared under reducing and nonreducing conditions (compare species at arrows, lane 7 and 8). Thus the IDP2 and the PEER cell lines appear to express similar types of TCR γ,δ -T3 complexes, in which the TCR γ and γ subunits are not covalently linked.

6.2.7. Cell Lines Created From WT31−T3+Cells in Normal WT31−T3+Peripheral Blood We wished to determine if this second δ TCAR was also expressed as a component of the T cell population in normal peripheral blood. Two-colour cytofluorographic analysis comparing staining of human peripheral blood lymphocytes (PBL) with mAb βF1 and OKT®3 showed a discrete population representing 2-5% of the T3+PBL that appeared to be TCR α,β negative. To examine this lymphocyte population, normal adult PBL were subjected to cytofluorographic cell sorting after staining with mAb WT31. Unstained PBL were isolated and propagated in vitro in IL-2-containing conditioned media receiving biweekly additions of irradiated autologous feeder cells and phytohaemagglutinin (PHA-P). The cell line derived, WT31−PBL line was cloned by limiting dilution with plating at 0.5 cell per well and the cloned cells were propagated as for the polyclonal cell line. Several such peripheral blood derived T cell clones were obtained, and PBL Clone 1 (PBL C1) was studied in detail. By cytofluorographic analysis, this clone was T3+T11−but T4−T8−and WT31−. The expression of TCR α,β and γ mRNA from PBL C1 was determined by Northern blot analysis. By comparison with the WT31+βF1+T cell tumor HPB-MLT, only very low levels of TCR α and β mRNA were detected. In contrast, abundant TCR γ mRNA was noted; interestingly, the TCR γ mRNA was slightly smaller than the 1.6 kilobase (kb) message found in HPB-MLT and in the TCR γ -expressing IDP2 cell line. Consistent with these observations, WT31 reactivity was not detected in cytofluorographic analysis and only scant levels of TCR α and β polypeptides were found by immunoprecipitation using mAb βF1 (FIG. 1B, lanes In contrast it is likely that the trace levels of TCR α and β protein detected in PBL C1 are accounted for by the 1–2% contamination with irradiated autologous feeder cells used in the propagation of this clone.

6.2.8. Different Species of γTCR Can be Identified by Gel Electrophoresis

Figure 1B:
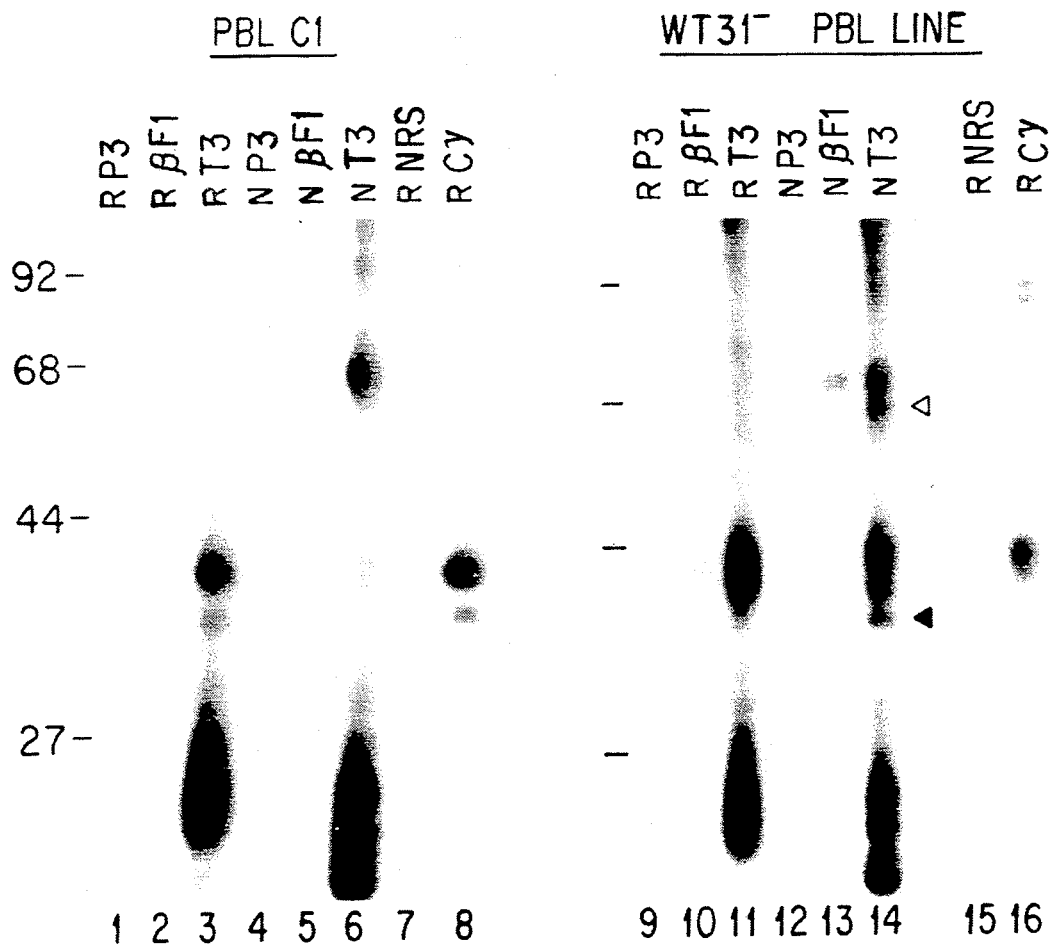

Two abundant chains (40 kD and 36 kD) were observed associated with T3 under reducing conditions in SDS-PAGE analysis (FIG. 1B, lane 3). Anti-Cγ sera immunoprecipitated both of these polypeptides from reduced and denatured PBL C1 lysates (FIG. 1B, lane 8). To determine if these 40 kD and 36 kD TCR γ polypeptides were part of a disulphide-linked dimer, co-immunoprecipitations with anti-T3 were examined under nonreducing conditions. A single band of $M_r$ (70 kD) was observed indicating that, unlike IDP2 and PEER cells, PBL CI expresses a T3-associated TCR γ gene product that is part of a disulphide-linked dimeric complex. As a TCR γ partner (δ) was present on the non-disulphide linked form of this receptor comples on IDP2 and PEER cells, we examined whether the disulphide-linked form of the receptor on PBL C1 was composed of a homo- or a heterodimer. Immunoprecipitates were analysed by two-dimensional gel electrophoresis (nonequilibrium pH gel electrophoresis (NEPHGE) followed by SDS-PAGE. Under reducing conditions, both the TCR γ species (40 kD and 36 kD) were found to have identical charges, and displayed heterogeneity typical for a sialylated glycoprotein. These characteristics are like those described previously for differentially glycosylated TCR polypeptides having the same amino-acid backbone. Thus, these species may represent differentially glycosylated forms of the same TCR γ peptide. This conclusion is supported by the results of metabolic pulse-labelling (below) which revealed only a single precursor TCR γ species in PBL C1.

A disulphide-linked dimer composed of one or both of these TCR γ species should have a focusing position similar to either of the two components alone when analysed by NEPHGE or equilibrium isoelectric focusing (IEF). But a heterodimer composed of TCR γ and a distinct polypeptide might have a different charge and focusing position. The position of the disulphide-linked dimer was therefore examined by carrying out NEPHGE under nonreducing conditions, followed by SDS-PAGE under nonreducing conditions. Strikingly, the position of the disulphide-linked dimer was substantially more acidic than that of the TCR polypeptides examined under reducing conditions. This result suggests that the TCR γ species were covalently linked to a polypeptide of distinct NEPHGE mobility. Thus, although a TCR γ partner could not be directly visualized (either because it was inadequately labelled with $^{125}I$ or because it did not resolve in the focusing system used here), the TCR γ polypeptide on PBL C1 appeared to be expressed as a part of a disulphide-linked heterodimer.

Experiments using equilibrium IEF (rather than NEPHGE) confirmed this observation.

6.2.9. γTCR Species have Different Peptide Backbond Sizes

A further distinction between the disulphide-linked and non-linked forms was the size of the mature TCR γ glycopeptide (55–60 kD on IDP2 and PEER versus 40 kD and 36 kD on PBL C1) To assess how much of this radical size difference is due to differential glycosylation and how much to different peptide backbones, TCR peptides were analysed in cells pulse-labelled with $^{35}S$-methionine. After solubilization under denaturing and reducing conditions, the lysates were immunoprecipitated with anti-Cγ sera and examined by two-dimensional gel electrophoresis. Immunoprecipitates were either treated with endoglycosidase H (endo-H) to remove immature high-mannose glycans from pulse-labelled material, or were mock treated. Two TCR γ polypeptides (46 kD and 43 kD) of identical NEPHGE mobility were synthesized by the IDP2 cell line. Treatment with endo-H reduced both forms to a 40 kD form, suggesting that the 46 kD and 43 kD forms carried different numbers of carbohydrates, and that a single TCR γ polypeptide backbone (40 kD) was synthesized by IDP2 cells. In contrast, a more basic, 38 kD glycosylated form was synthesized by PBC C1, which after endo-H digestion displayed a nonglycosylated 31 kD peptide backbone. Thus the TCR γ polypeptides on the non-disulphide-linked (IDP2) and the disulphide-linked (PBL C1) forms characterized here have radically different peptide backbone sizes (40 kD and 31 kD respectively). The fact that the glycosylated TCR γ peptides observed by pulse-labeling are of different molecular weight than those found by cell surface iodination presumably results from the different types of carbohydrates they carry, namely high-mannose versus complex.

6.2.10. Both Disulphide Linked AND Non-Covalently Associated γTCR are Present in Normal Peripheral Blood We next wished to determine if both a disulphide-linked and noncovalently associated form occurred in normal adult peripheral blood. The polyclonal peripheral blood cell line (WT31−PBL line) from which PBL C1 had been cloned was therefore studied in greater detail. WT31−PBL line was homogeneously T3+T11+and contained 95% WT31−T4−T8−with 5% contaminating WT31+T3+cells. When examined by immunoprecipitation from iodinated, solubilized cells, weak but detectable reactivity with mAb βF1 was observed (FIG. 1B, lanes 10 reduced and 13 nonreduced), consistent with the expected 5% TCR α,β positive lymphocytes. In contrast, anti-T3 mAb immunoprecipitated large amounts of both T3 and associated polypeptides of 35–45 kD under reducing conditions (FIG. 1B, lane 14). Less than half of the T3-associated polypeptides were disulphide-linked. This material included disulphide-linked TCR α,β peptides located above the open arrow, lane 14 (size identified by the βF1 precipitate, lane 13) and disulphide-linked TCR γ peptides of smaller size (open arrow, lane 14). Strikingly, the majority of the T3-associated species were not disulphide-linked and migrated with the same mobility under both reducing and nonreducing conditions. Notably, a fraction of these non-linked species displayed a marked increase in SDS-PAGE mobility under nonreducing conditions, similar to the TCR δ on the IDP2 and PEER cells (see FIG. 1B, lane 14, solid arrow). Reactivity with anti-Cγ sera confirmed that most of the labelled material associated with T3 expressed on WT31−PBL line was TCR γ gene products (lane 16).

Thus, the protein product of the TCR γ gene occurs on T3+lymphocytes in adult peripheral blood in both disulphide-linked and unlinked molecular γ forms.

Moreover, the non disulphide-linked form of TCR may be further divided into 55-60 kD glycosylated (IDP2 and PEER) or 35-45 kD glycosylated (thymic T cell clone C11 (Bank et al., 1986, Nature 322:179-181) and WT31−PBL Line) species.

6.2.11. Genomic Rearrangements of γTCR and βTCR Genes

TCR γ and β gene rearrangements were examined in T cells known to express the TCR γ polypeptide on their cell surfaces. Southern blot analysis was carried out using the 0.8 kb EcoRI-HindIII human $J_{\gamma 1,3}$ probe. This probe detects germline bands of 23 kb and 12 kb in a BamHI digest of genomic DNA. The 23 kb band encompasses $C_{\gamma 1}$ and the 12 kb encodes $C_{\gamma 2}$. Using this probe, IDP1, PBL C1 and PBL C2 (also derived from the WT31−PBL LINE) showed rearrangements of the TCR gene (both PBL C1 and PBL C2 displayed an identical rearrangement).

Seven rearrangements in PBL using the $J_{\gamma 1,3}$ probe and EcoRI-digested genomic DNA in Southern blot analyses have been detected (Quertermous et al., 1986, Science 23:252-255). Six (I, II, III, IV, VII and V) of these seven rearrangements are seen in PBL, fetal thymus, and newborn thymus genomic DNA. Four rearrangements (I, II, VI and VII) either are not used by peripheral blood lymphocytes which express the TCR γ polypeptide or cells demonstrating them were lost under the propagation conditions used for the WT31−PBL line. Nevertheless, the WT31−PBL line DNA revealed at least three of these rearrangements (III, IV and VI) and these same rearrangements were used by IDP2, PBL C1 and PBL C2, and all of these rearrangements are displayed in fetal thymus.

The TCR β gene was also rearranged in IDP2, PBL C1 and PBL C2 cells. The 1.1 kb EcoRI-HindIII $C_{\beta 2}$ probe detects a germline band of 20 kb which encompasses both Cβ constant regions in a BamHI digest of genomic DNA (Duby et al., 1986, Proc. Natl. Acad. Sci. U.S.A. 83:14890-4894). We observed one predominant TCRβ rearrangement for IDP2 and two identical rearrangements for PBL C1 and PBL C2. It is assumed that these TCR β rearrangements are nonproductive based on the immunoprecipitations and Northern analyses for these cell lines. As both PBL C1 and PBL C2 have the same TCR γ and δ rearrangements, they appear to be clonal and derived from the same cell within the WT31−PBL line.

6.2.12. γTCR Cells Have Spontaneous Effector Cytotoxic Capability

As TCR γ-expressing cells were found in adult peripheral blood, functional studies were carried out to determine whether they have effector capabilities. When IDP2 and PBL C1 were examined for their ability to lyse target cells in $^{51}$Cr release assays, they proved to have spontaneous effector cytotoxic capability. Although the IDP2 cell line did not lyse the majority of natural killer (NK) targets or PHA blasts of allogeneic PBL, they were selectively capable of lysing $^{51}$Cr-labelled MOLT-4 cells. In two of six similar assays, weak lysis (10-15% $^{51}$Cr release) of K562 targets was also observed. Lysis of MOLT-4 cells was not inhibited by a variety of mAb directed against monomorphic MHC Class I (W6/32 anti-HLA-A, B, C, 4E and 131) or Class II (LB3.1 and anti-Leu 10) determinants, although we previously found that these mAb efficiently block killing by both MHC Class I and Class II allospecific CTL (Brenner et al., 1985, J. Immunol. 135:384-390). These data suggest that lysis of MOLT-4 cells was MHC class I and II independent. Only anti-T3 mAb partially blocked the specific lysis of MOLT-4 cells. On the other hand, when triggered by prebinding of anti-T3 mAb to IDP2, as has been previously reported for thymic-derived CII[7], $^{51}$Cr-labelled target cells that express Fc receptors for IgG (for example, U937), were efficiently lysed. Such killing could be completely inhibited by aggregated human IgG, confirming that this T3-mediated lysis occurred through a mechanism of enhanced conjugate formation via IgG Fc receptors. The paradoxical augmentation of lysis by anti-T3 mAb for some targets (U937) and the blocking of lysis for specifically recognized targets (MOLT-4) might result from the competing effects of triggering and increasing conjugate formation via T3 but sterically blocking antigen recognition via the TCR.

PBL C1 proved a more efficient killer cell than IDP2. PBL C1 displayed sponteous cytolytic activity against K562 cells (MHC Class I and II negative) showing nearly 50% specific $^{51}$Cr release when examined at an effector target (E:T) ratio of 20:1. Moreover, PBL C1 also lysed MOLT-4 cells and to a lesser extent, CEM cells. No lysis of Daudi, U937, or either autologous or allogeneic PBL was detected. Triggering with anti-T3 mAb induced PBL C1 to lyse the U937 cell line. Further, lysis of K562 was slightly augmented while that of MOLT-4 was partially inhibited. Taken together, the spontaneous cytolytic activity of IDP2 and PBL C1 on tumour targets such as K562 and MOLT-4 and the failure to block such activity by a MHC mAb indicates that these TCR γ lymphocytes are non-MHC class I and class II restricted cytotoxic T lymphocytes.

6.3. Discussion

Framework monoclonal antibodies against the TCR α, β molecules, βF1 and WT31, were used to identify and isolate the WT31−βF1−T3+lymphocyte population from the peripheral blood lymphocytes of two immunodeficiency patients. By the criteria of both immunoprecipitation analysis with framework monoclonal antibodies and Northern blot analysis using TCR α and TCR β specific cDNA probes, polyclonal human T cell lines of this phenotype were shown to express neither TCR α, β mRNA transcripts nor polypeptides. Nevertheless, chemical cross-linking studies using the cleavable DSP reagent revealed the existence of a protein complex associated with the T3 glycoprotein on the surface of these cells. The heavier of the two subunits that cross-linked to T3 ($M_r$ 55,000) was also immunoprecipitated by two different antisera, one generated against a 17 amino acid synthetic peptide corresponding to a part of the variable region and another generated against a 20 amino acid synthetic peptide corresponding to a part of the constant region of the deduced amino acid sequence of a rearranged TCR γ gene (Murre et al., 1985, Nature 316:549-552; Dialynas et al., 1986, Proc Natl. Acad. Sci. U.S.A. 83:2619-2623). Thus, the $M_r$ 55,000 protein is the TCR γ protein encoded by the rearranging TCR γ gene (Saito et al., 1984, Nature, 309:757-762). The $M_r$ 40,000 polypeptide is a fourth T3-associated protein designated TCR δ. The TCR γ and TCR δ polypeptides form a T3-associated heterodimeric structure on these cells γ(R γδ-T3) that is analogous to the previously described T cell receptor complex (TCR α,β).

The TCR γ lymphocytes examined here exhibit non-MHC restricted cytolytic activity and may be similar to other T3+NK-like cells whose T-cell receptors have not yet been definitively characterized. (DelaHera et al., 1985, Proc. Natl. Acad. Sci. U.S.A. 82:6268-6271; Nowill et al. 1986, J. Exp. Med. 163:1601-01606; Lanier et al, 1986, J. Exp. Med. 164:339-344; Moingeon et al., 1986, Nature 323:638-640).

As NK-like lymphocytes, they may participate in host immune surveillance against malignancy. The specificity of lysis observed suggests TCR γ mediated antigen-specific recognition of some but not all tumour targets. As anti-T3 mAb could trigger nonspecific lysis of some target cells or alternatively block specific lysis of other targets, the T3 molecule on these cells appears to be functional.

7. Example: Production of Monoclonal Antibodies Specific for the γ TCR and δ TCR CHAINS

7.1 Materials and Methods

7.1.1. Culture Method

The PEER cell line described hereinabove was cultured in vitro in a medium composed of RPMI 1640, 10% calf serum, penicillin-streptomycin, and L-glutamine. The culture was fed twice a week and was kept at 37° C. in a humidified incubator with 5% $CO_2$.

7.1.2. Hybridoma Production for Monoclonal Antibodies Specific for the TCR γ Chain A BALB/c mouse was immunized intraperitoneally (I.P.) with $2 \times 10^7$ PEER cells suspended in 0.2 ml of phosphate buffered saline (PBS). The mouse was boosted by I.P. injection every 10 days with $2 \times 10^7$ PEER cells for a total of 20 injections. Three days before fusion, the mouse was boosted by intravenous (I.V.) injection with $2 \times 10^7$ PEER cells for 3 sequential daily I.V. injections. The mouse was sacrificed and the spleen was removed at the last I.V. injection. Immune spleen cells were fused with mouse myeloma cell P3×63Ag8.653 in the presence of polyethylene glycol 1500 at the ratio of 5:1 by standard procedures. After fusion, cells were suspended in the culture medium containing hypoxanthine $(1 \times 10^{-}M)$, aminopterin $(8 \times 10^{-}M)$, and thymidine $(1.6 \times 10^{-5} M)$ and plated at $2 \times 5$ cells per well in microliter plates which contained $2 \times 10^5$ cells per well in microliter plates which container $2 \times 10^5$ BALB/c thymocytes per well as feeder cells. The cultures were fed with the same medium on day 7. Beginning on day 14, cultures were fed with the same medium lacking aminopterin.

7.1.3. Hybridoma Screening for Monoclonal Antibodies Specific for the TCR γ Chain Since both the γ and δ chains of the T cell antigen receptor protein on PEER cells are complexed with CD3 antigen, antibodies against the PEER T cell antigen receptor should be able to co-modulate these surface proteins with an anti-CD3 monoclonal antibody such as OKT®3 (Meuer et al., 1983, J. Exp. Med. 157:705-719). Such co-modulation was employed as the primary screening for desirable hydridomas as follows. Each of the hybridoma culture supernatants was harvested and screened for its ability to co-modulate surface CD3 protein complexes with an anti-CD3 monoclonal antibody. One hundred microliters of a culture supernatant were added to each well of a 96-well microtiter plate containing $5 \times 10^5$ PEER cells per well. After overnight incubation at 37° C., fluorescein isothiocyanate-conjugated OKT®3 was added to each well and cultured for an additional 30 minutes at 0° C. Samples were then analyzed by flow cytometry. Supernatants which induced a significant decrease in fluorescence intensity were selected and further characterized by the immunoprecipitation methods described below. The cells in selected wells which secreted anti-human T cell antigen receptor proteins were subsequently cloned by the limiting dilution method.

7.1.4. Immunoprecipitation

PEER cells were radiolabeled with $^{125}I$ and solubilized in Tris buffered saline (TBS) containing 1% Nonidet P-40 as described hereinabove. Immunoprecipitation was performed by incubating $^{125}I$-labeled PEER cell lysates with each of the selected supernatants under reducing conditions. After immunoprecipitation, the samples were analyzed by 10% sodium dodecyl sulfate-polyacrylamide gel electrophoresis (SDS-PAGE). The gels were dried and autoradiographed, and the molecular weight of proteins was determined by comparison with molecular weight standards (Brenner et al., 1987, Nature 325:689-694).

7.1.5. Production A Monoclonal Antibody Specific For the TCR δ Chain

Monoclonal antibodies were made by immunizing BALB/c mice with immunoprecipitated TCR γ,δ-CD3 from the PEER cell line. Briefly, 1 gram of PEER cells was solublized in 0.3% CHAPS detergent and immunoprecipitated with 5 microliters of UCHTI ascites and fixed *Staphylococcus aureas* Cowan I strain bacteria as the immunoadsorbant similar to the procedure described in Brenner et al. (1987, J. Immunol. 138:1502-1509). The washed immune complexes were injected intraperitoneally at 4 week intervals for a total of 5 immunizations. The mice were then sacrificed and the spleen cells fused to P3×63Ag8.653 myeloma cells. The hybridomas were grown in HAT selection, screened and characterized by immunoprecipitation on $^{125}I$-labeled PEER cells and other cells as described in Brenner et al. (1987, Nature 325:689-694).

7.2. Results and Discussion

The antibody in hybridoma 34D12 supernate immunoprecipitated a 55 kD protein and a 20 kD protein under reducing conditions from the iodinated lysate of PEER cells. This 55 kD protein corresponds to the γ chain of the T cell antigen receptor and the 20 kD protein corresponds to T3 protein on PEER cells.

In a separate experiment a monoclonal against the T cell antigen receptor δ chain, i.e., 4A1, was produced and characterized. 4AI specifically reimmunoprecipitated a T cell antigen receptor δ chain (40 kD) from IDP2 cells (Brenner et al., 1987, Nature 325:689-694). 4AI has also been shown to immunoprecipitate the T cell antigen receptor γ,δ complex from several other T cell antigen receptor γ, δ positive cell lines, including IDP2 Molt-13 and PBL line 2.

8. Example: Cloning of the T Cell Antigen Receptor Delta Gene

8.1. Materials and Methods

8.1.1. Northern Blot Analysis

5 μg total RNA samples were electrophoresed through 1.5% agarose gels containing 2.2 M formaldehyde and transferred to nitrocellulose. Filters were probed with nick-translated 0-240 or chicken actin (Oncor), or with nick-translated 0-240, a 330 bp EcoRI-SacI fragment of 0-240/38 (V probe; see FIG. 2) labelled by hexanucleotide priming, or a 550 bp HaeIII fragment of 0-240 (3' UT; see FIG. 2) labeled by nick-translation. Filters were washed with 1×SSC, 0.5% SDS at 23° C. followed by 0.1×SSC at 50° C.

8.1.2. Southern Blot Analysis using Group O Clones

Genomic DNA samples were digested with restriction enzymes, electrophoresed through 0.7% agarose, transferred to nitrocellulose, and probed with nick-translated group 0 clones. Filters were washed with 1×SSC, 0.5% SDS at 23° C. followed by 0.1×SSC, 0.1% SDS at 68° C. or 0.2×SSC, 0.1% SDS at 55° C. PBMC and PBL L1 were derived from the same individual. A diminished signal in PBMC presumably resulted from deletion in most T cells in the sample. The remaining signal (largely B cells and monocytes) served as a germline control for PBL C1. On this basis, the observed 9.0 kb fragment is interpreted as a polymorphism rather than a rearrangement.

8.1.3. Sequence Analysis of Group 0 cDNA Clones

Nucleotide sequences of clones 0-240, 0-254, 0-240/38 and 0-240/47 were determined using the dideoxy chain termination method via the strategy outlined in FIG. 2.

8.2. Experimental Results

8.2.1. Selection of Putative δTCR cDNA Clones

A T cell-specific cDNA probe was generated by synthesizing high specific activity, $^{32}$P-labeled first strand cDNA from IDP2 poly-A+RNA, and subjecting this material to two cycles of hybridization with human B cell line JY poly-A+RNA followed by hydroxylapatite chromatography (Davis, M. M., et al., 1984, Proc. Natl. Acad. Sci. U.S.A. 81:2194). The twice-subtracted single-stranded material was used to probe 40,000 plaques of an IDP2 λgt10 cDNA library (Krangel, M. D., et al., 1987, Science 237:64), and 391 (1%) hybridizing plaques were obtained. Subsequent analysis organized these clones into 14 cross-hybridizing groups, composed of as many as 139, and as few as 2 members. Three groups were identified as TCR γ (10 members), TCR β (20 members), and CD3 δ/ε (γ members), based upon hybridization with appropriate probes. Representative members of the remaining 11 groups (A,B,C,D,E,G,I,K,M,O,R) were $^{32}$P-labelled and used to probe Northern blots. One group (O, consisting of 6 members) detected transcripts expressed in IDP2 and TCRγδ cell line PEER (Weiss, A., et al., 1986, Proc. Natl. Acad. Sci. U.S.A. 83:6998-7002; Brenner, M., et al., 1987, Nature 325:689-694; Littman, D. R., et al., 1987, Nature 326:85), but not expressed in JY and the TCR αβ cell line HPB-ALL. Based on this result, two group O clones (O-240 and -254) were selected for further study.

8.2.2. Northern Blot Analysis

Northern blot analysis of a larger panel of RNA samples using O-240 as a probe revealed the expression of cross-hybridizing transcripts in four TCR γδ cell lines (IDP2, PEER, Molt-13, and PBL L1 (Brenner, M., et al., 1987, Nature 325:689-694). Four distinct transcripts, of 2.2 kb, 1.7 kb, 1.3 kb, and 0.8 kb were detected. However, transcripts were undetectable in B cell line JY, myeloid cell line HL60, TCR αβ T cell line HPB-ALL and surface TCR−T cell line SKW3. Transcripts were barely detectable in RNA from fresh or phytohemagglutinin-activated peripheral blood mononuclear cells (PHA PBMC), of which only a small fraction express TCR γδ.

8.2.3. Evidence for Rearrangement of the Locus Defined by the Group O Clones Analysis of genomic DNA digested with a variety of enzymes revealed no evidence for rearrangement of O-240 hybridizing sequences in TCR γδ T cells. However, although a 9.5 kb XbaI fragment (and a 9.0 kb polymorphic fragment) was detected in B cells, myeloid cells and TCR γδ T cells, this fragment was deleted on both chromosomes in all other T cell examined. This represents somatic deletion rather than polymorphism, since pairs of B and T cells lines derived from the same individual were analyzed (SB and HSB; 8392 and 8402). These results suggest that deletion of sequences detected by O-240 may accompany rearrangement at either the TCR α or TCR β locus.

Initial sequence analysis of clones O-240 (1.5 kb) and O-254 (0.7 kb) revealed that they both extend from an endogenous EcoRI site at the 5' terminus through a poly-A tail and an EcoRI site in the linker at the 3' terminus. These clones were derived from a cDNA library constructed without methylation of EcoRI sites. In order to obtain information 5, to the natural EcoRI site, O-240 was used to probe an EcoRI methylated IDP2 λgt10 cDNA library. Two clones that spanned the EcoRI site, O-240/38 (1.3 kb) and O-240/47 (1.4 kb), were selected for detailed study. In contrast to the results obtained using probes derived from the 3, end of the group O end of O-240/38 detected discrete rearrangements in both EcoRI and PvuII digests of genomic DNA from five out of five TCR γδ cell lines. Of the three germ line fragments in each digest detected by this probe, rearrangements of the 3.3 kb EcoRI and 23.0 kb PvuII fragment appeared to be shared by the five TCR γδ cell lines, whereas rearrangements of the 6.6 kb EcoRI and 2.0 kb PvuII fragments distinguished the different cell lines. As opposed to these discrete rearrangements, a heterogeneous smear of rearrangements was detected in EcoRI digests of two samples of fetal thymus DNA.

8.2.4. Sequencing of Group O Clones

The comparative organization and sequencing strategies used to characterize clones O-240, O-254, O-240/38 and O-240/47 are presented in FIG. 2. Partial restriction maps and the locations of probes V, VJC and 3'UT (hatched bars) are presented. Poly-A tails are noted. FIG. 3 shows the composite nucleotide and deduced amino acid sequences of the group O cDNA clones. O-240/38 begins within codon γ of the composite sequences, whereas O-240 and O-254 begin with codon 150. Within the coding region, sequences agree at all positions except for codon 161 (GTG in O-254 and O-240/38, TTG in O-240). This discrepancy is presumed to result from a reverse transcriptase error in O-240. The composite sequence contains a long open reading frame of 293 amino acids clearly composed of V-, J- and C-like elements similar to those of TCR and immunoglobulin genes. Strikingly, the putative C region sequence is 79% identical at the nucleotide level, and 73% homologous at the amino acid level, to the sequence of a novel murine TCR constant region gene (Cx) recently reported by Chien et al. (1987, Nature 327:677) to reside within the TCR α locus. The high degree of sequence homology indicates that the group O clones reported here represent the human homologue of murine Cx. Thus, the deletion of this sequence in TCR αβ T cells suggests that the human constant region, like its murine counterpart, maps 5' to Cα within the human TCR α locus.

The 5' ends of O-240/38 and O-240/47 define a partial putative leader (L) sequence and a variable (V) region sequence. The precise processing point between these segments defining the amino terminus of the mature protein is unknown. However, processing of the TCR δ chain in HPB-MLT has been suggested to occur between A(-1) and Q(+1) since the amino terminus of TCR α is blocked (Sim, G. K., et al., 1984, Nature 312:771-775). By analogy, we have tentatively assigned the processing point to this location in our sequence, since in the region from −4 to +8 the two sequences are identical in 11/12 residues.

The putative V region displays 57% amino acid sequence identity with a human Vα sequence (PGA5; Sim, G. K., et al., 1984, Nature 312:771-775), 26% identity with a human Vβ sequence (YT35; Yanagi, Y., et al., 1984, Nature 308:145-149), and 21% identity with a human Vγ sequence (Vγ2, LeFranc, M-P., et al., 1986, Cell 45:237-246). Comparisons among Vα subgroup sequences and among Vβ subgroup sequences can be used to identify consensus residues that occur in 50% or more of Vα or Vβ subgroups. The deduced O-composite V region amino acid sequence was compared to Vα and Vβ subgroup consensus sequences. Consensus residues were assigned based upon their appearance in 50% or more of Vα or Vβ subgroups, using the data compiled in Toyonaga and Mak (1987, Ann. Rev. Immunol. 5:585).

The V region sequence reported here matches the Vα consensus in 75% of the residues (30/40). By contrast, it only matches the Vβ consensus in 49% of these residues (17/35). For comparison, the randomly selected Vα sequences 1.1, 6.1, and 12.1 match the Vα consensus in 70%, 73% and 73% of these positions, respectively, whereas the Vβ sequences 2.2, 5.4 and 8.1 match at 40%, 53% and 60%. Thus, this V region is clearly Vα-like, since it is as close to the consensus as other Vα sequences.

The deduced O-composite J region amino acid sequence was compared to Jα, Jβ and Jγ consensus residues. Consensus residues were assigned based upon their appearance in 40% or more of the Jα, Jβ and Jγ sequences compiled in references (Toyonaga and Mak, 1987, Ann. Rev. Immunol. 5:585; and Quertermous et al., 1987, J. Immunol. 138:2687-111 2690). Amino acids 112-125 displayed significant homology to human TCR consensus J region sequences and with the J region associated with murine Cx. However, amino acids 94-111 are homologous to neither V nor J sequences, and homology with the murine clone is minimal in this region as well. Whether and how much of this area is encoded by a separate D element or results from so called N-region diversity (Tonegawa, S., 1983, Nature 302:575) remains to be determined. Clearly, as the amino acid sequence remains in frame across the V(D)J junction, the IDP2 group O cDNA clones correspond to transcripts from a productively rearranged gene.

The putative constant region sequence includes an immunoglobulin-like region with two cysteine residues separated by 51 amino acids, a connector region carrying a cysteine residue which is typically believed to mediate interchain disulfide bonds between TCR components, and an intramembraneous region. Two potential sites of N-linked glycosylation are situated immediately amino-terminal to the first cysteine and carboxy-terminal to the second cysteine. Whereas Cβ and Cγ display putative intracellular tails which are highly charged, the IDP2 group O sequence contains a single basic residue followed by four hydrophobic amino acids.

The 3' untranslated (3'UT) sequences indicate the use of alternative polyadenylation sites. Whereas the O-240 3' UT extends some 950 bp to an ATTAAA polyadenylation signal, that of O-254 extends only 260 bp, with polyadenylation following the sequence TATAAA. Both sequences differ from the consensus AATAAA by a single nucleotide. Potential for additional heterogeneity exists, since the sequence TATAAA occurs twice more within the O-240 sequence (13 bp 3' to the signal used in O-254 and 130 bp 5' to the signal used in O-240). Variation in the site of polyadenylation is at least partially responsible for the transcript heterogeneity observed in Northern blots. Whereas the 2.2 and 1.3 kb transcripts are selectively detected by a V region probe, an O-240-specific 3' UT probe detects only the 2.2 and 1.7 kb transcripts. Thus in IDP2, PEER and PBL L1 the two most abundant species (2.2 and 1.3 kb) represent differentially polyadenylated trancripts. The minor 1.7 and 0.8 kb species therefore represent transcripts lacking V regions and are presumably transcribed from partially rearranged genes. By contrast, TCR β mRNA heterogeneity primarily results from the latter mechanism (Yoshikai, Y., et al., 1984, Nature 312:521).

8.3. Discussion

The group O cDNA clones appear to encode the IDP2 TCR δ peptide. They detect transcripts that are expressed specifically in TCR γδ T cells and are encoded by genes specifically rearranged in the same cells. Transcript levels correlate well with the level of expression of cell surface TCR δ polypeptide, which is lower in PEER than in IDP2, and lower still in MOLT-13.

Furthermore, the sequence of the group 0 clones is composed of V, J and C elements which are homologous to those of other TCR and immunoglobulin genes. The cDNA clones derived from IDP2 mRNA remain in frame across the V-J junction, indicating that they would encode a functional polypeptide in these cells. The predicted molecular weight of the polypeptide is 31.3 kD, with two potential N-linked glycosylation sites. As demonstrated below, these predictions agree well with the properties of the TCR δ peptide of IDP2 cells. Furthermore, it is demonstrated below by in vitro transcription and translation analysis that clone O-240/38 encodes a polypeptide immunologically cross-reactive with the IDP2 TCR δ protein.

Human TCR γ and δ peptides can exist in a disulfide-linked form or an unlinked form in different cell lines (Brenner et al., 1987, Nature 325; 689-694; Borst et al., 1987, Nature 325:683; Moingeon et al., 1987 Nature 325:723; Lanier et al., 1987, J. Exp. Med. 165:1076; Lefranc et al., 1986, Proc. Natl. Acad. Sci. U.S.A. 83:9596; Toyonaga and Mak, 1987, Ann. Rev. Immunol. 5:585). This structural heterogeneity is known to be controlled at least in part by TCR γ constant region usage, since the Cγ-1 gene encodes a cysteine in the membrane proximal connector region which is absent in Cγ-2 (Krangel, M. S., et al., 1987, Science 237:64; Littman, D. R., et al., 1987, Nature 326:85; Lefranc, M. P., et al., 1986, Proc. Natl. Acad. Sci. U.S.A. 83:9596). IDP2 uses the Cγ-2 gene, lacks this cysteine, and displays a nondisulfide linked receptor on the cell surface (Brenner, M., et al., 1987, Nature 325:689-694; Krangel, M. S., et al., 1987, Science 237:64). One might have predicted that the IDP2 TCR δ peptide would lack the analogous cysteine as well. However our cDNA sequences predict that IDP2 TCR δ carries a cysteine in the membrane proximal connector that would be available for disulfide linkage. Moreover, Southern blots provide evidence for only a single TCR δ constant region gene. Thus, it appears that a single TCR δ gene product could interact with TCR δ peptides encoded by Cγ-1 to form a disulfide-linked complex, or with TCR δ peptides encoded by Cγ-2 to form a nonlinked complex.

In contrast to TCR δ and TCR γ, only a limited number of functional TCR δ V regions exist (Lefranc, M.-P., e tla., 1986, Cell 45:237-246). Thus the TCR δ V gene pool size will be important in determining the number of antigens that may be recognized by TCR γδ lymphocytes. Recent nucleotide sequence analysis indicates that the IDP2, PBL C1 and Molt-13 TCR δ chains all use the same V region, an observation consistent with genomic rearrangment data. This result suggests a limited TCR δ V repertoire.

9. Example: Generation of Monoclonal Antibody Anti-TCRδ1 Specifically Reactive with the δTCR Subunit Constant Region, and Characterization of the δ Polypeptide

9.1. Materials and Methods

9.1.1. Cytofluorographic Analysis of T Cell Lines with Anti-TCR δ

The anti-TCRδ1 mAb, which is specifically reactive with the δTCR constant region, was made as follows: One gram of PEER cells were solubilized in 50 ml of 0.3% CHAPS (3-[3-cholamidopropyl)dimethylammonio]1-propanesulfonate) detergent and were immunoprecipitated with 1µl of UCHT1 (Beverley, P. C., and Callard, 1981, Eur. J. Immunol. 11:329-334) ascites, 500 µl of mAb 187.1 culture supernatant and Staphylococcus aureus Cowan I strain (SACI). Four intraperitoneal injections at six week intervals were carried out followed by a final boost of γδTCR (without CD3) isolated by selective elution of γδTCR from the immune complexes using 2% TX-100. The eluted material was administered both intravenously and intraperitoneally; four days after this boost, the mice were sacrificed and fusion carried out as previously described (Brenner, M. B., et al., 1987, J. Immunol. 138:1502-1509).

γδTCR T cell lines PEER and IDP2 or αβTCR cell lines HPB-MLT and JURKAT were stained with 50 µl of anti-TCRδ1 culture supernatant followed by staining with FITC-conjugated goat anti-mouse IG F(ab)'₂ fragments with analysis on an Ortho cytofluorograph. Control was the mAb secreted by P3×63.Ag8 hybridoma (P3) and anti-CD3 mAb was anti-Leu 4 (Ledbetter, J. A., et al., 1981, J. Exp. Med. 153:310).

9.1.2. Immunochemical Analysis of the Specificity of mAb Anti-TCRδ1

Surface ¹²⁵I-labeled IDP2 cells were solubilized and their proteins immunoprecipitated using control mAb P3, anti-Leu 4, anti-TCRδ1, or anti-Cγ serum. Precipitated samples were analyzed by SDS-PAGE followed by autoradiography. In CHAPS detergent, TCR γδ and CD3 remained associated and were immunoprecipitated as a complex by anti-Leu 4 (FIG. 4, lanes 3 and 4). However, after solubilization in 2% TX-100 detergent, anti-TCRδ1 immunoprecipitated TCR γδ (lane 5). After separation of the TCR γδ-CD3 component chains, anti-TCRδ1 immunoprecipitated TCR δ alone (lane γ and 8), while anti-Cγ serum immunoprecipitated TCR γ alone (lane 9). For chain separation experiments (lane 7-9), anti-Leu 4 immunoprecipitates from CHAPS solubilized IDP2 cells were boiled in 1% SDS and were then diluted with 4 volumes of 2% TX-100 followed by immunoprecipitation with anti-TCR δ1 or anti-Cγ serum. This follows procedures used previously (Brenner, M. B., et al., 1986, Nature 322:145).

9.1.3. N-Linked Glycosylation of the δTCR Polypeptide

¹²⁵I-labeled IDP2 cells were solubilized in 0.3% CHAPS, immunoprecipitated with anti-Leu 4 and resolved by SDS-PAGE. Control lane is mock-digested IDP2 δTCR polypeptide. N-glycanase digestion of δTCR polypeptide was performed as follows: δTCR was eluted from a gel slice followed by N-glycanase (Genzyme Corp.) digestion (10 U/ml) carried out in 30 µl 0.17% SDS, 1.25% Nonidet P-40, 0.2 M sodium phosphate buffer pH 8.6 for 16 hours at 37° C. (Tarentino, A. L., et al., 1985, Biochemistry 24:4665). The digested or mock-incubated TCR δ samples were analyzed by SDS-PAGE and visualized by autoradiography.

9.1.4. Recognition of In Vito Translation Products of cDNA Clone IDP2 O-240/38 by mAb Anti-TCRδ1

A plasmid designated pGEM3-O-240/38 was constructed as follows and used for in vitro transcription-translation. The IDP2 0-240/38 cDNA clone 1.5 kb insert begins within codon γ of the composite Group 0 sequence and includes the remaining coding region and most of the 3' untranslated region. This insert was cleaved as a single EcoRI fragment from λgt10 arms by partial EcoRI digestion (to prevent cleavage of the internal EcoRI site). This fragment was subcloned into a Bluescript+vector (Stratagene). The insert was then removed from the vector as a single BamHI-SalI fragment (ends are from the Bluescript vector polylinker) facilitating directional cloning into pGEM-3 (Promega Biotech) downstream of the Tγ promoter. The resultant pGEM3-O-240/38 plasmid was linearized with SalI and capped transcripts synthesized using Tγ RNA polymerase (Krangel, M. S., et al., 1987, Science 237:64). Integrity and size of the transcripts were monitored via an aliquot of the reaction mixture containing ³²P-ATP. A single RNA species of 1.5 kb was observed. In vitro translation in the presence of ³⁵S-methionine was performed in a rabbit reticulocyte lystate. After in vitro translation, the samples were boiled in 1% SDS with 2 mM dithiothreitol followed by the addition of 10 volumes of 2% TX-100 in Tris buffered saline pH 7.5. Samples were immunoprecipitated with control mAb P3 (FIG. 5, lanes 1 and 3) or with anti-TCRδ1 mAb (lanes 2 and 4) and analyzed by SDS-PAGE followed by fluorography (Bonner, W. J. and Laskey, R. A., 1974, Eur. J. Biochem. 46:83-88).

9.2. Results

We have generated a monoclonal antibody, anti-TCRδ1, that is specifically reactive with the δTCR constant region.

The γδTCR-CD3 complex from the PEER cell line (Weiss, A., et al., 1986, Proc. Natl. Acad. Sci. U.S.A. 83:6998–7002; Brenner, M. B., et al., 1987, Nature 325:689–694) was used as immunogen in the production of antibody-secreting hybridoma cell lines. Hybridomas were screened both by cell surface binding (cytofluorographic analysis) and by immunoprecipitation of PEER cell proteins followed by SDS-PAGE analysis. Two hybridoma supernatants (5A6 and 4A1) bound to the surface of PEER cells. After subcloning, one mAb (5A6.E9) was characterized further. This mAb bound to the surface of TCR γδ lymphocytes (PEER, IDP2) but failed to react with TCR αβ TCR cells (HPB-MLT, JURKAT) or with non-T leukocytes. Although the immunogen was composed of a complex of TCR γδ and CD3, the greater affinity of the mAb for TCR γδ cell lines suggested the mAb was not directed against CD3 determinants.

The specificity of the mAb was determined in immunoprecipitation studies using various detergents which affect the association of the proteins comprising the receptor complex. After $^{125}$I-labeled IDP2 cells are solubilized in CHAPS detergent, TCR γ and δ, and CD3 γ, δ and ε subunits remained part of an associated complex immunoprecipitated by anti-CD3 (FIG. 4, lanes 3, 4). However, if radiolabeled IDP2 cells were solubilized in 2% TX-100 detergent, TCR γδ and CD3 became largely dissociated, and the use of anti-CD3 mAb resulted in selective precipitation of CD3 (FIG. 4, lane 5). Under these latter conditions, mAb 5A6.E9 immunoprecipitated γδTCR as a heterodimer without associated CD3 (FIG. 4, lane 6). This observation provided the first direct evidence that TCR γ and TCR δ exist as a non-disulfide-linked heterodimer. To determine whether mAb 5A6.E9 reacts with TCR γ, TCR δ, combinatorial determinant, immunoprecipitation of separated polypeptide chains was performed. An anti-Leu 4 immunoprecipitate from radiolabeled, CHAPS-solubilized IDP2 cells was boiled in 1% SDS to dissociate the TCR γ, TCR δ, and CD3 proteins. After dilution with four volumes of 2% TX-100, mAb 5A6.E9 specifically immunoprecipitated the 40 kD (TCR δ) species (FIG. 4, lane 7). When an aliquot of the same immunoprecipitate was analyzed under reducing conditions (FIG. 4, lane 8) a dramatic shift in SDS-PAGE mobility was observed. This phenomenon is characteristic of TCR δ from the IDP2 and PEER cell lines (Brenner, M. B., et al., 1987, Nature 325:689–694). In contrast, when the separated chains were immunoprecipitated with anti-Cγ sera, the 55 kD species (γTCR), but not the 40 kD species (δTCR) was immunoprecipitated (FIG. 4, lane 9). Based on these biochemical and surface binding studies, mAb 5A6.E9 is referred to as anti-TCRδ1.

In addition to PEER and IDP2, anti-TCRδ1 also immunoprecipitated TCR δ from other TCR γδ cell lines including MOLT-13 and PBL Line 2. Further experiments have shown that anti-TCRδ1 reacts with a determinant encoded by a TCR δ constant (C) gene segment.

We have isolated cDNA clones from the IDP2 cell line (e.g., IDP2 0-240/38) by the subtractive approach representing a candidate gene which may encode the TCR δ subunit. Genes to which IDP2 group 0 cDNA clones hybridize in Southern blotting experiments are expressed and rearranged in TCR γδTCR lymphocytes but are typically not expressed (and are often deleted) in αβTCR cells. By sequence comparison with other TCR genes, these cDNA clones appear to be composed of novel V, D (?), J, and C gene segments. The IDP2 Group 0 composite DNA sequence contains a long open reading frame predicting a polypeptide with two potential asparagine-linked glycosylation sites and a molecular weight of 31.3 kilodaltons. To determine the molecular weight of the unglycosylated TCR δ protein and the number of asparagine-linked carbohydrates that are present on the mature IDP2 TCR δ polypeptide, gel purified TCR δ was either treated with N-glycanase or mock-incubated and analyzed by SDS-PAGE. Removal of N-linked carbohydrates resulted in a 5 kD decrease in apparent molecular weight (40 kD to 35 kD), suggesting the presence of two (2.5-3 kD) N-linked glycans on the IDP2 δTCR. This correlates well with the number of N-linked glycans predicted by the translated amino acid sequence in FIG. 3. The apparent molecular weight of the protein is in general agreement, differing from that predicted by 3.7 kD.

Given the reactivity of anti-TCRδ1 on IDP2 cells, the specificity for the TCR δ polypeptide, and the recognition of partially denatured (SDS boiled) TCR δ, we tested whether this mAb would recognize directly polypeptide encoded by the candidate TCR δ cDNA clone. Thus, the insert from cDNA clone IDP2 0-240/38 was subcloned into the pGEM-3 expression vector downstream of the Tγ promoter. Transcripts generated in vitro with Tγ RNA polymerase were then used in a rabbit reticulocyte lysate system to direct the synthesis of protein in the presence of $^{35}$S-methionine. Following in vitro transcription-translation, the reactions were boiled in 1% SDS, diluted with ten volumes of 2% TX-100, and then immunoprecipitated with either an isotype-matched control mAb or with anti-TCRδ1. Anti-TCRδ1 mAb specifically immunoprecipitated a predominant species (34 kD) (FIG. 5, lane 4). No such band was observed in immunoprecipitates when control mAbs were used (lane 3), when RNA transcripts were omitted (lanes 1 and 2), or when TCR γ constructs were used. Thus, the radiolabeled species immunoprecipitated by mAb anti-TCRδ1 corresponds to a polypeptide whose synthesis was specifically directed by the IDP2 0-240/38 cDNA clone. This polypeptide (34 kD) is very similar in size to the N-glycanase treated IDP2 TCR δ chain (35 kD). The IDP2 0-240/38 clone lacks a natural ATG initiation codon as well as the leader sequence. There are two potential internal ATG codons (at residues 12 and 44) within the V region of this clone (FIG. 5). Use of these codons to initiate synthesis could result in more than one polypeptide species possibly accounting for the minor species noted (FIG. 5, lane 4).

9.3. Discussion

Taken together, the correlation between predicted and determined extent of glycosylation and peptide size, the selective expression and rearrangement in TCR γδ cells, and the direct serological recognition of the polypeptide encoded by IDP2 0-240/38, argue compellingly that this candidate cDNA represents the gene encoding the IDP2 TCR δ subunit.

10. EXAMPLE: GENERATION OF MONOCLONAL ANTIBODY δTCAR-3 SPECIFICALLY REACTIVE WITH THE TCR DELTA SUBUNIT VARIABLE REGION

10.1. Materials and Methods

10.1.1. Immunoprecipitation and SDS-Page Analysis of T Cell Antigen Receptor The δTCAR-3 mAb, specifically reactive with the variable region of the δTCR chain, was generated as follows: One mouse was immunized with $2 \times 10^7$ Molt-13 cells by intraperitoneal injection. One month later the mouse was boosted with $1 \times 10^7$ Molt-13 cells by intravenous injection each day for 3 sequential days, and then immune splenocytes were fused with mouse myeloma P3x63Ag8.653 cells in the presence of 50% polyethylene glycol 1500. The hybridomas were screened by analyzing the CD3 co-modulation with flow cytometry. The analysis of CD3 co-modulation was based on the observation that antibody to T cell antigen receptor, when incubated with the cells, caused the internalization of the CD3 complex (Lanier, L. L., et al., 1986, J. Immunol. 137:2286; Meuer, S. C., et al., 1983, J. Exp. Med. 157:705).

Molt-13, PEER, and HPB-ALL cell lines were iodinated using the lactoperoxidase technique. The $^{125}$I-labeled cells were solubilized in Tris-buffered saline (pH 8) containing 1% Triton X-100. Lysates were immunoprecipitated using δTCAR-3 antibody or βF1 antibody. βF1 is a framework monoclonal antibody to the β chain and is described elsewhere (Brenner, M. B., et al., 1987, J. Immunol. 138:1502–1509).

All samples were analyzed by SDS-PAGE under reducing or non-reducing conditions (FIG. 25). Molt-13 and PEER are both CD4$^-$8$^{31}$ WT31$^-$. HPB is CD4+8+WT31+.

δTCAR-3 immunoprecipitated non-disulfide-linked γ and δ chains from Molt-13 and PEER, while βF1 immunoprecipitated disulfide-linked α and β chains from HPB-ALL.

10.1.2. Immunoprecipitation of δ Chain by δTCAR-3 Antibody

FIG. 6 shows $^{125}$I-labeled Molt-13 cells solubilized in Tris-buffered saline (pH 8) containing 0.3% CHAPS or in 1% Triton X-100. In 1% Triton X-100, the γδTCR dissociates from the CD3 complex, while in 0.3% CHAPS, the γδTCR remains associated with the CD3 complex. Prior to immunoprecipitation, the $^{125}$I-labeled lysates used in lanes 3, 4, and γ of FIG. 6 were denatured by adding SDS to a final concentration of 1% followed by heating for 5 minutes at 68° C. After cooling, iodoacetamide was added to a final concentration of 20 mM. The mixture was then diluted with 4 volumes of 1.5% Triton X-100 in Tris-buffered saline (pH 8). This denaturing process completely dissociates γ chain, δ chain, and CD3 proteins from one another. All samples were analyzed by SDS-PAGE under non-reducing conditions (N) except for the sample in lane 4 which is under reducing conditions (R). Note the difference in mobility of δ chain under reducing and non-reducing conditions. The anti-Cγ antiserum was generated by immunizing a rabbit with a 20 amino acid synthetic peptide from the γ constant region (residues 117–136).

10.1.3. Analysis of Cell Surface Staining by Flow Cytometry $5 \times 10^5$ cells were incubated with the appropriate antibodies (NMS (normal mouse serum), δTCAR-3, OKT3, or WT31) at 4° C. for 30 minutes and then washed two times with 0.2% BSA in PBS (pH 7.4). Following incubation with fluorescein-conjugated goat anti-mouse IgG for 30 minutes at 4° C. After washing, the cells were incubated with fluorescein (FITC)-conjugated OKT3 for 30 minutes at 4° C. and then cells were analyzed on an Ortho cytofluorograph.

10.1.4. Color Cytofluorographic Analysis of a δTCAR-3+ and OKT®3+ Peripheral Blood Lymphocytes The peripheral blood lymphocytes were first incubated with δTCAR-3 at 4° C. for 30 minutes. After washing, cells were incubated with phycoerythrin (PE)-conjugated goat anti-mouse IgG for an additional 30 minutes at 4° C. After washing, the cells were incubated with fluorescein (FITC)-conjugated OKT3 for 30 minutes at 4° C. and then cells were analyzed on an Ortho cytofluorograph.

10.1.5. Measurement of Intracytoplasmic $Ca^{2+}$ Concentration ($[Ca^{2+}]_i$) Versus Time Molt-13 cells were labeled with the acetoxymethyl ester form of the $Ca^{2+}$-sensitive probe fura-2 (2 μM from a 1 mM stock in DMSO, Molecular Probes, Eugene, Oregon) at a concentration of $10^7$ cells/ml in RPMI 1640 plus 10% fetal bovine serum for 30 minutes at 37° C. Cells were then washed and resuspended at $10^7$ cells/ml in Hanks balanced salt solution (HBSS) plus 5% fetal bovine serum and kept in the dark at room temperature until use. Immediately prior to fluorescent measurement, $2 \times 10^6$ cells were centrifuged and then resuspended in 2 ml of fresh HBSS and placed in a quartz cuvette at 37° C. and constantly stirred. Fluorescence was measured on the cell suspension in a SPF-600C fluorometer (SLM Aminco, Urbana, Illinois), the excitation wavelength alternating between 340 (+2) and 380 (+2) nm and emission was detected at 510 (+5) nm. The ratio of 350/380 was automatically calculated (1 ratio every 2 seconds), plotted, and stored in an IBM PC AT. Quantitiation of $[Ca^{2+}]_i$ from the fluorescence ratio was performed as described by Grynkiewicz, et al. (105). Addition of irrelevant antibodies did not alter $[Ca^{2+}]_i$ while cell lysis resulted in a $[Ca^{2+}]_i$ of 1 μM.

10.2. Results and Discussion

We have generated a monoclonal antibody, δTCAR-3, that is directed against a variable region of the TCR δ chain and which can be used to characterize the δ polypeptide. This monoclonal antibody binds to T cells bearing the γδTCR and also elicits a fura-2 $Ca^{2+}$ signal upon binding to Molt-13 cells.

The δTCAR-3 monoclonal antibody was generated by immunizing a mouse with the Molt-13 cell line which has a CD3+4-8-WT31-phenotype. The hybridomas were first screened by CD3 co-modulation as described in Materials and Methods. The positive clones were further screened by immunoprecipitation. δTCAR-3 did not immunoprecipitate any polypeptide from HPB-ALL. In contrast, βF1, a framework monoclonal antibody specific to the β chain (Brenner, M. B., et al., 1987, J. Immunol. 138:1502–1509), immunoprecipitated in (Brenner, M. B., the αβTCR heterodimer from the HPB-ALL cell line. The immunoprecipitated γδTCR receptor from both Molt-13 and PEER cells, when analyzed under either reducing or non-reducing conditions, displays a heterodimeric structure indicating a non-disulfide linked γδTCR receptor in these two cell lines. There is a slight shift in mobility of the δ chain under reducing conditions relative to that observed under non-reducing conditions, a phenomenon which has been noted previously in IDP2 and PEER cell lines (Brenner, M. B., et al., 1987, Nature 325:689–694), suggesting the existence of intrachain disulfide linkages. In order to demonstrate that the δTCAR-3 antibody recognizes a CD3-associated γδTCR, immunoprecipitations were performed using $^{125}$I-labeled Molt-13 cell lysates solubilized in 0.3% CHAPS detergent (FIG. 6, lane 1). Under these conditions, the CD3 complex remains associated with the receptor, and both γδ heterodimer and the CD3 complex are immunoprecipitated by δTCAR-3. However, when $^{125}$I-labeled lysates were solubilized in 1% Triton X-100 detergent which largely dissociates the CD3 complex from the γδ receptor, only γδTCR heterodimer is immunoprecipitated by δTCAR-3 (FIG. 6, lane 2). As a control, the anti-CD3 antibody, UCHT-1 (Beverley, P. C. and Callard, R. E., 1981, Eur. J. Immunol. 11:329–334) immunoprecipitates only the CD3 complex, but not the γδ heterodimer (FIG. 6, lane 5).

The specificity of δTCAR-3 was further analyzed by using immunoprecipitations of denatured, $^{125}$I-labeled Molt-13 lysates in which γ, δ and CD3 proteins were completely dissociated. δTCAR-3 specifically immunoprecipitated the δ chain which has an apparent molecular weight of 38 kD under non-reducing conditions (FIG. 6, lane 3) and 40 kD under reducing conditions (FIG. 6, lane 7). These data indicate that δ TCAR-3 is δ chain specific.

γTCAR-3 not only immunoprecipitates γ,δTCR heterodimer from the PEER and Molt-13 cell lines, it also binds to the surface of these cell lines and to the IDP2 clone (Brenner et al., 1987, Nature 325:689–694). It does not bind to the αβTCR-bearing HPB-ALL and Jurkat cell lines. In contrast, WT31 (Tax, W. J. M., et al., 1983, Nature 304:445–447), a framework monoclonal antibody to the αβreceptor, reacts with αβTCR TCR positive HPB-ALL and Jurkat cell lines, but not with γδTCR positive Molt-13, PEER, and IDP2 cells. When normal peripheral blood lymphocytes (PBL) were examined, a subpopulation (0.9–2.4%) of CD3+lymphocytes were positive with δTCAR-3. When δTCAR-3, immobilized on tissue culture plates was used for culture of normal human PBL, it selectively stimulated the proliferation of the γδTCR positive subpopulation. After 45 days in culture, the γδTCR subpopulation represented 96% of the total cell count.

Antibodies to the αβTCR T cell antigen receptor stimulate a rise in the cytoplasmic free calcium ion concentration $[Ca^{2+}]_i$ (Weiss, A., et al., 1986, Ann. Rev. Immunol. 4:593). Incubation of Molt-13 cells with δTCAR-3 elicited a rapid increase in $[Ca^{2+}]_i$ similar to the response induced by T3 antibodies. Moreover, δTCAR-3 similarly stimulated a $Ca^{2+}$ flux in PEER cells and in the γδTCR positive cell line generated from PBL as described above. We have also observed that incubation of Molt-13, PEER, and IDP2 cells with δTCAR-3 causes the co-modulation of the CD3 protein complex.

11. EXAMPLE: THREE FORMS OF THE HUMAN T CELL RECEPTOR γδ: PREFERENTIAL USE OF ONE FORM IN SELECTED HEALTHY INDIVIDUALS

In the examples herein, the structure of a new form of the human γδTCR, consisting of a 40 kD TCR γ glycoprotein (termed Form 2bc) noncovalently associated with a TCR δ chain, is presented. The three human forms of the γTCR protein are compared, namely the disulfide-linked 40 kD δTCR Form 1, the non-disulfide-linked 55 kD γTCR Form 2abc, and the non-disulfide linked 40 kD γTCR Form 2bc. All three forms are found in association with δTCR.

11.1. Materials and Methods

11.1.1. Antibodies

Monoclonal antibodies used were anti-Leu4 (anti-CD3) (Ledbetter et al., 1981, J. Exp. Med. 153:310–323), βF1 (anti-βTCR) (Brenner et al., 1987, J. Immuno). 138:1502–1509), anti-TCRδ1 (anti-δTCR) P3 (control) (secreted by P3×63.Ag8; Kohler and Milstein, 1975, Nature 256:495–497), 187.1 (rat anti-mouse κ light chain) (Yelton et al., 1981, Hybridoma 1:5–11), and WT31 (stains αβTCR lymphocytes brightly) (Spits et al., 1985, J. Immunol. 135:1922–1928). Anti-Cγb peptide serum (anti-TCR γ) was generated against a 22 amino acid synthetic peptide (Gln-Leu-Asp-Ala-Asp-Val-Ser-Pro-Lys-Pro-Thr-Ile-Phe-Leu-Pro-Ser-Ile-Ala-Glu-Thr-Lys -Cys) (described more fully in copending application Serial No. 882,100 filed Jul. 3, 1986, which is incorporated by reference in its entirety).

11.1.2. Cell Lines

PEER (Weiss et al., 1986, Proc. Natl. Acad. Sci. U.S.A. 83:6998–7002) and MOLT-13 (isolated by J. Minowada, Loh et al., 1987, Nature 330:569–572) are T leukemic cell lines. Umbilical cord blood derived clone WM-14 (Alarcon et al., 1987, Proc. Natl. Acad. Sci. U.S.A. 84:3861–3865) and peripheral blood derived cell line IDP2 (described more fully in copending U.S. application Ser. No. 882,100 filed Jul. 3, 1986, which is incorporated by reference in its entirety) and thymus-derived Clone II (Bank et al., 1986, Nature 322:179–181) were cultured as described earlier. Peripheral blood derived cell line 2 (PBL-L2) was isolated by sorting peripheral blood isolated lymphocytes that did not stain with mAb WT31. The isolated cells were then expanded in vitro in RPMI 1640 medium supplemented with 10% (v/v) conditioned medium containing IL-2 and 10% (v/v) human serum, and stimulated every 3 weeks with irradiated autologous feeder cells.

11.1.3. Iodination and Immunoprecipitation $2 \times 10^7$ cells were isolated by Ficoll-diatrizoate (Organon Teknika Corp.) centrifugation and iodinated on ice in 0.5 ml of phosphate-buffered saline, pH 7.4 (PBS) containing 1 mM $MgCl_2$, 5 mM glucose by adding 100 μg of lactoperoxidase (80–100 U/mg, Sigma) and 1 mCi of $Na^{125}I$ (New England Nuclear). Ten μl of a 0.03% hydrogen peroxide solution was added at 5 minute intervals over a reaction period of 30 minutes. Cells were solubilized overnight in detergent supplemented TBS (50 mM Tris-Base pH 7.6, 140 mM NaCl) containing 1 mM phenylmethylsulfonyl fluoride (PMSF, Sigma) and 8 mM iodoacetamide (IAA, Sigma). As indicated, different detergents used in this study were 0.3% (w/v)

3-[(3-cholamidopropyl) dimethylammonio]1-propanesulfonate (CHAPS, Sigma), 1% (w/v) digitonin (Aldrich) and Triton X-100 (TX-100, Sigma). After 20 minutes of centrifugation at 10,000 g to remove insoluble material, detergent lysates were precleared by a 30 minute incubation with 4 μl of normal rabbit serum (NRS) and 400 μl of 187.1 hybridoma culture medium, followed by addition of 200 μl of a 10% (w/v) cell suspension of fixed Staphylococcus aureus Cowan I (Pansorbin, Calbiochem). After a one-hour incubation, Pansorbin was removed by centrifugation. Specific precipitations were carried out by adding 0.25 μl βF1 ascites, 1 μl mg/ml anti-Leu4 or 0.25 μl P3 ascites, together with 150 μl of 187.1 culture supernatant to each sample, followed by a one-hour incubation. 100 μl of 10% (v/v) Protein A-Sepharose (Pharmacia) was added and the mixture was rocked for 1 hour at 4° C. Immunoprecipitates were washed five times with 0.1% (v/v) Triton X-100 containing TBS and analyzed by SDS-PAGE (Laemmli, 1970, Nature 227:680–685).

For immunoprecipitations with the anti-Cγb peptide serum, iodinated cells were solubilized in 1% (w/v) sodium dodecyl sulfate (SDS) containing TBS and then boiled for 3 minutes. After cooling, 5 volumes of 2% (v/v) Triton X-100 in TBS containing PMSF and IAA was added, together with 200 μl of a mixture of 1 mg/ml DNAse and 0.5 mg/ml RNAse in 50 mM MgCl$_2$. Preclearing and immunoprecipitations were performed as described above, omitting the addition of 187.1 mAb. Immunoprecipitates were washed in TBS containing 0.5% (v/v) Triton X-100, 0.5% (w/v) deoxycholate (DOC), 0.05% (w/v) SDS.

11.1.4. Biosynthetic Labelling $4 \times 10^7$ exponentially growing cells were resuspended in 4 ml of methionine and cysteine-free RPMI 1640 (Select-Amine kit, Gibco) supplemented with 10% dialyzed FCS and 20 mM Hepes. After a 30 minute starvation period at 37° C., 1 mCi of $^{35}$S-methionine and 1 mCi of $^{35}$S-cysteine were added, allowing a 15 minute labelling period. Cells were harvested and solubilized in 2% (v/v) Triton X-100, TBS. Preclearing and imaunoprecipitations were performed as described above. The immunoprecipitates were washed four times in 0.5% (v/v) Triton X-100, 0.5% (w/v) deoxycholic acid, 0.05% (w/v) SDS, TBS followed by three washes in 0.5% (v/v) Triton X-100, 0.5 M NaCl, 5 mM EDTA, 50 mM Tris, pH 7.6. The samples were analyzed by SDS-PAGE and visualized by standard fluorography procedures (Bonner and Laskey, 1974, Eur. J. Biochem. 46:83–88).

11.1.5. Gel Purification of δTCR Proteins

Surface iodinated cells were solubilized in 0.3% (w/v) CHAPS-TBS and immunoprecipitated using 50 μl of anti-Leu4-coupled Sepharose beads. The immunoprecipitated species were resolved by SDS-PAGE under nonreducing conditions and the wet gel was exposed for 24 hours at 4° C. on XAR-5 film (Kodak) to visualize radiolabelled δTCR proteins. The gel regions corresponding to δTCR were excised, incubated in 5% (v/v) 2-mercaptoethanol containing sample buffer and resolved a second time by SDS-PAGE. Because of the characteristic SDS-PAGE mobility shift upon reduction, δTCR protein could be separated and then purified from contaminants. TCR proteins were eluted from gel slices by overnight incubation in 0.05% (w/v) SDS, 50 mM ammonium bicarbonate buffer at 37° C. and lyophilized.

11.1.6. Endoglycosidase Digestion

For endoglycosidase H (Endo H) digestions, immunoprecipitated material or gel purified protein was boiled for 3 minutes in a 40 μl 1% (w/v) SDS solution containing 0.14 M 2-mercaptoethanol. After cooling, the mixture was diluted with 360 μl of 0.15 M acetate buffer, pH 5.5 containing 1 mM PMSF. Five μl Endo H (1U/ml- Endo-β-N-acetylglucosaminidase H, Genzyme) was incubated with half of the above solution for 14 hours at 37° C., while the other half was mock treated.

For N-glycanase (N-GLY) digestion, gel purified material was boiled for 3 minutes in 35 μl of 0.5% (w/v) SDS, 0.10 M 2-mercaptoethanol. Then, 100 μl of 0.2 M sodium phosphate (pH 8.6), 1.25% (v/v) Triton X-100 was added. Half of the mixture was incubated with 1 μl N-Glycanase (250 U/ml, peptide-N-[N-acetyl-β-glucosaminyl]asparagine amidase; Genzyme) and incubated for 16 hours at 37° C., while the other half was mock treated.

After digestion, 10 μg bovine serum albumin was added as carrier and samples were recovered by trichloroacetic acid precipitation. Protein pellets were taken up in sample buffer containing 5% (v/v) 2-mercaptoethanol.

11.1.7. Production of Monoclonal Antibody Anti-Cγml

Part of the Cγ CI and CII exons of HPB-MLT pTγ-1 was isolated using the BamHI and PstI sites at nucleotide positions 571 and 848 (Dialynas et al., 1986, Proc. Natl. Acad. Sci. USA 83:2619–2623) and was cloned into expression vector pRIT2T (Pharmacia). The resulting Protein A fusion protein was expressed in *E. coli* N4830. Bacteria were lysed with lysozyme and the fusion protein was isolated by purification over a IgG Sepharose column. Mice were injected intraperitoneally with 100 μg of fusion protein in Freund's adjuvant at days 0, 7 and 28. Twenty-eight days later 100 μg of fusion protein in PBS was injected intravenously. After three days splenocytes were isolated and fused with the hybridoma P3X63Ag8.653 as described (Brenner et al., 1987, J. Immunol. 138:1502–1509). Hybridomas were screened by enzyme-linked immunoabsorbent assay (ELISA).

Although anti-Cγml (IgG$_1$) does not recognize the native γδTCR/CD3 complex in cytofluorographic analysis nor the γδTCR heterodimer from TX-100 solubilized cells in immunoprecipitation, it does recognize biosynthetically labelled γTCR precursor and mature γTCR proteins after separation of CD3/γδTCR proteins into individual chains. In this way, anti-Cδml was shown to recognize the γTCR protein after separating CD3/γδTCR complexes into individual chains by boiling anti-CD3 immunoprecipitates in 1% (w/v) SDS in TBS (FIG. 8, lane 3).

11.1.8. Isolation and Sequencing of a Molt-13 γTCR cDNA Clone

Poly (A)+RNA was prepared from MOLT-13 cells by urea/lithium chloride precipitation followed by oligo (dT) cellulose affinity chromatography. A λgt 10 cDNA library was prepared from poly(A)+RNA by the method of Huynh et al., 1985 (DNA Cloning, Glover, D. M. ed. IRL Press, Oxford, I:49–78) using Mung Bean Nuclease for the hairpin loop cleavage (McCutcham et al., 1984, Science 225:626–628). The cDNA library was amplified on the *E. coli* strain C600 Hfl and screened by plaque filter hybridization with $^{32}$P-labelled PTγI(Dialynas et al., 1986, Proc. Natl. Acad. Sci. U.S.A. 83:2619–2623). Positive clones Were analyzed for size and restriction enzyme map, and cDNA clone M13k was selected for sequencing. The cDNA of M13k was excised from λgt 10 phage with the endonuclease EcoRI and further digested with appropriate restriction enzymes. The fragments were subcloned into M13 vectors and sequenced by the dideoxy chain termination method (Sanger et al., 1977, Proc. Natl. Acad. Sci. U.S.A. 74:5463–5467) using the modified T7 polymerase (Sequenase, United States Biochemical Corp.)

Clone M13k corresponds to a full length, in frame, γTCR transcript, including 36 nucleotides of 5' untranslated region and 72 nucleotides of 3' noncoding region (FIG. 10). The nucleotide sequence of the V region is identical to the genomic Vγ1.3 sequence (nomenclature Lefranc et al., 1986a, Cell 45:237–246; Strauss et al., 1987, Science 237:1217–1219), except for a C to T (Ile to Val) change of nucleotide 53 in the putative signal sequence. The J region is identical to the Jγ2.3 sequence (nomenclature based on Lefranc et al, 1986b, Nature 319:420–422; Quertermous et al, 1987, J. Immunol. 138:2687–2690). Interestingly, 8 nucleotides occur at the V-J junction which do not appear to be encoded by the genomic V or J sequences and presumably represents an N-region. The C region sequences match the corresponding genomic sequence (Lefranc et al., 1986c, Proc. Natl. Acad. Sci. U.S.A. 83:9596–9600), with the exception of nucleotide 559 (G to C; Val to Ile) and nucleotide 908 (T to C; Met to Thr).

11.2. Results

11.2.1. Novel γδTCR Protein Complex

Preliminary studies of peripheral blood γδTCR lymphocytes revealed the presence of a CD3-associated complex that was different from the known human γδTCR forms. In an attempt to delineate this form, we produced and characterized a number of cell lines derived from normal human donors. Peripheral blood lymphocytes were stained with monoclonal antibody (mAb) WT31, which brightly stains resting αβTCR lymphocytes. Cells that did not stain were isolated by cell sorting and then expanded in vitro in IL-2 containing medium. Peripheral blood lymphocyte line 2 (PBL-L2) obtained in this way, proved to be homogeneously CD3+CD4−CD8−, a cell surface phenotype characteristic of γδTCR lymphocytes.

To visualize γδTCR complexes on PBL-L2 cells, immunoprecipitations with an anti-CD3 mAb were carried out from cell surface $^{125}$I-labelled cells solubilized in CHAPS or digitonin. In these detergents, the physical association between the CD3 complex and γδTCR subunits is preserved. SDS-PAGE of anti-CD3 immunoprecipitates from PBL-L2 cells resolved 40 kD and 44 kD proteins (referred to as 40 kD) that were identified as γTCR subunits by anti-Cγb serum, an antiserum directed against a γTCR constant region peptide (FIG. 7A; see methods section).

These γTCR proteins on PBL-L2 are noncovalently associated with a δTCR subunit, which is visible as a weakly iodinated protein in the anti-CD3 immunoprecipitation analyzed under nonreducing conditions (FIG. 7A, lane 6, closed arrow). This weakly iodinated protein represents the δTCR subunit on PBL-L2 cells, since it is not recognized by anti-Cγb serum (FIG. 7A, lane 8). In addition, it displays the same SDS-mobility shift comparing analysis under nonreducing and reducing conditions as was noted for the δTCR proteins on IDP2 and PEER cells (see infra; described more fully in copending U.S. application Ser. No. 016,252 filed Feb. 19, 1987 which is incorporated by reference herein in its entirety). The δTCR protein could not be visualized after reduction (FIG. 7A, lane 3), because it migrated with a mobility of 40 kD (see infra) and then was obscured by the similar sized γTCR protein (open arrow).

This δγTCR form is not only present on normal peripheral blood T-lymphocytes, but is also observed on thymus-derived Clone II cells (FIG. 7D; and on the T-leukemic cell line MOLT-13 (FIG. 7E). These three cell lines possess γTCR species that display differential glycosylation resulting in a γTCR protein doublet observed on PBL-L2 (40 kD and 44 kD; FIG. 7A, lane 8) and Clone II cells (40 kD and 44 kD; FIG. 7D, lane 8) or a diffusely labelled γTCR protein band observed on MOLT-13 cells (40 to 46 kD; FIG. 7E, lane 6). Two-dimensional gel analysis [nonequilibrium pH gradient electrophoresis (NEPHGE) followed by SDS-PAGE]of the MOLT-γTCR protein band resolved two parallel γTCR species (40 kD and 44 kD), of which the 44 kD γTCR species contained an additional high mannose (or hybrid) N-linked glycan compared to the 40 kD γTCR species. Thus, the γTCR subunits of this receptor complex isolated from three different cell sources (peripheral blood, thymus, and leukemia) reveal cell surface species of 40 kD that are noncovalently associated with δTCR partner chains.

For comparison to the γδTCR form on PBL-L2, Clone II and MOLT-13 cells, we examined the previously known forms on the IDP2 and WM-14 cell lines. The IDP2 cell line (described more fully in copending U.S. application Ser. No. 882,100 filed Jul. 3, 1986, which is incorporated by reference herein in its entirety) contains a larger, 55–60 kD γTCR protein (referred to as 55 kD), which is recognized by anti-Cγb serum (FIG. 7B). When the anti-CD3 immunoprecipitate is examined under nonreducing conditions, it is evident that the IDP2 γTCR protein is associated noncovalently with its γTCR partner chain (FIG. 7B, lane 4, solid arrow). Upon reduction, the γTCR protein displays a decrease in SDS-PAGE mobility to a relative molecular mass of 40 kD (compare FIG. 7B, lane 4, closed arrow, with FIG. 7B, lane 2, open arrow).

In contrast to the noncovalently associated γδTCR forms, the peripheral blood-derived T cell clone, WM-14, bears a disulfide-linked TCR dimer of 70 kD (FIG. 7C, lane 7), that was recognized by anti-Cγ serum (Alarcon et al, 1987, Proc. Natl. Acad. Sci. U.S.A. 84:3861–3865). This dimer is also recognized by anti-TCRδ1, a mAb directed against the δTCR subunit (FIG. 7C, lane 5), and therefore represents a γδTCR heterodimer. Analysis under reducing conditions reveals three γTCR proteins of 36 kD, 40 kD and 43 kD (referred to as 40 kD). Thus, the CD3-associated complex on PBL-L2, Clone II and MOLT-13 cells constitutes a novel γδTCR heterodimer compared to the previously known forms, since its TCR δ subunit is 40 kD (similar in size to the disulfide-linked Cγ1 encoded γTCR protein on WM-14 cells), yet it is not disulfide-linked to its partner chain (similar to the 55 kD, Cγ2 encoded γTCR protein on IDP2 cells). To understand the molecular basis of this complex more detailed structural analysis of its γTCR and δTCR subunits was carried out as described infra, using the MOLT-13 cell line as an example.

11.2.2. Core Polypeptide Size of Molt-13 γTCR Subunit

Figure 9B:
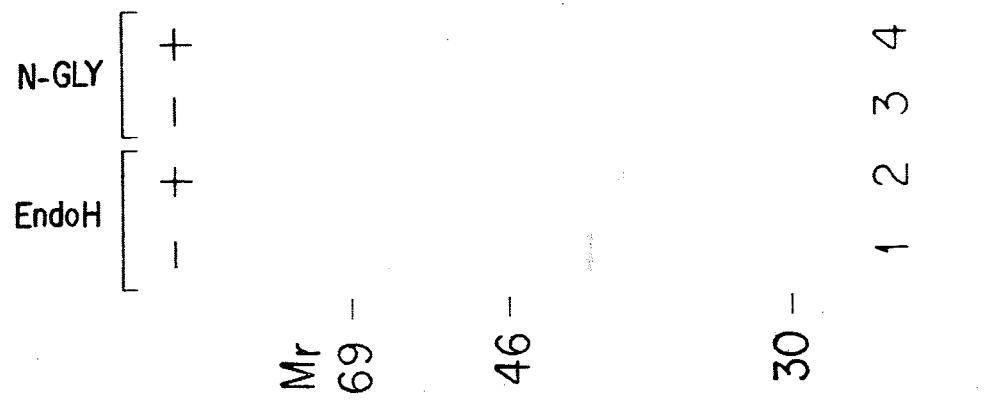
Figure 9A:
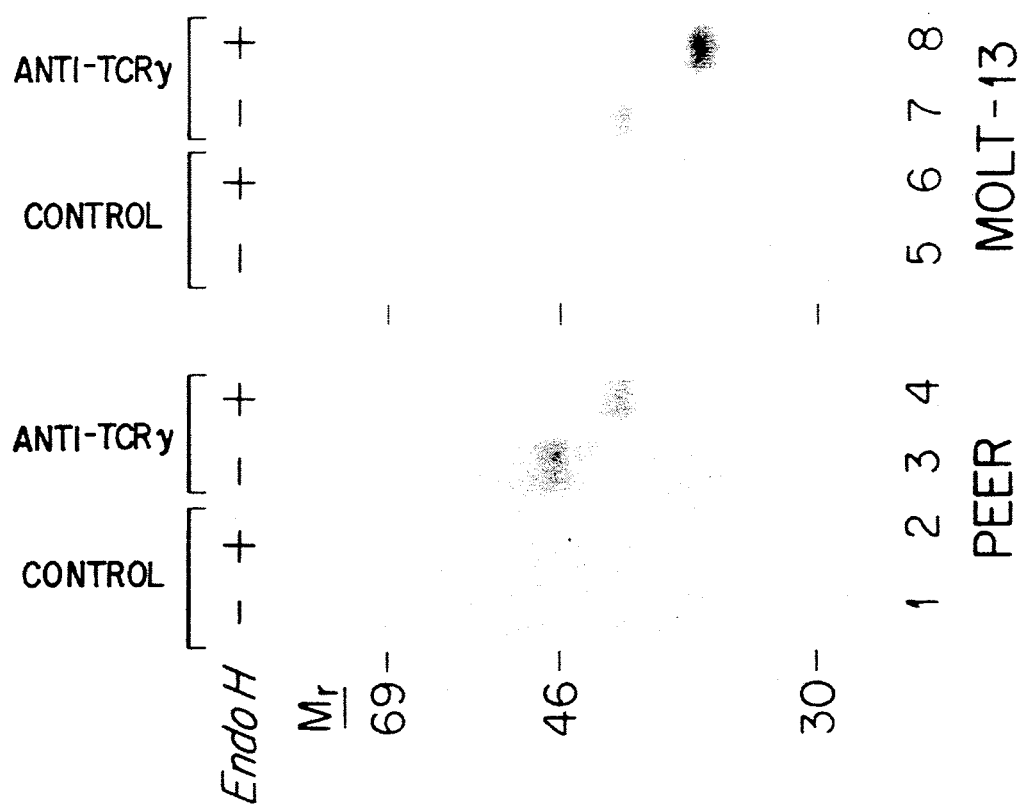

To determine the size of the γTCR core polypeptide of MOLT-13 cells (40 kD γTCR glycoprotein), and compare it with that of PEER cells (55kD γTCR glycoprotein), both cell lines were biosynthetically labelled for 15 minutes in the presence of $^{35}$S-methionine and $^{35}$S-cysteine, solubilized in Triton X-100 and then immunoprecipitated with anti-Cγm1, a monoclonal antibody that specifically recognizes the γTCR chain (FIG. 9A, see methods section). Immunoprecipitated material was subsequently digested with endoglycosidase H (Endo H) to remove the immature N-linked glycans. The MOLT-13 γTCR polypeptide backbone has a relative molecular mass of 35 kD (FIG. 9A, lane 8), which is 5 kD smaller than the PEER γTCR core polypeptide (40 kD; FIG. 9A, lane 4) or the IDP2 γTCR core polypeptide (40 kD; described more fully in copending U.S. application Ser. No. 016,252, filed Feb. 19, 1987, incorporated by reference herein in its entirety). It can be concluded that MOLT-13 cells express a γTCR core polypeptide that is distinct from the IDP2 and PEER γTCR core polypeptides based on its being 5 kD smaller. In addition, only 5-11 kD of size on the mature MOLT-13 γTCR cell surface glycoprotein are accounted for by post-translational processes (40-46 kD surface size minus 35 kD core size), where 15-20 kD of relative molecular mass can be accounted for by post-translational processes on the PEER and IDP2 δTCR glycoproteins (55-60 kD surface size minus 40 kD core size). Assuming that all post-translational processes are N-linked glycans and that each glycan chain accounts for approximately 3 kD of relative molecular mass, we predict that 2 to 3 N-linked glycans are attached to the MOLT-13 γTCR protein, while 5 N-linked glycans are added to the polypeptides on PEER and IDP2 cells. Experiments using N-glycanase to remove N-linked carbohydrates from cell surface γTCR proteins showed that the majority of the post-translational processes that are added to the core polypeptide are indeed N-linked glycans.

11.2.3. Primary Sequence of Molt-13 γTCR

To understand the structure of the constant region gene segment encoding the MOLT-13 γTCR subunit, the sequence of a cDNA clone representing the MOLT-13γTCR transcript was determined. A λgt10 library from MOLT-13 derived poly-A+RNA was constructed and probed with a human γTCR cDNA clone, pTγ-1 (Dialynas et al., 1986, Proc. Natl. Acad. Sci. U.S.A. 83:2619-23). Based on size and limited restriction enzyme mapping one clone, M13k, was selected and its nucleotide sequence determined (FIG. 10). Clone M13k represents a full length, in-frame γTCR transcript, using a Vγ1.3 gene segment joined to a Jγ2.3 gene segment (Lefranc et al., 1986, Cell 45:237-246; Lefranc et al., 1986, Nature 319:420-422; nomenclature based on Strauss et al., 1987, Science 237:1217-19; Quertermous et al., 1987, J. Immunol. 138:2687-2690). The constant region sequence was found to be nearly identical to a recently reported non-functional γTCR (Pellici et al., 1987, Science 287:1051-1055) and to the Cγ2 genomic sequence containing two CII exon copies b and c (Lefranc et al., 1986, Proc. Natl. Acad. Sci. U.S.A. 83:9596-9600)(see methods section for detailed account). This represents the first in-frame transcript encoding a γTCR protein expressed on the cell surface that utilizes a Cγ2 gene segment with two CII exon copies.

The deduced amino acid sequence of this cDNA clone predicts a polypeptide backbone size of 34.8 kD which is in good agreement with biochemical data described above. Surprisingly, six potential N-linked carbohydrate attachment sites are encoded by this transcript. Since the biochemical data suggest that only 2 to 3 N-linked glycans are attached to the polypeptide chain, it indicates that not all potential sites are used.

To reflect Cγ gene segment usage, we have denoted the disulfide-linked γδTCR form expressed by PBL-CI and WM-14 as "Form 1", since such disulfide-linked γTCR chains utilize the Cγ1 gene segment (Krangel et al., 1987, Science 237, 64-67). The large (55 kD), nondisulfide-linked γTCR subunit of the γδTCR form expressed on IDP2 and PEER cells is encoded by Cγ2 gene segments containing three CII exon copies, namely copy a, copy b and copy c (Krangel et al., supra; Littman et al., 1987, Nature 326:85-88) and therefore this γδTCR form is called herein "Form 2abc" In concordance, the form characterized on MOLT-13 cells is referred to as "Form 2bc".

11.2.4. Preferential Cγ Gene Segment Usage

To determine the presence of these three γ,δTCR forms in freshly isolated peripheral blood we analyzed the mononuclear cells from ten healthy subjects, using biochemical analysis with mAb anti-TCRδ1 (described in Section 9, supra; reactive with the δTCR constant region). This antibody reacts with the great majority, if not all γ,δTCR lymphocytes. In subject 1, anti-TCRδ1 immunoprecipitates (analyzed under nonreducing conditions) demonstrated the presence of both disulfide-linked γ, δTCR complexes as a 70 kD protein band (Form 1) and nondisulfide-linked γ,δTCR complexes as a broad 40 kD protein band (Form 2bc). This indicated that the Cγ1 and Cγ2 constant regions are both used by the expressed γ,δTCR of this individual. However, the amount of Form 2bc varied among individuals. We noted a smaller fraction of Form 2bc in subject 2 compared to subject 1 by comparing the intensity of the 40 kD protein bands in both individuals. Even more strikingly, only disulfide-linked γ, δTCR complexes could be detected on the mononuclear cells of three of the ten individuals examined, even after long exposure of the autoradiographs. None of the analyzed individuals revealed the 55 kD, nondisulfide-linked γ, δTCR complex (Form 2abc) in peripheral blood.

11.2.5. Characterization of the δTCR SUBUNIT

In contrast to the striking structural differences in size and glycosylation of the γTCR proteins, δTCR subunits from different cell sources proved to be markedly similar. The relative molecular mass of the δTCR glycoprotein on MOLT-13 cells was directly determined to be 40 kD using the anti-δTCR mAb (FIG. 8, lane 4), confirming that it is similar in size to the δTCR glycoprotein on IDP2 cells (FIG. 7B, lane 2, open arrow).

To also compare δTCR polypeptide backbone sizes, cell surface $^{125}$I-labelled δTCR protein from MOLT-13 cells was digested with N-glycanase to remove asparagine-linked glycans (of the high mannose, hybrid, and complex-type; Tarentino et al., 1985, Biochem. 24:4665-4671; Hirani et al., 1987, Anal. Biochem.

162:485–492). The δTCR core polypeptides of MOLT-13 cells has a relative molecular mass of 35 kD (FIG. 9B, lane 4), which is similar to that of the δTCR backbone of IDP2 cells (35 kD; see Section 8, supra, and copending U.S. application Ser. No. 115,256, filed Oct. 29, 1987).

In addition, digestion of cell surface $^{125}$I-labelled MOLT-13 δTCR protein with endoglycosidase H (Endo H, removing only high mannose and certain hybrid N-glycans; Tarentino et al., 1974, J. Biol. Chem. 249:811–817; Trimble and Maley, 1984, Anal. Biochem. 141:514–522) caused a decrease in relative molecular mass of 2.5 kD, (FIG. 9B, lane 2) consistent with the presence of one carbohydrate moiety, leaving a relative mass of 2.5 kD of Endo H resistant carbohydrates attached to the polypeptide. Since there are two potential N-glycan attachment sites present in the δTCR constant domain (See Section 8 supra; copending U.S. application Ser. No. 115,256, filed Oct. 29, 1987; Loh et al., 1987, Nature 330:569–572), these data show that both are used, but that their N-glycans are processed differently, namely one as a high mannose N-glycan (Endo H-sensitive) and the other as a complex N-glycan (Endo H-resistant, but N-glycanase sensitive). In contrast to the different amounts of attached N-linked carbohydrate on δTCR polypeptide chains, the δTCR subunits expressed on PEER, IDP2 and MOLT-13 cells all revealed the same peptide core sizes and the presence of two N-linked glycans (FIG. 9B).

11.3. Discussion

In this example, three protein forms of the human γTCR glycoprotein are compared, namely the disulfide-linked 40 kD γTCR (Form 1), the nondisulfide-linked 55 kD γTCR (Form 2abc) and the nondisulfide-linked 40 kD γTCR protein (Form 2bc). All three forms are shown to be associated with a δTCR subunit. Complementary DNA sequences representing the first two γTCR forms have been published (Krangel et al., 1987, Science 237:64–67; Littman et al., 1987, Nature 326:85–88). The constant region of γTCR Form 1 (on PBL-C1) is encoded by the Cγ1 gene segment containing a single CII exon, while γTCR Form 2abc (on IDP2 and PEER cells) utilizes the Cγ2 gene segment containing CII exon copy a, copy b and copy c. The cDNA sequence corresponding to a γTCR chain of Form 2bc was shown to contain a Cγ2 gene segment utilizing only two CII exon copies, namely copy b and copy c. Similarly, it seems likely that the gene structure of the γTCR connector region of Clone II and PBL-L2 (non-disulfide-linked, 40 kD γTCR protein) will also be like the MOLT-13 structure determined here, namely of Form 2bc. Since the γTCR constant region used is the same for all these forms (see Section 8 and copending U.S. application Ser. No. 115,256, filed Oct. 29, 1987) a complete comparison of the structures of the three γδTCR forms in man now can be made (FIG. 11).

Two Cγ2 polymorphic genomic forms exist in man (Lefranc et al., 1986, Nature 319:420–422; Pellici et al., 1987, Science 237:1051–1055). The two transcript forms (Form 2abc and Form 2bc) are probably the product of these different allelic types. To date, no allelic form of γTCR polypeptides have been found in mice. We conclude that the dramatic difference in γTCR cell surface protein size between Form 2abc (55 kD) and Form 2bc (40 kD) is largely determined by the amount of attached N-link carbohydrates, most likely reflecting the number of N-linked glycans. Backbone sizes of IDP2 γTCR (Form 2abc) and MOLT-13 γTCR (Form 2bc) proteins have been measured to be 40 kD and 35 kD respectively, on the basis of SDS-PAGE, which correlates well with their predicted molecular masses of 36.6 kD and 34.8 kD respectively, calculated on the basis of cDNA sequences. It is clear that this small difference in backbone size (5 kD in SDS-PAGE), accounted for mainly by one CII exon encoded peptide of 16 amino acids, contributed to, but could not solely explain the observed difference in molecular mass between the 55 kD and 40 kD nondisulfide-linked γTCR surface forms. Form 2abc γTCR polypeptides possess 5 potential N-linked glycan attachment sites that are probably all used, in contrast to the MOLT-13 γTCR polypeptide which bears one additional potential attachment site, while carrying only 2 to 3 N-linked glycans. The reason for this limited use of potential attachment sites is unknown, but may result from the influence of the CII exon encoded peptides on the conformation of the γTCR protein. The CII exon encoded peptides and their neighboring amino acids make up a connector region between the plasma membrane and the immunoglobulin-like constant domain. This region contains most of the N-linked glycan attachment sites. We conclude that the CII exon copies appear to determine the protein form not only by determining polypeptide backbone size, and by creating the ability to disulfide-link chains, but also by influencing the amount of attached carbohydrates.

δTCR complementary DNAs of IDP2 (see Section 8, supra), PEER (Loh et al., 1987, Nature 330:569–592) and MOLT-13 cells have been sequenced and were found to be identical, except for the diversity/N-region interspacing the variable and constant region gene segments. The δTCR protein on WM-14 cells has a relative molecular mass of 43 kD, which is similar to the δTCR protein described previously (Borst et al., 1987, Nature 325:683–688; Lanier et al., 1987, J. Exp. Med. 165:1076–1094) but is 3 kD larger than the other γTCR chains. These 43 kD δTCR proteins might indicate the presence of an additional N-linked glycosylation site in a different δ variable domain.

Structural differences comparable to those described for γTCR constant region segments have not been observed for αTCR and βTCR genes (Yoshikai et al., 1985, Nature 316:837–840; Toyonaga et al., 1985, Proc. Natl. Acad. Sci. U.S.A. 82:8624–8628; Royer et al., 1984, J. Exp. Med. 160:947–952; Kronenberg et al., 1985, Nature 313:647–653). There is possible structural similarity in the number of human CII exon repeats with the length in murine Cγ regions, of which the Cγ1, Cγ2 and Cγ4 constant regions encode for 15, 10 and 33 amino acid connector region, respectively (Garman et al, 1986, Cell 45:733–742; Iwamoto et al., 1986, J. Exp. Med. 163:1203–1212). The connector regions in mouse, however, reflect a difference in the size of the relevant exon, not the multiple use of exons as is seen in Form 2abc γTCR and Form 2bc γTCR in humans. Also, the murine γTCR only exist in disulfide linked forms in contrast to the two nondisulfide linked human forms.

Importantly, the human γ, δ TCR forms do not appear to be used equally. In some individuals (selected for high percentages of γ,δTCR lymphocytes) a single form (Form 1) predominates, suggesting that either positive selection occurs for this form or that there is selection against other γ, δTCR forms.

12. EXAMPLE: CHARACTERIZATION OF A HUMAN δ T CELL ANTIGEN RECEPTOR GENE AND A V_δ SPECIFIC MONOCLONAL ANTIBODY

We have isolated γTCR cDNA and a rearranged δTCR gene from a human γδ T cell clone, AK119. From these DNA clones, a V-J_δ probe was obtained, and used to determine the diversity of γTCR gene rearrangements in a panel of 13 human γ, δ cell clones and γ, δ human T cell tumor lines. Altogether, five different rearrangements were detected, which corresponded to rearrangements using 2 to 5 different V_δ genes. One particular rearrangement was always seen in human γ, δ T cells that reacted with mAb TCSδ1 (δTCAR-3). In addition, TCSδ1 immunoprecipitated the δTCR polypeptide from a human γ,δ tumor cell line, Molt 13. We provide evidence that monoclonal antibody TCSδ1 recognizes an epitope encoded in the AK119 V_δ gene or in a combination epitope of the rearranged AK119 Vδ-Jδ gene.

12.1. MATERIALS AND METHODS

12.1.1. ISOLATION AND SEQUENCING OF AK119 δTCR cDNA CLONES

A cDNA library was generated from the PBL T cell clone, AK119, by the method of Gubler and Hoffmann (Gubler and Hoffman, 1983, Gene 25:263). About 100,000 plaques of an amplified library were screened using a $^{32}$P-labeled nick-translated Cδ probe, isolated from a δTCR clone called O-024 (see Section 8, supra). The longest hybridizing cDNA clone (1.3 kb clone C119 δ3) was selected for sequence analysis by the dideoxy chain termination method.

12.1.2. Cloning a Rearranged δTCR GENE

A 3.5 kb genomic DNA clone containing the rearranged Vδ gene was obtained from AK119 cells as follows. EcoRI digested DNA was size fractionated on a preparative agarose gel, ligated into λgt10, packaged and transfected into *E. coli*. Recombinant phage were screened with a $^{32}$P-labeled nick translated 550 bp EcoRI fragment derived from the cDNA clone, c119 δ3. A rearranged clone called r119 δ1 which contains a 0.8 kb HincII fragment (V region specific) and a 1 kb HincII-EcoRI fragment (V-J region) were isolated.

12.1.3. DNA Preparation

Fetal and newborn thymic tissues were collected in accordance with accepted guidelines regarding patients' rights and approval. T cell clones were obtained from peripheral blood, pleural exudate or cerebrospinal fluid by limiting dilution and were cultured in vitro (Hafler et al., 1985, Ann Neurol. 18:451; Van de Griend et al., 1987, J. Immunol. 138:1627). In all cases, DNA was prepared by digestion with proteinase K in 1% sodium dodecyl sulfate, followed by extraction with phenol/chloroform and ethanol precipitation.

12.1.4. Southern Blot Analysis

Genomic DNA was digested with EcoRI, size fractionated on a 0.9% agarose gel and transferred to nitrocellulose. Hybridization was carried out with $^{32}$P-nick translated probes as previously described (Maniatis, 1982, Molecular Cloning: A Laboratory Manual, Cold Spring Harbor Laboratory, Cold Spring Harbor, New York).

12.1.5. Cytofluorometric Analysis

Normal peripheral blood mononuclear cells (PBMC), obtained from volunteers, were isolated by fractionation on a Ficoll gradient. PBMC and PBL T cell clones were stained by indirect immunofluorescence using mAb TCSδ1 (referred to previously as δTCAR-3; see Section 10, supra) and fluorescein-conjugated goat antimouse IgG (Becton Dickinson) and analyzed in a fluorescence activated flow cytometer.

12.2. Results

12.2.1. Diversity of δTCR Gene Rearrangements

Using a Cδ probe, we isolated a 1.3 kb δTCR cDNA clone, termed c119 δ3, from a λgt10 cDNA library of the T cell clone AK119. The 5' end of c119δ3 was sequenced and found to use previously identified V_δ and J_δ genes (see copending applications U.S. Ser. No. 187,698, filed Apr. 29, 1988, and U.S. Ser. No. 115,256, filed Oct. 29, 1987, incorporated by reference in their entirety; Loh et al., 1987, Nature 330:569). The sequence of the V-J junction indicated that C119 δ3 has an in frame V-J joint.

A 550 basepair (bp) EcoRI fragment encoding all the variable and joining region and part of the constant region (V-J-C probe) was obtained from c119 δ3 and used in Southern blot analysis of EcoRI digested genomic DNA from AK119. This probe detects a germline 3.2 kb V_δ and a germline 1.0 kb C_δ band. AK119 showed an extra rearranged 3.5 kb band that is identical to a common δTCR rearrangement (see copending applications Serial No. 187,698 filed Apr. 29, 1988, and U.S. Ser. No. 115,256, filed Oct. 29, 1987; Loh et al., 1987, supra) (rearrangement II in FIG. 12). This 3.5 kb band was cloned from a Eco RI size-fractionated λgt10 genomic library using the V-J-C cDNA probe. The cloned rearranged γTCR gene was called r119 δ1. The localization of the variable and joining region was determined using J oligonucleotide probes and Variable region specific probes. From r119δ1, a 1 kb V-J probe was isolated by digestion with HincII and EcoRI enzymes.

This V-J probe was used to determine the diversity of δTCR gene rearrangements in a panel of 13 human γδTCR positive T-cell clones and 3 human γδTCR positive tumor cell lines. As shown in FIG. 12, five common rearrangements, numbered I-V, are seen in the polyclonal newborn thymocyte sample (lane 11). These rearrangements are representative of rearrangements used by the human γδT cell clones. Only rearrangement II hybridized to the HincII - HincII V_δ specific probe. Although we do not know that all these rearrangements represent V-D-J rather than D-J rearrangements, some of them must represent rearrangements of new variable regions to the previously characterized J_δ gene segment because these cells express a functional δTCR polypeptide chain on their cell surfaces. We have not ruled out the possibility that these new rearrangements represent rearrangements of a single new V_δ gene to other J_δ genes, yet to be identified. Our data is consistent with the fact that there must be 2-5 variable region genes that can be used in δTCR gene rearrangements.

12.2.2. Determining the Specificity of mAb TCSδ1

TCSδ1, previously referred to as δTCAR-3, was generated by fusing splenocytes from mice immunized with the human tumor γδTCR T cell line MOLT-13 with a mouse myeloma line. When used in fluorescent activated cell sorter analysis, TCSδ1 reacted only with some, but not all, human γδ T cells. The results are given in Table II. There is a perfect correlation with usage of the AK119 V$_δ$ gene (rearrangement II) with positive staining by TCSδ1. This data provides strong evidence that the epitope recognized by TCSδ1 is encoded in the AK119 V$_δ$ gene or in combinatorial epitope of the rearranged AK119 V$_δ$-J$_δ$ gene.

TABLE II

Correlation between staining by mAb TCSδ1 and a specific V$_{67}$ rearrangement

| | δ rearrangement[1] | TCSδ1 |
|---|---|---|
| human γδTCR T cell clones | | |
| AK4 | V/?[2] | −[4] |
| AK615 | I/IV | − |
| AK925 | III/? | nd |
| 1004 | I/IV | − |
| 1005 | I/IV | − |
| 1011 | I/IV | − |
| 1012 | I/IV | − |
| 1015 | I/? | − |
| 1018 | IV/? | − |
| Wi.1 | I/? | − |
| 1019 | II/IV | nd |
| AK119 | II/? | + |
| Wi.K | II/III | + |
| human γδTCR T cell tumor lines | | |
| Peer | II/? | + |
| Molt-13 | II/V | + |
| DND41 | II/VI[3] | + |

[1]δTCR rearrangements detected with V-J probe, numbered I-V as in FIG. 12.
[2]Only 1 rearrangement was identified in each case even though no germline J$_{67}$ was detected.
[3]A new rearrangement is observed which is not seen in newborn or fetal thymocytes. This rearrangement has been assigned rearrangement VI.
[4]+ means positive staining. − means negative staining. nd means not determined.

12.3. Discussion

The direct correlation between the usage of the AK119 V$_δ$ gene (namely the rearranged 3.5 kb fragment or rearrangement II) and staining by TCSδ1 provided evidence that the TCSδ1 epitope is encoded in the AK119 gene or in a combinatorial Vδ-Jδ region. This is the first V$_δ$ or Vδ-Jδ specific mAb that can be used to stain cell surface δTCRs. The generation of variable region specific mAbs is useful for studying the usage of V$_δ$ genes in different tissues, during different stages of development, and in disease.

Our studies have also shown that the repertoire of the TCR-δ gene is not as restricted as previously described in copending U.S. application Ser. No. 115,256, filed Oct. 29, 1987, and Loh et al., 1987, supra.

13. EXAMPLE: T CELL γδ COMPLEX, NOT ASSOCIATED WITH CD3, IS IDENTIFIED IN HUMAN ENDOMETRIAL GLANDULAR EPITHELIUM

We have tested a panel of four mAbs to γδTCR in pregnant and non-pregnant uteri. γδTCR was not detecte stromal lymphocytes, but was localized in the cytoplasm of the endometrial glandular epithelium from most pregnant uteri. These antibodies also reacted with endometrial glandular epithelium in a majority of non-pregnant uteri; the reactivity was most consistent in secretory phase glands than that in the proliferative phase of menstrual cycle. However, the γδTCR was not associated with CD3 complex, as shown by the lack of reactivity with three different mAbs to CD3. The γδTCR-positive glandular epithelial cells did not react with two mAbs to γδTCR, and they were also CD4- and CD8- negative.

13.1. Materials and Methods

13.1.1. SPECIMENS

Twenty first trimester samples were obtained from elective aspirations of normal pregnancies between 6 to 12 weeks of gestation. Tissues (1 cm$^3$) were snap frozen in liquid nitrogen-cooled isopentane, and stored at −20° C. Twenty fresh fragments of non-pregnant endometrium were obtained from curettage or hysterectomy specimens within 30 minutes of surgery. Fragments (5–10 mm size) were quenched in liquid nitrogen-cooled isopentane and stored in liquid nitrogen until use. The remaining endometrial tissue was processed for routine histological examination. All operations were performed for non-endometrial pathology and only histologically normal tissues in accord with menstrual dates were included. Ten specimens were proliferative, and ten were from the secretory phase of the menstrual cycle. Cryostat sections (5 μm) of frozen tissues were stained with hematoxylin and eosin to allow morphology and ensure adequate representation of functionalis and basalis and accordance with appearance in routine paraffin sections.

13.1.2. Monoclonal Antibodies

Twenty monoclonal antibodies were employed in the present study. The reference and the concentration of each antibody are outlined in Table III.

TABLE III

| MONOCLONAL ANTIBODIES | | | |
|---|---|---|---|
| Antibody | Antigen | Ig Class | Concentration* |
| WT31 | CD3-TCR α/β | IgG1 | 1:5 (diluted As) |
| βF1 | TCR β chain | IgG1 | 20 μg/ml (Ig) |
| γ3 | TCR γ chain | IgG1 | 1:200 (As) |
| TCSδ1 | TCR δ chain | IgG1 | 25 μg/ml (Ig) |
| TS-8 | TCR δ chain | IgG1 | 20 μg/ml (Ig) |
| TCRδ-1 | TCR δ chain | IgG1 | 1:500 (As) |
| Leu-4 | CD3 | IgG1 | 2.5 μg/ml (Ig) |
| OKT3 | CD3 | IgG1 | 20 μg/ml (Ig) |
| UCHT-1 | CD3 | IgG1 | 1:50 (Ig) |
| OKT4 | CD4 | IgG1 | 5 μg/ml (Ig) |
| T811 | CD8 | IgG1 | 2.5 μg/ml (Ig) |
| B1G6 | β2M | IgG2a | 4 μg/ml (Ig) |
| W6/32 | HLA-A,B,C | IgG2a | 20 μg/ml (Ig) |
| DR1 | HLA-DR | IgG1 | 50 μg/ml (Ig) |
| B8.12.2 | HLA-DR | IgG2b | 4 μg/ml (Ig) |
| 80 | Keratin | IgG1 | 1:20 (Sup) |
| GB5 | Epithelium | IgG1 | 1:1 (Sup) |
| GB24 | Epithelium | IgG1 | 1:1 (Sup) |
| GB17 | Trophoblast | IgG1 | 1:1 (Sup) |
| GB25 | Trophoblast | IgG1 | 1:1 (Sup) |

*Ig: purified immunoglobulin; As: ascites; Sup: culture supernatant.

The antibodies used included antibodies to TCR, leukocyte, MHC, trophoblast, and epithelial antigens. WT31 reacts with a common epitope on the αβTCR complex (Spits et al., 1985, J. Immunol. 135:1922–1928). βF1 is directed against a framework epitope on TCR β chain. γ3 was raised against a synthetic peptide from Cγ constant region. TCSδ1 and TS-δ were raised against Molt 13 cells. TCRδ1 was raised against PEER cells (Band et al., 1987, Science 238:682). TCSδ1 and TCRδ1 recognize non-competing epitopes on the TCR δ chain. GB5 reacts with amniotic epithelium, most epithelial cells (Hsi & Yeh, 1986, J. Reprod. Immunol. 9:11–21), as well as with uterine glands and spiral arteries. GB24 reacts with different subsets of trophoblasts, most epithelia and peripheral blood lymphocytes. GB17 recognizes 170 kD peptide from syncytiotrophoblast. GB25 reacts with villous trophoblasts. GB17, GB24 and GB25 react with trophoblasts from first trimester and term placentae.

13.1.3. Immunohistology

The whole procedure was performed at room temperature, and the time for each incubation was 30 minutes unless otherwise specified. Between each incubation, the cryostat sections were washed once for 5 minutes in 0.15 M phosphate buffered saline (PBS), pH 7.2 for immunofluorescence; and they were washed twice with 0.05 M Tris-buffered saline (TBS), pH 7.6, each for 5 minutes for immunoperoxidase. The omission of primary antibodies and the replacement of TCR antibodies by irrelevant antibodies were used as negative controls.

13.1.4. Immunofluorescence

Sections were air-dried and incubated with monoclonal antibodies at the appropriate concentration (see Table III). They were then incubated with a 1:40 dilution of fluorescein isothiocyanate (FITC) conjugated F(ab')$_2$ fragment of rabbit immunoglobulin (Ig) to mouse Ig (Dakopatts A/S, Denmark), and mounted in 1% n-propyl gallate (Sigma) in PBS and glycerol.

13.1.5. Double-Labeling Experiment

Sections were incubated with a 1:100 dilution of FITC conjugated goat anti-human factor VIII related protein (Atlantic Antibodies, Maine, USA). They were then reacted with monoclonal antibodies, and incubated with 1:400 dilution of biotinylated rabbit Ig anti-mouse Ig (Dako). The sections then were reacted with 1:50 dilution of biotinylated phycoerythrin strepavidin complex (Amersham International PLC, U.K.). The sections were fixed with stabilizer for 20 minutes, dried and mounted in the mounting medium provided in the phycoerythrin-based cytochemical kit (Amersham).

13.1.6. Immunoperoxidase Staining

Sections of pregnant endometrium were air-dried and fixed in acetone for 5 minutes. They were incubated with monoclonal antibodies, and reacted with 1:400 dilution of biotin-conjugated rabbit Ig anti-mouse Ig (Dako). Then they were incubated with 1 drop of avidin-biotinylated horseradish peroxidase complex (ABC) (Dako). The reaction was developed with 3-amino-9-ethyl carbazole (AEC) (0.4 mg/ml) (Sigma) in 0.1 M phosphate citrate buffer, pH 5.5 containing 0.03% $H_2O_2$ for 8 minutes and rinsed in distilled $H_2O$. The sections were counterstained with Mayer's hematoxylin (Sigma) for 15 minutes, rinsed in distilled $H_2O$ and plunged into 0.1 M $NaHCO_3$, pH 8.3. The sections were mounted in glycergel (Dako).

Acetone-fixed sections of non-pregnant endometrium were labeled using a streptavidin-biotin-peroxidase kit (Zymed, Calif., USA). Sections were incubated sequentially with primary monoclonal antibody for 30 minutes, biotinylated anti-mouse immunoglobulin for 10 minutes and streptavidin-peroxidase for 5 minutes according to the supplier's instructions. The reaction was developed with AEC, and the sections were highly counterstained with hemotoxylin and mounted in an aqueous mountant.

13.1.7. Microscopy

The preparations were examined with a Zeiss Axiphot microscope fitted for bright field, phase contrast and epi-illumination fluorescence microscopy. The photographs were taken with Ektachrome ASA 200 daylight films for immunofluorescence, and ASA 160 tungsten or Tmax 100 films for immunoperoxidase by using an integrated camera system.

13.2. Results

13.2.1. Detection of TCR

Six monoclonal antibodies directed against TCR were employed. WT31 and $\beta$F1 react with the $\alpha\beta$ complex; TCS$\delta$1, TS-8, TCR$\delta$1 and 73 recognize the $\alpha\beta$ complex. TCS$\delta$1 TS-8, TCR$\delta$1 and $\gamma$3 reacted with the uterine glands in thirteen out of twenty pregnant specimens; the reactivity was located in the cytoplasm of the columnar epithelium, and in some glands, negative cells could be seen. Occasionally, fewer positive epithelial cells were found in the degenerative endometrial glands. These four antibodies showed similar reaction patterns; the intensity between them varied slightly. Double labeling with TCS$\delta$1 and anti-factor VIII showed that the blood vessels identified by anti-factor VIII did not react with TCS$\delta$1. WT31 and $\beta$F1 did not react with uterine glands, but they did label a few cells situated close to the uterine glands in the maternal decidua, as well as very few cells in the intervillous space. No reactivity was identified in the chorionic villi. As a control experiment, WT31, $\beta$F1 and leu 4, but not TCS$\delta$1, reacted with $\alpha/\beta$TCR+positive Jurkat cells by using membrane immunofluorescence and analyzing by flow cytometry.

In non-pregnant endometrium, TCS$\delta$1 reacted with gland epithelium in all except 3 specimens (2 proliferative, 1 secretory). In secretory phase endometrium, the majority of glands labeled with TCS$\delta$1 but occasional glands were completely non-reactive. Within any one glandular structure a variable proportion of epithelial cells did not stain, normally a small minority. The reaction was localized in the cytoplasm of the epithelial cells at the upper portion towards the lumen. Reactivity of TCS$\delta$1 with glands was also detected in proliferative endometrium, but staining was often weaker than in secretory phase samples and a higher proportion of glands were non-reactive. Individual negative cells were identified within the TCS$\delta$1-positive glands. The three other monoclonal antibodies directed against the TCR $\gamma\delta$ complex showed reaction patterns with endometrial glands similar to TCS$\delta$1, although the reaction intensity varied, being more intense with TCS$\delta$1 and least with TCR$\delta$1. WT31, $\beta$F1 and UCH1 failed to react with glandular epithelium, but occasional scattered stromal lymphocytes were reactive.

13.2.2. Detection of Leukocyte Antigens and MHC Antigens

Five monoclonal antibodies to CD3, CD4 and CD8 were utilized. In pregnant endometrium, OKT3 and leu 4 which recognize the CD3 complex, reacted with various numbers of leucocytes in the maternal decidua and in the intervillous space. However, none of these two antibodies labeled uterine endometrial glands. Anti-CD4 and anti-CD8 antibodies also reacted with some lymphocytes; some CD8-positive lymphocytes were identifed as clusters around the $\gamma,\delta$TCR CD8-positive glands, but neither antibodies showed any reactivity with uterine glands. In non-pregnant uterine specimens, UCHTI, which is another monoclonal antibody directed against the CD3 complex, labeled lymphocytes within endometrial stroma and the reaction pattern was similar to that observed with βF1. CD3 lymphocytes were scattered throughout the functionalis and formed aggregates within the basalis. Scattered CD8-positive lymphocytes were detected. CD4 was present on the majority of macrophages in endometrial stroma. CD3, CD4 and CD8 were not detected on endometrial gland epithelium in any specimen.

In pregnant uterine specimens, monoclonal antibodies to β2-microglobulin (BIG6) and to the common determinant of HLA-A,B,C (W6/32) reacted strongly with the stromal tissues of maternal decidua and those of chorionic villi. In contrast, the syncytiotrophoblast of chorionic villi and uterine glandular epithelium was completely non-reactive. Two monoclonal antibodies to HLA-DR (one of which (B8.12.2) was labeled with biotin), reacted with the cells in the fibrinoid attaching to the chorionic villi, as well as many cells in the maternal decidua. However, the uterine epithelium was completely non-reactive. In contrast to pregnant specimens, reactivity for β2-microblobulin and MHC class I antigens was detected in non-pregnant endometrium in glands and stroma. MHC class II antigens were reactive with macrophages within endometrial stroma and there was also labeling of occasional glandular epithelial cells in accord with previous results (Bulmer & Johnson, 1985, Immunology 55:35-44).

13.2.3. Detection of Epithelial Antigens and Trophoblast Antigens

An antibody to keratin which reacts with epithelial cells was used as an aid to identify endometrial glands. This antibody reacted with syncytiothrophoblast and cytotrophoblasts of chorionic villi, as well as uterine glandular epithelium. GB5' which reacts with many epithelial cells, did not react with the trophoblasts in chorionic villi. On the contrary, this antibody reacted with endometrial glands, and showed weaker reactivity with spiral arteries, as previously reported (Bulmer et al., 1987 Am. J. Reprod. Immunol. Microbiol. 14:79-83). The reactivity was localized at the basal surface of uterine glands.

GB17, GB24 and GB25 recognize different trophoblast antigens, and all react with syncytiotrophoblast. Additionally, GB24 and GB25 detect cytotrophoblasts. In the first trimester placentae, only GB24 reacted with endometrial glands, producing intense labeling at the basal surface of the glandular epithelium. GB17 and GB25 were non-reactive.

13.3. Discussion

The results showed that by using a panel of four monoclonal antibodies, γδTCR was detected in the cytoplasm of the endometrial glandular epithelium from most non-pregnant and pregnant uteri, whereas α,βTCR was not detected. Surprisingly, the presence of γδTCR was not associated with CD3 complex. These TCR γ,δ-positive glandular epithelium were also CD4· and CD8-negative. The identity of the uterine glands was pinpointed and confirmed by several immunological markers, i.e., epithelial antigens (anti-keratin-, GB24-, GB5-positive) (Bulmer et al., 1987, Am. J. Reprod. Immunol. Microbiol. 14:79-83); trophoblast antigens (GB17-, GB25-negative); blood clotting factor (anti-factor VIII-negative); and class I and II MHC antigens (W6/32-and anti-DR-negative) (Johnson & Bulmer, 1984, J. Immunol. 132:1608-1610). The possibility of cross-reactivity was minimized by the following controls: (1) Several antibodies of the same specificity from different sources gave identical results; (2) Many other antibodies to different antigens showed diverse reactivity patterns; (3) The omission of primary monoclonal antibodies was completely non-reactive. On the other hand, several non-pregnant and pregnant uteri did not react with any of the four antibodies to γδTCR, the reason for which is yet to be determined.

A striking phenomenon during early pregnancy is that uterine glandular epithelial cells lose class I MHC antigens, although glands in non-pregnant endometrium are consistently class I MHC-positive (Johnson & Bulmer, 1984, J. Immunol. 132:1608-1610). In contrast, extravillous trophoblasts express a novel type of class I MHC antigens with a 41 kD β2-microglobulin-associated heavy chain (Ellis et al., 1986, Immunology 59:595-60). Furthermore, in non-pregnant uteri, the reactivity of anti-γδγTCR antibody in the uterine glands was more consistent in the secretory phase than in the proliferative phase of the menstrual cycle, suggesting that the expression of some antigens on these glandular epithelium may be under local hormonal regulation.

14. EXAMPLE: HUMAN LYMPHOCYTES BEARING γδTCR ARE PHENOTYPICALLY DIVERSE

A direct quantitative and phenotypic cytofluorographic analysis of TCRγδ+lymphocytes as well as an immunohistologic study of their tissue distribution and microanatomy was performed using mAb anti-TCRδ1 which is specific for a framework determinant on human TCR δ chains. TCRγδ+lymphocytes ranging between >0.5 to 16% of CD3+cells were found in fetal and postnatal thymus, fetal and adult peripheral lymphoid organs and adult peripheral blood. While TCRγδ+lymphocytes comprised a small subpopulation of T cells (mean of 4% in most individuals) occasionally >10 to 16% of CD3+cells expressed γδTCR. Virtually all TCRγδ+thymocytes/lymphocytes expressed CD7, CD2 and CD5 but were heterogeneous with respect to their expression of CD1, CD4, CD8, CD28, CD11b, CD16 and Leu7.

γδTCR was initially identified on cell lines which had a "double negative" (CD4−CD8−) phenotype. We describe herein the identification of γδ+T cells which are CD4+.

14.1. Materials and Methods

14.1.1. Tissue Sampling

Fetal tissue (thymus, spleen, small and large intestine, liver, lung, kidney, adrenal gland) was obtained at the time of postmortem examination from electively aborted fetuses (n=9, gestational ages, as determined by crown rump length, menstrual records, and fetal morphology were 10, 14, 17, 18 20, and 21 weeks). Consent forms and collecting practices were approved by the Committee for the Protection of Human Subjects from Research Risks. Full-term neonatal (n =3) and postnatal thymi (n =18, age range =6 weeks to 6 years) were obtained from normal children undergoing corective cardiac surgery. Adult human peripheral blood was donated by randomly selected healthy volunteers (n =29, age range 23 to 54 years). Specimens of adult tissue (bone marrow, n =1; tonsil, n=9; lymph node, n=8; spleen, n=7; smal, n=12, and large, n=5' intestine; liver, n=5; lung, n=4; skin, n=10, kidney, n=1;

brain, n=4; heart, n=1; ovary, n=1; adrenal gland, n=1) were obtained from specimens removed for diagnostic or therapeutic purposes or at the time of autopsy.

14.1.2. Monoclonal Antibodies

The mAb used for phenotyping are listed in Table IV.

conjugated streptavidin (Becton Dickinson & Co.) as the second step reagent(s). For three-color immunofluorescence, cells were stained with FITC-, PE-and biotin-conjugated mAb together with APC-conjugated streptavidin (Becton Dickinson & Co.) Labelled cells were analyzed by a FACS 440 or FACStar flow cytometer.

TABLE IV

| | MONOCLONAL ANTIBODIES USED FOR PHENOTYPING | | | | | | | |
|---|---|---|---|---|---|---|---|---|
| pnTh | 1/25 (2 mo.) | 3/25 (8 mo.) | 4/4 (1½mo.) | 4/7 (1 yr.) | 4/29 (7 mo.) | 5/1 (2 mo.) | 6/30 (11 mo.) | 6/25 (4 yrs.) |
| CD45 | 100% | 100% | | | | | | |
| CD7 | — | — | | | | | 60% | |
| CD2 | 100 | 100 | | | 100% | | 100 | |
| CD5 | 100d | — | | | 100d | | 100 | |
| CD1 | — | — | | | | | — | |
| CD4 | — | — | | | | | — | |
| CD8 | — | — | 100 | 100 | — | — | — | |
| CD3 | 100 | 100 | 100 | 100 | 100 | 100 | 100 | 100 |
| αTCRδ1 | 100 | 100 | 100 | 100 | 100 | 100 | 100 | 100 |
| δTCS-1 | 100(80,70) | 34 | 100 | 100 | — | 100 | 10 | |
| BB3 | 30 | 3 | | | — | | 4 | |
| TiγA | — | — | | | — | — | 18 | |
| TCSC9 | 100 | 6 | | | — | | 30 | |
| TCSC12 | 100 | 7 | | | — | | 30 | |
| TCSC13 | | | | | — | | | |
| WT31 | — | — | | | 100d | | — | |
| HLA-DR | 100 | 100 | | | | | 100 | |
| IL-2R | 100 | 50 | | | | | 50 | |
| TFR | 100 | 50 | | | | | | |
| VLA-1 | 100 | 100 | | | | | | |
| LFA-1 | 100 | 100 | | | | | | |
| LFA-3 | 100 | 100 | | | | | | |
| CD28 | 100d | — | | | | | | |
| HB5 | — | — | | | | | | |
| CD16 | | | | | | | — | |
| Cγ1 | + | + | + | + | | | | |
| Cγ2abc | + | | | + | | | | |
| Cγ2bc | + | + | + | + | | | | |

Anti-Leu mAb were purchased from Becton Dickinson & Co., Mountain View, CA; OKT mAb were purchased from Ortho Diagnostic Systems Inc., Raritan, N.J.; mAb T3b was provided by Dr. J. E. de Vries; mAb 64.1 and 9.3 were provided by Dr. J. A. Hansen; mAb WT31 was provided by Dr. W. J. M. Tax. Isotype matched control Ig that do not react with human leukocytes were used as controls.

14.1.3 Immunofluorescence Analysis of Thymocytes, Peripheral Blood Mononuclear Cells (PBMC), and Splenocytes After removing the capsule and blood clots, thymocyte suspensions were prepared by gently teasing thymic tissue into single cell suspensions using the entire thymic lobule to ensure that cortical and medullary thymocytes were accurately represented. For splenocyte suspensions, spleens were minced to prepare a single cell suspension. Viable mononuclear cells from thymus and spleen were isolated using Ficoll/Hypaque. The mononuclear cell fraction from peripheral blood was isolated using Ficoll/Hypaque. For single color analysis thymocytes/PBMC/splenocytes were resuspended in phosphate buffered saline (PBS), 1% fetal calf serum (FCS), 0.02% $NaN_3$ at $2 \times 10^6$ cells/ml containing appropriately diluted mAb and incubated for 30 minutes at 4° C. After two washes in PBS/1% FCS, antibody binding was visualized by using FITC-labelled $F(ab')_2$ goat anti-mouse immunoglobulin (Ig) (Tago, Inc., Burlingame, Calif.). Two-color staining was performed using FITC-conjugated mAb or unconjugated mAb together with FITC-conjugated goat anti-mouse Ig and either PE- or biotin-conjugated mAb with PE-

14.1.4. Immunohistologic Analysis of Cryostat Sections of Lymphoid and Nonlymphoid Organs Tissue samples were processed according to standard methods. Tissues were snap-frozen in liquid nitrogen with quenching in 2-methylbutane or in cryostats and stored at −70° C. until us e. Four-micrometer serial cryostat sections were mounted on glass slides, air dried and stored at −20° C. until use. After 5 minutes, acetone fixation tissue sections were immunostained using a 3-stage biotin-avidin-peroxidase procedure as previously described (Cerf-Bensussan et al., 1983, J. Immunol. 130:2615; Picker et al., 1987, Am. J. Pathol. 128:181). Briefly, cryostat sections were first exposed to normal horse serum (2.5% in PBS) to inhibit nonspecific binding of horse Ig, followed by an overnight incubation with the appropriately diluted mAb. The subsequent step to block endogenous peroxidase activity with $H_2O_2$ was followed by incubation first with biotin-conjugated horse anti-mouse Ig serum and second with avidin-conjugated horseradish peroxidase (both from Vector Laboratories, Inc., Burlingame, Calif.). Sections were then subjected to a 3-amino-9-ethylcarbazole (Aldrich Chemical Co. Inc., Milwaukee, Wis.) reaction. After nuclear counterstaining with hematoxylin, sections were mounted in Dako glycergel (Dako, Accurate Chemical, Westbury, N.Y.). In kidney and liver sections endogenous biotin activity was blocked as previously described (Tuazon et al., 1987, Am. J. Pathol 129:119). In all tissues except gut epithelium and epidermis, percentages of anti-TCRδ1 and anti-Cγm1 reactive cells within the CD3+cell population were enumerated by counting all CD3+/TCRγδ+cells respectively in 5 high power fields of each section evaluated using a calibrated optical grid. In cryostat sections of gut a stretch of a total 20 mm epithelium was screened for the relative number of CD3+ and TCRγδ+cells respectively. Quantification of intraepidermal TCRγδ+lymphocytes was performed in immunostained epidermal sheet preparations as previously described (Groh et al., 1986, J. Invest. Dermatol. 86:115).

14.2 Results

14.2.1 Reactivity of mAB Anti-TCRδ1 mAb anti-TCRδ1 is directed against an epitope on the TCRδ chain. It binds, without exception, to all CD3+TCRαβ−T cell clones and polyclonal cell lines examined, including cells bearing TCRγ and δ subunits encoded by a variety of TCRγ and TCRδ variable and constant region gene segments. To further examine the reactivity of anti-TCRδ1, we determined its ability to bind to CD3+peripheral blood lymphocytes (PBL) lacking TCRαβ expression based on their staining behavior with mAb WT31. As demonstrated earlier (Van de Griend et al., 1988, J. Immunol. 140:1107), WT31 strongly binds to the surface of TCRαβ+cells but weakly stains cultured TCRγδ lymphocytes. In preliminary experiments, we thus determined the antibody concentrations required to synchronously demonstrate moderate-strong WT31 staining indicative of TCRαβ expression as well as lack of, or weak WT31 reactivity (WT31$^{dull}$, suggestive of TCRγδ expression. Exposure of PBMC to WT31 and FITC-goat anti-mouse Ig revealed a population of heterogeneously intense WT31+cells ranging from WT31$^{dull}$ to WT31$^{bright}$ green staining. Staining of PBMC with biotinylated anti-TCRδ1 followed by PE-streptavidin revealed staining of the TCRγδ+lymphocyte population in red. However, two color staining using both of these mAb not only revealed two distinct populations, but also, that all TCRγδ+weakly react with WT31. This result was confirmed by similar two color cytofluorographic analysis of PBMC with anti-CD3 and WT31 which revealed two distinct CD3+populations: one that is weakly reactive with WT31 and another more strongly stained with WT31 and clearly double positive for WT31 and CD3. Concomitant staining of PBMC with anti-CD3 in red and with both WT31 and anti-TCRδ1 in green revealed one double-stained population, indicating that WT31 and anti-TCRδ1 together react with all detectable CD3+lymphocytes. This type of analysis was carried out on PBL samples from 16 different individuals with similar results indicating that WT31 and anti-TCRδ1 together reacted with all CD3+cells in peripheral blood. Taken together, the analysis of individual T cell lines and clones known to use different TCRδ gene segments and the mAb reactivity with all WT31− or WT31$^{dull}$ cells in peripheral blood, argue strongly that the anti-TCRδ1 mAb reacts with a framework determinant present on all TCRγδ bearing lymphocytes.

14.2.2 The Number and Phenotype of γδTCR Lymphocytes in Peripheral Blood and Spleen The proportion of anti-TCRδ1+cells ranged between 0.5 and 16.3% (mean 4.9%) of CD3+PBL in 26 of 29 donors studied. Serial measurements performed on some individuals revealed that the percentages of anti-TCRδ1+PBL did not appear to fluctuate with time and remained nearly constant over a period of at least 6 months. In 3 of 29 samples anti-TCRδ1 reactivity was below the limit of detection by cytofluorography (i.e., they contained <0.5% reactive cells). However, in at least some of these individuals, TCRγδ+cells were successfully cloned from peripheral blood suggesting that even when undetectable by cytofluorographic staining, γδTCR bearing cells appeared to be present in all individuals.

Anti-TCRδ1+PBL have been further examined by two and three color cytofluorographic analysis for the expression of other cell surface molecules relevant to T cell function and differentiation, for example, CD7, CD2, CD5' CD1, CD4, CD8, IgG Fc-receptors (CD16), CR3 receptor (CD11b), the NK cell marker Leu 7, the monocyte/macrophage determinant CD14 and the B cell antigen CD19 (Table IV). For technical reasons, this analysis was performed on PBMC samples obtained from 12 different subjects containing >2% TCRγδ+cells among their CD3+PBL. In 5 of 5 samples all anti-TCRδ1+PBL were CD7+, CD5+ and CD2+, although CD5 expression by these cells was 5-fold less than on TCRαβ lymphocytes. CD1 was consistently absent from TCRγδ+PBL. Although not emphasized previously in 3 of 7 individuals examined, ~1-4% of the anti-TCRδ1+cells expressed CD4 (FIG. 13a,b). In contrast, in 7 of 7 individuals, a sizable portion (~10-70%) of anti-TCRδ1+lymphocytes expressed CD8, however at lower levels than on TCRαβ cells (FIG. 13c,d). In 1 of 5 subjects, ~10% of anti-TCRδ1+cells coexpressed low levels of CD16, and in 5 of 5 subjects CD11b (CR3) was present in low amounts on ~50% anti-TCRδ1+cells. However, precise quantitation was difficult due to the low amounts of CD16 and CD11b expression. The same was true for the expression of the Leu 7 antigen by some anti-TCRδ1+reactive lymphocytes in 3 of 5 individuals. Anti-Leu M3 (CD14) and anti-Leu12 (CD19) did not stain any peripheral TCRγ1+cells. Furthermore these cells did not express IL-2R and HLA-DR while the T cell antigen CD28 which is expressed by virtually all TCRαβ+cells and is involved in T cell activation was expressed on 50% of anti-TCRδ1+cells in 5 of 5 individuals studied. The phenotype of TCRγδ bearing lymphocytes is summarized in Table IV, supra.

TCRγδ+splenocytes comprised between >0.5 and 15% of CD3+cells in the organ and their phenotype was similar to TCRγδ+PBL.

15. THREE T CELL ANTIGEN RECEPTOR γδ ISOTYPIC FORMS RECONSTITUTED BY PAIRING OF DISTINCT TRANSFECTED γTCR CHAINS WITH A SINGLE δTCR SUBUNIT

As described in the example herein, the role of the γTCR polypeptide in the formation of the γδ heterodimer was explored. We examined by transfection the γδTCR complexes formed by the association of γTCR chains corresponding to the three γTCR forms (Forms 1, 2abc, and 2bc) with a single resident δTCR chain. γTCR DNA encoding either Form 1 or Form 2abc of the γTCR polypeptide was transfected into the MOLT-13 cell line, which constitutively expresses a γδ heterodimer comprised of form 2bc γTCR polypeptide noncovalently associated with δTCR polypeptide. Transfected cells were capable of expressing, together with the γδTCR characteristic of the MOLT-13 cell line, γδ heterodimers comprised of either Form 2abc γTCR noncovalently associated with δTCR or Form 1 γTCR covalently linked to δTCR. Furthermore, the glycosylation of the transfected γTCR gene products was identical to the glycosylation of these genes in their native cell lines. Thus, the degree of glycosylation and the ability to form disulfide linkages are properties determined by the γTCR gene. γTCR constant region CII exon usage determines not only the presence or absence of disulfide linkage between TCR γ and δ polypeptides, but also the amount of carbohydrate attached to the γTCR chain, which is largely responsible for the differences in size of the cell surface γTCR proteins.

15.1. Materials and Methods

15.1.1. Cell Lines

MOLT-13, a TCR γδ+T leukemia cell line (Section 8, supra), and peripheral blood derived TCR γδ+cell lines PBL C1 and IDP2 were cultured as previously described.

15.1.2. Antibodies

The monoclonal antibodies (mAb) used were: Anti-leu-4 (anti-human CD3; IgG1) (Ledbetter, J. A. et al., 1981, J. Exp. Med. 153:310 323), anti-TCRδ1 (anti-human TCRδ chain constant region; IgG1) (See Section 9; Band, H., et al., 1987, Science 238:682–684), anti-Ti-γA (anti-Vγ2; IgG2a) (Jitsukawa, S., et al., 1987, J. Exp. Med. 166:1192–1197), anti-Cγm1 (anti-human γTCR contant region; see Section 11.1.7), p3 (IgGI secreted by the p3×63Ag8 myeloma) (Koehler, G., and Milstein, C., 1975, Nature 256:495–497), and 187.1 (rat anti-mouse λ light Chain-specific) (Yelton, D. E., et al., 1981, Hybridoma 1:5–11).

15.1.3. Isolation and Sequencing of Molt-13 δTCR cDNA Clones

A complementary DNA (cDNA) library prepared from MOLT-13 poly A+RNA in the vector λgt10 (Huynh, et al., 1985, in DNA Cloning, ed. Glover, D. M. (IRL Press, Oxford), Volume 1, pp. 49–78) was screened by hybridization with $^{32}$P-labeled human γTCR cDNA clone IDP2 0-240/38 (See Section 8). Clones were selected for detailed analysis on the basis of size and limited restriction enzyme mapping. Nucleotide sequence was determined in M13 vectors by dideoxy chain termination method (Sanger et al., 1977, Proc. Natl. Acad. Sci. U.S.A. 74:5463–5467) using the modified T7 polymerase (Sequenase, United States Biochemical Corp.) (Potter et al., 1984, Proc. Natl. Acad. Sci. U.S.A. 81:7161–7165).

15.1.4. Construction of Expression Plasmids and Transfections

γTCR cDNAs (PBL C1.15 and IDP2.11r) (Krangel, M. S., et al., 1987, Science 237:64–67) were cloned into pFneo mammalian expression vector (Saito, T., et al., 1987, Nature 325:125–130; Ohashi, P., et al., 1985, Nature 316:606–609) downstream from Friend spleen focus forming virus (SFFV) long terminal repeat (LTR), as shown schematically in FIG. 14B. The plasmid constructs were transfected into MOLT-13 cells by electroporation (Potter, H., et al., 1984, Proc. Natl. Acad. Sci. 81:7161–7165). Transfectants were selected and maintained in medium containing 2 mg/ml of G418 (480 μg/mg solid by bioassay; GIBCO), and cloned by limiting dilution.

15.1.5. Iodination and Immunoprecipitation

Cell surface labeling with $^{251}$I using lactoperoxidase, solubilization in 3-[(3-cholamidopropyl) dimethylammonio] 1-propanesulfonate (CHAPS; Sigma Chemical Co., St. Louis, Mo.), immunoprecipitation with various antibodies, nonequilibrium pH gradient gel electrophoresis (NEPHGE), and SDS polyacrylamide gel electrophoresis (SDS-PAGE) were performed as described (See Section 11.1.3; Brenner, M. B., et al., 1986, Nature 322:145–149; Brenner, M. B., et al., 1987, Nature 325:689–694). Specific immunoprecipitations were carried out with 1 μg anti-leu-4, 0.1 μl anti-TCRδ1 ascites, or 1 μl P3 ascites, together with 150 μl of 187.1 culture supernatant. For anti-T9-γA, 1 μ1 of ascites was used without 187.1.

15.1.6. Biosynthetic Labeling

Exponentially growing cells were incubated for 30 minutes in methionine- and cysteine-free medium followed by a 15 minute pulse labeling at 37° C. with $^{35}$S-methionine and $^{35}$S-cysteine, and immunoprecipitations were carried out as described in Section 11.1.3, supra. Immunoprecipitates were either treated with endoglycosidase-H (endo-H) or were mock-incubated, separated by SDS-PAGE, and visualized by fluorography (Bonner, W. M. and Laskey, R. A., 1974, Eur. J. Biochem. 46:83–88).

15.2. Results

We investigated the products resulting from association of structurally distinct γTCR gene products with a single δTCR protein in order to demonstrate the role of the γTCR gene, and in particular the TCR CII exons, in determining the structural differences between various γTCR isotypes. For this purpose, MOLT-13, a T leukemia cell line that expresses the 40 kD nondisulfide-linked γTCR polypeptide (Form 2bc), was used as a recipient for γTCR chain cDNA clones corresponding to the other two forms of the receptor (Forms 1 and 2abc). Complete sequences of the cDNA clones representing these γTCR chains are described in FIG. 10 (Form 2bc), and in Krangel et al. (1987, Science 237:64–67) (Forms 1 and 2abc) and they are schematically represented in FIG. 14A.

15.2.1. A single Functional δTCR Chain is Present in the Molt-13 Cell Line

δTCR gene rearrangement studies of the MOLT-13 cell line (see Section 8) suggested that only a single functional δTCR gene product was expressed in this cell line. However, to demonstrate directly that a single functional transcript for δTCR is made in MOLT-13 cells, cDNA clones cross-hybridizing with a δTCR cDNA probe (Section 8) were isolated from a MOLT-13 cDNA library prepared in λgt10 and the sequence of selected cDNA clones was determined. This analysis revealed that MOLT-13 cells express transcripts corresponding to one functionally rearranged and one aberrantly rearranged δTCR gene. The cDNA clone corresponding to the functionally rearranged δTCR gene has the same V (Vδ1), J (Jδ1, and C gene segments described earlier for the IDP2 cell line (see Section 8, supra). The MOLT-13 δTCR cDNA clone, however, possesses a distinct nucleotide sequence between the V and J gene segments arising from D segment utilization (MOLT-13 probably uses only Dδ2), imprecise joining, and N-region diversity at the V-D and D-J junctions (see Section 8). The MOLT-13 δTCR cDNA also predicts a cysteine residue in the membrane proximal connector region of the constant gene segment that would be available for disulfide linkage to γTCR gene products that utilize the Cγ1 gene segment. Although the MOLT-13 cell line expresses a nondisulfide-linked γ,δTCR receptor, the presence of a cysteine residue in the membrane proximal connector region of its δTCR chain leaves open the possibility that this δTCR subunit might be capable of participating in either a nondisulfide-linked or a disulfide-linked complex.

15.2.2. γTCR Gene Product Determines the Form of the Receptor

The MOLT-13 cells transfected with γTCR cDNA constructs were abbreviated as M13.PBL C1γ (for MOLT-13 cells transfected with PBL C1-derived γTCR cDNA) and M13.IDP2γ (for MOLT-13 cells transfected with IDP2-derived γTCR cDNA). The bulk transfectant cell lines and representative subclones derived from these lines were analyzed by Northern blot analysis with γTCR (VJC) or Vγ2-specific cDNA probes. In addition to the resident 1.6 kb MOLT-13 γTCR transcript, a second γTCR transcript initiating in the SFFV LTR of the expression plasmid) was observed in transfectant lines and their clones. The 1.8 kb transcript specifically hybridized with a Vγ2 probe that does not cross-hybridize with the Vγ1.3 present in the resident MOLT-13 γTCR transcript, and thus the 1.8 kb transcript represents the transcript of the transfected γTCR cDNAs (which utilize a Vγ2 segment).

Figures 15A, 15B, 15C:
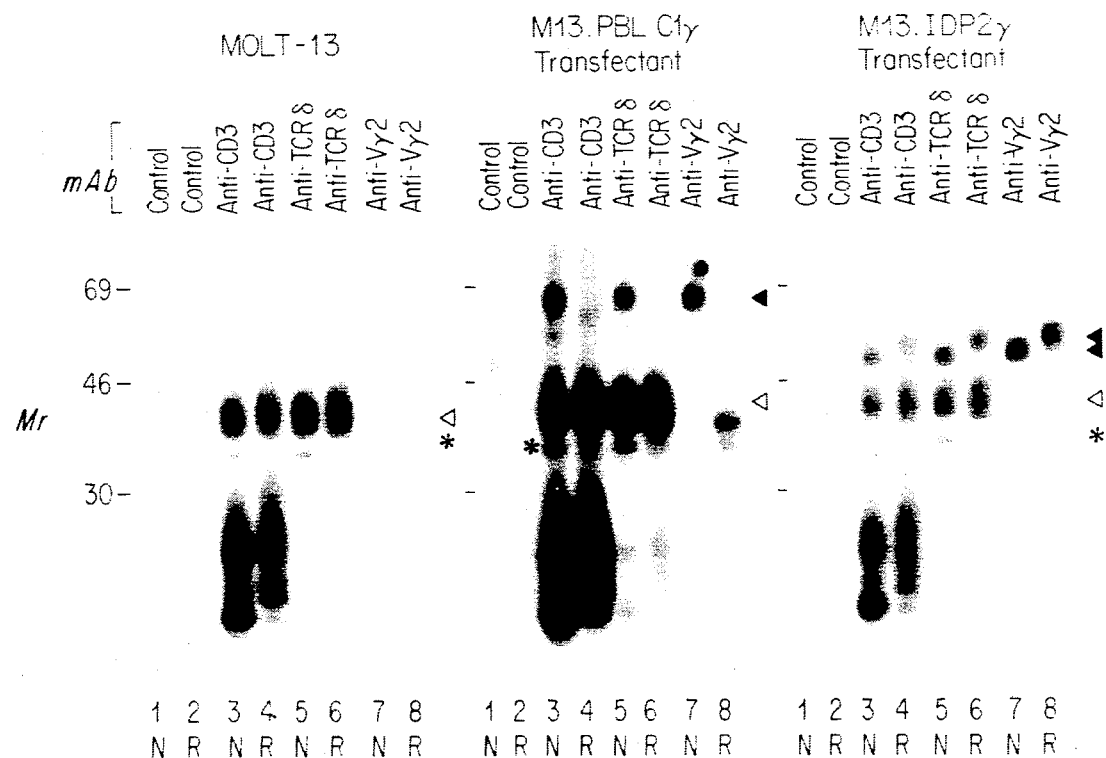
Figures 15D, 15E:
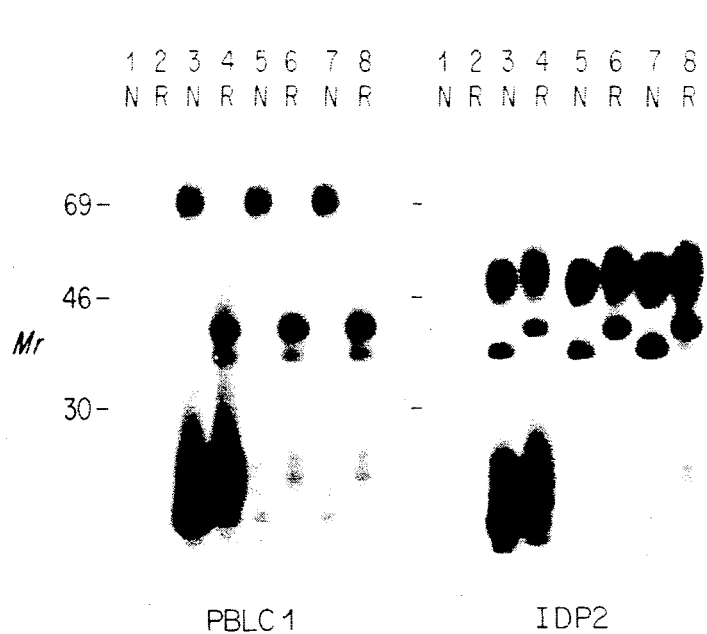

To biochemically characterize the γTCR protein(s) expressed on the surface of the transfectants, a representative clone derived from each line was analyzed by immunoprecipitation of surface iodinated cells with P3 (control), anti-leu-4 (anti-CD3), anti-TCRδ1 (anti-δTCR), or anti-Ti-γA mAbS. Anti-Ti-γA (Jitsukawa, S., et al., 1987, J. Exp. Med. 166:1192–1997) appears to specifically recognize the γ,δTCR cells that utilize the Vγ2 gene segment as the variable portion of their γTCR chains. Untransfected (FIG. 15A) as well as the transfected MOLT-13 cells (FIG. 15B and 15C) express the expected parental γTCR (40 kD; see open arrow) and δTCR subunits (see asterisk). Note that anti-Vγ2-specific mAb (anti-Ti-γA) fails to react with the resident MOLT-13 γTCR chain (FIG. 15A, lanes 7 and 8). Anti-CD3 immunoprecipitates of M13.PBL C1γ transfectant cells revealed an additional CD3-associated species (68 kD) when examined under nonreducing conditions (FIG. 15B, lane 3, see solid arrow). On both PBL C1 cells (FIG. 15D, lanes 3 and 4) and the M13.PBL C1γ transfectant cell line (FIG. 15B, lanes 3 and 4), the 68 kD complex yielded 40 and 36 kD species upon reduction (in the case of the M13.PBL C1γ transfectant, these bands are clearly visualized in the anti-Vγ2 immunoprecipitate, see FIG. 15B, lanes 7 and 8, solid arrows). These 40 and 36 kD species represent differentially glycosylated γTCR polypeptides. In these immunoprecipitates, the δTCR chain (40 kD reduced) comigrates with the 40 kD γTCR polypeptide and is therefore not visualized (however, see below).

Importantly these experiments show that the resident δTCR chain of the MOLT-13 cell line, normally part of a nondisulfide-linked complex, associates with the PBL C1 γ TCR protein to form a disulfide-linked γ,δTCR heterodimer in the transfectant cell line. In contrast, the IDP2-derived γTCR protein (55 kD) in the M13.IDP2 transfectant cell line formed a nondisulfide-linked complex with the resident MOLT-13 δTCR chain (FIG. 15C, lanes 3 and 4). Immunoprecipitates carried out with anti-TCRδ1 mAb (specific for δTCR peptide) confirmed that the endogenous (FIGS. 15A, D and E, lanes 5 and 6) as well as the transfected γTCR chains (FIG. 15B and C, lanes 5 and 6) from all these cell lines were associated directly with the δTCR chain. Anti-Ti-γA specifically immunoprecipitated the 68 kD disulfide-linked γ,δTCR heterodimer from the M13.PBL C1 transfectant cells (FIG. 15B, lanes 7 and 8), and the 55 kD γTCR chain, along with the 40 kD γTCR chain, from the M13.EDP2γ transfectant cells (FIG. 15C, lanes 7 and 8), confirming that the γTCR chains that are part of these complexes correspond to the transfected PBL C1 and IDP2-derived cDNAs, respectively.

To further characterize the various γTCR proteins biochemically, two-dimensional (2D) gel analyses (NEPHGE followed by SDS-PAGE) of surface $^{125}$I-labeled cells were carried out. Superimposition of the 2D patterns of resident (MOLT-13) and transfected (PBL C1 or IDP2) γTCR chains relative to the positions of the CD3 components allowed comparison of the relevant γTCR species. In the immunoprecipitates from MOLT-13 cells, the γTCR chains resolved as two discrete parallel series of iodinated species. MOLT-13 cells transfected with the PBL C1 or the IDP2 TCR cDNAs revealed the resident MOLT-13 γTCR polypeptide series, but in addition, showed radiolabeled species that were identical in 2D gel patterns to the γTCR polypeptides of PBL C1 or IDP2 cells, respectively. Thus, the 2D gel biochemical analyses confirmed that the transfected γTCR chains were expressed and processed similarly in MOLT-13 transfectants and in the parental cell lines, PBL C1 and IDP2.

15.2.3. Polypeptide Backbone Sizes of the Transfected γTCR Chain Proteins

The peptide backbone sizes of the transfected γTCR chains were determined by endoglycosidase-H treatment of the material immunoprecipitated from metabolically pulse-labeled cells. Immunoprecipitates carried out with anti-Cγm1 (specific for γTCR chain) identified 35.5 and 34 kD species in untransfected MOLT-13 cells (FIG. 16, lane 4) that represent endogenous MOLT-13 γTCR polypeptides. The smaller of these two polypeptides (see open arrows) corresponds to the expected polypeptide core size of the MOLT-13 γTCR polypeptide, whereas the larger polypeptide appears to represent a partially processed intermediate. In addition to these resident MOLT-13 γTCR polypeptides, a polypeptide with a deglycosylated size of 41 kD was immunoprecipitated by anti-Cγm1 from the M13.IDP2γ transfectant, (FIG. 16, lane 8, see solid arrow). The size of this transfectant-specific γTCR polypeptide agrees well with the deglycosylated IDP2 γTCR polypeptide core size determined earlier in IDP2 cells. As expected, M13.PBL C1γ transfectant cells revealed an additional γTCR protein with a deglycosylated size of 32 kD (FIG. 16, lane 12, see solid arrow) which compares well with the γTCR polypeptide backbone size determined for the PBL C1 cell line. This 32 kD species was specifically immunoprecipitated by the Vγ2- specific mAb, anti-Ti-γA (FIG. 16, lane 13, see solid arrow), thereby allowing unambiguous assignment of resident and transfected γTCR species in this cell line. Thus, the determined backbone sizes of the transfected γTCR chains, derived from IDP2 and PBL C1 cell lines, match the backbone sizes of these polypeptides in their parent cell lines. By comparing the γTCR polypeptide core sizes with those of the cell surface proteins, we infer that the MOLT-13, IDP2, and PBL C1 derived γTCR chains carry 6, 14, and 8 kD N-linked carbohydrate, respectively.

15.3. Discussion

Three biochemically distinct forms of the human γδTCR subunit structure occur. In the present work, we show that a single δTCR polypeptide can associate with γTCR chains representing each of the three receptor forms to reconstitute the appropriate γ,δTCR heterodimers. The resident γTCR polypeptide of MOLT-13 (form 2bc) is 40 kD and is noncovalently associated with the δTCR subunit. When the γTCR cDNA clones corresponding to the disulfide-linked receptor of PBL C1 (Form 1), or the 55 kD non-disulfide-linked receptor of the IDP2 cell line (Form 2abc) were transfected into the MOLT-13 cell line, the γδTCR forms corresponding to those found in the cDNA-donor cell lines were reconstituted. The present transfection studies provide direct evidence that disulfide linkage is dictated by γTCR constant segment usage, since the resident MOLT-13 δTCR chain was shown to participate in a disulfide-linked receptor complex with the PBL C1-derived γTCR chain (Form 1), and a nondisulfide-linked receptor complex with the IDP2-derived γTCR chain (Form 2abc).

We have shown that the remarkable difference in size between the 55 kD (Form 2abc) and 40 kD (Form 2bc) non-disulfide-linked γTCR polypeptides is primarily due to different amounts of N-linked carbohydrate attached to the TCR polypeptide backbone (See Section 11.2.2, supra). Thus, either 15 kD (Form 2abc on 1Dp2 or pEER) or only 5 kD (Form 2bc on MOLT-13) of N-linked carbohydrate is attached to these γTCR polypeptides even though the same number (five each) of N-linked glycan acceptor sites are encoded by the constant region gene segments used in both of these forms. Four of these N-linked glycosylation sites are present in or around the CII exon-encoded connector region. In the example herein, we show that the amount of N-linked carbohydrate attached to the transfected γTCR proteins is identical to that seen in their parent cell lines, based on a comparison of peptide core size and mature cell surface size of the protein products of transfected γTCR cDNA clones. Thus, the conformation of the two Cγ2 encoded protein segments must differ sufficiently to result in drastic difference in glycosylation. The major difference between Cγ segments of these two forms is that copy "a" of the CII exon is present in the 55 kD γTCR chain of Form 2abc and it is absent from the 40 kD γTCR chain of Form 2bc. Thus the presence or absence of this CII exon copy may be largely responsible for the glycosylation differences that account for the γTCR polypeptide sizes.

The variation in structure of human γδTCR isotypic forms is unprecedented among T cell receptors as no such parallel is observed in αβTCR.

16. EXAMPLE: DIVERSITY AND ORGANIZATION OF HUMAN T CELL RECEPTOR δ VARIABLE GENE SEGMENTS

Previous studies of the human T cell receptor δ gene identified a single commonly used Vδ segment, denoted Vδ1. In order to better understand the extent of the human δTCR V gene repertoire, TCR transcripts and gene rearrangements were examined in a new panel of cloned human γδTCR lymphocytes. Through this analysis we identified and determined the structures of two new Vδ segments, denoted Vδ2 and Vα These Vδ segments are different from previously characterized Vα segments, supporting the notion that the human Vδ and Vα repertoires are distinct. Examination of Vγ gene segment usage in these cells revealed that the Vδ2 gene segment is used in conjunction with the Vγ2 gene segment. Blot hybridization indicated that the Vδ2 gene segment lies between Vα17.1 and Dδ-Jδ-Cδ, and within 100 kb of the latter. Analysis of genomic clones indicated that the Vδ3 gene segment lies in an inverted orientation, about 2 kb 3' of Cγ. This implies that rearrangement of Vδ3 to Dδ-Jδ-Cδ occurs by inversion. Together with previous mapping studies, these results indicate that human Vδ segments are dispersed, rather than clustered, within the TCR α/δ locus. The analysis of rearrangements in polyclonal thymocyte DNA suggests that there may be a limited number of additional Vδ gene segments yet to be characterized.

16.1. Materials and Methods

16.1.1. γδTCR+Cell Lines

The derivation and characteristics of peripheral blood-derived cell line IDP2 (see Section 6; Brenner et al. 1986, Nature 322:145) and leukemic cell line Molt-13 (Loh et al., 1987, Nature 330:569; Hochstenbach et al., 1988, J.Exp.Med. 168:761) have been described previously. The cloned T cell line WM-4 was derived from umbilical cord blood cells (Alarcon et al., 1987, Proc. Natl. Acad. Sci U.S.A. 84:3861). The T cell clones LB117, LB207, LB213 and LB220 were obtained by stimulating the PBL from a healthy donor with Burkitt's lymphoma cells, followed by cloning using limiting dilution and feeder cell mixtures as described previously (Yssel et al., 1984, J. Immunol. Methods 72:219). The T cell clones were maintained in Yssel's medium and were expanded in IL-2 by weekly stimulation with feeder cells (Yssel et al., supra.)

16.1.2. DNA Probes

The δTCR DNA probes used in this study were as follows: C δ; cDNA O-240 (see Section 8); Jδ1, a 1.7 kb genomic XbaI fragment (id.); Jδ3, a 1.1 kb BamHI-XbaI genomic fragment (previously called Jδ2) (id.); Vδ1, a 300 bp EcoRI-ScaI fragment of cDNA O-240/47 (id.); Vδ2, a 430 bp EcoRI-NcoI fragment of cDNA LB117δ(1-7); and Vδ3, a 435 bp EcoRI-TaqI fragment of cDNA WM14δ(2-1). The γTCR DNA probes used in this study were as follows: Jγ1.3/2.3, an 800 bp Jγ1.3 genomic HindIII-EcoRI fragment (Quertermous et al., 1987, J. Immunol. 138:2687); Vγ1, a 350 bp EcoRI-KpnI fragment of Vγ1.3 cDNA M13k (Hochstenbach et al., 1988, J. Exp. Med. 168:761); Vγ2, a 445 bp EcoRI-AccI fragment of cDNA PBLC1.15 (Krangel et al., 1987, Science 237:64); Vγ3, a 300 bp EcoRI fragment of cDNA pTγ15; Vγ4, a 400 bp SspI-EcoRI fragment of rearranged genomic clone pTγR4 containing both V and J sequences. Fragments were purified through low gelling temperature agarose and labelled to high specific activity by the random priming method (Feinbert et al., 1983, Anal. Biochem. 132:6).

16.1.3. Preparation and Blot Hybridization Analysis of RNA and DNA Samples Total cellular RNA and high molecular weight genomic DNA were prepared from a single frozen pellet of approximately $5 \times 10^7$ cells in each instance. Cells were lysed for RNA preparation by the urea-lithium chloride method (Auffray et al., 1980, Eur. J. Biochem. 170:303). 90% of the lysate was sheared and used for RNA preparation, whereas 10% of the lysate was diluted into 15 volumes of 15 mM NaCl/10 mM Na$_2$EDTA/10 mM Tris HCl, pH 8.0/0.4% SDS/100 µg/ml proteinase K and used for the preparation of genomic DNA (Wigler et al., 1979, Cell 16:777). Yields averaged 85 µg RNA and 50 µg DNA.

RNA was electrophoresed through 1.5% agarose gels containing 2.2 M formaldehyde (Lehrach et al., 1977, Biochem. 16:4743) and was then blotted onto and UV-crosslinked to Hybond-N membranes (Amersham), according to the manufacturer's instructions. Genomic DNA was digested with the appropriate restriction enzyme, electrophoresed through 0.7% agarose gels, and was similarly blotted onto and UV-crosslinked to Hybond-N membranes. Filters were prehybridized at 50° C. and hybridized at 42° C. in 50% formamide/4.8×SSC/5×Denhardt's/0.5% SDS/200 µg/ml boiled salmon sperm DNA/50 mM Hepes pH 7.0. High stringency washes were in 0.1×SSC/0.1% SDS at 50° C. for Northern blots and at 60° C. for Southern blots. Blots were stripped prior to reprobing by incubation for 1-2 hours at 68° C. in the prehybridization solution.

16.1.4. cDNA Library Construction and Analysis cDNA libraries containing 200,000 to 300,000 recombinants were constructed from LB117 RNA, WM14 RNA, and a mixture of LB207, LB210 and F7 RNA. Poly-A+RNA prepared from approximately 80 µg total RNA was converted to double stranded cDNA using AMV Reverse Transcriptase, Klenow, Mung Bean Nuclease, and EcoRI Methylase. EcoRI linkered, size fractionated cDNA was cloned into the EcoRI site of the vector λgt10 (Huynh et al., 1985, in DNA Cloning, A Practical Approach, Vol. I., Glover, D. M., ed., IRL Press, Oxford, p. 49). Following screening with the appropriate probes, the 5' EcoRI fragments (FJC$_\delta$) of positive clones and subfragments thereof were subcloned into either Bluescript (Stratagene) or M13mp18, and nucleotide sequences were determined on both strands by the dideoxy chain termination method (Sanger et al., 1977, Proc. Natl. Acad. Sci. U.S.A. 74:5463; Biggin et al., 1983, Proc. Natl. Acad. Sci. U.S.A. 80:3963) using modified T7 polymerase (Tabor and Richardson, 1987, Proc. Natl. Acad. Sci. U.S.A. 84:4767; Sequenase, U.S. Biochemicals).

16.1.5. Analysis of Genomic Clones

An 11 kb BamHI-KpnI fragment carrying the 3' portion of Vδ3, and a 3 kb KpnI-BamHI fragment carrying the 5' portion of Vδ3 were isolated from cosmid K7A and subcloned into Bluescript. Sequences were determined by the dideoxy chain termination method using double stranded templates and exonuclease III generated deletions (Chen et al., 1985, DNA 4:165; Henikoff, 1984, Gene 28:351; Erase-a-base System, Promega Biotec) according to the manufacturer.

16.2. Results

16.2.1. Two Novel Human Vδ Segments

In previous studies it was shown that the TCR γδ peripheral blood T cell lines IDP2, PBL C1 and PBL L1, and the leukemic T cell lines PEER and Molt-13 all displayed functional rearrangements using the Vδ1 and Jδ1 gene segments (see Section 8; Hata et al., 1987, Science 238:687; Loh et al., 1987, Nature 330:569; Hata et al., 1988, Science 240:1541; see Section 17, infra). In order to identify TCR T cell lines using distinct Vδ segments, RNA samples from a panel of seven γδTCR lymphocyte peripheral blood clones were examined by blot hybridization using Vδ1 and δ probes. As in RNA from the previously studied IDP2 cell line, a Cδ probe revealed TCR δ RNA species indicative of differentially polyadenylated transcripts arising from fully rearranged genes (2.2 and 1.3 kb) in all cell lines (FIG. 17A). In addition, this probe detected differentially polyadenylated transcripts arising from partially or unrearranged genes (1.7 and 0.8 kb) in some cell lines. However, aside from IDP2 RNA, only a single cell line (F7) revealed transcripts (2.2 and 1.3 kb) detected by a Vδ1 probe (FIG. 17B). The remaining cell lines (LB117, LB207, LB210, LB213, LB220, WM14), which expressed full length Vδ1 negative transcripts of 2.2 and 1.3 kb, were presumed to be using distinct Vδ gene segments.

In order to determine whether the Vδ1 negative cell lines all employed the same novel Vδ segment, XbaI digests of genomic DNA samples were analyzed by blot hybridization using Jδ1 and Jδ3 probes (FIG. 18A, B). The Jδ1 probe detects a single germline fragment of 1.7 kb in SB (B cell) and HL60 (myeloid cell), and two rearrangements in the γδTCR cell lines IDP2 and Molt-13. Of these rearrangements, the 6.4 kb fragment shared by IDP2 and Molt-13 represents rearrangement to Vδ1 (see Section 17, infra). The 2.9 kb rearrangement in IDP2 is quite common, and is thought to represent either D-J or D-D-J, whereas the 7.2 kb rearrangement in Molt-13 has not been detected elsewhere. As expected, the Vδ1 positive cell line F7 shares the 6.4 kb Vδ1-Jδ1 rearrangement with IDP2 and Molt-13. On the other hand, the Vδ1 negative cell lines display three distinct Jδ1 rearrangements, two of which (4.2 kb and 1.9 kb) had not been observed previously. These were presumed to reflect rearrangement to two novel Vδ segments, designated Vδ2 (4.2 kb) and Vδ3 (1.9 kb).

Based upon the above assignments, neither LB207 nor LB213 carries a functional Jδ1 rearrangement. We have previously described a distinct Jδ segment (Jδ2) that is homologous to the murine Jδ2 element and is located about 10 kb 3' of Jδ1. Since it is now clear that an additional J segment lies between these two J segments (Takihara et al., 1988, Proc. Natl. Acad. Sci. U.S.A. 85:6097; Boehm et al., 1988, EMBO J. 7:385), it seems appropriate to rename the most 3' Jδ segment as Jδ3. Our Jδ3 probe detects a 5.0 kb germline XbaI fragment that carries both Jδ2 and Jδ3, and therefore should detect rearrangements to either of these Jδ segments. Notably, the Jδ3 probe detects a 3.4 kb rearrangement specific to LB207 and LB213, indicating the likelihood of functional rearrangement to either Jδ2 or Jδ3 in these cell lines. Based upon the disposition of XbaI sites flanking Jδ1, Jδ2 and Jδ3, we predicted that in these instances Jδ3 had rearranged to the same V segment (Vδ2) identified by the 4.2 kb Jδ1 rearrangement.

In order to confirm these interpretations and characterize the novel V segments, we generated cDNA libraries from LB117 and from WM14 poly-A+RNA. Using a Cδ probe we identified cDNA clones representing the transcripts of the functionally rearranged δTCR gene in each cell line. The nucleotide and deduced amino acid sequences of these cDNA clones are presented in FIG. 19A and B, and the deduced amino acid sequences for the V segments are compared both to each other and to that of $V_\delta 1$ in FIG. 19C. LB117 ($V_\delta 2$) and WM14 ($V_\delta 3$) clearly use $V_\delta$ segments distinct from the $V_\delta 1$ segment and from each other. Both cDNAs display potential contributions from the $D\delta 1$ and $D\delta 2$ elements as well as from N-region nucleotides within the junctional region, both utilize the $J_\delta 1$ segment, and both maintain an open reading frame across the V-D-D-J junction.

The $V_\delta 1$, $V_\delta 2$ and $V_\delta 3$ gene segments are all distinct from previously reported $V\alpha$ segments, further supporting the notion that the human $V\alpha$ and $V\delta$ repertoires are distinct. Furthermore, they display only low levels of amino acid sequence identity with each other, matching at 23-33% of the residues in various pairwise comparisons (FIG. 19C). Nevertheless there are striking homologies with particular murine $V_\delta$ segments (FIG. 19C). For example, human $V_\delta 1$ matches a member of the murine $V_\delta 6$ family at 58% of the residues, and human $V_{67}3$ matches murine $V_\delta 5$ at 66% of the residues (Elliot et al., 1988, Nature 331:627). Such high levels of interspecies sequence conservation despite low levels of intraspecies sequence conservation most probably indicate that these pairs of V segments have evolved from distinct ancestral V segments whose existence predates the divergence of mouse and man. Similar observations have been made for particular human and murine $V\beta$ (Lai et al., 1988, Nature 331:543) and $V\gamma$ (Pelkonen et al., 1987, EMBO J. 6:1941) gene segments.

16.2.2. Rearrangement and Expression of δTCR and γTCR Gene Segments

In order to further characterize the δTCR rearrangements in the remaining γδTCR cell lines in the panel, $V_\delta 2$ and $V_\delta 3$ specific probes were generated and were used to probe both Northern blots (FIG. 17C, D) and Southern blots (FIG. 20A, B). All $V_\delta 1$ negative cell lines expressed either $V_\delta 2$ or $V_\delta 3$ transcripts, although one cell line, LB210, expressed both. The $V_\delta 2$ gene segment was found on a 3.7 kb germline XbaI fragment that was rearranged either to a 4.2 kb fragment (corresponding to rearrangement to $J_\delta 1$) or to a 3.4 kb fragment (corresponding to rearrangement to $J_\delta 2$ or $J_\delta 3$). The $V_\delta 3$ gene segment was found on a 9.4 kb germline XbaI fragment that was rearranged to a 1.9 kb fragment (corresponding to rearrangement to $J_\delta 1$) in two cell lines. As expected from the analysis of Northern blots, LB210 displayed rearrangements of both $V\delta 2$ and $V\delta 3$. An additional $V\delta 3$ rearrangement of approximately 1.0 kb, not detected by $J_\delta 1$ and $J_\delta 3$ probes, may reflect rearrangement of $V_\delta 3$ to Dδ. Such V-D rearrangements have been documented for murine δTCR (Chien et al., 1987, Nature 330:722).

In order to determine which of the two rearrangements ($V_\delta 2$ or $V_\delta 3$ to $J_\delta 1$) in LB210 was productive, and which of the $J_\delta$ segments ($J_\delta 2$ or $J_\delta 3$) was rearranged to $V_\delta 2$ in LB207, a cDNA library generated from RNA of both cell lines was screened with a $V_\delta 2$ cDNA probe, as well as with $J_\delta 1$ and $J_\delta 3$ specific oligonucleotide probes. Two cDNA clones that used the $V_\delta 2$ segment along with either $J_\delta 1$ (LB210) or $J_\delta 3$ (LB207) were characterized. Their nucleotide and deduced amino acid sequences are presented in FIG. 19A. Both cDNA clones maintain an open reading frame across the V-D-D-J junction and thus they represent the functional transcripts in the respective cell lines. Thus in LB210, which displays both $V_\delta 2$ and $V_\delta 3$ rearrangements and transcripts, the $V_\delta 2$ rearrangement is productive. Further, in LB207, and likely in LB213, productive rearrangements of $V_\delta 2$ to $J_\delta 3$ have occurred. This is the first evidence for functional utilization of the human $J_\delta 3$ element.

We assessed $V_\gamma$ and $J_\gamma$ segment usage within this panel by analyzing Northern blots with $V\gamma 1$ family, $V\gamma 2$, $V\gamma 3$, and $V\gamma 4$ probes (FIG. 17 E, F, G, and H, respectively) and Southern blots of KpnI digested genomic DNA with $J\gamma 1.3/2.3$ and $V_\gamma 2$ probes (FIG. 21 A and B, respectively; nomenclature according to Strauss et al., 1987, Science 237:1237 and Quertermous et al., 1987, J. Immunol. 138:2687). As shown by Huck and Lefranc (1987, FEBS Lett. 224:291), the linkage of human $J\gamma$ segments predicts that a $J\gamma 1.3/2.3$ probe can detect all γTCR gene rearrangements in KpnI digests of human genomic DNA. Additional analysis using a $V\gamma 2$ probe served to specifically identify $V\gamma 2$ rearrangements, and further, to distinguish between rearrangements to $V\gamma 1$ and $V\gamma 3$, since the germline $V\gamma 2$ gene segment would be deleted upon rearrangement of $V\gamma 1$ gene segments, but retained upon rearrangement of $V\gamma 3$.

All cell lines within the panel displayed two $J\gamma$ rearrangements (FIG. 21A). In some cases Northern blots allowed an assessment of which rearrangement was productive, since only one transcript was detected (FIG.21E,F,G,H). Further, cells that had productively rearranged the $V\gamma 2$ gene segment could be identified using the mAb anti-TiγA, which specifically stains the surface of lymphocytes using this V segment (Triebel et al., 1988, J. Exp. Med. 167:694). All cells that displayed a $V\gamma 2$ to $J\gamma$ rearrangement were found to be TiγA+ by surface fluorescence. As a result, unambiguous assignment of the productive rearrangement could be made in most instances.

A summary of the $V\gamma$ and $V\gamma$ transcripts and $J\gamma$ and $J_\delta$ rearrangements detected in all of the clonal cell lines that we have examined so far is presented in Table V.

TABLE V*

| | δTCR | | | | δTCR | | | |
|---|---|---|---|---|---|---|---|---|
| | Rearrangements | | Transcripts | | Rearrangements | | Transcripts | |
| Cell Line | p | n | p | n | p | n | p | n |
| IDP2 | $V_\delta 1$-$J_\delta 1$ | $D_\delta$-$J_\delta 1$ | $V_\delta 1$ | — | $V_\gamma 2$-$J_\gamma 2.3$ | $V_\gamma 3$-$J_\gamma 1.1$ | $V_{65}2$ | ($V_\gamma 3$) |
| PBL C1 | $V_\delta 1$-$J_\delta 1$ | $D_\delta$-$J_\delta 1$ | $V_\delta 1$ | — | $V_\gamma 2$-$J_\gamma 1.3$ | ND | $V_{65}2$ | ND |
| MOLT-13 | $V_\delta 1$-$J_\delta 1$ | ?-$J_\delta 1$ | $V_\delta 1$ | — | $V_\gamma 1.3$-$J_\gamma 2.3$ | $V_\gamma 1$-$J_\gamma 1.1$ | $V_{65}1$ | ND |
| PEER | $V_\delta 1$-$J_\delta 1$ | deletion | $V_\delta 1$ | — | $V_\gamma 1.8$-$J_\gamma 2.3$ | $V_\gamma 2$-$J_\gamma 2.3$ | $V_{65}1$ | $V_\gamma 2$ |
| LB117 | $V_\delta 2$-$J_\delta 1$ | $D_\delta$-$J_\delta 1$ | $V_\delta 2$ | — | $V_\gamma 2$-$J_\gamma 1.2$ | $V_\gamma 1$-$J_\gamma 2.1$ | $V_{65}2$ | — |
| LB207 | $V_\delta 2$-$J_\delta 3$ | $D_\delta$-$J_\delta 1$ | $V_\delta 2$ | — | $V_\gamma 2$-$J_\gamma 1.3/2.3$ | $V_\gamma 1$-$J_\gamma 1.3/2.3$ | $V_{65}2$ | — |
| LB210 | $V_\delta 2$-$J_\delta 1$ | $V_\delta$-$J_\delta 1$ | $V_\delta 2$ | ($V_\delta 3$) | $V_\gamma 2$-$J_\gamma 1.2$ | $V_\gamma 3$-$J_\gamma 1.3/2.3$ | $V_{65}2$ | $V_{65}3$ |
| LB213 | $V_\delta 2$-$J_\delta 3$ | | $V_\delta 2$ | — | $V_\gamma 2$-$J_\gamma 1.2$ | $V_\gamma 3$-$J_\gamma 1.1$ | $V_{65}2$ | ($V_\gamma 3$) |
| LB220 | $V_\delta 2$-$J_\delta 1$ | $D_{67}$-$J_\delta 1$ | $V_\delta 2$ | — | ND | ND | $V_{65}2$ | $V_\gamma 3$ |
| WM14 | $V_\delta 3$-$J_\delta 1$ | $D_{67}$-$J_\delta 1$ | $V_\delta 3$ | — | [$V_\gamma 1$-$J_\gamma 1.3/2.3$] | [$V_\gamma 1$-$J_\gamma 1.1$] | $V_{65}1$ | — |

TABLE V*-continued

| | δTCR | | | | δTCR | | | |
|---|---|---|---|---|---|---|---|---|
| | Rearrangements | | Transcripts | | Rearrangements | | Transcripts | |
| Cell Line | p | n | p | n | p | n | p | n |
| F7 | $V_\delta 1$-$J_\delta 1$ | $V_\delta 1$-$J_\delta 1$ | $V_\delta 1$ | — | $V_\gamma 1$-$J_\gamma 1.1$ | $V_\gamma 4$-$J_\gamma 1.3/2.3$ | $V_\gamma 6$ 1 | — |

*Nomenclature used to denote δTCR gene segments is that of Strauss et al., 1987, Science 237:1237, and Quertermous et al., 1987, J. Immunol 138:2687. The assignments reflect the data obtained in this study as well as in Loh et al., 1987, Nature 330:569 and Hata, 1988, Science 240:1541; see Section 17, infra). The assignment of rearrangements and transcripts as either (p) productive or (n) nonproductive results from a combination of blot hybridization data, cDNA sequences, and staining with mAb anti-TiγA. Unambiguous assignment of the productive rearrangement could be made in each case, except for the γTCR rearrangements in WM14, which are bracketed. Vγ1 family segments are denoted explicitly when the information is available from sequence analysis (e.g., Vγ1.8), or simply as Vγ1 when the assignment relies solely on hybridizaton data that does not distinguish Vγ1 family segments from one another. Transcripts detected at very low levels are in parentheses.

All of the cell lines studied appear to productively rearrange one of the three characterized human Vδ segments, and either a Vγ1 family member or Vγ2. A striking finding of this analysis was that all cell lines within the panel that display productive rearrangement of the Vδ2 segment also display productive rearrangement of the Vγ2 gene segment. This relationship is not reciprocal, in that the Vγ2 gene segment is used in conjunction with either Vδ1 or Vδ2. The Vγ2- Vδ2 cell lines within the panel use either Jγ1.2 (Jγ7γP: 12.0 kb rearrangement) or Jγ1.3/2.3 (7.5 kb rearrangement) (FIG. 21 and Table V) and either Jδ1 or Jδ3, indicating no specific restrictions on J segment utilization. These data may suggest that δTCR chains using the Vδ2 gene segment may only be correctly assembled and expressed on the cell surface in association with γTCR chains using the Vδ2 gene segment. Alternatively, the data may reflect either positive selection for this particular receptor, or negative selection for receptors expressing Vδ2 in conjunction with other Vγ segments.

16.2.3. Additional J 1 Rearrangements in Newborn Thymus DNA

Since we found that there was no evidence for the utilization of additional Vδ segments within this panel of cell lines, we sought to determine whether additional Jδ rearrangements could be detected in XbaI digests of newborn thymus DNA. A total of seven Jδ1 rearrangements were detected in each of two DNA samples. Those of 6.4 kb, 4.2 kb and 1.9 kb correspond to rearrangement to Vδ1, Vδ2 and Vδ3, respectively, whereas that of 2.9 kb corresponds to the common rearrangement (thought to be partial D-J or D-D-J) shared by many cell lines. Of the three remaining Jδ1 rearrangements (8.2 kb, 3.4 kb and 2.4 kb; open triangles), one might reflect the second partial rearrangement (D-J or D-D-J). Thus the Jδ1 probe may detect rearrangements to two or three as yet unidentified V segments. The low frequency of rearrangements by the Jδ3 probe precluded an analysis of rearrangements to the Jδ2 or Jδ3 gene segments in total thymocyte populations. However, these data suggest strongly that the number of frequently rearranged human Vδ segments will not be large.

16.2.4. Spersed Organization of Human Vδ Segments Within the α/δTCR Gene Locus Our initial studies of the genomic organization of the α/δTCR locus revealed that the Vδ1 genomic segment was a large distance from the Cδ locus, with one $V_\alpha$ segment ($V_\alpha 13.1$) immediately 5' of Vδ1, and at least one $V_\alpha$ segment ($V_\alpha 17.1$) between Vδ and Dδ1-Jδ-Cδ. These data indicated that $V_\alpha$ and Vδ segments were interspersed within the locus. In order to determine whether Vδ segments were clustered or dispersed, we determined the locations of the newly identified Vδ2 and Vδ3 segments. As seen in FIG. 18C, the F7 cell line, which has rearranged Vδ1 to Jδ1 on both chromosomes (FIG. 18A,B) has deleted both copies of the Vδ2 gene segment. This places the Vδ2 gene segment in the region between Vδ1, Vδ2 locus. However, whereas the $V_\alpha 17.1$ gene segment appears to map by field inversion gel electrophoresis (FIGE) to the SalI and SfiI fragments carrying Vδ, Vδ2 maps to the SfiI and SalI fragments carrying Dδ-Jδ-Cδ. Thus, Vδ2 lies between $V_\alpha 17.1$ and Dδ-Jδ-Cδ, and must be within 100 bp 5' of the latter (FIG. 22).

It is intriguing that like F7, Molt-13 also has deleted both copies of the Vδ2 gene segment. Molt-13 displays a productive Vδ1 to Jδ1 rearrangement on one chromosome, and an unidentified Jδ1 rearrangement on the other chromosome, with one copy of Vδ1 in the germline configuration (see Section 17, infra). This, together with FIGE mapping suggests that the nonproductive Jδ1 rearrangement in Molt-13 involves an unidentified region mapping between Vδ17.1 and Vδ2.

Unlike Vδ2, the Vδ3 gene segment is not deleted upon rearrangement of Vδ1 to Jδ1 (FIG. 20B), indicating that it does not lie between these gene segments. Further, Vδ3 rearrangements to Jδ1 were detected by a Cδ probe (FIG. 20B,C), indicating that Vδ3 lies extremely close to Cδ. The analysis of cosmid clones spanning the Cδ region demonstrated that Vδ3 lies in an inverted orientation, roughly 2–3 kb 3' of the Cδ segment (FIG. 22). Following subcloning and fine mapping of the KpnI-BamHI fragments spanning this region, the nucleotide sequence of the germline Vδ3 segment was determined (FIG. 23). This analysis revealed a structure typical of other TCR V segments, including separate exons encoding the leader peptide and the main body of the V segment, and heptamer and nonamer recombination signals flanking the 3' end of the second exon, thereby establishing its boundary (FIG. 23). The location and orientation of the Vδ3 segment relative to Cδ is analogous to that described for murine $V_\beta 14$ relative to $C_\beta 2$ (Malissen et al., 1986, Nature 319:28 and implies that rearrangement of Vδ3 occurs by inversion of Dδ-Jδ-Cδ. These data provide further support for the notion that a limited number of human Vδ segments are dispersed throughout the human α/δTCR locus.

16.3. Discussion

Studies have identifed two Dδ segments, three Jδ segments, and one C segment, nested within the αTCR locus, and located just upstream of the $J_\alpha$ region (see Sections 8, 18; Takihara et al., 1988, Proc. Natl. Acad. Sci. U.S.A. 85:6097; Boehm et al., 1988, EMBO J. 7:385; Isobe et al., 1988, Proc. Natl. Acad. Sci. U.S.A. 85:3933; Griesser et al., 1988, Eur. J. Immunol. 18:641). An estimated 50–100 $V_\alpha$ segments are situated in the region 5' of the $D_\delta$, $J_\delta$, $C_\delta$, $J_\alpha$ and $C_\alpha$ segments (Toyonaga and Mak, 1987, Ann. Rev. Immunol. 5:585; Griesser et al., supra). Despite the large number of V segments available for recombination, all productive $\delta$TCR gene rearrangements in previously examined $\gamma\delta$TCR cell lines involve a single V segment, denoted $V_\delta 1$ (see Section 8, supra; Loh et al., 1987, supra; Section 17, infra). This V segment is distinct from previously characterized $V_\alpha$ segments, yet is situated among $V_\alpha$ segments, at least 180 kb 5' of $J_\delta 1$ (see Section 18). These observations suggested a limited repertoire of germline $\delta$TCR gene segments, and a highly controlled rearrangement process that is able to segregate $\delta$TCR and $\alpha$TCR recombinational events and repertoires, despite the interspersion of $\delta$TCR and $\alpha$TCR gene segments.

Our analysis of a larger panel of $\gamma\delta$TCR cell lines has now allowed the identification of two additional $V_\delta$ segments, termed $V_\delta 2$ and $V_\delta 3$. Like $V_\delta 1$, these $V_\delta$ segments are distinct from previously characterized $V_\alpha$ segments. Blot hybridization experiments indicate that $V_\delta 2$ lies within 100 kb 5' of the $C_\delta$ region, and analysis of cosmid clones reveals that $V_\delta 3$ lies roughly 2–3 kb 3 of $C_\delta$. These results clearly demonstrate that $V_\delta$ segments are not present as a discrete cluster within the locus, but rather are dispersed throughout the locus. It follows that the segregation of $V_\alpha$ and $V_\delta$ rearrangements must be mediated by local signals marking particular V segments, rather than long range signals marking large segments of the locus. Such signals might include unique promoter or other elements that could help to modulate the accessibility of particular V segments to recombinases at a specific time in development (Alt et al., 1987, Science 238:107), but probably do not include the heptamer and nonamer recombination signals flanking the V segments, since they are indistinguishable.

Of the three human $V_\delta$ segments characterized, two display quite high amino acid sequence identity with particular murine $V_\delta$ segments. Identity is 58% in a comparison of human $V_\delta 1$ to a murine $V_\delta 6$ family member, and 66% in a comparison of human $V_\delta 3$ to murine $V_\delta 5$. Conservation extends to genomic organization as well, since murine $V_\delta 5$, like human $V_\delta 3$, lies 3' to the $C_\delta$ segment, in an inverted orientation, whereas murine $V_\delta 6$, like human $V_\delta 1$, lies at some distance 5' to $C_\delta$.

The analysis of $J_\delta 1$ rearrangements in newborn thymus DNA supports the likelihood that there may be two or three additional $V_\delta$ segments utilized within this polyclonal population that are not represented within the clonal cell lines that we have examined to date. It is also possible that distinct and novel $V_\delta$ segments may be rearranged at a selective time in thymic development and/or in $\gamma\delta$TCR cells populating distinct sites in the periphery and hence might not be represented in the polyclonal samples we have analyzed.

It is important to note that the vast majority of $J_\delta 1$ rearrangements detected in newborn thymocyte DNA must occur in cells that do not express functional $\gamma\delta$TCR on their surfaces, since only a few percent of the thymocytes in these samples stained with the mAb anti-TCR$\delta$1. Based upon the intensity of the rearrangements relative to control single copy examples in clonal cell lines, we assume that the fraction of thymocytes displaying $J_\delta 1$ rearrangements is much higher. This would argue that the detection of a limited number of $J_\delta 1$ rearrangements could not reflect selection for the expression of functional receptors, but rather must reflect specificity in the rearrangement process per se.

The $\gamma\delta$TCR V segment repertoires appear to be both limited and of similar size in man and mouse. In man, there are at most seven functional $V_\gamma$ segments (in four families), and at least three functional $V_\delta$ segments. In mouse there are six functional $V_\gamma$ segments (in five families) and at least nine functional $V_\delta$ segments (in six families) (Elliot et al., 1988, Nature 331:627). These numbers are significantly lower than those estimated for $\alpha\beta$TCR, which range from 30–100 for each V segment (Toyonaga and Mak, 1987, Ann. Rev. Immunol. 4:529; Kronenberg et al., 1986, Ann. Rev. Immunol. 4:529). Our limited panel analysis suggests that the total number of $V_\gamma$-$V_\delta$ pairs may be limited. Thus, the $\gamma\delta$TCR might interact with a discrete set of putative restricting elements or antigen presenting molecules.

17. EXAMPLE: EXTENSIVE JUNCTIONAL DIVERSITY OF REARRANGED HUMAN T CELL RECEPTOR δ GENES

The human T cell receptor $\delta$ ($\delta$TCR) gene encodes one component of the $\gamma\delta$TCR-CD3 complex found on subsets of peripheral blood and thymic T cells. Human $\delta$TCR diversity was estimated by characterizing rearrangements in $\gamma\delta$TCR cell lines and determining the structures of complementary DNA clones representing functional and nonfunctional transcripts in these cell lines. One $V\delta$ segment and one $J\delta$ segment were identified in all functional transcripts, although a distinct $J\delta$ segment was identified in a truncated transcript. Further, one $D\delta$ element was identified, and evidence for the use of additional $D\delta$ element was obtained. Thus human $\delta$TCR genes appear to use a limited number of germline elements. However, the apparent use of two $D\delta$ elements in tandem coupled with imprecise joining and extensive incorporation of N nucleotides generates unprecedented variability in the junctional region.

17.1. Materials and Methods

17.1.1. Detection of δTCR Gene Rearrangements in γδTCR+Cell Lines

High molecular weight genomic DNA was digested with XbaI, electrophoresed through 0 7% agarose, and transferred to Hybond membranes (Amersham). Filters were probed with appropriate DNA fragments labeled by hexamer priming (Feinberg et al., 1983, Anal. Biochem. 132:6), and were washed with 1×SSC and 0.5% SDS at 23° C. and then with 0.1×SSC and 0.1% SDS at 60° C. SB (B cell line), HL60 (myeloid cell line), and PBMC (fresh peripheral blood mononuclear cells) served as germline controls. Molt-13 and PEER are $\gamma\delta$TCR leukemic cell lines, IDP2 is a long-term IL-2-dependent $\gamma\delta$TCR cell line, and PBL L1 is a oligoclonal IL-2-dependent $\gamma\delta$TCR cell line. Ethidium bromide staining revealed that PBL L1 DNA was overloaded, and PBMC DNA underloaded, relative to the other samples. A phage λ HindIII digest provided molecular weight markers.

17.1.2. Determining the Structure of δTCR V-J Junctional Regions

Lambda gt10 cDNA libraries (Krangel et al., 1987, Science 237:64) were screened with probe IDP2 O-240 (see Section 8, supra), labeled by nick-translation, the 5' EcoRI fragments (extending from the EcoRI linker at the 5' end to the natural EcoRI site 75 bp into the C segment) were subcloned, and their sequences were determined on both strands by the dideoxy chain termination method (Sanger et al., 1977, Proc. Natl. Acad. Sci. U.S.A. 74:5463; Tabor and Richardson, 1987, ibid 84:4767). The sequences proved identical to the V, J, and C sequences of IDP2 δTCR, except in the junctional region. Only the junctional region is shown in FIG. 25. Sequences are aligned in the V and J segments with (—) denoting identities. The boundaries of the germline V and J segments, including heptamer and nonamer recombination signals, are presented. Functional sequences are not aligned. Codon numbering is for IDP2 δTCR (Section 8; Hata et al., 1987, Science 238:678).

17.2. Results and Discussion

In order to investigate the variability of δTCR, we obtained and analyzed cDNA clones representing seven distinct δTCR transcripts from four γδTCR cell lines. These clones displayed use of a single δTCR V segment and a predominant δTCR J segment, suggesting limited germline diversity. However, they showed unprecedented variability in the V-J junctional region.

We used a V-specific probe derived from the IDP2 δTCR cDNA clone O-240/47 (Section 8, supra) to examine δTCR rearrangements in XbaI digests of genomic DNA from five different γδTCR cell lines (FIG. 24A). This probe detects a single germline fragment of 7.5 kb that is rearranged to a 6.2 kb fragment on one chromosome in Molt-13 (Loh et al., 1987, Nature 330:569), IDP2 (see Section 6; Brenner et al., 1986, Nature 322:145), PEER (Weiss et al., 1986, Proc. Natl. Acad. Sci. U.S.A. 83:6998; Brenner et al., 1987, Nature 325:689; Litman et al., 1987, ibid. 326:85), PBL L1 (Brenner et al., 1987, supra) (FIG. 24A) and PBL C1. We also subcloned a genomic fragment encoding the Jδ segment present in the IDP2 δTCR cDNA clone Jδ1). This probe detects a single 1.7 kb germline fragment that is rearranged on both chromosomes in all γδTCR cell lines examined (FIG. 24B). One rearranged band, of 6.2 kb, corresponds exactly to the rearranged fragment detected by the V-specific probe, indicating the rearrangement of a common V segment to a common J segment in Molt-13, IDP2, PEER, PBL L1 (FIG. 24B), and PBL C1. The Jδ1 probe also detects a second rearranged band of 2.7 kb that is shared by IDP2, PBL L1, and PBL C1. By contrast, Molt-13 displays a distinct rearranged fragment of 7.2 kb detected by the Jδ1 probe, whereas PEER displays no detectable second rearrangement and has presumably deleted Jδ1 on this chromosome. The polyclonal γδTCR cell line PBL L1 displays an additional minor Jδ1 rearrangement of 1.8 kb. It is likely that some of the rearrangements detected by the Jδ1 probe reflect partial (D-J and D-D-J) joins on one chromosome.

In order to investigate in more detail the functionally rearranged δTCR genes in these cells, we isolated and characterized cDNA clones encoding the expressed δTCR polypeptides. Nucleotide sequence analysis identified one functional transcript in γδ peripheral blood clone PBL C1, one functional transcript in leukemic γδTCR cell line Molt-13, and two functional transcripts in the oligoclonal γδTCR peripheral blood cell line PBL L1 (PBL L1a and PBL L1b) (FIG. 25A). The V, J, and C segments of these clones are identical to those of previously characterized IDP2 (see Section 8; Hata et al., 1987, supra) and PEER (Loh et al., 1987, supra) δTCR cDNA clones. However, by comparison to the structures of the germline V and J segments (FIG. 25A), the 3' boundaries of the V segment and the 5' boundaries of the J segment vary. Strikingly, the regions between the 3' end of the V segment and 5' end of the J segment range from a few as 9 to as many as 51 nucleotides. The junctional segments are therefore longer, and the variability among sequences more extensive, than is typically observed for other rearranged TCR genes (Toyanaga and Mak, 1987, Ann. Rev. Immunol. 5:585; Kronenberg et al., 1986, Ann. Rev. Immunol. 4:529).

An alignment of the junctional sequences of these cDNA clones as well as of a cDNA clone representing a nonfunctional δTCR transcript in PBL L1 (PBL L1c) and a cDNA clone representing a functional δTCR transcript in PEER cells is presented in FIG. 25B. Although there is a wide variation in the junctional sequences, two discrete blocks of nucleotide homology are apparent. Segments of the sequences CTCCCT and ACTGGGGGATACG appear in most cDNA clones. Because these sequences are shared among the clones, they are likely to be germline encoded and represent at least portions of two distinct Dδ elements. The germline structure of the 3'Dδ element, flanked by conserved heptamer and nonamer recombination signals (Early et al., 1980, Cell 19:981), has been determined (FIG. 25B). This D element conforms to the known properties of δTCR D elements in that it is G-rich, is joined in an imprecise fashion, and is translatable in all three reading frames (Kavaler et al., 1984, Nature 310:421; Siu et al., 1984, Nature 311:344; Clark et al., 1984, Nature 311:387). Two reading frames are actually used among the five functionally rearranged δTCR genes analyzed here (FIG. 25A). The use of a 5' Dδ element is inferred from the sequence conservation noted.

The sequences interspersed between the boundaries of the V, D, and J elements display little identity with each other. Some of these nucleotides may derive from the putative 5, D elements or perhaps from additional D elements. However, most of them almost certainly do not, and therefore likely represent the incorporation of template-independent N region nucleotides, a process thought to be mediated by the activity of terminal transferase (Alt and Baltimore, 1982, Proc. Natl. Acad. Sci. U.S.A. 79:4118). The tentative assignments in FIG. 25B suggest extensive N nucleotide incorporation at multiple sites in the junctional region.

We also identified a cDNA clone representing a second transcript from the Molt-13 cell line (Molt-13t). This cDNA has C sequences identical to those of other cDNA clones but lacks V sequences and thus appears to represent a truncated nonfunctional transcript. Notably, the region immediately 5' of the C segment is related to, although distinct from, the J segment (Jδ1) found in the functional cDNA clones (FIG. 26). The two J sequences display only 53% identity (26/49) at the nucleotide level and 44% identity (7/16) at the amino acid level. Further, the Molt-13t J segment (Jδ2) is 8 bp longer. Despite these differences, Jδ2 differs from the core of most highly conserved TCR J residues (Toyanaga and Mak, 1987, Ann. Rev. Immunol. 5:585) (FG-G[T/S]-L-V; FG-GT-L-V-P for Jα) in only a single position, although this substitution (I for T) is unusual. At its 5' boundary, the Molt-13t Jδ2 sequence is bounded by the consensus heptamer-like sequence TAATGTG. This is separated by 12 bp from the sequence GTTACCTGT, which displays only limited similarity to the consensus nonamer recombination signal GGTTTTTGT (Early et al., 1980, Cell 19:981). A genomic fragment encoding the Jδ2 segment detects a single germline fragment of 5.1 kb that is unrearranged in all γδTCR cell lines examined (FIG. 24C). Since Molt-13 has undergone two different Jδ1 rearrangements, and since the region upstream of the germline Jδ2 segment displays a sequence identical to that of Molt-13t (FIG. 26), the Molt-13t cDNA clone must represent a transcript initiating upstream from Jδ2 on a chromosome that has undergone rearrangement at Jδ1. The lack of rearrangement to Jδ2 in this panel of γδTCR cells may reflect the divergent nonamer-like recombination signal flanking this element.

Heptamer- and nonamer-like elements separated by 23 bp flank the 3' ends of the Vδ segment and the identified Dδ segment, whereas similar elements separated by 12 bp flank the 5' ends of the Dδ and Jα segments. On the basis of the so-called 12/23 rule (Early et al., supra) and the apparent incorporation of two Dδ elements in tandem into the junctional region, the putative 5' Dδ segment would be predicted to be flanked by recombination signals spaced like those of the 3' Dδ element. This arrangement of recombination signals would allow for the incorporation of 0, 1, or perhaps more D elements between the V and J segments, further increasing the potential for diversity at the junction. Indeed, the alignments in FIG. 25B suggest that rearranged δTCR genes in peripheral blood cell lines (IDP2, PBL C1, and PBL L1) incorporate both Dδ elements, whereas those in the leukemic cell lines (PEER and Molt-13) incorporate only the 3' Dδ element.

Our studies indicate that germline human δTCR diversity may be quite limited. That only a single Vδ and Jδ segment are found in all functionally rearranged genes characterized here is unlikely to be due to the selective expansion of certain clones of γδTCR lymphocytes as a result of a common cell source or particular culture conditions, since IDP2, PBL C1, and PBL L1 are peripheral blood cell lines whereas Molt-13 and PEER are leukemic cell lines and all are derived from different individuals. Preliminary characterization of a distinct panel of γδTCR cell lines indicates the use of two additional Vδ segments. However, the repertoire of germline δTCR V and J segments appears to be much closer to that of γTCR than to that of αTCR or βTCR and in fact might be smaller than that of γTCR.

In contrast to be the limited germline diversity indicated by these sequences, the level of δTCR junctional diversity is unprecedented. The apparent incorporation of multiple D elements in tandem distinguishes δTCR from both the βTCR and immunoglobulin heavy chain genes. This feature, in conjunction with imprecise joining, multiple sites of insertion and extensive incorporation of N nucleotides, and translation in multiple reading frames, generates tremendous diversity in a small segment of the polypeptide. This suggests that the δTCR variable domain may form a relatively conserved framework, with a single hypervariable region at the V-D-J junction. Junctional variability appears to be an important factor in γTCR diversity as well. The contrasts between these patterns of diversity and those of αTCR and βTCR should reflect differences in the types of antigens and restricting elements recognized by the αβ and γδTCRs.

18. EXAMPLE: GENOMIC ORGANIZATION OF THE HUMAN T CELL ANTIGEN RECEPTOR α/δ LOCUS

Two clusters of overlapping cosmid clones comprising about 100 kilobases (kb) at the human T cell antigen receptor α/β locus were isolated from a genomic library. The structure of the germ-line Vδ1 variable gene segment was determined. Vδ1 is located 8.5 kb downstream of the Vα13.1 gene segment, and both V segments are arranged in the same transcriptional orientation. The Vα17.1 segment is located between Vδ1 and the Dδ, Jδ, Cδ region (containing the diversity, joining, and constant gene segments). Thus, Vδ and Vα segments are interspersed along the chromosome. The germ-line organization of the Dδ2, Jδ1, and Jδ2 segments was determined. Linkage of Cδ to the Jα region was established by identification of Jα segments within 20 kb downstream of Cδ. The organization of the locus was also analyzed by field-inversion gel electrophoresis. The unrearranged Vδ1 and Dδ, Jδ, Cδ regions are quite distant from each other, apparently separated by a minimum of 175-180 kb.

18.1. Materials and Methods

18.1.1. Isolation and Characterization of Genomic Clones

A cosmid library from the human homozygous B-lymphoblastoid cell line MANN has been described (Blanck et al., 1988, J. Immunol. 141:1734–1737). Random-primed DNA probes (Feinberg et al., 1873, Anal. Biochem. 132:6-13) included δTCR cDNA clones 0-240 (specific for the constant segment Cδ) (see Section 8) and 0-240(VDJδ) (see Section 8) and 142-base-pair (bp) EcoRV-NaeI (Vα) and 37-bp Nae I-EcoRV (Jα) fragments of cDNA L17α (Leiden et al., 1986, Immunogenetics 24:17-23). Jδ1, Jδ2, and Dδ2 oligomers were labeled by using polynucleotide kinase and [γ$^{32}$P]ATP (Maniatis et al., 1982, Molecular Cloning: A Laboratory Manual, Cold Spring Harbor Laboratory, Cold Spring Harbor, N.Y.). Gel-purified DNA fragments were subcloned into Bluscript plasmid (Stratagene, LaJolla, Calif.), and sequences were determined on both strands (except where noted) by the dideoxy chain-termination method (Tabor et al., 1987, Proc. Natl. Acad. Sci. U.S.A. 84:4767–4771) usig double-stranded templates and exonuclease III-generated deletions (Chen et al., 1985, DNA 4:165–170; Tabor et al., 1987, supra; Promega Biotech, Madison, Wis.).

18.1.2. Field Inversion Gel Electrophoresis (FIGE)

DNA samples were prepared in agarose blocks by modifications of previous procedures (Van Ommen, et al., 1986, in Human Genetic Diseases: A Practical Approach, ed. Davies, K. E., IRL, Oxford, pp. 113–133). After digestion of DNA with restriction endonucleases, FIGE (Carle, et al. 1986, Science 232:65–68) was carried out for 36 hours in a 295×135×3 mm vertical 1% agarose gel (containing 45 mM Tris, 45 mM boric acid, 1 mM EDTA, and 0.3 μg of ethidium bromide per ml), with a PC 750 pulse controller (Hoefer, San Francisco). The gel was UV-irradiated and the DNA was transferred by electroblotting onto a Hybond-N membrane (Amersham) and UV-crosslinked to the membrane as described by the manufacturer.

18.2. Results

18.2.1. Isolation and Characterization of Cosmids Containing Vδ and Cδ Gene Segments A genomic cosmid library from homozygous human lymphoblastoid cell line MANN (Blanck et al., 1988, J. Immunol. 14:1734–1737) Was screened by colony hybridization with a labeled VDJCδ cDNA probe (see Section 8). Restriction enzyme digests of DNA prepared from those cosmids spanning the largest distances in the Vδ and Cδ regions were electrophoresed in 1% agarose and blots were prepared. Restriction maps were constructed based upon ethidium bromide staining as well as blot hybridization with available cDNA fragments and synthetic oligonucleotides and are presented in FIG. 27. The depicted orientation of the Vδ cosmids relative to the Cδ cosmids is supported by genomic rearrangement data presented in FIG. 29.

18.2.2. Vδ1 Genomic Segment

The Vδ1 segment was initially localized to a 10 kb XbaI fragment and was fine-mapped within this fragment to a 3 kb EcoRI fragment (FIG. 28A). The sequence spanning the Vδ1 segment is presented in FIG. 28B. The intron-exon organization was determined by comparison with available cDNA sequences (see Section 8). As for other TCR V segments, the Vδ1 segment is composed of two exons, one encoding the majority of the leader sequence and the second encoding the remainder of the leader sequence and the majority of the V domain. These exons are separated by a 223-bp intron that displays conserved splice donor and acceptor sequences. Heptamer and nonamer recombination signals separated by 23 bp flank the 3' end of the coding region.

18.2.3. Vα Segments Lie Upstream and Downstream of Vδ1

Blots carrying digests of Vδ1 cosmids were examined at low stringency with Vδ and Vα probes to study the possible association of additional V segments with the 45 kb region surrounding Vδ1. A single weakly hybridizing 3.6 kb XbaI-Asp718 fragment was identified in cosmid K3A by using a V fragment of cDNA L17α (Leiden et al., 1986, Immunogenetics 24:17-23) (Vδ17.1 in the nomenclature of Takihara et al., 1988, Eur. J. Immunol. 18:282-287) as a probe. This fragment was subcloned and fine-mapped, and the nucleotide sequence was determined (FIG. 28C). The sequence extending from the Asp718 site toward Vδ1 revealed an open reading frame representing the 3' portion of a V segment, identified as Vα13.1 based upon 100% nucleotide identity with a published cDNA sequence (Klein et al., 1987, Proc. Natl. Acad. Sci. U.S.A. 84:6884-6888). This V segment lies roughly 8.5 kb 5, of Vδ1, and both segments are organized in the same transcriptional orientation. Notably, the heptamers flanking Vα13.1 and Vδ1 are identical, and the nonamers differ at only two positions.

By analyzing Southern blots of XbaI-digested genomic DNA samples from γδTCR cell lines, we identified one cell line F7, that displays Vδ1 to (D-D)Jδ1 rearrangement on both chromosomes. As shown in FIG. 29, whereas IDP2 cells display two distinct Jδ1 rearrangements, one of 6.2 kb to Vδ1 (see Section 17) and one of 2.7 kb presumed to be D-J or D-D-J, the cell line F7 displays only a 6.2 kb Jδ1 rearrangement. Since F7 retains no germ-line copies of Jδ1 and has not rearranged Jδ2, it must carry two rearrangements of Vδ1 to Jδ1, a conclusion supported by the intensity of hybridization with the Jδ1 probe. Further analysis revealed that both IDP2 and F7 retain two copies of Vα13.1 but have deleted one copy and two copies, respectively, of a genomic segment mapping just 3' to Vδ1 (FIG. 29). This indicates that Vδ1 rearrangement occurs by deletion and orients Vα13.1, Vδ1 and Dδ, Jδ, Cδ as shown in FIG. 27. Strikingly, the Vα17.1 gene segment, like the segment mapping 3' of Vδ1, has been deleted on one chromosome in IDP2 and on both chromosomes in F7 (FIG. 29). These results indicate that Vα17.1 lies 3' of Vδ1, between Vδ1 and Dδ, Jδ, Cδ, and provides evidence for the interspersion of Vα and Vδ gene segments.

18.2.4. Dδ, Jδ, and Cδ Segments

Hybridization with a Cδ specific cDNA probe (Section 8, supra) localized the Cδ gene segment to a 9.4-kb XbaI fragment in cosmids K7A and K3B. The Jδ1 and Jδ2 segments were mapped by using synthetic oligonucleotides whose design was based upon putative J sequences identified in various cDNA clones (see Section 17). Jδ2 was localized to a 1.1 kb BamHI-XbaI fragment, present in both K7A and K3B, that mapped 1.5 kb upstream of the fragment carrying Cδ. Jδ1 was localized to a 1.7 kb XbaI fragment, present only in K3B, that mapped about 8 kb further upstream. The sequences spanning the Jδ1 and Jδ2 segments are presented in FIG. 30A and B. Both Jδ segments are flanked by heptamer and nonamer elements separated by 12 bp at their 5' ends and by conserved splice donor sites at their 3' ends. Homology between the two J segments is low. Notably, Jδ2 displays an unusual substitution relative to the core of amino acids that are highly conserved in J segments (Phe-Gly-Xaa-Gly-Ile rather than Phe-Gly-Xaa-Gly-Thr). Furthermore, the nonamer element flanking this J segment is particularly divergent from the consensus nonamer sequence. These observations may explain why this Jδ sement appears to be utilized less frequently than Jδ1 (see Section 17).

A comparison of the junctional sequences of a panel of human δTCR cDNA clones revealed two conserved sequences suggestive of the use of two germ-line Dδ elements (see Section 17), as has been demonstrated form murine δTCR (Chien et al., 1987, Nature 330:722-727; Elliot et al., 1988, Nature 331:627-631). By using a synthetic oligonucleotide probe, the putative 3' D element (Dδ2) was localized to a 3.9 kb XbaI fragment that mapped immediately 5' to the XbaI fragment carrying Jδ1. Nucleotide sequence analysis identified this Dδ element of 13 bp as nucleotides 3525-3537 of the fragment (FIG. 30C). This element is flanked by heptamer and nonamer elements separated by 12 bp at its 5' end and by 23 bp at its 3' end. Comparison with available cDNA sequences revealed that the Dδ2 element can be used in multiple translational reading frames (see Section 17, supra).

18.2.5. Linkage of the Cδ and Jα Regions

By using a small cDNA fragment carrying Jα sequences as a probe, a 1.6 kb XbaI-SalI fragment of K7A that mapped roughly 20 kb downstream of Cδ was identified. The sequence of this fragment revealed two typical Jα segments separted by about 900 bp. It is possible that other Jα segments lie between these segments and Cδ.

18.2.6. Field Inversion Gel Electrophoresis (FIGE)

Figure 31B:
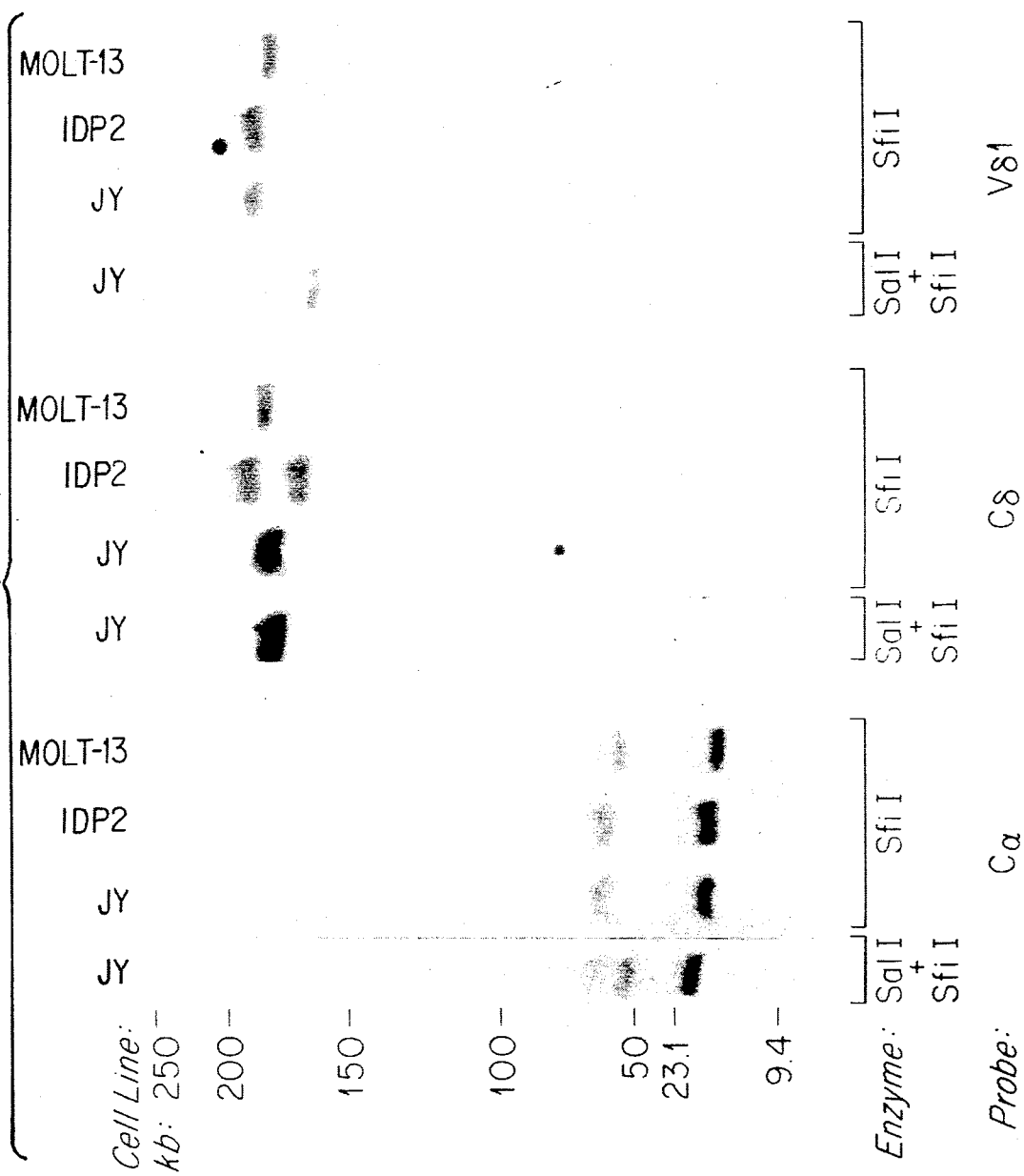
Figure 31D:
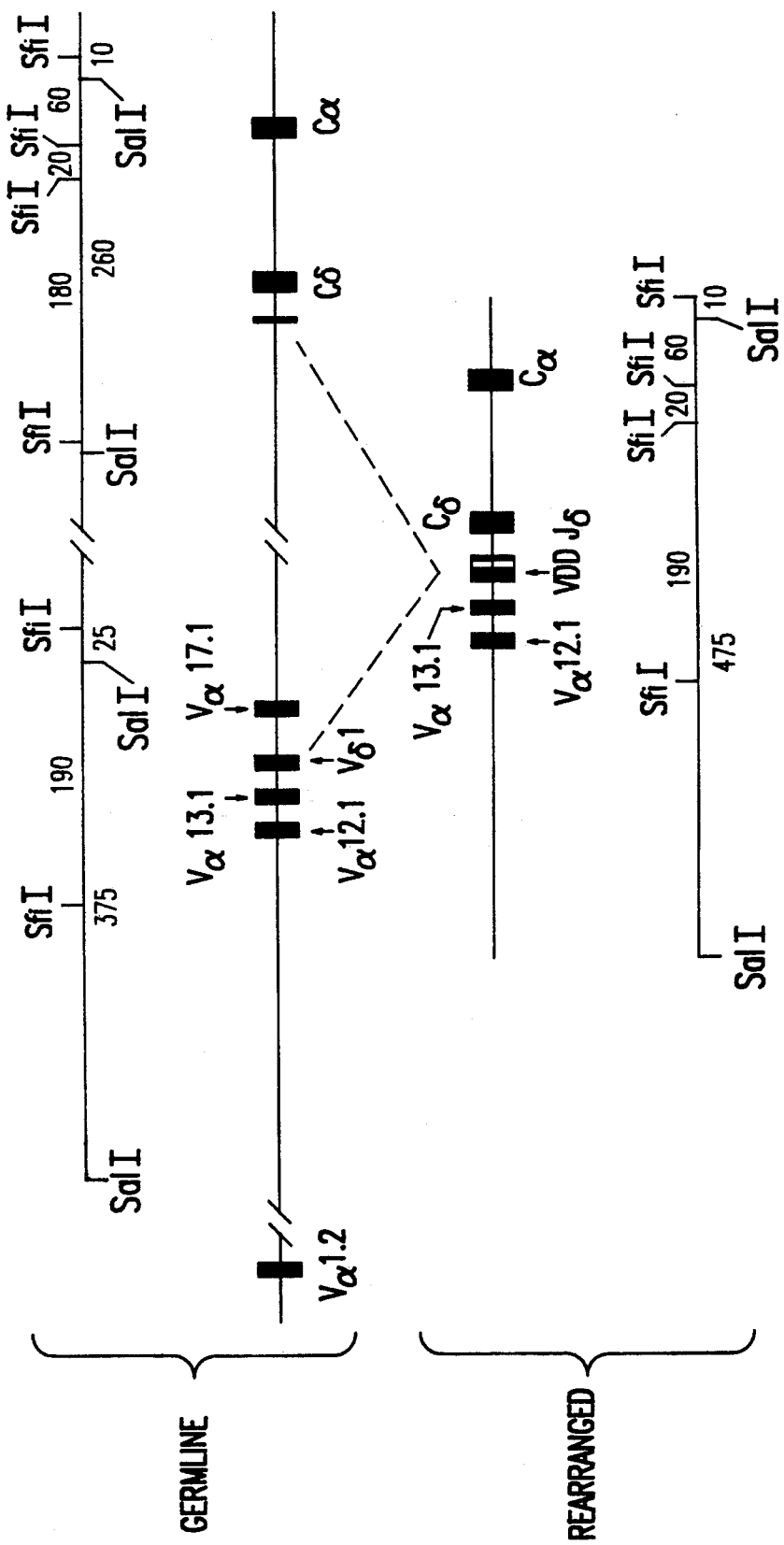

The relative organization of Vα, Vδ, Cδ, and Cα segments within the TCR α/δ locus was further investigated by FIGE. High molecular weight genomic DNA obtained from cells displaying the germ-line configuration at this locus and cells displayig VDDJδ rearrangements were examined. The Cα and Cδ gene segments were localized to the same 260 kb germ-line SalI fragment in JY and IDF (FIG. 31A), whereas the Vδ1 segment was localized to a distinct SalI fragment of 375 kb in the small cell lines. In addition, a higher molecular weight SalI fragment was reproducibly detected, by using a Vδ1 probe, in IDF DNA but not in JY DNA (FIG. 31A and C); this fragment might be a partial digestion product. By contrast, the Cα, Cδ, and Vδ1 segments were all localized to distinct SfiI fragments in JY DNA (FIG. 31B). The Cα probe detected two fragments, of 60 kb and 20 kb, due to the presence of an SfiI site within one intron of the Cα gene segment (Yoshikai et al., 1985, Nature 316:837-840). The Cδ probe detected an SfiI fragment of roughly 180 kb, whereas the Vδ1 probe detected a fragment of 190 kb. These fragments were clearly distinguishable based on double digestion with SalI plus SfiI (FIG. 31B). These data are summarized in the map of the unrearranged chromosome presented in FIG. 31D.

Two Vα segments, Vδ17.1 and Vδ12.1 (Sim, et al., 1984, Nature 316:837-840) were localized to the same SalI and SfiI fragment as Vδ1. As described above, deletional analysis mapped Vα17.1 3' to Vδ1 (FIG. 29). Since Vδ1 is deleted on a chromosome that has rearranged Vδ12.1, the latter must map 5' to the former. Cosmid analysis mapped Vα13.1 immediately 5' to Vδ1 (FIGS. 27 and 28). One other Vα segment tested, Vα1.2 (Yanagi et al., 1985, Proc. Natl. Acad. Sci. U.S.A. 82:3430-3434), mapped to distinct SalI and SfiI fragments (FIG. 31C). These fragments are presumed to map distal to those carrying Vδ1, Vα17.1, and Vα12.1, since a chromosome that has rearranged Vα1.2 has deleted Vδ1. Whether these sets of fragments are linked is not known.

DNA from the γδTCR cell lines PEER, IDP2, and Molt-13 was analyzed in order to determine the structure of chromosomes carrying a functionally rearranged δTCR gene. PEER displayed a single SalI fragment of 475 kb that hybridized with Cα, Cδ, and Vδ probes (FIG. 31A). IDP2 displayed a rearranged fragment of the same size that hybridized with all three probes. As expected, the rearranged fragment did not hybridize with a Vα17.1 probe. In addition, IDP2 displayed apparent germ-line fragments originating from the nonproductively rearranged chromosome (note that the germ-line IDP2 pattern detected by the Vδ1 probe resembles that of IDF rather than that of JY (FIG. 31A). IDP2 and Molt-13 displayed 190 kb SfiI fragments hybridizing with both Vδ1 and Cδ probes, as well as an additional (nonproductively) rearranged fragment in each cell line detected by the Cδ probe (FIG. 31B). These data are summarized in the map of the rearranged chromosome presented in FIG. 31D.

Given that the arrangement of Vδ1 to Dδ-Jδ occurs by deletion (FIG. 29), it is possible to estimate the minimal distance between these segments. If the SfiI fragments carrying Vδ1 (190 kb) and Cδ (180 kb) were adjacent to each other, the detection of a rearranged SfiI fragment of 190 kb would imply the deletion of 180 kb in the process of rearrangement (190+180-190=180). Similarly, the detection of 475 kb would predict the deletion of 175 kb in the process of rearrangement (375+25+260-10-475=175). Thus, Vδ1 lies a minimum of 175 to 180 kb away from Jδ1. However, since the SfiI fragments in question may not be adjacent in the germ-line configuration, this distance could be greater.

18.3. Discussion

The results of these and other studies indicate that the human δTCR gene segments are nested within the αTCR locus on human chromosome 14. Within the locus are 50-100 Vα segments, 50-100 Jα segments, and two Jδ segments, all of which take part in recombinational events leading to the assembly of functional αTCR and δTCR genes. In contrast to αTCR, there are only a limited number of δTCR germ-line segments. The diversity of δTCR is nevertheless high, because the use of multiple D elements and extensive incorporation of N nucleotides generates tremendous variability of the V-D-D-J junction. It is rather striking that the αTCR and δTCR genes maintain distinct strategies to generate diversity despite their nested chromosomal arrangement.

It is striking finding of this study that Vδ1 is situated within 8.5 kb of a known Vα segment, Vα13.1, yet at quite some distance from Dδ, Jδ, Cδ. Although we have not determined this distance directly, our data imply that Vδ1 and Dδ, Jδ, Cδ are separated by a minimum of 175 to 180 kb. Further, at least one Vα segment, Vα17.1, lies between Vδ1 and Dδ, Jδ, Cδ. Thus Vδ and Vδ segments are not segregated from each other and in fact are interspersed within the locus. Murine Vα and Vα segments may be similarly interspersed (Elliot et al., 1988, Nature 331:627-631).

Since Vδ1 rearrangements, but not Vα13.1 and Vα17.1 rearrangements, to Dδ, Jδ, Cδ have been detected in the γδTCR lymphocytes, V-segment utilization cannot be controlled by proximity to Dδ, Jδ, Cδ and/or the gross organization of the V segments on the chromosome. Proximity has been invoked to explain the hierarchy of rearrangements at the immunoglobulin heavy-chain locus (Yancopoulas et al., 1984, Nature 311:727-733). In addition, specificity is unlikely to be provided by the recombination signals flanking the V segments, since those flanking Vα1 and Vα13.1 are virtually identical to each other, suggesting the use of a common recombination machinery (Yancoupoulas et al., 1986, Cell 44:251-259). If control of rearrangement is mediated through modulation of the accessibility of particular segments of the chromosome, as has been suggested (Yancoupoulas et al., 1985, Cell 40:271-281; Blackwell et al., 1986, Nature 324:585-589), the data presented in this paper would imply that such accessibility is limited to within 8 kb 5' of Vδ1. Alternatively, there may be other elements involved in regulating the recombinational events within the locus.

19. DEPOSIT OF HYBRIDOMAS

The following hybridoma cell lines, producing the indicated monoclonal antibody, have been deposited with the American Type Culture Collection (ATCC), Rockville, Md., on the indicated dates, and have been assigned the listed accession numbers:

| Hybridoma | Monoclonal Antibody | Date of Deposit | Accession Number |
| --- | --- | --- | --- |
| δTCAR-3 | TCSδ1 (δTCAR-3) (anti-Vδ) | 10/29/87 | HB 9578 |
| 5A6.E9 | anti-TCRδ1 (anti-Cδ) | 7/27/88 | HB 9772 |
| #3 | anti-Cγm1 (anti-Cγ) | 7/27/88 | HB 9773 |

The present invention is not to be limited in scope by the cell lines deposited since the deposited embodiments are intended as single illustrations of one aspect of the invention and any cell lines which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Throughout this specification, various publications are cited, the disclosures of which are incorporated by reference herein.

What is claimed is:

1. A method for expressing a γ,δ T cell antigen receptor heterodimer, which comprises culturing a transfected cell capable of expressing a nucleic acid encoding a gamma T cell antigen receptor polypeptide and capable of expressing a nucleic acid encoding a delta T cell antigen receptor polypeptide, under conditions such that both the encoded gamma T cell antigen receptor polypeptide and the encoded delta T cell antigen receptor polypeptide are expressed by the cell.

2. A composition comprising isolated cells which (a) express a γ, δ T cell antigen receptor heterodimer; and (b) express the CD4 antigen.

3. A composition comprising isolated cells which express a γ,δ T cell antigen receptor heterodimer; which heterodimer is not associated with a CD3 complex.

4. The composition of claim 3 in which the cells are endometrial glandular epithelial cells.

5. A method for expressing a portion of a γ,δ T cell antigen receptor heterodimer, which comprises culturing a transfected cell capable of expressing a nucleic acid sequence encoding a portion of a γ (gamma) T cell antigen receptor polypeptide, which portion is selected from the group consisting of an epitope of a constant region of a γ chain of a T cell antigen receptor, an epitope of a variable region of a γ chain of a T cell antigen receptor and an epitope of a joining region of a γ chain of a T cell antigen receptor, and capable of expressing a portion of a δ T cell antigen receptor polypeptide, which portion is selected from the group consisting of an epitope of a constant region of a δ chain of a T cell antigen receptor, an epitope of a variable region of a δ chain of a T cell antigen receptor, an epitope of a joining region of a δ chain of a T cell antigen receptor and an epitope of diversity region of a δ chain of a T cell antigen receptor and subjecting the cell to conditions such that both nucleic acid sequences are expressed by the cell, in which the portion of the γ polypeptide is associated with the portion of the δ polypeptide.

6. A composition comprising isolated cells which (a) express at least a portion of a γ,δ T cell antigen receptor heterodimer, which portion of a γ,δ T cell antigen receptor comprises a portion of a γ polypeptide selected from the group consisting of an epitope of a constant region of a γ chain, an epitope of a variable region of a γ chain, and an epitope of a joining region of a γ chain, associated with a portion of a δ polypeptide selected from the group consisting of an epitope of a constant region of a δ chain, an epitope of a variable region of a δ chain, an epitope of a joining region of a δ chain, and an epitope of a diversity region of a δ chain; and (b) express the CD4 antigen.

7. A composition comprising isolated cells which express at least a portion of a γ, δ T cell antigen receptor heterodimer, which portion of a γ, δ T cell antigen receptor comprises a portion of a γ polypeptide selected from the group consisting of an epitope of a constant region of a γ chain, an epitope of a variable region of a γ chain, and an epitope of a joining region of a γ chain, associated with a portion of a δ polypeptide selected from the group consisting of an epitope of a constant region of a δ chain, an epitope of a variable region of a δ chain, an epitope of a joining region of a δ chain, and an epitope of a diversity region of a δ chain; which heterodimer is not associated with a CD3 complex.

8. A composition of claim 7 in which the cells are endometrial glandular epithelial cells.

9. A composition comprising isolated cells which (a) express at least a portion of a γ, δ T cell antigen receptor heterodimer, which portion of a γ, δ T cell antigen receptor comprises a portion of a γ polypeptide selected from the group consisting of an epitope of a constant region of a γ chain, an epitope of a variable region of a γ chain, and an epitope of a joining region of a γ chain, associated with a portion of a δ polypeptide selected from the group consisting of an epitope of a constant region of a δ chain, an epitope of a variable region of a δ chain, an epitope of a joining region of a δ chain, and an epitope of a diversity region of a δ chain; and (b) express the CD3 antigen.

10. A composition comprising a transfected cell which expresses a γ,δ T cell antigen receptor heterodimer.

11. A composition comprising a transfected cell which expresses at least a portion of a γ,δ T cell antigen receptor heterodimer, which portion of a γ, δ T cell antigen receptor comprises a portion of a γpolypeptide selected from the group consisting of an epitope of a constant region of a γ chain, an epitope of a variable region of a γ chain, and an epitope of a joining region of a γ chain, associated with a portion of a δ polypeptide selected from the group consisting of an epitope of a constant region of a δ chain, an epitope of a variable region of a δ chain, an epitope of a joining region of a δ chain, and an epitope of a diversity region of a δ chain.

12. The method according to claim 1 in which the cell constitutively expresses the nucleic acid encoding a γ T cell antigen acceptor polypeptide and expresses the nucleic acid encoding a δ T cell antigen receptor polypeptide which was transfected into the cell.

13. The method according to claim 1 in which the cell expresses the nucleic acid encoding a γ T cell antigen receptor polypeptide which was transfected into the cell and constitutively expresses the nucleic acid encoding a δ T cell antigen receptor polypeptide.

14. The method according to claim 1 in which the cell expresses the nucleic acid encoding a γ T cell antigen receptor polypeptide which was transfected into the cell and expresses the nucleic acid encoding a δ T cell antigen receptor polypeptide which was transfected into the cell.

15. The method according to claim 1 in which the cell is a T cell.

16. The method according to claim 1 in which the nucleic acid encoding a γ T cell antigen receptor polypeptide is selected from the group consisting of (i) a nucleic acid comprising a single CII exon; (ii) a nucleic acid comprising two CII exons; and (iii) a nucleic acid comprising three CII exons.

17. The method according to claim 1 in which the γ T cell antigen receptor polypeptide and the δ T cell antigen receptor polypeptide are non-covalently associated.

18. The method according to claim 1 in which the γ T cell antigen receptor polypeptide and the δ T cell antigen receptor polyppetide are covalently associated.

19. The method according to claim 5 in which the cell constitutively expresses the nucleic acid encoding at least a portion of the γ T cell antigen receptor polypeptide and expresses the nucleic acid encoding at least a portion of the δ T cell antigen receptor which was transfected into the cell.

20. The method according to claim 5 in which the cell expresses the nucleic acid encoding at least a portion of the gamma T cell antigen receptor polypeptide which was transfected into the cell and constitutively expresses the nucleic acid encoding at least a portion of the delta T cell antigen receptor polypeptide.

21. The method according to claim 5 in which the cell expresses the nucleic acid encoding at least a portion of the γ T cell antigen receptor polypeptide which was transfected into the cell, and expresses the nucleic acid encoding at least a portion of the δ T cell antigen receptor polypeptide which was transfected into the cell.

22. The method according to claim 5 in which the cell is a T cell.

23. The method according to claim 5 in which the nucleic acid encoding at least a portion of the γ T cell antigen receptor polypeptide is selected from the group consisting of (i) a nucleic acid comprising a single CII exon; (ii) a nucleic acid comprising two CII exons; and (iii) a nucleic acid comprising three CII exons.

24. The method according to claim 5 in which the portion of the γ T cell antigen receptor polypeptide and the portion of the δ T cell antigen receptor polypeptide are non-covalently associated.

25. The method according to claim 5 in which the portion of the γ T cell antigen receptor polypeptide and the portion of the δ T cell antigen receptor polypeptide are covalently associated.

* * * * *